United States Patent
Li et al.

(10) Patent No.: US 6,498,151 B2
(45) Date of Patent: Dec. 24, 2002

(54) ARYLDIFLUOROMETHYLPHOSPHONIC ACIDS WITH SULFUR-CONTAINING SUBSTITUENTS AS PTP-1B INHIBITORS

(75) Inventors: Chun Sing Li, Dollard Des Ormeaux (CA); Christopher Bayly, Beaconsfield (CA); Jacques Yves Gauthier, Laval (CA); Yves Leblanc, Kirkland (CA); Cheuk Kun Lau, Ile Bizard (CA); Patrick Roy, Dollard Des Ormeaux (CA); Michel Therien, Laval (CA); Zhaoyin Wang, Kirkland (CA); Claude Dufresne, Dollard Des Ormeaux (CA); Rejean Fortin, Montreal-Nord (CA)

(73) Assignee: Merck Frosst Canada & Co., Kirkland (CA)

(*) Notice: Subject to any disclaimer, the term of this patent is extended or adjusted under 35 U.S.C. 154(b) by 0 days.

(21) Appl. No.: 09/813,489

(22) Filed: Mar. 21, 2001

(65) Prior Publication Data
US 2002/0091104 A1 Jul. 11, 2002

Related U.S. Application Data
(60) Provisional application No. 60/191,369, filed on Mar. 22, 2000.

(51) Int. Cl.$^7$ ................ C07D 239/95; C07D 277/36; C07F 9/38; A61K 31/675; A61P 5/48

(52) U.S. Cl. ................ 514/80; 514/82; 514/86; 514/89; 514/92; 514/93; 514/94; 514/100; 514/107; 514/113; 514/124; 514/127; 514/128; 514/141; 544/243; 544/244; 546/22; 546/23; 546/24; 548/112; 548/113; 548/119; 548/415

(58) Field of Search ................ 514/80, 82, 86, 514/89, 92, 93, 94, 160, 167, 113, 124, 127, 128, 141; 544/243, 244; 546/22, 23, 24; 548/112, 113, 119, 415; 549/220, 218; 562/23, 24; 558/386; 560/9; 662/20, 11

(56) References Cited

U.S. PATENT DOCUMENTS 6,066,715 A  5/2000  Desmarias et al.

FOREIGN PATENT DOCUMENTS

| WO | WO 97/40017 | 10/1997 |
| WO | WO 98/20156 | 5/1998 |
| WO | WO 99/31066 | 6/1999 |
| WO | WO 99/47529 | 9/1999 |
| WO | WO 00/17211 | 3/2000 |
| WO | WO 00/69889 | 11/2000 |
| WO | WO 01/46203 | 6/2001 |
| WO | WO 01/46204 | 6/2001 |
| WO | WO 01/46205 | 6/2001 |
| WO | WO 01/46206 | 6/2001 |

OTHER PUBLICATIONS

Beers, Scott A.; Malloy, Elizabeth A.; Wu, Wei; Wachter, Michael P.; Gunnia, Uma; Cavender, Druie; Harris, Crafford; Davis, Janet; Brosius, Ruth; Pellegrino–Gensey, J. Lee; Siekierka, John, Bioorg. Med. Chem., 5(12), 2203–2211 (English) 1997..*
Pierre L. Beaulieu, et al., J. Med. Chem. 1999, 42, 1757–1766.
K. Blades, et al., Chem. Commun., 1615–1616, 1996.
Terrence R. Burke, Jr., et al., Bioorganic & Medicinal Chemistry Letters 9 (1999) 347–352.
Neil A. Caplan, et al., Bioorganic & Medicinal Chemistry Letters 8 (1998) 515–520.
Paul S. Charifson, et al., Biochemistry 1997, 36, 6283–6293.
G. Stuart Cockerill, et al., Tetrahedron Letters 40 (1999) 2601–2604.
G. Stuart Cockerill, et al., J. Chem. Soc., Perkin Trans. 1, 2000, 2591–2599.
Sylvie Desmarais, et al., Biochem. J. (1999) 337, 219–223.
Mikhail F. Gordeev, et al., Tetrahedron Letters, vol. 35, No. 41, pp. 7585–7588, 1994.
Hong, J. Enzyme Inhib., vol. 12, pp. 191–203, 1997.
Christopher C. Kotoris, Bioorganic & Medicinal Chemistry Letters 8 (1998) 3275–3280.
Christopher c. Kotoris, J. Org. Chem. 1998, 63, 8052–8057.
Scott D. Taylor, et al., Bioorganic & Medicinal Chemistry 6 (1998) 1457–1468.
Scott D. Taylor, et al., Tetrahedron Letters, vol. 37, No. 45, pp. 8089–8092, 1996.
Scott D. Taylor, et al., Tetrahedron 54 (1998) 1691–1714.
Qingping Wang, et al., Bioorganic & Medicinal Chemistry Letters 8 (1998) 345–350.
Zhu–Jun Yao, et al., Tetrahedron 55 (1999) 2865–2874.
Bin Ye, et al., Tetrahedron, vol. 52. No. 30., pp. 9963–9970, 1996.
Tsutomu Yokomatsu, et al., Tetrahedron 54 (1998) 9341–9356.
Tsutomu Yokomatsu, et al., Bioorganic & Medicinal Chemistry Letters 9 (1999) 529–532.

* cited by examiner

Primary Examiner—Mark L. Berch
(74) Attorney, Agent, or Firm—James L. McGinnis; Melvin Winokur

(57) ABSTRACT

The invention encompasses the novel class of compounds represented by the formula below, which are inhibitors of the PTP-1B enzyme.

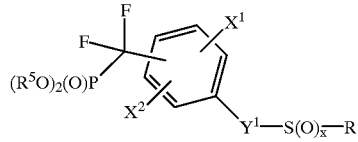

The invention also encompasses pharmaceutical compositions and methods of treating or preventing PTP-1B mediated diseases, including diabetes.

26 Claims, No Drawings

ARYLDIFLUOROMETHYLPHOSPHONIC ACIDS WITH SULFUR-CONTAINING SUBSTITUENTS AS PTP-1B INHIBITORS

CROSS REFERENCE TO RELATED APPLICATION

U.S application Ser. No. 09/398,356, filed on Sep. 17, 1999, now U.S. Pat. No. 6,174,874, issued Jan. 6, 2001; U.S. application Ser. No. 09/570,092, filed May 12, 2000, now U.S. Pat. No. 6,365,592; U.S. application Ser. Nos. 09/745,199, 09/745,211, 09/745,220 and 09/745,222, all filed on Dec. 21, 2000; and U.S. application Ser. No. 09/813,499, filed on even date herewith, all contain related subject matter. This application claims priority from U.S. Provisional application Ser. No. 60/191,369, filed on Mar. 22, 2000, which is incorporated by reference into this application in its entirety.

BACKGROUND OF THE INVENTION

This invention relates to a novel class of phosphonic acid derivatives that are inhibitors of PTP-1B.

Protein tyrosine phosphatases are a large family of transmembrane or intracellular enzymes that dephosphorylate substrates involved in a variety of regulatory processes (Fischer et al., 1991, Science 253:401–406). Protein tyrosine phosphatase-1B (PTP-1B) is a ~50 kd intracellular protein present in abundant amounts in various human tissues (Charbonneau et al., 1989, Proc. Natl. Acad. Sci. USA 86:5252–5256; Goldstein, 1993, Receptor 3:1–15).

Determining which proteins are substrates of PTP-1B has been of considerable interest. One substrate which has aroused especial interest is the insulin receptor. The binding of insulin to its receptor results in autophosphorylation of the domain (White & Kahn, 1994, J. Biol. Chem. 269:1–4). This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45:1379–1385 ("Seely") studied the relationship of PTP-1B and the insulin receptor in vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995, J. Biol. Chem. 270:20503–20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1 tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Recently, Kennedy et al., 1999, Science 283: 1544–1548 showed that protein tyrosine phosphatase PTP-1B is a negative regulator of the insulin signalling pathway, suggesting that inhibitors of this enzyme may be beneficial in the treatment of Type 2 diabetes. Mice lacking PTP-1B are resistant to both diabetes and obesity.

Therefore, inhibitors of PTP-1B improve insulin-sensitivity. They may have utility in controlling or treating Type 2 diabetes, in improving glucose tolerance, and in improving insulin sensitivity in patients in need thereof. The compounds may also be useful in treating or controlling other PTP-1B mediated diseases, and may be useful in the treatment of cancer, neurodegenerative diseases and the like.

SUMMARY OF THE INVENTION

Compounds represented by formula I, including pharmaceutically acceptable salts thereof, and prodrugs thereof, are PTP-1B inhibitors that may be useful in the treatment of diabetes and related medical conditions. They may also be useful in the treatment of other PTP-1B mediated diseases.

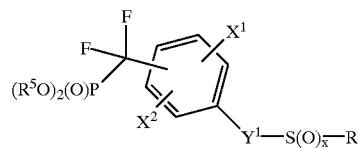

In the compounds of formula I:

$X^1$ and $X^2$ are each independently selected from the group consisting of: H, OH, halogen, CN, $CO_2H$, $CO_2C_{1-6}$ alkyl, $CO_2C_{1-6}$alkenyl, $OC_{1-6}$alkyl, $OC_{2-6}$alkenyl, $C(O)C_{1-6}$alkyl, $C(O)C_{2-6}$alkenyl, $OC(O)C_{1-6}$alkyl, $OC(O)C_{2-6}$alkenyl, $S(O)_xC_{1-6}$alkyl, $S(O)_xC_{2-6}$alkenyl, $C_{1-6}$ alkyl, $C_{2-6}$alkenyl, $C_{2-6}$alkynyl, $S(O)_2NR^1R^2$, $C(O)NR^1R^2$, and $NR^1R^2$, wherein each alkyl group and each alkenyl group in each substituent may optionally be substituted with one or more substituents that are independently selected from the following groups of substituents: (a) 1–13 halogen atoms, and (b) 1–2 substituents independently selected from $OC_{1-3}$ alkyl, $C(O)C_{1-3}$alkyl, $OC(O)C_{1-3}$alkyl, $CO_2H$, and $CO_2C_{1-3}$ alkyl;

$R^5$ is H;

$R^1$ and $R^2$ are each independently selected from the group consisting of H and $C_{1-4}$alkyl, wherein said alkyl substituents are optionally substituted with 1–9 halogen atoms;

Each halogen is independently selected from I, Cl, Br and F;

Each x is independently 0, 1, or 2;

$Y^1$ is selected from the group consisting of a bond, a $C_{1-6}$ alkylene group, and a $C_{2-6}$ alkenylene group, wherein said alkylene group and said alkenylene group are optionally substituted with one or more substituents independently selected from (a) 1–12 halogen atoms and (b) 1–2 substituents independently selected from OH and $OC_{1-4}$ alkyl, said $OC_{1-4}$ alkyl being optionally substituted with 1–9 halogen atoms;

R is selected from the group consisting of $C_{1-10}$ alkyl, $C_{2-10}$alkenyl, $C_{2-10}$alkadienyl, $C_{2-10}$alkynyl, $Ar^1$, and $Het^1$, wherein said alkyl, alkenyl, alkadienyl, and alkynyl are optionally substituted with one or more substituents independently selected from (a) 1–21 halogen atoms, (b) one substituent selected from $Ar^1$ and $Het^1$, and (c) 1–2 substituents independently selected from OH, CN, $CO_2H$, $CO_2C_{1-6}$ alkyl, $CO_2C_{2-6}$ alkenyl, $OC_{1-3}$alkyleneO$C_{1-3}$alkyl, $OC_{1-6}$alkyl, $OC_{2-6}$ alkenyl, OC(O)C$_{1-6}$alkyl, OC(O)C$_{2-6}$alkenyl, C(O)C$_{1-6}$alkyl, C(O)C$_{2-6}$alkenyl, Aryl, C(O)Aryl, OC(O)Aryl, OAryl, CO$_2$Aryl, S(O)$_x$C$_{1-6}$alkyl, S(O)$_x$C$_{2-6}$alkenyl, S(O)$_x$Aryl, S(O)$_2$NR$^1$R$^2$, C(O)NR$^1$R$^2$, NR$^1$R$^2$, and a 5–6-membered heterocycle having 1–2 heteroatoms selected from N, S and O in the ring, wherein said alkyl groups and said alkenyl groups of said substituents are optionally substituted with 1–13 halogen atoms;

Het$^1$ is a 5–10 membered aromatic ring system comprising 1 ring or 2 rings fused together and 1–4 heteroatoms selected from O, N, S(O)$_x$, and combinations thereof, and 0–2 carbonyl groups, wherein one of said fused rings is optionally a benzene ring, and said Het$^1$ is optionally substituted with one or more groups independently selected from (a) one group selected from CO$_2$H, CF$_2$CO$_2$H, P(O)(OR$^5$)$_2$, and SO$_2$R$^4$, and (b) 1–3 groups independently selected from R$^3$;

Ar$^1$ is phenyl or napthyl, wherein phenyl is optionally substituted with one or more groups independently selected from (a) one group selected from CF$_2$P(O)(OR$^5$)$_2$, CO$_2$H, CF$_2$CO$_2$H, P(O)(OR$^5$)$_2$, SO$_2$R$^4$, and Ar$^2$, and (b) 1–5 groups selected from R$^3$, and wherein naphthyl is optionally substituted with one or more groups independently selected from (a) one group selected from CO$_2$H, CF$_2$CO$_2$H, P(O)(OR$^5$)$_2$, SO$_2$R$^4$, and Ar$^2$, and (b) 1–5 groups selected from R$^3$;

Ar$^2$ is phenyl, naphthyl or a 5–10 membered aromatic ring system comprising 1 ring or 2 rings fused together and 1–4 heteroatoms independently selected from O, N, S(O)$_x$, and combinations thereof, and 0–2 carbonyl groups, wherein one of said fused rings is optionally a benzene ring, wherein Ar$^2$ is optionally substituted with one or more substituents independently selected from (a) one group selected from CF$_2$P(O)(OR$^5$)$_2$, CO$_2$H, CF$_2$CO$_2$H, P(O)(OR$^5$)$_2$, and SO$_2$R$^4$, and (b) 1–2 groups selected from R$^3$;

R$^3$ is selected from the group consisting of halogen, OH, CN, CO$_2$H, NO$_2$, CO$_2$C$_{1-10}$alkyl, CO$_2$C$_{2-10}$ alkenyl, OC$_{1-10}$alkyl, OC$_{2-10}$ alkenyl, C$_{1-10}$ alkyl, C$_{2-10}$ alkenyl, OC(O)C$_{1-10}$alkyl, OC(O)C$_{2-10}$alkenyl, C(O)C$_{1-10}$alkyl, C(O)C$_{2-10}$alkenyl, C(O)Aryl, OC(O)Aryl, OAryl, CO$_2$Aryl, S(O)$_x$C$_{1-10}$alkyl, C$_{1-3}$alkyleneS(O)$_x$C$_{1-10}$alkyl, S(O)$_x$C$_{2-10}$alkenyl, S(O)$_2$NR$^1$R$^2$, C(O)NR$^1$R$^2$, NR$^1$R$^2$, NR$^1$S(O)$_2$R$^2$, NR$^1$C(O)C$_{1-6}$alkyl, NR$^1$C(O)H, Aryl, and Het, wherein each alkyl group and each alkenyl group of each substituent is optionally substituted with one or more substituents independently selected from (a) 1–21 halogen atoms and (b) 1–2 substituents independently selected from OH, OC$_{1-3}$ alkyl, CO$_2$H, CO$_2$C$_{1-3}$alkyl, C(O)C$_{1-3}$alkyl, OC(O) C$_{1-3}$alkyl, S(O)$_x$Aryl, S(O)$_x$C$_{1-3}$alkyl and phenyl, wherein said phenyl is optionally substituted with 1–3 substituents independently selected from OCH$_3$, OCF$_3$, S(O)$_2$ NR$^1$R$^2$, Br, Cl, and F, wherein the C$_{1-3}$ alkyl groups of said substituents are optionally substituted with one or more substituents independently selected from (a) 1–7 halogen atoms and (b) 1–2 phenyls which are optionally substituted with 1–3 substituents independently selected from halogen and SO$_2$NR$^1$R$^2$;

Aryl is a 6–14 membered aromatic carbocyclic moiety comprising 1 ring or 2–3 fused rings, wherein said Aryl is optionally substituted with 1–3 substituents independently selected from C$_{1-3}$alkyl, halogen, OH, OC$_{1-3}$ alkyl, C(O)C$_{1-3}$alkyl, OC(O)C$_{1-3}$alkyl, CO$_2$H, CO$_2$C$_{1-3}$alkyl, NR$^1$R$^2$, S(O)$_x$C$_{1-4}$alkyl and SO$_2$NR$^1$R$^2$, wherein said alkyl groups in said substituents are optionally substituted with 1–7 halogen atoms;

Het is a 5–10 membered aromatic ring system containing 1–4 heteroatoms selected from N, S(O)$_x$, O, and mixtures thereof, and 0–2 carbonyl groups, wherein said Het comprises 1 ring or 2 fused rings, one of which fused rings may be a benzene ring, and said Het is optionally substituted with 1–3 substituents independently selected from C$_{1-3}$alkyl, halogen, OC$_{1-3}$ alkyl, C(O)C$_{1-3}$alkyl, OC(O)C$_{1-3}$alkyl, CO$_2$H, CO$_2$C$_{1-3}$alkyl, NR$^1$R$^2$, S(O)$_x$C$_{1-4}$alkyl and SO$_2$NR$^1$R$^2$, wherein said alkyl groups are optionally substituted with 1–7 halogen atoms;

Alkyl, alkenyl, alkadienyl and alkynyl are linear, branched or cyclic hydrocarbon structures, or combinations thereof containing the indicated number of carbon atoms and substituted as indicated, wherein alkyl, alkenyl, alkadienyl and alkynyl are respectively saturated, contain one double bond, contain 2 double bonds, or contain one triple bond; and R$^4$ is phenyl or C$_{1-4}$ alkyl, wherein said phenyl is optionally substituted with one or more substituents independently selected from (a) 1–3 halogen atoms and (b) 1–2 C$_{1-3}$ alkyl or C$_{1-3}$alkoxy groups, which are optionally substituted with 1–7 halogen atoms, and said C$_{1-4}$ alkyl is optionally substituted with one or more substituents independently selected from (a) 1–9 halogen atoms and (b) 1–2 C$_{1-3}$ alkoxy groups, which are optionally substituted with 1–7 halogen atoms.

Methods of treating and controlling diabetes, obesity, and other diseases and conditions using the compounds of Formula I are taught herein. Pharmaceutical compositions and combination treatments are also disclosed herein.

DETAILED DESCRIPTION OF THE INVENTION

The compounds of Formula I have numerous embodiments.

One embodiment includes compounds of Formula I as described below:

X$^1$ and X$^2$ are each independently selected from the group consisting of: H, OH, halogen, CN, CO$_2$H, CO$_2$C$_{1-6}$ alkyl, CO$_2$C$_{2-6}$alkenyl, OC$_{1-6}$alkyl, OC$_{2-6}$alkenyl, C(O)C$_{1-6}$alkyl, C(O)C$_{2-6}$alkenyl, OC(O)C$_{1-6}$alkyl, OC(O)C$_{2-6}$alkenyl, S(O)$_x$C$_{1-6}$alkyl, S(O)$_x$C$_{2-6}$alkenyl, C$_{1-6}$ alkyl, C$_{2-6}$alkenyl, S(O)$_2$NR$^1$R$^2$, C(O)NR$^1$R$^2$, and NR$^1$R$^2$, wherein each alkyl group and each alkenyl group in each substituent is optionally substituted with one or more substituents independently selected from (a) 1–13 halogen atoms and (b) 1–2 substituents independently selected from OC$_{1-3}$ alkyl, C(O)C$_{1-3}$alkyl, OC(O)C$_{1-3}$alkyl, CO$_2$H, and CO$_2$C$_{1-3}$alkyl;

R$^5$ is H;

R$^1$ and R$^2$ are each independently selected from the group consisting of H and C$_{1-4}$alkyl, wherein said alkyl substituents are optionally substituted with 1–9 halogen atoms;

Each halogen is independently selected from I, Cl, Br and F;

Each x is independently 0, 1, or 2;

Y$^1$ is selected from the group consisting of a bond, a C$_{1-4}$ alkylene group, and a C$_{2-4}$ alkenylene group, wherein said alkylene group and said alkenylene group are optionally substituted with one or more substituents independently selected from (a) 1–8 halogen atoms and (b) 1–2 substituents independently selected from OH and OC$_{1-4}$ alkyl, said OC$_{1-4}$ alkyl being optionally substituted with 1–9 halogen atoms;

R is selected from the group consisting of $C_{1-10}$ alkyl, $C_{2-10}$alkenyl, $C_{2-10}$alkadienyl, $C_{2-10}$alkynyl, $Ar^1$, and $Het^1$, wherein said alkyl, alkenyl, alkadienyl, and alkynyl are optionally substituted with one or more substituents independently selected from (a) 1–21 halogen atoms, (b) one substituent selected from $Ar^1$ and $Het^1$, and (c) 1–2 substituents independently selected from OH, CN, $CO_2H$, $CO_2C_{1-6}$ alkyl, $CO_2C_{2-6}$ alkenyl, $OC_{1-6}$alkyl, $OC_{2-6}$ alkenyl, $OC(O)C_{1-6}$alkyl, $OC(O)C_{2-6}$alkenyl, $C(O)C_{1-6}$alkyl, $C(O)C_{2-6}$alkenyl, $C(O)$Aryl, $OC(O)$Aryl, $OAryl$, $CO_2Aryl$, $S(O)_xC_{1-6}$alkyl, $S(O)_x$ $C_{2-6}$alkenyl, $S(O)_2NR^1R^2$, $C(O)NR^1R^2$, and $NR^1R^2$, wherein said alkyl groups and said alkenyl groups of said substituents are optionally substituted with 1–13 halogen atoms;

$Het^1$ is a 5–10 membered aromatic ring system comprising 1 ring or 2 rings fused together and 1–4 heteroatoms selected from O, N, $S(O)_x$, and combinations thereof, and 0–2 carbonyl groups, wherein one of said fused rings is optionally a benzene ring, and said $Het^1$ is optionally substituted with one or more substituents independently selected from (a) one group selected from $CO_2H$, $CF_2CO_2H$, $P(O)(OR^5)_2$, and $SO_2R^4$, and (b) 1–2 groups independently selected from $R^3$;

$Ar^1$ is phenyl or napthyl, wherein phenyl is optionally substituted with one or more groups independently selected from (a) one group selected from $CF_2P(O)(OR^5)_2$, $CO_2H$, $CF_2CO_2H$, $P(O)(OR^5)_2$, $SO_2R^4$, and $Ar^2$, and (b) 1–2 groups selected from $R^3$, and wherein naphthyl is optionally substituted with one or more groups independently selected from (a) one group selected from $CO_2H$, $CF_2CO_2H$, $P(O)(OR^5)_2$, $SO_2R^4$, and $Ar^2$, and (b) 1–2 groups selected from $R^3$;

$Ar^2$ is phenyl, naphthyl or a 5–10 membered aromatic ring system comprising 1 ring or 2 rings fused together and 1–4 heteroatoms selected from O, N, $S(O)_x$, and combinations thereof, and 0–2 carbonyl groups, wherein one of said fused rings is optionally a benzene ring, wherein $Ar^2$ is optionally substituted with one or more substituents independently selected from (a) one group selected from $CF_2P(O)(OR^5)_2$, $CO_2H$, $CF_2CO_2H$, $P(O)(OR^5)_2$, and $SO_2R^4$, and (b) 1–2 groups selected from $R^3$;

$R^3$ is selected from the group consisting of halogen, OH, CN, $CO_2H$, $CO_2C_{1-10}$ alkyl, $CO_2C_{2-10}$ alkenyl, $OC_{1-10}$ alkyl, $OC_{2-10}$ alkenyl, $C_{1-10}$ alkyl, $C_{2-10}$ alkenyl, $OC(O)C_{1-10}$alkyl, $OC(O)C_{2-10}$alkenyl, $C(O)C_{1-10}$alkyl, $C(O)C_{2-10}$alkenyl, $C(O)$Aryl, $OC(O)$Aryl, $OAryl$, $CO_2Aryl$, $S(O)C_{1-10}$alkyl, $S(O)_xC_{2-10}$alkenyl, $S(O)_2NR^1R^2$, $C(O)NR^1R^2$, $NR^1R^2$, Aryl, and Het, wherein each alkyl group and each alkenyl group of each substituent is optionally substituted with one or more substituents independently selected from (a) 1–21 halogen atoms and (b) 1–2 substituents independently selected from OH, $OC_{1-3}$ alkyl, $CO_2H$, $CO_2C_{1-3}$alkyl, $C(O)C_{1-3}$alkyl, $OC(O)C_{1-3}$alkyl, and phenyl, wherein said phenyl is optionally substituted with $OCH_3$, $OCF_3$, or 1–3 halogen atoms selected from Cl and F, and said $C_{1-3}$ alkyl groups of said substituents are optionally substituted with one or more substituents independently selected from (a) 1–7 halogen atoms and (b) 1–2 phenyls, wherein said phenyls are optionally substituted with 1–3 halogen atoms;

Aryl is a 6–14 membered aromatic carbocyclic moiety comprising 1 ring or 2–3 fused rings, wherein said Aryl is optionally substituted with 1–3 substituents independently selected from $C_{1-3}$alkyl, halogen, $OC_{1-3}$ alkyl, $C(O)C_{1-3}$alkyl, $OC(O)C_{1-3}$alkyl, $CO_2H$, and $CO_2C_{1-3}$ alkyl, wherein said alkyl groups in said substituents are optionally substituted with 1–7 halogen atoms;

Het is a 5–10 membered aromatic ring system containing 1–4 heteroatoms selected from N, $S(O)_x$, O, and mixtures thereof, and 0–2 carbonyl groups, wherein said Het comprises 1 ring or 2 fused rings, one of which fused rings may be a benzene ring, and said Het is optionally substituted with 1–3 substituents independently selected from $C_{1-3}$alkyl, halogen, $OC_{1-3}$ alkyl, $C(O)C_{1-3}$alkyl, $OC(O)C_{1-3}$alkyl, $CO_2H$, and $CO_2C_{1-3}$ alkyl, wherein said alkyl groups are optionally substituted with 1–7 halogen atoms; and $R^4$ is phenyl or $C_{1-4}$ alkyl, wherein said phenyl is optionally substituted with one or more substituents independently selected from (a) 1–3 halogen atoms and (b) 1–2 $C_{1-3}$ alkyl or $C_{1-3}$alkoxy groups, which are optionally substituted with 1–7 halogen atoms, and said $C_{1-4}$ alkyl is optionally substituted with one or more substituents independently selected from (a) 1–9 halogen atoms and (b) 1–2 $C_{1-3}$ alkoxy groups, which are optionally substituted with 1–7 halogen atoms.

In one embodiment of the compounds of Formula I, the halogen atom substituents are independently selected from Cl, Br, and F.

In another embodiment, $X^1$ is H, and $X_2$ is a halogen atom, $CH_3$, $OCH_3$, OH or $CO_2H$.

Another embodiment comprises compound of Formula I, wherein $X^1$ is H, $X^2$ is selected from the group consisting of Cl, F, and Br, and the $Y^1$substituent on the phenyl ring to which $Y^1$ is attached is in the position para to $CF_2 P(O)(OR^5)_2$. In one subset of compounds of this embodiment, $X^2$ is Br and is ortho to $CF_2P(O)(OR^5)_2$.

Other embodiments comprise compounds in which $Y^1$ is a bond, $CH_2$, or linear $C_{2-4}$alkylene. A subset of these includes compounds in which $Y^1$ is a bond, $CH_2$, or $C_2H_4$.

Another preferred group of compounds comprises those compounds in which the group $Y^1$ of Formula I is alkylene or alkenylene, where each carbon atom that makes up $Y^1$ is linear or monobranched. Similarly, all the carbon atoms that make up the main carbon chain in the group R are linear or monobranched, where R can be alkyl, alkenyl, alkadienyl or alkynyl. Carbon atoms are defined as linear when they are bonded by only single bonds and they have no hydrocarbon branches on any carbon atom, and are defined as monobranched when there is one hydrocarbon branch on the carbon. Dibranched carbons have two hydrocarbon substituents (i.e. they are quaternary carbon atoms). In other embodiments, only the first two carbons of $Y^1$ and R on each side of the S atom must be linear or monobranched.

Another preferred embodiment comprises compounds in which R is $C_{1-4}$ alkyl, $C_{2-4}$ alkenyl or $C_{2-4}$alkynyl, and is substituted with one $Ar^1$ and optionally with 1–2 substituents selected from Aryl and (C=O)Aryl; and $Ar^1$ is phenyl which is optionally substituted with (a) one group $CF_2P(O)(OR^5)_2$ and/or (b) 1–2 groups $R^3$, or a combination of these. In preferred compounds, $Ar^1$ is phenyl optionally substituted with 1–2 $R^3$. $R^3$ is selected from Br, Cl, F, OH, and $C_{1-3}$ alkyl. A preferred embodiment includes compounds in which $R^3$ is Br. Compounds in which R is selected from $C_{1-4}$ alkyl and $C_{2-4}$ alkenyl are also preferred, as are compounds in which $Y^1$ is a bond, $C_{1-4}$alkylene or $C_{1-4}$ alkenylene.

Another subset of compounds includes compounds in which R is selected from the group consisting of $C_{1-4}$ alkyl, $C_{2-4}$ alkenyl, and $C_{2-4}$alkynyl, and R is substituted with one $Ar^1$;

Ar$^1$ is phenyl or naphthyl and is substituted with Ar$^2$;

Ar$^2$ is a 5–10 membered aromatic ring system comprising 1 ring or 2 rings fused together and 1–4 heteroatoms selected from O, N, S(O)$_x$, and combinations thereof, and 0–2 carbonyl groups, wherein one of said fused rings is optionally a benzene ring, and Ar$^2$ is optionally substituted with one or more substituents independently selected from (a) one group selected from P(O)(OH)$_2$ and CO$_2$H and (b) 1–2 groups R$^3$;

R$^3$ is selected from halogen, C$_{1-10}$ alkyl, OC$_{1-10}$ alkyl, C(O)Aryl, and Aryl, where said C$_{1-10}$ alkyl and OC$_{1-10}$ alkyl are optionally substituted with 1–2 substituents independently selected from OC$_{1-3}$ alkyl, phenyl, and CO$_2$H; and X$^1$, X$^2$, R$^1$, R$^2$, R$^4$, R$^5$, x, Y$^1$, Aryl, Het, and Het$^1$ are as defined prevously.

Another group of desirable compounds includes compounds in which R is selected from the group consisting of C$_{1-4}$ alkyl and C$_{2-4}$ alkenyl, and R is substituted with one Ar$^1$;

Ar$^1$ is phenyl or naphthyl and is substituted with Ar$^2$;

Ar$^2$ is a 5–10 membered aromatic ring system comprising 1 ring or 2 rings fused together and 1–4 heteroatoms selected from O, N, S(O)$_x$, and combinations thereof, and 0–2 carbonyl groups, wherein one of said fused rings is optionally a benzene ring, and Ar$^2$ is optionally substituted with one or more substituents independently selected from (a) one group selected from P(O)(OH)$_2$ and CO$_2$H and (b) 1–2 groups R$^3$;

R$^3$ is selected from C$_{1-10}$ alkyl, OC$_{1-10}$ alkyl, C(O)Aryl, and Aryl, where said C$_{1-10}$ alkyl and OC$_{1-10}$ alkyl are optionally substituted with 1–2 substituents independently selected from OC$_{1-3}$ alkyl, phenyl, and CO$_2$H; and X$^1$, X$^2$, R$^1$, R$^2$, R$^4$, R$^5$, x, Y$^1$, Aryl, Het, and Het$^1$ are as defined previously.

In preferred embodiments of the two groups of compounds described above, Ar$^2$ is quinoline.

In another embodiment of the compounds having formula I:

R is selected from the group consisting of C$_{1-4}$ alkyl, C$_{2-4}$ alkenyl and C$_{2-4}$alkynyl and is substituted with one Ar$^1$;

Ar$^1$ is phenyl and is substituted with one Ar$^2$;

Ar$^2$ is phenyl, and is optionally substituted with one or more substituents which are independently selected from (a) one substituent selected from P(O)(OR$^5$)$_2$, CO$_2$H, and SO$_2$R$^4$, and/or (b) 1–2 groups R$^3$;

R$^4$ is phenyl or C$_{1-4}$ alkyl;

R$^3$ is selected from OH, Br, OC$_{1-10}$ alkyl, C$_{1-10}$ alkyl, Aryl, and C$_{2-10}$ alkenyl, where each alkyl group and each alkenyl group is optionally substituted with OC$_{1-3}$ alkyl or phenyl; and X$^1$, X$^2$, R$^1$, R$^2$, R$^5$, x, Y$^1$, Aryl, Het and Het$^1$ are as defined previously.

Another embodiment of the invention includes compounds in which X$^1$ and X$^2$ are each independently selected from the group consisting of H, Cl, Br, F, C$_{1-3}$alkyl, OC$_{1-3}$alkyl, OH, CO$_2$H, and CO$_2$C$_{1-3}$alkyl;

R$^5$ is H;

Y$^1$ is selected from the group consisting of a bond and a C$_{1-4}$ alkylene group;

R is selected from the group consisting of C$_{1-8}$ alkyl, C$_{2-8}$ alkenyl, C$_{2-8}$ alkynyl, Ar$^1$, and Het$^1$, wherein said C$_{1-8}$alkyl, C$_{2-8}$ alkenyl and C$_{2-8}$alkynyl are optionally substituted with one or more groups independently selected from (a) 1–5 halogen atoms selected from Cl, Br, and F, (b) one Ar$^1$ or Het$^1$, and (c) 1–2 substituents independently selected from OH, CN, CO$_2$H, CO$_2$C$_{1-6}$ alkyl, CO$_2$C$_{2-6}$ alkenyl, OC$_{1-6}$alkyl, OC$_{2-6}$ alkenyl, OC(O)C$_{1-6}$alkyl, OC(O)C$_{2-6}$ alkenyl, C(O)C$_{1-6}$alkyl, C(O)C$_{2-6}$alkenyl, Aryl, C(O)Aryl, OC(O)Aryl, OAryl, CO$_2$Aryl, S(O)$_x$C$_{1-6}$alkyl, S(O)$_x$C$_{2-6}$alkenyl, S(O)$_2$NR$^1$R$^2$, C(O)NR$^1$R$^2$, and NR$^1$R$^2$, wherein said alkyl groups and said alkenyl groups of said substituents are optionally substituted with 1–5 halogen atoms selected from Cl, Br, and F;

x is 0, 1, or 2;

R$^1$ and R$^2$ are each independently selected from the group consisting of H and C$_{1-4}$alkyl, wherein said alkyl substituents are optionally substituted with 1–5 halogen atoms selected from Cl, Br, and F;

Het$^1$ is a 5–10 membered aromatic ring system comprising 1 ring or 2 rings fused together and 1–4 heteroatoms selected from O, N, S(O)$_x$, and combinations thereof, and 0–2 carbonyl groups, wherein one of said fused rings is optionally a benzene ring, and said Het$^1$ is optionally substituted with (a) one group selected from CO$_2$H, CF$_2$CO$_2$H, P(O)(OR$^5$)$_2$, and SO$_2$R$^4$, and/or (b) 1–2 groups independently selected from R$^3$;

Ar$^1$ is phenyl, optionally substituted with (a) one group selected from CF$_2$P(O)(OR$^5$)$_2$, CO$_2$H, CF$_2$CO$_2$H, P(O)(OR$^5$)$_2$, SO$_2$R$^4$, and Ar$^2$, and (b) 1–2 groups selected from R$^3$;

Ar$^2$ is phenyl, naphthyl or a 5–10 membered aromatic ring system comprising 1 ring or 2 rings fused together and 1–4 heteroatoms selected from O, N, S(O)$_x$, and combinations thereof, and 0–2 carbonyl groups, wherein one of said fused rings is optionally a benzene ring, wherein Ar$^2$ is optionally substituted with (a) one group selected from CF$_2$P(O)(OR$^5$)$_2$, CO$_2$H, CF$_2$CO$_2$H, P(O)(OR$^5$)$_2$, and SO$_2$R$^4$, and (b) 1–2 groups selected from R$^3$;

R$^3$ is selected from the group consisting of Cl, Br, F, OH, CN, CO$_2$H, CO$_2$C$_{1-3}$ alkyl, CO$_2$C$_{2-3}$ alkenyl, OC$_{1-10}$ alkyl, OC$_{2-10}$ alkenyl, C$_{1-10}$ alkyl, C$_{2-10}$ alkenyl, OC(O)C$_{1-3}$alkyl, OC(O)C$_{2-3}$alkenyl, C(O)C$_{1-3}$alkyl, C(O)C$_{2-3}$alkenyl, C(O)Aryl, OC(O)Aryl, OAryl, CO$_2$Aryl, S(O) C$_{1-6}$alkyl, S(O)$_x$C$_{2-6}$alkenyl S(O)$_2$NR$^1$R$^2$, C(O)NR$^1$R$^2$, NR$^1$R$^2$, NR$^1$S(O)$_2$R$^2$, NR$^1$C(O)C$_{1-6}$alkyl, NR$^1$C(O)H, Aryl, and Het, wherein each alkyl group and each alkenyl group of each substituent is optionally substituted with one or more groups independently selected from (a) 1–3 halogen atoms selected from Cl, Br, and F, and (b) 1–2 substituents independently selected from OH, OC$_{1-3}$ alkyl, CO$_2$H, CO$_2$C$_{1-3}$alkyl, C(O)C$_{1-3}$alkyl, OC(O)C$_{1-3}$alkyl, and phenyl, wherein said phenyl is optionally substituted with 1–3 groups independently selected from OCH$_3$, OCF$_3$, Cl and F, and said C$_{1-3}$ alkyl groups of said substituents are optionally substituted with one or more substituents independently selected from (a) 1–3 halogen atoms independently selected from Cl, Br and F, and (b) 1–2 phenyl moieties;

Aryl is a phenyl or naphthyl moiety, wherein said Aryl is optionally substituted with 1–3 substituents independently selected from C$_{1-3}$alkyl, Cl, F, Br, OC$_{1-3}$ alkyl, C(O)C$_{1-3}$alkyl, OC(O)C$_{1-3}$alkyl, CO$_2$H, and CO$_2$C$_{1-3}$ alkyl, wherein said alkyl groups in said substituents are optionally substituted with 1–3 halogen atoms selected from Cl, Br, and F;

Het is a 5–10 membered aromatic ring system containing 1–4 heteroatoms selected from N, $S(O)_x$, O, and mixtures thereof, and 0–2 carbonyl groups, wherein x is 0, 1, or 2, wherein said Het comprises 1 ring or 2 fused rings, one of which fused rings may be a benzene ring, and said Het is optionally substituted with 1–3 substituents independently selected from $C_{1-3}$alkyl, Cl, Br, F, $OC_{1-3}$ alkyl, $C(O)C_{1-3}$alkyl, $OC(O)C_{1-3}$alkyl, $CO_2H$, and $CO_2C_{1-3}$alkyl, wherein said alkyl groups in said substituents are optionally substituted with 1–3 halogen atoms selected from Cl, Br, and F; and $R^4$ is phenyl or $C_{1-4}$ alkyl.

Preferred compounds from the group described immediately above include those compounds in which:

$Y^1$ is selected from the group consisting of a bond and a $C_{1-3}$ alkylene group; and R is selected from the group consisting of $C_{1-8}$ alkyl, $C_{2-8}$ alkenyl, $Ar^1$, and $Het^1$, wherein said $C_{1-8}$alkyl and $C_{2-8}$ alkenyl are optionally substituted with one or more groups independently selected from (a) 1–5 halogen atoms selected from Cl, Br, and F, (b) one $Ar^1$ or $Het^1$, and (c) 1–2 substituents independently selected from OH, CN, $CO_2H$, $CO_2C_{1-6}$ alkyl, $CO_2C_{2-6}$ alkenyl, $OC_{1-6}$alkyl, $OC_{2-6}$ alkenyl, $OC(O)C_{1-6}$alkyl, $OC(O)C_{2-6}$ alkenyl, $C(O)C_{1-6}$alkyl, $C(O)C_{2-6}$alkenyl, $C(O)$Aryl, $OC(O)$Aryl, OAryl, $CO_2$Aryl, $S(O)_xC_{1-6}$alkyl, $S(O)_xC_{2-6}$alkenyl, $S(O)_2NR^1R^2$, $C(O)NR^1R^2$, and $NR^1R^2$, wherein said alkyl groups and said alkenyl groups of said substituents are optionally substituted with 1–5 halogen atoms selected from Cl, Br, and F.

The invention also comprises prodrugs of the compounds of Formula I. In these, one or more of $R^5$ is a moiety that is converted to H or a pharmaceutically acceptable salt under physiological conditions during or after administration to a mammalian patient, and the remainder of $R^5$ moieties are each H or a pharmaceutically acceptable salt therof.

Finally, a large number of specific compounds are disclosed. The structures of 209 compounds are illustrated in Table 1, and their syntheses are described in Examples 1–209. Structures of additional compounds are illustrated as Examples 210–258 in Table 2.

Methods of treating, preventing, or controlling diabetes and other diseases using the compounds of Formula I are disclosed herein. A method of treating, controlling or preventing diabetes and complications thereof in a mammalian patient in need of such treatment includes administering to the patient an anti-diabetic effective amount of a compound of Formula I. A method of treating, controlling or preventing obesity in a mammalian patient in need of such treatment comprises the administration to the patient of an anti-obesity effective amount of a compound in accordance with claim 1. Such methods also include the administration of a second compound, which may be an anti-diabetic compound, an anti-obesity compound, or an HMG-CoA reductase inhibitor, in an amount effective to treat, control or prevent diabetes or obesity, or to improve a poor lipid profile.

A method of treating, controlling or preventing atherosclerosis in a mammalian patient in need of such treatment comprises administering to the patient an effective amount of a compound of Formula I and an effective amount of an HMG-CoA reductase inhibitor.

More generally, compounds of Formula I may be used as the active compound in a method for treating, preventing, or controlling one or more diseases or conditions selected from Type 1 diabetes, Type 2 diabetes, inadequate glucose tolerance, insulin resistance, obesity, hyperlipidemia, hypertriglyceridemia, hypercholesterolemia, low "H levels, atherosclerosis, vascular restenosis, inflammatory bowel disease, pancreatitis, adipose cell tumors, adipose cell carcinoma, liposarcoma, dyslipidemia, cancer, and neurodegenerative disease. The method comprises the administration of an effective amount of the compound of Formula I. Combination treatments can also be used in which case, the method comprises the administration of a compound of Formula I and an effective amount of one or more pharmaceutically active compounds selected from the group consisting of an HMG-CoA reductase inhibitor, an anti-obesity agent, and an antidiabetic compound.

Pharmaceutical compositions also can be made using the compounds of Formula I. Compositions that are suitable for the treatment, prevention or control of one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease contain an effective amount of a compound of Formula I in combination with a pharmaceutically acceptable carrier.

Such pharmaceutical compositions may also include a second anti-diabetic agent or an anti-obesity agent. They may also include a cholesterol lowering agent. Pharmaceutical compositions may therefore include: (1) an effective amount of a compound of Formula I, (2) an effective amount of one or more pharmaceutically active compounds selected from the group consisting of an HMG-CoA reductase inhibitor, an anti-obesity agent, and an anti-diabetic agent, and (3) a pharmaceutically acceptable carrier.

Such pharmaceutical compositions that contain a second active compound or composition and that are suitable for the treatment, prevention or control of one or more diseases or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, may be comprised of the following:

(1) an effective amount of a compound of Formula 1;
(2) an effective amount of one or more pharmaceutically active compounds listed below; and
(3) a pharmaceutically acceptable carrier; where the pharmaceutically active compounds are selected from the group consisting of:
  (a) insulin sensitizers including (i) PPARγ agonists such as the glitazones (e.g. troglitazone, pioglitazone, englitazone, MCC-555, rosiglitazone, and the like), and compounds disclosed in WO 97/27857, 97/28115, 97/28137 and 97/27847; (ii) biguanides such as metformin and phenformin;
  (b) insulin or insulin mimetics;
  (c) sulfonylureas such as tolbutamide and glipizide, or related materials;
  (d) α-glucosidase inhibitors (such as acarbose);
  (e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) inhibitors of cholesterol absorption for example beta-sitosterol and acyl CoA:cholesterol acyltransferase inhibitors, such as for example melinamide and (vi) probucol;
(f) PPARα/γ agonists;
(g) antiobesity compounds such as appetite suppressants, fenfluramine, dexfenfluramine, phentirarnine, sulbitramine, orlistat, neuropeptide Y5 inhibitors (NP Y5 receptor antagonosts), leptin, which is a peptidic hormone, $\beta_3$ adrenergic receptor agonists, and PPARγ antagonists and partial agonists;
(h) ileal bile acid transporter inhibitors; and
(i) insulin receptor activators.

The pharmaceutically active compounds that are used in the combination pharmaceutical compositions with the compounds of this invention may be summarized as follows:
(a) insulin sensitizers, PPAR-gamma agonists, partial agonists, and antagonists, PPAR-alpha agonists, PPAR-delta agonsts, and biguanides;
(b) insulin and insulin mimetics;
(c) sulfonylureas;
(d) α-glucosidase inhibitors;
(e) cholesterol lowering agents selected from the group consisting of (i) HMG-CoA reductase inhibitors; (ii) sequestrants, (iii) nicotinyl alcohol, nicotinic acid and salts thereof, (iv) PPARα agonists, (v) inhibitors of cholesterol absorption; and (vi) probucol;
(f) PPARα/γ agonists;
(g) antiobesity compounds selected from the group consisting of appetite suppressants, fenfluramine, dexfenfluramine, phentiramine, sulbitramine, orlistat, neuropeptide Y5 inhibitors (NP Y5 receptor antagonosts), leptin, $\beta_3$ adrenergic receptor agonists, and PPARγ antagonists and partial agonists;
(h) ileal bile acid transporter inhibitors; and
(i) insulin receptor activators.

Abbreviations
The following abbreviations have the indicated meanings:
AA=arachidonic acid
Ac=acetyl
AIBN=2.2'-azobisisobutyronitrile
Bn=benzyl
BSA=bovine serum albumin
Bz=benzoyl
CHO=chinese hamster ovary
CMC=1-cyclohexyl-3-(2-morpholinoethyl) carbodiimidemetho-p-toluenesulfonate
DAST=diethylamino sulfur trifluoride
DBU=diazabicyclo[5.4.0]undec-7-ene
DMAP=4-(dimethylamino)pyridine
DMF=N,N-dimethylformamide
DMSO=dimethyl sulfoxide
Et$_3$N=triethylamine
HATU=O-(7-azabenzotriazol-1-yl)-1,1,3,3-tetramethyluronium hexafluorophosphate
HBSS=Hanks balanced salt solution
HEPES=N$^1$-[2-Hydroxyethyl]piperazine-N$^4$-[2-ethanesulfonic acid]
HWB=human whole blood
KHMDS=potassium hexamethyldisilazane
LDA=lithium diisopropylamide
LPS=lipopolysaccharide
mCPBA=metachloro perbenzoic acid
MMPP=magnesium monoperoxyphthalate
Ms=methanesulfonyl=mesyl
Ms0=methanesulfonate=mesylate
NBS=N-bromosuccinimide
NCS=N-chlorosuccinirnide
NIS=N-iodosuccinimide
NSAID=non-steroidal anti-inflammatory drug
Oxone®=potassium peroxymonosulfate
PCC=pyridinium chlorochromate
PDC=pyridinium dichromate
PPA=polyphosphoric acid
PTP=protein tyrosine phosphatase
r.t.=room temperature
rac.=racemic
Tf=trifluoromethanesulfonyl=triflyl
TFA=trifluoroacetic acid
TFAA=trifluoroacetic anhydride
Tf0=trifluoromethanesulfonate=triflate
THF=tetrahydrofuran
TLC=thin layer chromatography
Ts=p-toluenesulfonyl=tosyl
TsO=p-toluenesulfonate=tosylate
Tz=1H (or 2H)-tetrazol-5-yl Alkyl group abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Dose Abbreviations
bid=bis in die=twice daily
qid=quater in die=four times a day
tid=ter in die=three times a day Alkyl means linear, branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, cyclopropylmethyl, methylcyclopropy, adamantyl, cyclododecylmethyl, 2-ethyl-1-bicyclo[4.4.0]decyl and the like.

Fluoroalkyl means alkyl groups of the indicated number of carbon atoms in which one or more hydrogens is replaced by fluorine. Examples are —CF$_3$, —CH$_2$CH$_2$F, —CH$_2$CF$_3$, c-Pr-F$_5$, c-Hex-F$_{11}$ and the like. Haloalkyl has the analogous meaning for replacement of one or more hydrogen atoms with any halogen (Cl, Br, F, and/or I).

Alkenyl means linear, branched and cyclic structures, and combinations thereof containing a double bond with the indicated number of carbon atoms. Examples of alkenyl groups include allyl, 2-butenyl, 3-butenyl, 2-pentenyl, 2-cyclopentenyl, 3-cyclopentenyl, 2-methyl-cyclohexenyl, 2-cyclohexenyl, 3-cyclohexenyl and the like. Alkadienyl means the diunsaturated counterpart to alkenyl.

Alkynyl means linear, branched and cyclic structures, and combinations thereof containing a triple bond with the indicated number of carbon atoms. Examples of alkynyl groups include propargyl, 2-butynyl, 3-butynyl, 2-pentynyl, cyclopropylethynyl, and the like.

Alkylene, alkenylene, alkynylene, fluoroalkylene, alkadienylene, and the like, where the suffix "ene" has been added to the name of the monovalent radicals alkyl, alkenyl, alkynyl, fluoroalkyl, alkadienyl, and the like, describe divalent radicals that are the same as their monovalent counterparts, except that two hydrogen atoms rather than one are removed so that the radical will have two points of attachment, in addition to attachments to substituents which may also be present.

Aryl groups include 6–14 membered carbocyclic aromatic ring systems comprising 1–3 phenyl rings. If two or more aromatic rings are present, then the rings are fused together, so that adjacent rings share a common side. Examples are benzene, naphthalene, anthracene and phenanthrene. Preferred aryl groups are benzene and naphthalene. Substitutions on these are defined herein.

Heteroaryl as used herein represents a 5–10 membered aromatic ring system comprising one ring or two fused rings, 1–4 heteroatoms selected from the groups consisting of N, O, S(O)$_x$, and mixtures thereof wherein x is 0, 1 or 2, and 0–2 carbonyl groups. Carbonyl groups, when present, are not counted as heteroatoms. Heteroaryl includes, but is not limited to, furanyl, diazinyl, imidazolyl, isoxazolyl, isothiazolyl, oxadiazolyl, oxazolyl, pyrazolyl, pyridyl, pyrrolyl, tetrazinyl, thiazolyl, thienyl, triazinyl, triazolyl, 1H-pyrrole-2,5-dionyl, 2-pyrone, 4-pyrone, pyrrolopyridine, furopyridine and thienopyridine. Heteroaryl also includes benzoheteroaryl, defined below. Preferred heteroaryls include imidazolyl, isoxazolyl, isothiazolyl, oxadiazolyl, oxazolyl, pyrazolyl, pyridyl, thiazolyl, and thienyl.

Benzoheteroaryl is a subset of heteroaryl and includes aromatic ring systems containing one or more heteroatoms which also have a fused 6-membered benzene ring, such as 2H-1-benzopyran-2-one, 4H-1-benzopyran-4-one, 2(3H) benzofuranone, 3(2H)benzofuranone, 2,3-dihydrobenzofuran, 2,3-dihydrobenzothiophene, indole, benzofuran, benzothiophene, benzimidazole, benzoxazole, benzothiazole, benzotriazole, benzothiadiazole, 1H-isoindole-1,3(2H)-dione, quinoline, and isoquinoline. Preferred benzoheteroaryl compounds include benzothiophene, benzothiazole, benzotriazole, benzothiadiazole, quinoline, and isoquinoline. Specific heteroaryls used in this invention include quinoline, thiazole, tetrazole, pyridine, pyrazole, oxadiazole, oxathiazole and oxazole.

Another subset of heteroaryls includes 5-membered heteroaryls, such as the following:

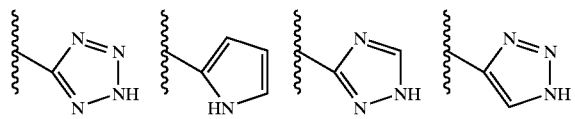

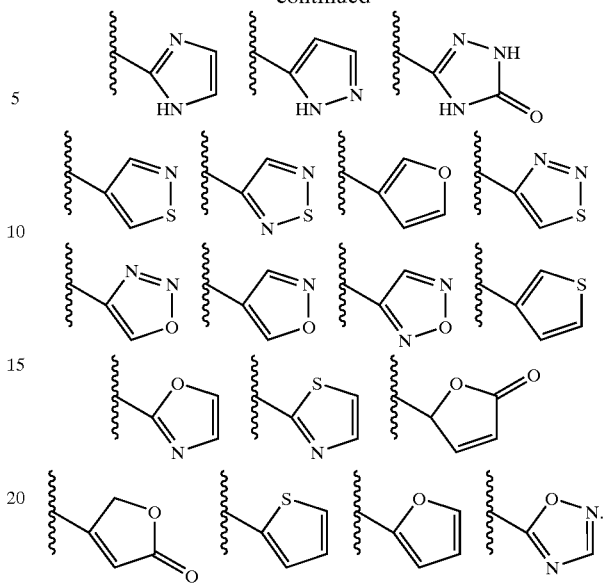

When a heteroaromatic ring is specified as optionally having one or more heteroatoms, this means that at least one heteroatom is present, selected from O, S, SO, SO$_2$ and N, and up to 4 such heteroatoms may be present, depending upon the size of the ring specified.

When a moiety is specified as being optionally substituted, then the same moiety may also remain unsubstituted, unless otherwise stated.

Finally, when a list of possible choices is provided for a given moiety, and the moiety is used in more than one position in a chemical formula, the selection of a choice for the moiety in each position is independent of other selections, unless the definition specifically says otherwise.

Metabolites—Prodrugs

Metabolites of the compounds of this invention that are therapeutically active and that are described by formula I also are within the scope of the claimed invention, as are prodrugs, which are compounds that are converted to the claimed active compounds or salts of the claimed active compounds after they have been administered to a patient. A non-limiting example of a prodrug of the phosphonic acids of this invention would be a monoester or diester of one or more phosphonic acid groups, where the ester functionality preferably has a structure that makes it easily hydrolyzed or metabolized after administration to a patient. Examples of prodrugs include C$_{1-6}$ alkyl esters of the phosphonic acids. Prodrugs that have structures that are more easily hydrolyzed or metabolized are generally more preferred. Examples are illustrated by the structures below, where R'=H or a C$_{1-6}$ alkyl group, and R"=C$_{1-6}$ alkyl group or —OC$_{1-6}$ alkyl group, and Q is the residue of the molecule that is attached to the —CF$_2$PO$_3$H$_2$ or —PO$_3$H$_2$ group in formula I. The alkyl groups and alkoxy groups may optionally be substituted with one or more substituents independently selected from 1–5 halogen atoms, a phenyl group, or a mixture of these. The phenyl group, if present, may optionally be substituted with 1–3 substituents independently selected from halogen, —CH$_3$, —CF$_3$, —OCH$_3$ and —OCF$_3$. In these compounds, and as defined in general throughout this application, the alkyl groups and the alkyl portions of Oalkyl groups may be linear or branched and may optionally be cycloalkyl or may include a cycloalkyl group in their structure. For examples of prodrug structures related to those shown below, see D. N. Srinivasta et al., Bioorganic Chemistry 12, 118–129 (1984).

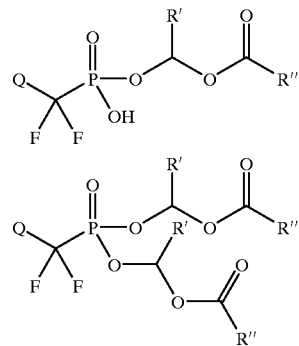

Other ester functionalities that may be used in the monoester or diester phosphonate prodrugs include phenyl esters and benzyl esters, where the phenyl ester groups have the structure —Ophenyl, and the benzyl ester groups have the structure —OCHR'phenyl, in which R' is H or $C_{1-6}$alkyl, and $C_{1-6}$alkyl is substituted as described above. In either case, phenyl is substituted as described above.

The prodrugs of this invention may therefore be defined as compounds having the formula I, in which at least one group $R^5$ is selected from the group consisting of $C_{1-6}$alkyl, phenyl, —CHR'phenyl, and —CHR'OC(=O)R", and the remaining groups $R^5$ are selected from H, $C_{1-6}$alkyl, phenyl, —CHR'phenyl and —CHR'OC(=O)R", wherein each group R' is H or $C_{1-6}$alkyl and each group R" is —$C_{1-6}$alkyl or —$OC_{1-6}$alkyl, where $C_{1-6}$alkyl and the alkyl portion of —$OC_{1-6}$alkyl may optionally be substituted with one or more substituents independently selected from 1–5 halogen atoms, a phenyl group, or a mixture of these. The phenyl group in —CHR'phenyl, the phenyl group that is an optional substituent on $C_{1-6}$alkyl and —$OC_{1-6}$alkyl, and the phenyl ester group that is obtained when $R^5$ is phenyl may optionally be substituted with 1–3 groups independently selected from halogen, —$CH_3$, —$CF_3$, —$OCH_3$ and —$OCF_3$. By this definition, at least one of the phosphonic acid groups is a monoester or diester, and each of the remaining phosphonic acid groups, if any, may be a free acid or a monoester or diester.

In preferred compounds, the groups $R^5$ that are not H may all be the same because of the difficulty of synthesizing different $R^5$ groups on the same phosphonates. In many cases, the prodrug will be a mixture of compounds having different levels of esterification on the phosphonic acid groups because of the difficulty of synthesizing and separating a discrete pure compound.

Optical Isomers—Diastereomers—Geometric Isomers

Some of the compounds described herein contain one or more asymmetric centers and may thus give rise to diastereomers and enantiomers, which in turn can be resolved as optical isomers. The present invention includes all such diastereomers and enantiomers, including racemic mixtures and resolved, enantiomerically pure forms, and pharmaceutically acceptable salts thereof. Some of the compounds described herein contain olefinic double bonds, and unless specified otherwise, include both E and Z geometric isomers.

Salts

The pharmaceutical compositions of the present invention comprise a compound of the current invention as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids.

It will be understood that in the discussion of methods of treatment or of specific compounds which follows, references to the compounds of Formula I and other formulae are meant to include the pharmaceutically acceptable salts.

Utilities

Inhibitors of PTP-1B may improve insulin-sensitivity and thus may have utility in preventing or treating diabetes, particularly Type 2 diabetes. They may also be useful for improving glucose tolerance and insulin-sensitivity when there is insulin-resistance, and for treating or preventing obesity in mammals that are in need of such treatments or that might benefit from such treatments. The compounds are expected to be useful for treating Type 2 diabetes (non-insulin dependent diabetes, or NIDDM). The compounds may also cause a beneficial reduction in triglycerides and lipids.

Compounds in the present class of phosphonic acids may have certain unexpected advantages. Some of the compounds may be selective in inhibiting PTP-1B in preference to T-Cell Protein Tyrosine Phosphatase (TCPTP). This may make it possible to avoid toxic side effects due to T-Cell inhibition.

The compounds of this invention in general exhibit good in vitro activity for inhibiting the PTP-1B enzyme. The compounds exemplified in this application in general have an $IC_{50}$ value of less than 1 $\mu$M for inhibition of the PTP-B enzyme, and in some cases less than 0.1 $\mu$M, as measured using the enzyume assay described herein in the assays section.

The PTP-1B inhibitors may also be useful in the treatment, prevention or control of a number of conditions that accompany type 2 diabetes, including hyperlipidemia, hypertriglyceridemia, hypercholesterolemia (including beneficially raising low HDL levels), atherosclerosis, vascular restenosis, pancreatitis, adipose cell tumors, adipose cell carcinomas such as liposarcoma, dyslipidemia, inflammatory bowel disease, inflammation in general, and other disorders where insulin resistance is a component. Finally, the compounds may be used to treat or prevent cancer, such as prostate cancer, neurodegenerative diseases and the like.

Pharmaceutical Compositions

For the treatment of any of these PTP-1B-mediated diseases the active compound may be administered orally, topically, parenterally, by inhalation spray or rectally in dosage units containing conventional pharmaceutically acceptable carriers. The term parenteral as used herein includes subcutaneous, intravenous, intramuscular and intrasternal injection and infusion techniques. In addition to the treatment of warm-blooded animals such as mice, rats, horses, cattle, sheep, dogs, cats, etc., the compounds of the invention are useful for the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxy-ethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical composition may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent, for example as a solution in 1,3-butanediol. Examples of vehicles and solvents include water, Ringer's solution and isotonic sodium chloride. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds may also be administered in the form of suppositories. These compositions can be prepared by mixing the drug with a suitable non-irritating excipient which is solid at ordinary temperatures but molten at the body temperature and will therefore release the drug. Such materials include cocoa butter and polyethylene glycols.

For topical use, creams, ointments, gels, solutions or suspensions containing the compound are employed. (For purposes of this application, topical application includes mouth washes and gargles.) Topical formulations may include cosolvents, emulsifiers, penetration enhancers, preservatives, emollients and the like.

The pharmaceutical composition may also be further comprised of a second anti-diabetic or anti-obesity effective compound.

Dose Ranges

Dosage levels on the order of from about 0.01 mg to about 100 mg/kg of body weight per day are useful in the treatment of the above-indicated conditions, or alternatively about 0.5 mg to about 7 g per patient per day. For example, the diseases and conditions described herein may be effectively treated by the administration of from about 0.01 to 50 mg of the compound per kilogram of body weight per day, or alternatively about 0.5 mg to about 3.5 g per patient per day.

The active ingredient is typically combined with the carrier to produce a dosage form suitable for the particular patient being treated and the particular mode of administration. For example, a formulation intended for the oral administration of humans may contain from about 0.5 mg to about 5 g of the active agent, compounded with an appropriate and convenient amount of carrier material which may vary from about 5 to about 95 percent of the total composition. Representative dosage forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It is understood that the specific dose level for any particular patient will depend upon a variety of factors including the age, body weight, general health, sex, diet, time of administration, route of administration, rate of excretion, drug combination and the severity of the particular disease undergoing therapy.

Combinations with Other Drugs

In further aspects, the invention encompasses pharmaceutical compositions for treating PTP-1B mediated diseases as defined above comprising an effective amount of the active compound and one or more other pharmaceutically active compounds, such as anti-diabetic compounds (for example, insulin, sulfonyl ureas, PPAR-alpha and/or -gamma ligands, including ligands that have both PPAR-alpha and -gamma activity), anti-obesity compounds, and compounds that improve the lipid profile of the patient.

Thus, the methods of treatment or prevention described herein may further be comprised of administering to said patient a second anti-diabetic compound in an amount effective to treat, control, or prevent diabetes, alone or in combination with the PTP-1B inhibitors of this invention.

Similarly, the methods of treatment or prevention described herein may further be comprised of administering to said patient an anti-obesity compound in an amount effective to treat, control or prevent obesity, alone or in combination with the PTP-1B inhibitors of this invention.

Similarly, the methods of treatment of diabetes may comprise the administration of a cholesterol biosynthesis inhibitor, particularly an HMG-CoA reductase inhibitor, such as lovastatin, simvastatin, pravastatin, fluvastatin, atorvastatin and rivastatin, in an amount effective to improve the lipid profile. In combination with a PTP-1B inhibitor, this may be beneficial in treating or preventing atherosclerosis and other conditions that often are associated with Type 2 diabetes.

Examples of other pharmaceutically active compounds that may be combined with a compound of Formula I and administered in combination with the PTP-1B inhibitors include, but are not limited to, the following compounds or compositions or groups of compounds or compositions that are used as anti-diabetes compounds (a, b, c, d, f, and i below), anti-obesity compounds (g below), and/or compounds or compositions for lipid profile control (e and h below):

(a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) inhibitors of cholesterol absorption for example beta-sitosterol and acyl CoA:cholesterol acyltransferase inhibitors for example melinamide and (vi) probucol;

(f) PPARα/γ agonists;

(g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, β3 adrenergic receptor agonists, and PPARγ antagonists and partial agonists;

(h) ileal bile acid transporter inhibitors; and (i) insulin receptor activators, such as those disclosed in copending, commonly assigned U.S. application Ser. Nos. 09/095,244 and 09/280,602.

Where a second pharmaceutical is used in addition to an active compound taught herein, the two pharmaceuticals may be administered together in a single composition, separately at approximately the same time, or on separate dosing schedules. The important feature is that their dosing schedules comprise a treatment plan in which the dosing schedules overlap in time and thus are being followed concurrently.

Assays for Demonstrating Biological Activity

Activity in the compounds of this application is demonstrated using the following assays for PTP-1B-inhibiting activity.

Phosphatase Assay Protocol

Materials:

EDTA—ethylenediaminetetraacetic acid (Sigma)

DMH—N,N'-dimethyl-N,N'-bis(mercaptoacetyl)-hydrazine (synthesis published in *J. Org. Chem.* 56, pp. 2332–2337,(1991) by R. Singh and G. M. Whitesides and can be substituted with DTT—dithiothreitol Bistris—2,2-bis(hydroxymethyl)2,2',2"-nitrilotriethanol-(Sigma) Triton X-100-octylphenolpoly(ethylene-glycolether) 10 (Pierce)

Antibody: Anti-glutathione S-transferase rabbit (H and L) fraction (Molecular Probes)

Enzyme: Human recombinant PTP-1B, containing amino acids 1–320, fused to GST enzyme (glutathione S-transferase) or to FLAG peptide purified by affinity chromatography (Huyer et al, 1997, J. Biol. Chem., 272, 843–852). Wild type contains active site cysteine (215), whereas mutant contains active site serine(215).

Tritiated peptide: Bz-NEJJ-CONH2, Mwt. 808, empirical formula, $C_{32}H_{32}T_2O_{12}P_2F_4$

| Stock Solutions | |
|---|---|
| (10X) Assay Buffer | 500 mM Bistris (Sigma), pH 6.2, MW = 209.2 |
| | 20 mM EDTA (GIBCO/BRL) |
| | Store at 4° C. |
| Prepare fresh daily: | |
| Assay Buffer (1X) (room temp.) | 50 mM Bistris |
| | 2 mM EDTA |
| | 5 mM DMH (MW = 208) |
| Enzyme Dilution | |
| Buffer (keep on ice) | 50 mM Bistris |
| | 2 mM EDTA |
| | 5 mM DMH |
| | 20% Glycerol (Sigma) |
| | 0.01 mg/ml Triton X-100 (Pierce) |
| Antibody Dilution | |
| Buffer (keep on ice) | 50 mM Bistris |
| | 2 mM EDTA |

$IC_{50}$ Binding Assay Protocol:

Compounds (ligands) which potentially inhibit the binding of a radioactive ligand to the specific phosphatase are screened in a 96-well plate format as follows:

To each well is added the following solutions @ 25° C. in the following chronological order:

1. 110 μl of assay buffer.
2. 10 μl. of 50 nM tritiated BzN-EJJ-CONH$_2$ in assay buffer (1×) @ 25° C.
3. 10 μl. of testing compound in DMSO at 10 different concentrations in serial dilution (final DMSO, about 5% v/v) in duplicate @ 25° C.
4. 10 μl. of 3.75 μg/ml purified human recombinant GST-PTP-1B in enzyme dilution buffer.
5. The plate is shaken for 2 minutes.
6. 10 μl. of 0.3 μg/ml anti-glutathione S-transferase (anti-GST) rabbit IgG (Molecular Probes) diluted in antibody dilution buffer @ 25° C.
7. The plate is shaken for 2 minutes.
8. 50 μl. of protein A-PVT SPA beads (Amersham) @ 25° C.
9. The plate is shaken for 5 minutes. The binding signal is quantified on a Microbeta 96-well plate counter.
10. The non-specific signal is defined as the enzyme-ligand binding in the absence of anti-GST antibody.
11. 100% binding activity is defined as the enzyme-ligand binding in the presence of anti-GST antibody, but in the absence of the testing ligands with the non-specific binding subtracted.
12. Percentage of inhibition is calculated accordingly.
13. $IC_{50}$ value is approximated from the non-linear regression fit with the 4-parameter/multiple sites equation (described in: "Robust Statistics", New York, Wiley, by P. J. Huber (1981) and reported in nM units.
14. Test ligands (compounds) with larger than 90% inhibition at 10 μM are defined as actives.

| Assay buffer | 50 mM Bis-Tris (pH = 6.3) |
|---|---|
| | 2 mM EDTA |
| | 5 mM N,N'-dimethyl-N,N'-bis(mercapto-acetyl)hydrazine (DMH) |
| Substrate | 10 mM fluorescein diphosphate (FDP) store at −20°C. |
| Enzyme dilution buffer | 50 mM Bis-Tris (pH = 6.3) |
| | 2 mM EDTA |
| | 5 mM DMH |
| | 20% (v/v) glycerol |
| | 0.01% Triton X-100 |

The assay was carried out at room temperature in 96 well plates. The reaction mixture in 170 μl contained 50 mM Bis-Tris (pH=6.3), 2 mM EDTA, 5 mM N,N'-dimethyl-N,N'bis(mercaptoacetyl)hydrazine (DMH) and 10 μM fluorescein diphosphare (FDP). 10 μl of 10 concentrations (serial dilution) of the test compound (inhibitor) dissolved in DMSO or DMSO alone for control was added to each well and the plate was mixed for 2 min. The reaction was initiated by adding 20 μl of diluted PTP-1B (50 nM in 50 mM Bis/Tris (pH=6.3), 2 mM EDTA, 5 mM DMH, 20% glycerol and 0.01% Triton X-100. The phosphatase activity was followed by monitoring the appearance of the fluorescent product fluorescein monophosphate (FMP) continuously for 15–30 min, using the Cytofluor II plate reader (PerSeptive Biosystems Inc.) with excitation of 440 nm (slit width 20 nm) and emission at 530 nm (slit width 25 nm). All the assays were done at least in duplicate. The initial rate of FMP formation is plotted against the concentration of inhibitor and the data was fitted to 4-parameter equation and the inflection point of the fit is the $IC_{50}$.

Pharmacokinetics in Rats

Per Os Pharmacokinetics in Rats

Procedure:

The animals are housed, fed and cared for according to the Guidelines of the Canadian Council on Animal Care.

Male Sprague Dawley rats (325-375 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.

Vehicles:

The following vehicles may be used in PO rat blood level determinations:

| PEG 200/300/400: | restricted to 2 mL/kg |
|---|---|
| Methocel 0.5%–1.0%: | 10 mL/kg |
| Tween 80: | 10 mL/kg |

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv\,(mg/kg)}{AUCiv}$$

The units of CL are mL/h·kg (milliliters per hour kilogram)

Intravenous Pharmacokinetics in Rats

Procedure:

The animals are housed, fed and cared for according to the Guidelines of the Canadian Council on Animal Care.

Male Sprague Dawley (325-375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1-2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles:

The following vehicles may be used in IV rat blood level determinations:

| Dextrose: | 1 mL/kg |
|---|---|
| 2-Hydroxypropyl-b-cyclodextrin | 1 mL/kg |
| DMSO (dimethylsulfoxide): | Restricted to a dose volume of 0.1 mL per animal |
| PEG 200: | Not more than 60% mixed with 40% sterile water - 1 mL/kg |

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv\,(mg/kg)}{AUCiv}$$

The units of CL are mL/h·kg (milliliters per hour kilogram).

PTP 1B Intact Cell Assay

This assay is the subject of copending, commonly assigned U.S. Provisional Application No. 60/123,243, filed Mar. 8, 1999, which patent application is incorporated herein by reference, and was recently published in Cromlish, Wanda A., Paul Payette and Brian P. Kennedy (1999) *Biochem Pharmocol* 58: 1539–1546.

Construction of Recombinant Baculovirus Transfer Vectors And Insect Cells

Briefly, using the Bac-to-Bac Baculovirus Expression System (Gibco-BRL, Mississauga, Ontario, Canada) PTP 1B cDNA (obtained from Dr. R. L. Erikson, Harvard University, USA), is cloned into the pFASTBAC donor plasmid engineered to include a FLAG sequence at the 5' end of the cDNA (PTP1B-FL). The recombinant plasmid is transformed into competent DH10BAC *E. Coli* cells. Following transposition and antibiotic selection, the recombinant bacmid DNA is isolated from selected *E. Coli* colonies and used to transfect sf9 insect cells (Invitrogen, San Diego, Calif., U.S.A.). The sf9 cells are cultured in spinner flasks at 28° C. in Graces supplemented medium (Gibco-BRL, Mississauga, Ontario, Canada) with 10% heat-inactivated fetal bovine serum (Gibco-BRL) following the protocol of Summers and Smith (*A manual for Methods for Baculovirus Vectors and Insect Culture Procedures (Bulletin No. 1555)*. Texas A & M University, Texas Agricultural Experiment Station, College Station, Tex., 1987).

Intact Cell Assay

Infected sf9 cells expressing PTP1B-FL and mock infected cells, are harvested at 29 hpi (hours post infection) by gentle centrifugation (Beckman GS-6R) at 460 rpm, (48 g) for 5 min. Cells are washed once in assay buffer (Hanks' solution buffered with 15 mM Hepes, pH 7.4, obtained from Sigma, St. Louis, Mo., U.S.A.) and recentrifuged at 300 rpm (21 g) for 10 min. The cells are then gently resuspended in assay buffer and examined using a hemacytometer for cell density and viability by trypan blue exclusion. Assays are performed using a Tomtec Quadra 96 pipeting robot, programmed to mix the cells gently after each addition. In 200 μL of assay buffer, 2×10⁵ PTP expressing cells or mock infected cells are dispensed into each well of 96-well polypropylene plates and pre-incubated either with a test compound or DMSO vehicle (3 μL), for 15 min at 37° C. The pre-incubated cells are challenged with a final concentration of 10 mM pNPP (p-nitrophenyl phosphate, obtained from Sigma-Aldrich Canada Ltd., Oakville, Ontario) for 15 min, centrifuged at 4° C. and the amount of substrate hydrolysis is determined spectrophotometerically at $OD_{405}$.

Oral Glucose Tolerance Test

Oral glucose tolerance tests are done on conscious Zucker obese fa/fa rats or obese ob/ob mice (age 12 weeks or older). The animals are fasted for 16–18 hours before use for experiments. A test compound or a vehicle is given either intraperitoneally or orally 60 minutes before oral administration of a glucose solution at a dose of 2 g/kg body weight. Blood glucose levels are measured using a Medisense glucometer from tail bled samples taken at different time points before and after administration of glucose. A time curve of the blood glucose levels is generated and the area-under-the-curve (AUC) for 120 minutes is calculated (the time of glucose administration being time zero). Percent inhibition is determined using the AUC in the vehicle-control group as zero percent inhibition.

In separate studies, C57BL/6J mice are fed a high fat (35%) and high carbohydrate (36%) diet obtained from Bioserv (Frenchtown, N.J.) for 3 to 4 weeks, at which time the mice gained 50–100% of the baseline body weight. Oral glucose tolerance tests are done in the same manner as described above.

EXAMPLES

The invention is further illustrated by the following non-limiting examples. The examples further illustrate the invention and should not be construed as limiting the invention in any way. New compounds according to this invention are summarized in Tables 1 and 2. Methods used to synthesize the compounds are then summarized under the title, Methods of Synthesis. Specific intermediates and methods of making them are presented in the Synthesis of Intermediates section. Finally, the actual syntheses of 209 compounds and their structures are provided in Examples 1–209 and in Table 1. The structures of many other compounds are provided in Table 2 as Examples 210–258.

In the various synthetic examples:

(i) all operations were carried out at room or ambient temperature, that is, at a temperature in the range 18–25° C., (ii) evaporation of solvent was carried out using a rotary evaporator under reduced pressure (600–4000 pascals: 4.5–30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (litre(s)), mL (millilitres), g (gram(s)), mg (milligrams(s)), mol (moles), mmol (millimoles), eq (equivalent(s)).

TABLE 1

| Structure | Example | Method |
|---|---|---|
| [structure 1] | 1 | C + L |
| [structure 2] | 2 | A + L |
| [structure 3] | 3 | M |

TABLE 1-continued

| Structure | Example | Method |
|---|---|---|
| (difluorophosphonomethyl-bromophenyl)-CH₂-S-CH₂-(phenyl-difluorophosphonomethyl), tetrasodium salt | 4 | A + L |
| (difluorophosphonomethyl-bromophenyl)-CH₂-S-CH₂-(phenyl-difluoro(diethylphosphonate)methyl) | 5 | M |
| (difluorophosphonomethyl-bromophenyl)-CH₂-S-CH₂-(phenyl-difluorophosphonomethyl) | 6 | M |
| (4-difluorophosphonomethylphenyl)-CH₂-S-CH₂-(biphenyl with isopentyloxy and phosphonic acid) | 7 | C + L |
| (difluorophosphonomethyl-bromophenyl)-CH₂-S-CH₂-(biphenyl with isopentyloxy and phosphonic acid) | 8 | C + L |
| (difluorophosphonomethyl-bromophenyl)-CH₂-S-CH₂-(difluorophosphonomethyl-bromophenyl) | 9 | A + L |

TABLE 1-continued

| | Example | Method |
|---|---|---|
| (structure) | 10 | L |
| (structure) | 11 | D + L |
| (structure) | 12 | E + L |
| (structure) | 13 | C + L |

TABLE 1-continued
| | Example | Method |
|---|---|---|
| 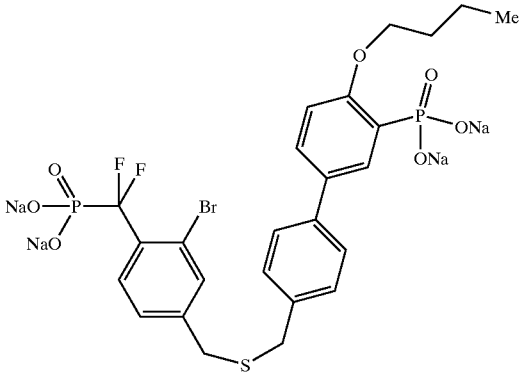 | 14 | C + L |
| 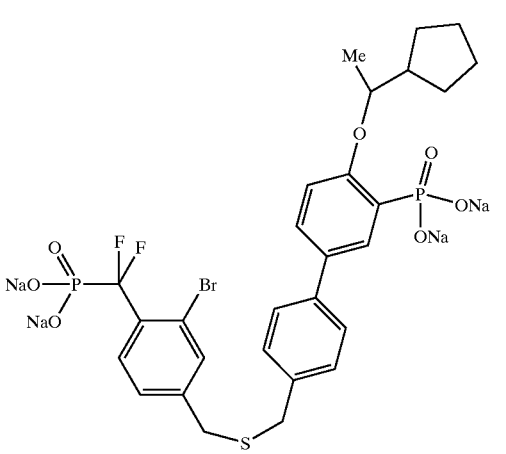 | 15 | C + L |
| 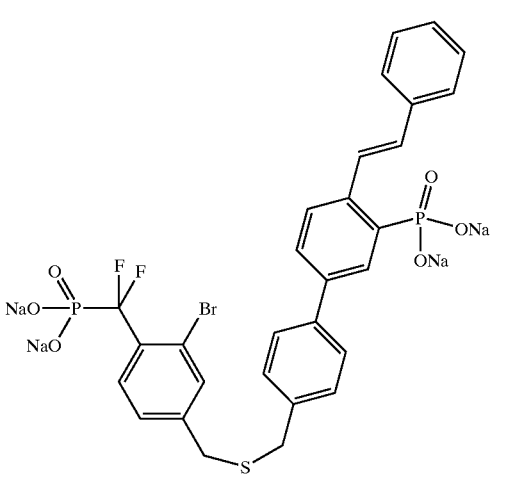 | 16 | E + L |

TABLE 1-continued

| Example | Method |
|---------|--------|
| 17 | F + L |
| 18 | F + L |
| 19 | G + L |

TABLE 1-continued

| Example | Method |
|---------|--------|
| 20 | F + L |
| 21 | F + L |
| 22 | H + L |

TABLE 1-continued

| | Example | Method |
|---|---|---|
| (structure) | 23 | I + L |
| (structure) | 24 | J + L |
| (structure) | 25 | J + L |

TABLE 1-continued

| Structure | Example | Method |
|---|---|---|
| (difluoro(phosphono)methyl)-bromo-benzyl-S-CH2-biphenyl | 26 | L |
| (difluoro(phosphono)methyl)-bromo-benzyl-S-CH2-(phenyl-SO2Me) | 27 | N + L |
| (difluoro(phosphono)methyl)-bromo-benzyl-S-biphenyl | 28 | P |
| (difluoro(phosphono)methyl)-bromo-benzyl-SO2-CH2-CH=CH-phenyl | 29 | M |
| (difluoro(phosphono)methyl)-bromo-benzyl-SO2-CH=CH-phenyl | 30 | O |
| (difluoro(phosphono disodium)methyl)-bromo-benzyl-S-Me | 31 | L |
| (difluoro(phosphono)methyl)-bromo-benzyl-S-CH2-cyclopropyl | 32 | L |

TABLE 1-continued

| | Example | Method |
|---|---|---|
| [structure] | 33 | P |
| [structure] | 34 | P |
| [structure] | 35 | U |
| [structure] | 36 | P |
| [structure] | 37 | L |
| [structure] | 38 | L |
| [structure] | 39 | L |
| [structure] | 40 | L |

TABLE 1-continued

| Example | Method |
|---|---|
| 41 | L |
| 42 | S |
| 43 | L |
| 44 | S |
| 45 | Q |
| 46 | P |
| 47 | P |
| 48 | Q |

TABLE 1-continued
| | Example | Method |
|---|---|---|
| 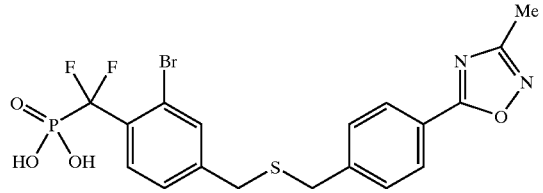 | 49 | Q |
| 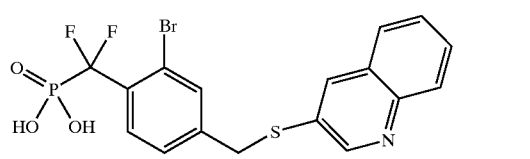 | 50 | U |
| 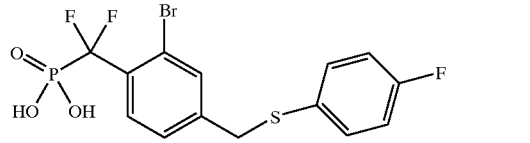 | 51 | P |
| 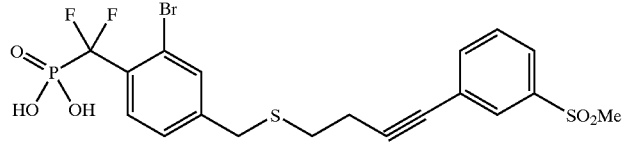 | 52 | Q |
| 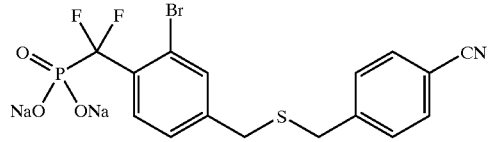 | 53 | L |
| 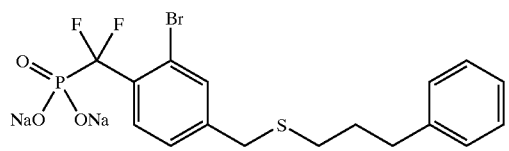 | 54 | Q |
| 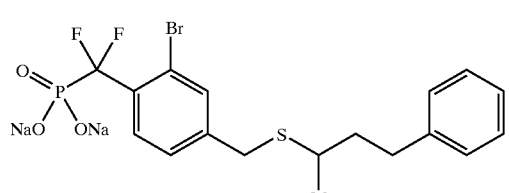 | 55 | Q |

TABLE 1-continued
| Example | Method |
|---|---|
| 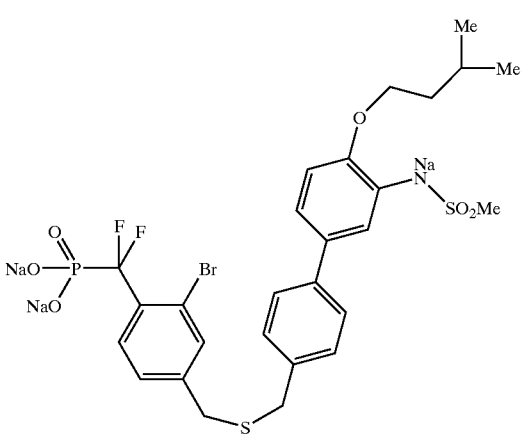 56 | Q |
| 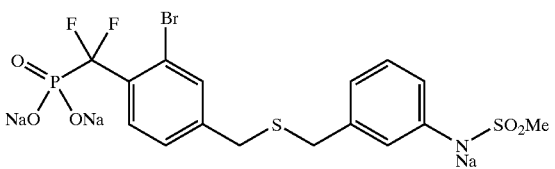 57 | Q |
| 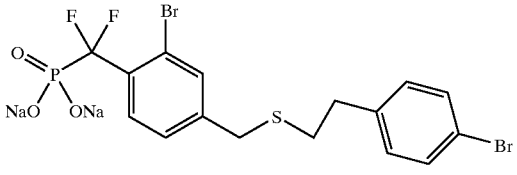 58 | Q |
| 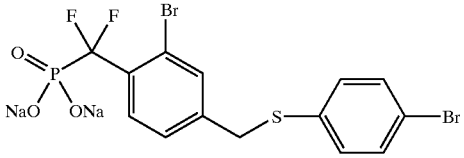 59 | P |
| 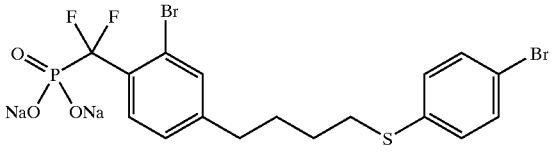 60 | R |
| 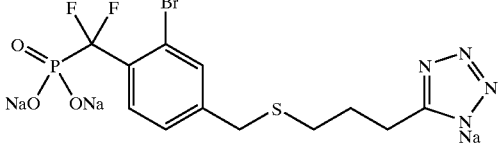 61 | Q |
| 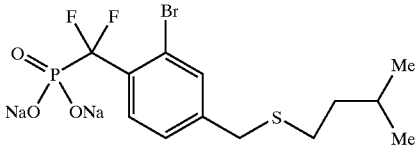 62 | P |

TABLE 1-continued

| Example | Method |
|---|---|
| 63 | P |
| 64 | Q |
| 65 | L |
| 66 | L |
| 67 | L |
| 68 | L |
| 69 | K, L, Q |
| 70 | L |
| 71 | L |

TABLE 1-continued

| Structure | Example | Method |
|---|---|---|
| (compound) | 72 | L |
| (compound) | 73 | L |
| (compound) | 74 | S |
| (compound) | 75 | L |
| (compound) | 76 | Q |
| (compound) | 77 | L |
| (compound) | 78 | L |

TABLE 1-continued

| Example | Method |
|---------|--------|
| 79 | L |
| 80 | L |
| 81 | L |
| 82 | L |
| 83 | L |
| 84 | L |
| 85 | L |
| 86 | L |

TABLE 1-continued

| | Example | Method |
|---|---|---|
| (structure) | 87 | L |
| (structure) | 88 | L |
| (structure) | 89 | L |
| (structure) | 90 | L |
| (structure) | 91 | Q |
| (structure) | 92 | L |
| (structure) | 93 | L |

TABLE 1-continued

| Example | Method |
|---------|--------|
| 94 | T |
| 95 | L |
| 96 | P |
| 97 | L |
| 98 | L |
| 99 | L |
| 100 | P |

TABLE 1-continued
| | Example | Method |
|---|---|---|
| 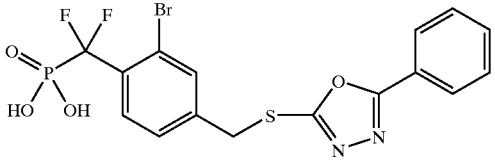 | 101 | P |
| 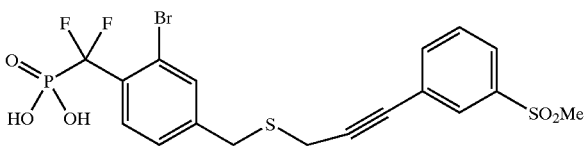 | 102 | Q |
| 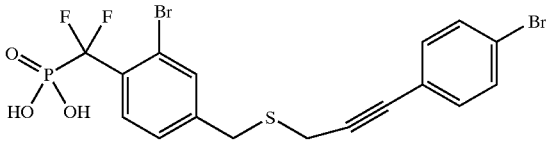 | 103 | Q |
| 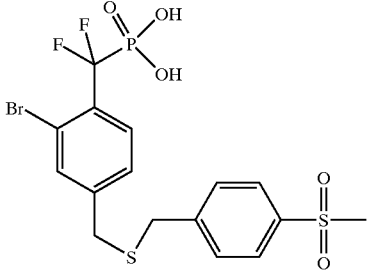 | 104 | L |
| 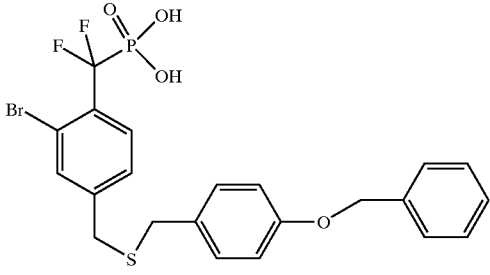 | 105 | L |
| 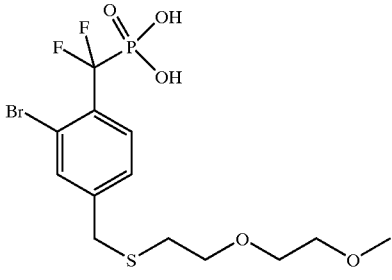 | 106 | L |

TABLE 1-continued

| Structure | Example | Method |
|---|---|---|
| (2-bromo-4-{[(4-acetamidobenzyl)thiomethyl]}phenyl)difluoromethylphosphonic acid | 107 | L |
| (2-bromo-4-{[2-(phenylsulfinyl)ethylthio]methyl}phenyl)difluoromethylphosphonic acid | 108 | L |
| (2-bromo-4-{[(3,3-dimethyl-2-oxobutyl)thio]methyl}phenyl)difluoromethylphosphonic acid | 109 | L |
| (2-bromo-4-{[(2,4,6-trimethylbenzyl)thio]methyl}phenyl)difluoromethylphosphonic acid | 110 | L |

TABLE 1-continued

| Structure | Example | Method |
|---|---|---|
| (2-bromo-4-((3-nitrobenzylthio)methyl)phenyl)difluoromethylphosphonic acid | 111 | L |
| (2-bromo-4-((3-phenoxypropylthio)methyl)phenyl)difluoromethylphosphonic acid | 112 | L |
| (2-bromo-4-((3-methoxybenzylthio)methyl)phenyl)difluoromethylphosphonic acid | 113 | L |
| (2-bromo-4-(((tetrahydro-2H-pyran-2-yl)methylthio)methyl)phenyl)difluoromethylphosphonic acid | 114 | L |
| (2-bromo-4-((4-(1,3-dioxoisoindolin-2-yl)butylthio)methyl)phenyl)difluoromethylphosphonic acid | 115 | L |

TABLE 1-continued
| | Example | Method |
|---|---|---|
| 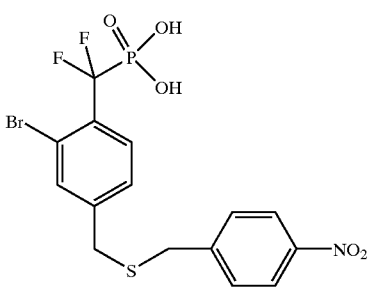 | 116 | L |
| 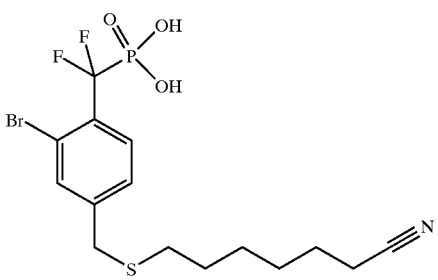 | 117 | L |
| 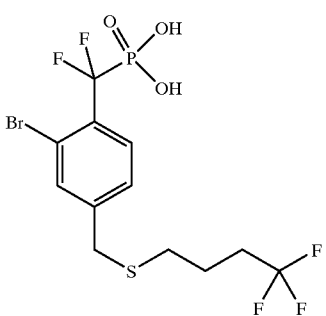 | 118 | L |
| 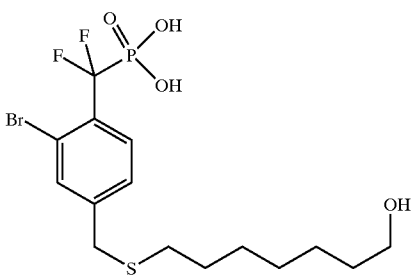 | 119 | L |

TABLE 1-continued

| | Example | Method |
|---|---|---|
| (structure) | 120 | L |
| (structure) | 121 | L |
| (structure) | 122 | L |
| (structure) | 123 | L |

TABLE 1-continued
| | Example | Method |
|---|---|---|
| 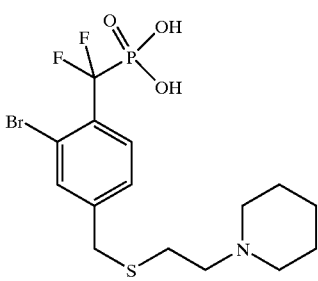 | 124 | L |
| 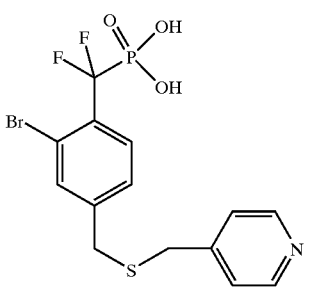 | 125 | L |
| 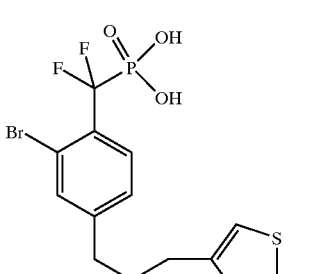 | 126 | L |
| 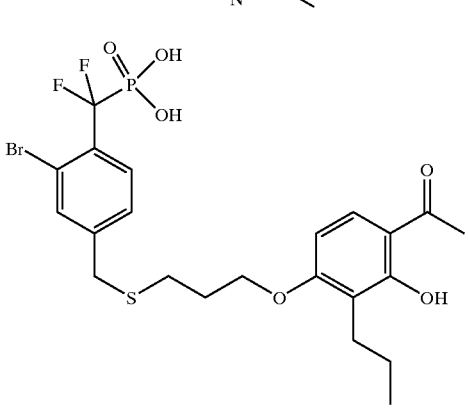 | 127 | L |
| 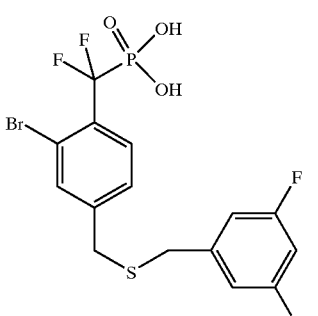 | 128 | L |

TABLE 1-continued
| | Example | Method |
|---|---|---|
| 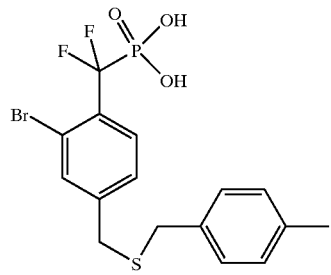 | 129 | L |
| 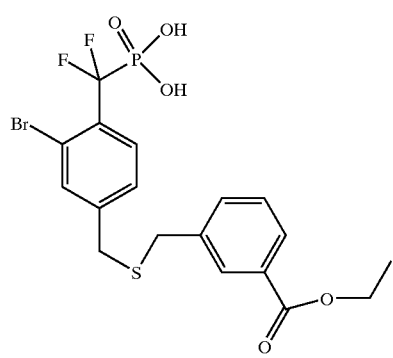 | 130 | L |
| 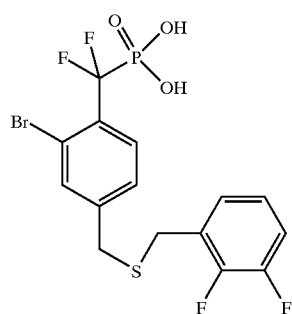 | 131 | L |
| 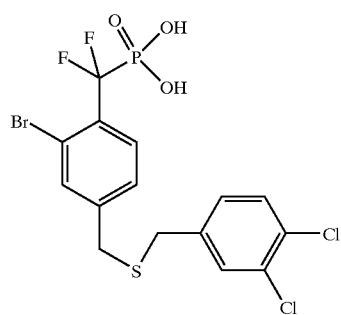 | 132 | L |

TABLE 1-continued

| Structure | Example | Method |
|---|---|---|
| (difluoro(phosphono)methyl)-bromo-phenyl-CH2-S-CH2-(2-biphenyl) | 133 | L |
| (difluoro(phosphono)methyl)-bromo-phenyl-CH2-S-CH2-(2,6-dichlorophenyl) | 134 | L |
| (difluoro(phosphono)methyl)-bromo-phenyl-CH2-S-CH2-(3-cyanophenyl) | 135 | L |
| (difluoro(phosphono)methyl)-bromo-phenyl-CH2-S-CH2-(2-trifluoromethylphenyl) | 136 | L |

TABLE 1-continued

| Structure | Example | Method |
|---|---|---|
| (2-bromo-4-((2-nitrobenzylthio)methyl)phenyl)difluoromethylphosphonic acid | 137 | L |
| (2-bromo-4-((3-trifluoromethylbenzylthio)methyl)phenyl)difluoromethylphosphonic acid | 138 | L |
| (2-bromo-4-((2-iodobenzylthio)methyl)phenyl)difluoromethylphosphonic acid | 139 | L |
| (2-bromo-4-((2-fluorobenzylthio)methyl)phenyl)difluoromethylphosphonic acid | 140 | L |
| (2-bromo-4-((3-fluorobenzylthio)methyl)phenyl)difluoromethylphosphonic acid | 141 | L |

TABLE 1-continued

| Structure | Example | Method |
|---|---|---|
| [2-bromo-4-[(2-chloro-4-fluorobenzylthio)methyl]phenyl]difluoromethylphosphonic acid | 142 | L |
| [2-bromo-4-[(3-iodobenzylthio)methyl]phenyl]difluoromethylphosphonic acid | 143 | L |
| [2-bromo-4-[((4-methylnaphth-1-yl)methylthio)methyl]phenyl]difluoromethylphosphonic acid | 144 | L |
| [2-bromo-4-[(2-chloro-6-fluorobenzylthio)methyl]phenyl]difluoromethylphosphonic acid | 145 | L |
| [2-bromo-4-[(3,5-dibromobenzylthio)methyl]phenyl]difluoromethylphosphonic acid | 146 | L |

TABLE 1-continued

| | Example | Method |
|---|---|---|
| [structure: 2-bromo-4-[(2-chlorobenzylthio)methyl]phenyl difluoromethylphosphonic acid] | 147 | L |
| [structure: 2-bromo-4-[(3-methylbenzylthio)methyl]phenyl difluoromethylphosphonic acid] | 148 | L |
| [structure: 2-bromo-4-[(2,3,5,6-tetrafluoro-4-trifluoromethylbenzylthio)methyl]phenyl difluoromethylphosphonic acid] | 149 | L |
| [structure: 2-bromo-4-[(3-chlorobenzylthio)methyl]phenyl difluoromethylphosphonic acid] | 150 | L |
| [structure: 2-bromo-4-[(2,5-difluorobenzylthio)methyl]phenyl difluoromethylphosphonic acid] | 151 | L |

TABLE 1-continued

| | Example | Method |
|---|---|---|
| (structure: 2-bromo-4-[(2,6-difluorobenzylthio)methyl]phenyl difluoromethylphosphonic acid) | 152 | L |
| (structure: 2-bromo-4-[(2,5-dichlorobenzylthio)methyl]phenyl difluoromethylphosphonic acid) | 153 | L |
| (structure: 2-bromo-4-[(2-methylbenzylthio)methyl]phenyl difluoromethylphosphonic acid) | 154 | L |
| (structure: 2-bromo-4-[(2,4-dichlorobenzylthio)methyl]phenyl difluoromethylphosphonic acid) | 155 | L |
| (structure: 2-bromo-4-[(1-methyl-1H-tetrazol-5-ylthio)methyl]phenyl difluoromethylphosphonic acid) | 156 | P |

TABLE 1-continued
| | Example | Method |
|---|---|---|
| 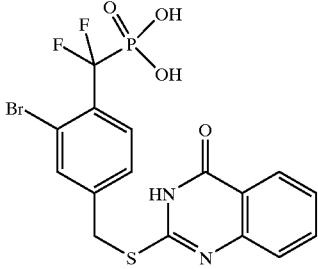 | 157 | P |
| 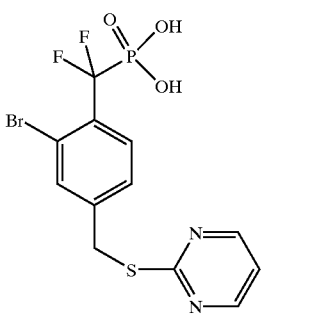 | 158 | P |
| 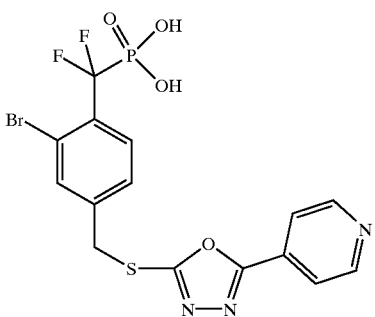 | 159 | P |
| 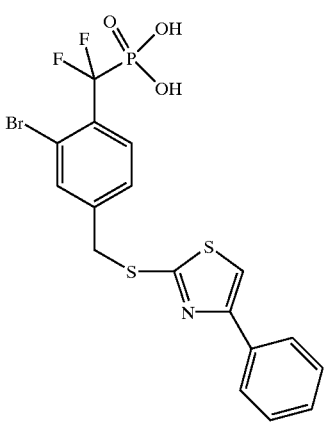 | 160 | P |

TABLE 1-continued

| | Example | Method |
|---|---|---|
| (structure) | 161 | P |
| (structure) | 162 | P |
| (structure) | 163 | P |
| (structure) | 164 | P |
| (structure) | 165 | P |

TABLE 1-continued

| | Example | Method |
|---|---|---|
| [structure: 2-bromo-4-(((1-methyl-1H-imidazol-2-yl)thio)methyl)benzyl difluoromethylphosphonic acid] | 166 | P |
| [structure: 2-bromo-4-(((4-acetamidophenyl)thio)methyl)benzyl difluoromethylphosphonic acid] | 167 | P |
| [structure: 2-bromo-4-(((3-chlorophenyl)thio)methyl)benzyl difluoromethylphosphonic acid] | 168 | P |
| [structure: 3-(((3-bromo-4-((difluoro(phosphono)methyl))benzyl)thio)benzoic acid] | 169 | P |
| [structure: 2-bromo-4-(((3-bromophenyl)thio)methyl)benzyl difluoromethylphosphonic acid] | 170 | P |

TABLE 1-continued

| Structure | Example | Method |
|---|---|---|
| (structure with bromophenyl-CF2-PO(OH)2 and CH2-S-(3,5-dichlorophenyl)) | 171 | P |
| (structure with bromophenyl-CF2-PO(OH)2 and CH2-S-(4-chlorophenyl)) | 172 | P |
| (structure with bromophenyl-CF2-PO(OH)2 and (CH2)2-S-(1-methyltetrazol-5-yl)) | 173 | R |
| (structure with bromophenyl-CF2-PO(OH)2 and (CH2)2-S-(4-oxoquinazolin-2-yl)) | 174 | R |
| (structure with bromophenyl-CF2-PO(OH)2 and (CH2)2-S-(pyrimidin-2-yl)) | 175 | R |

TABLE 1-continued

| Structure | Example | Method |
|---|---|---|
| (2-bromo-4-{3-[(5-pyridin-4-yl-1,3,4-oxadiazol-2-yl)sulfanyl]propyl}phenyl)(difluoro)methylphosphonic acid | 176 | R |
| (2-bromo-4-{3-[(5-pyridin-4-yl-1,3,4-oxadiazol-2-yl)sulfanyl]propyl}phenyl)(difluoro)methylphosphonic acid | 177 | R |
| (2-bromo-4-{3-[(5-(4-chlorophenyl)-1H-1,2,4-triazol-3-yl)sulfanyl]propyl}phenyl)(difluoro)methylphosphonic acid | 178 | R |
| (2-bromo-4-{3-[(pyridin-2-yl)sulfanyl]propyl}phenyl)(difluoro)methylphosphonic acid | 179 | R |
| (2-bromo-4-{3-[(quinolin-2-yl)sulfanyl]propyl}phenyl)(difluoro)methylphosphonic acid | 180 | R |

TABLE 1-continued

| Structure | Example | Method |
|---|---|---|
| (3-bromo-4-(difluoro(phosphono)methyl)phenyl)propylthio-5-methyl-1H-benzimidazole | 181 | R |
| (3-bromo-4-(difluoro(phosphono)methyl)phenyl)propylthio-5-methyl-1,3,4-thiadiazole | 182 | R |
| (3-bromo-4-(difluoro(phosphono)methyl)phenyl)propylthio-5-phenyl-1H-1,2,4-triazole | 183 | R |
| (3-bromo-4-(difluoro(phosphono)methyl)phenyl)propylthio-1-methylimidazole | 184 | R |
| (3-bromo-4-(difluoro(phosphono)methyl)phenyl)propylthio-4-acetamidophenyl | 185 | R |

TABLE 1-continued

| | Example | Method |
|---|---|---|
| (structure) | 186 | R |
| (structure) | 187 | R |
| (structure) | 188 | R |
| (structure) | 189 | R |
| (structure) | 190 | R |

TABLE 1-continued
| | Example | Method |
|---|---|---|
| 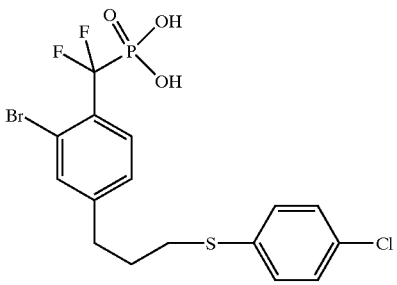 | 191 | R |
| 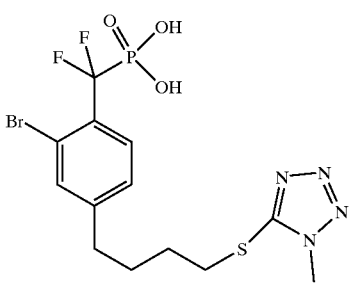 | 192 | R |
| 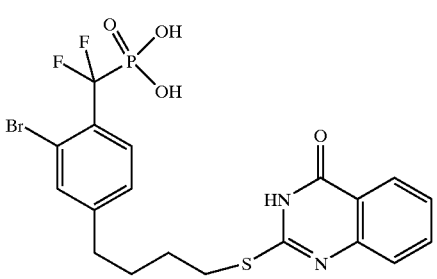 | 193 | R |
| 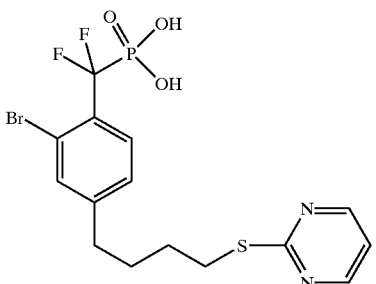 | 194 | R |
| 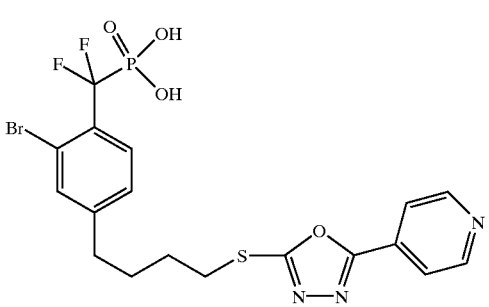 | 195 | R |

TABLE 1-continued
| | Example | Method |
|---|---|---|
| 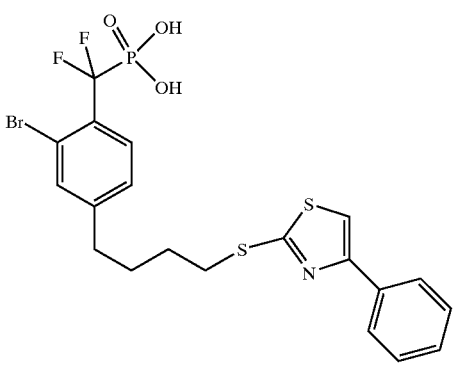 | 196 | R |
| 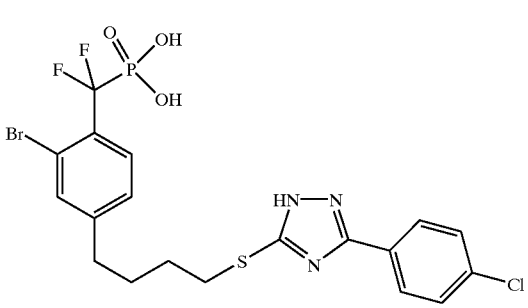 | 197 | R |
| 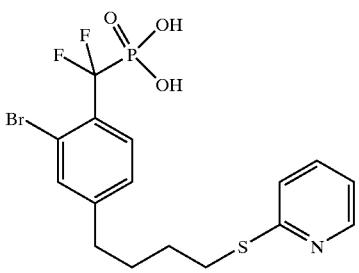 | 198 | R |
| 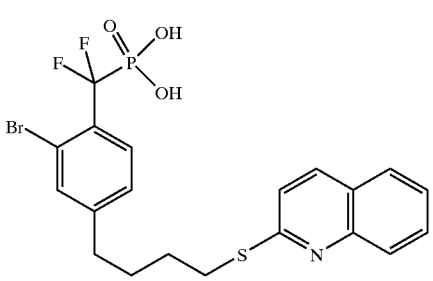 | 199 | R |
| 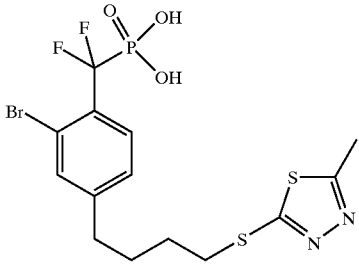 | 200 | R |

TABLE 1-continued
| | Example | Method |
|---|---|---|
| 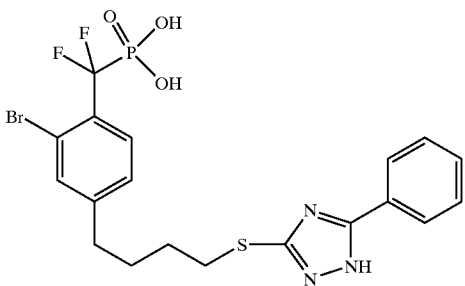 | 201 | R |
| 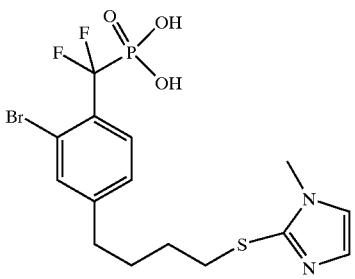 | 202 | R |
| 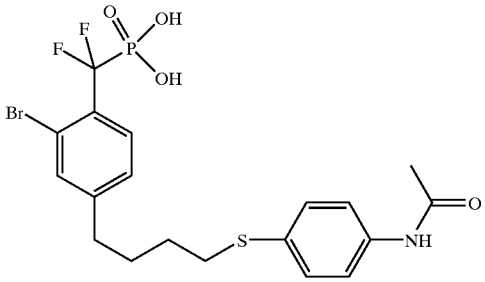 | 203 | R |
| 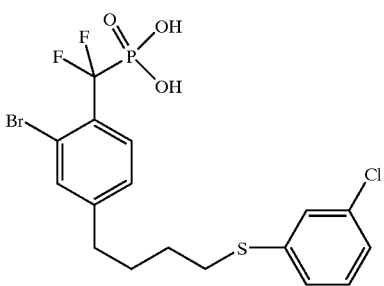 | 204 | R |
| 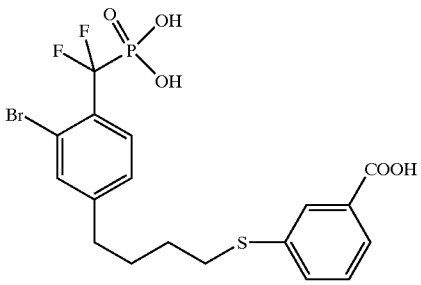 | 205 | R |

TABLE 1-continued

| | Example | Method |
|---|---|---|
| (structure) | 206 | R |
| (structure) | 207 | R |
| (structure) | 208 | R |
| (structure) | 209 | R |

TABLE 2

| | Example | Method |
|---|---|---|
| (structure) | 210 | |

TABLE 2-continued
| | Example | Method |
|---|---|---|
| 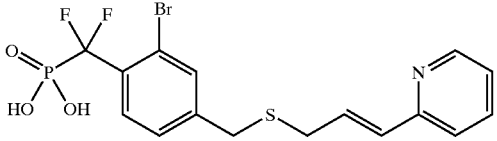 | 211 | |
| 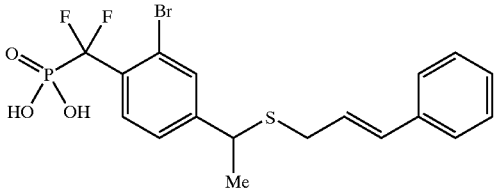 | 212 | |
| 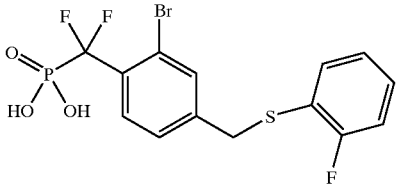 | 213 | |
| 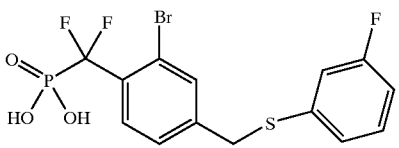 | 214 | |
| 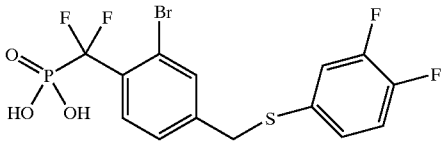 | 215 | |
| 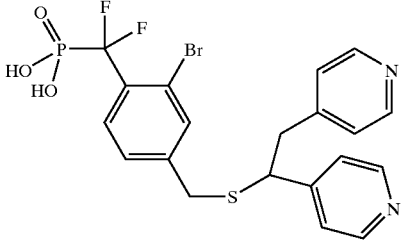 | 216 | |
| 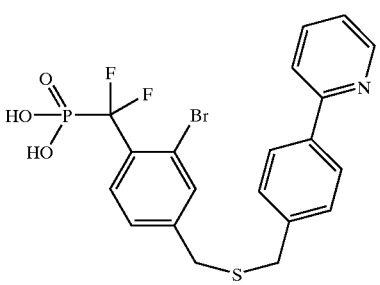 | 217 | |

TABLE 2-continued

| Structure | Example | Method |
|---|---|---|
| (difluoro(phosphono)methyl)-bromobenzyl-S-CH2CH2-N(Me)2 | 218 | |
| (difluoro(phosphono)methyl)-bromobenzyl-S-thiazol-2-yl | 219 | |
| (difluoro(phosphono)methyl)-bromobenzyl-S-(4,5-dimethylthiazol-2-yl) | 220 | |
| (difluoro(phosphono)methyl)-bromobenzyl-S-(4-methylthiazol-2-yl) | 221 | |
| (difluoro(phosphono)methyl)-bromobenzyl-S-(5-methylthiazol-2-yl) | 222 | |
| (difluoro(phosphono)methyl)-bromobenzyl-S-CH(Ph)-CH2-(pyridin-4-yl) | 223 | |
| (difluoro(phosphono)methyl)-bromobenzyl-S-CH2-CH=C(Me)2 | 224 | |
| (difluoro(phosphono)methyl)-bromobenzyl-S-Ph | 225 | |
| (difluoro(phosphono)methyl)-bromobenzyl-S-CH2-(4-(2-(hexafluoro-2-hydroxypropyl)thiazol-5-yl)phenyl) | 226 | |

TABLE 2-continued
| | Example | Method |
|---|---|---|
| 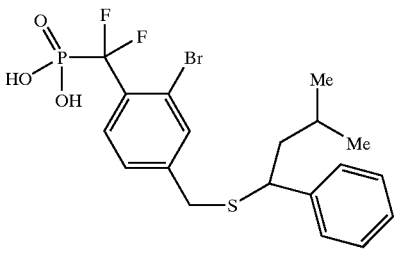 | 227 | |
| 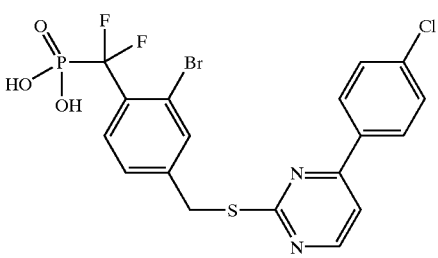 | 228 | |
| 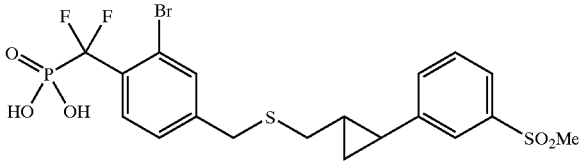 | 229 | |
| 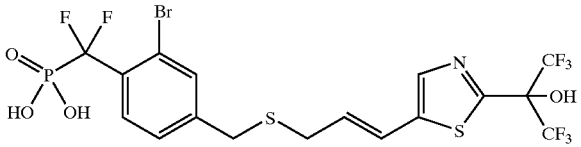 | 230 | |
| 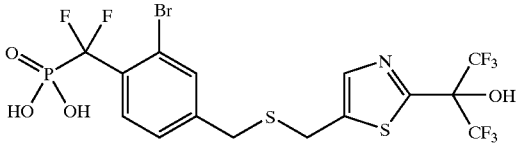 | 231 | |
| 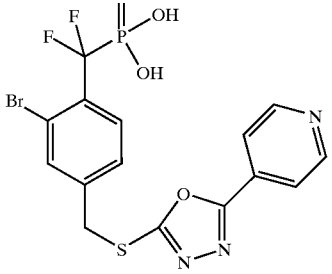 | 232 | |
| 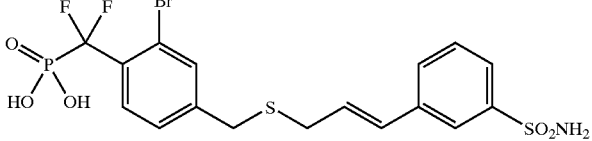 | 233 | |

TABLE 2-continued

| | Example | Method |
|---|---|---|
| [structure] | 234 | |
| [structure] | 235 | |
| [structure] | 236 | |
| [structure] | 237 | |
| [structure] | 238 | |

TABLE 2-continued

| | Example | Method |
|---|---|---|
| (structure) | 239 | |
| (structure) | 240 | |
| (structure) | 241 | |
| (structure) | 242 | |
| (structure) | 243 | |

TABLE 2-continued

| Example | Method |
|---------|--------|
| 244 | |
| 245 | |
| 246 | |
| 247 | |
| 248 | |

TABLE 2-continued
| | Example | Method |
|---|---|---|
| 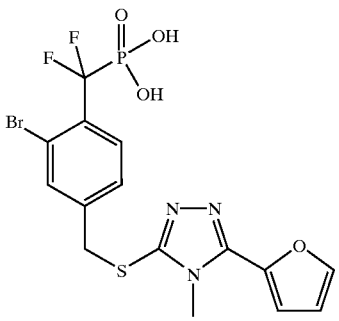 | 249 | |
| 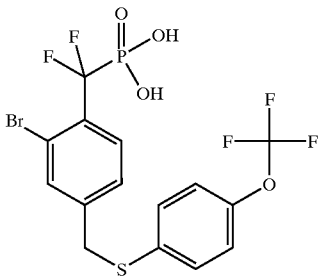 | 250 | |
| 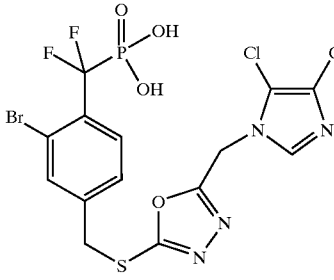 | 251 | |
| 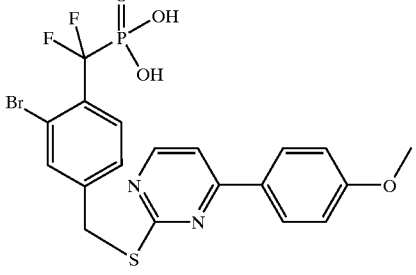 | 252 | |
| 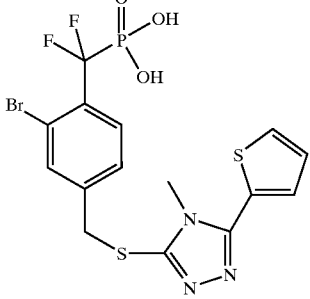 | 253 | |

TABLE 2-continued

| | Example | Method |
|---|---|---|
| (structure) | 254 | |
| (structure) | 255 | |
| (structure) | 256 | |
| (structure) | 257 | |
| (structure) | 258 | |

Methods of Synthesis

The compounds of the present invention can be prepared according to the following methods.

Method A

An appropriately substituted aniline 1, from commercial sources or prepared from readily available starting material, is diazotized and converted to the corresponding cyano intermediate 2 under Sandmyer's condition. Compound 2 is then reduced with DIBAL-H from −78° C. to room temperature to give the hydroxymethyl benzaldehyde 3. The hydroxyl group of 3 is converted to the bromo group by the treatment with a brominating mixture such as $POBr_3$ and DMF to give bromide 4. The aldehyde of 4 is reacted with an anion derived from dialkyl phosphite and a base such as $LiN(TMS)_2$ to afford the hydroxy intermediate 5. Oxidation of 5 with $MnO_2$ or under Swern's condition provides the ketophosphonate 6. Treatment with DAST then gives bromide 7.

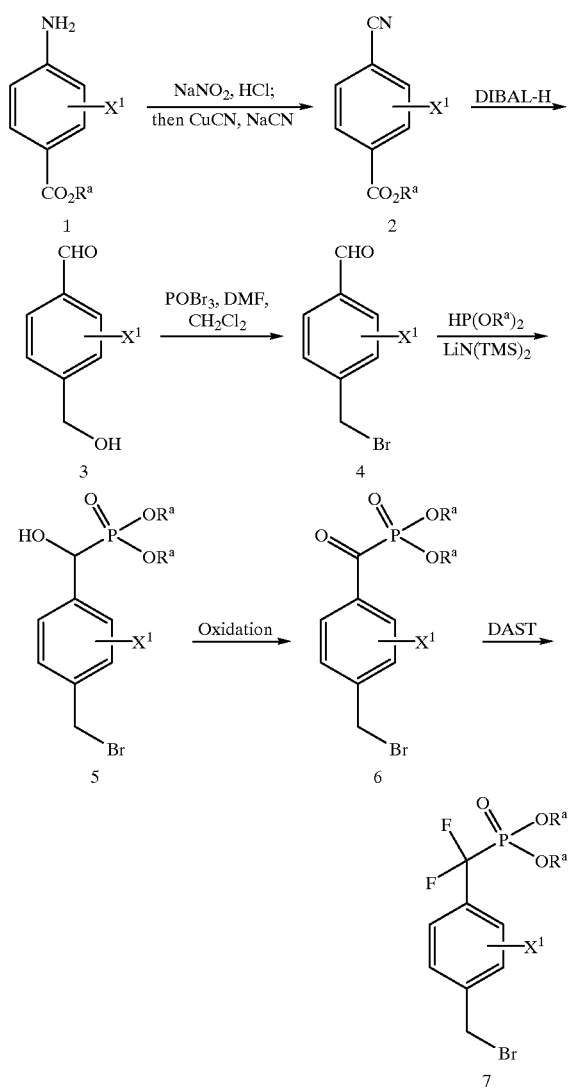

$R^a$ is a substituent, which is part of an ester group, and can be selected independently.

Method B

An appropriately substituted difluoromethylphosphonic acid dialkyl ester 7 is reacted with potassium thioacetate in DMF to give the corresponding thioacetate 8.

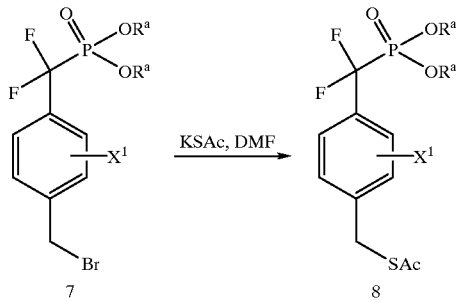

Method C

4'-Methoxy-4-methylbiphenyl 9 is prepared from the Suzuki reaction of 4-methylbenzeneboronic acid and 4-bromoanisole. The methyl ether is then cleaved with a Lewis acid such as $BBr_3$ to give phenol 10. The hydroxyl intermediate is converted to the phosphate intermediate 11 followed Purnanand's condition (Tet. Lett., 1989, 30, 1687). Base promoted rearrangement with a base such as LDA provides the hydroxyl phosphonate intermediate 12. Alkylation with an alkyl halide in the presence of a base such as NaOH in a solvent such as DMF or with an alcohol under Mitsunobu reaction condition gives an alkoxy phosphonate intermediate 13. Bromination with NBS provides the bromomethyl intermediate 14 for subsequent alkylation reaction.

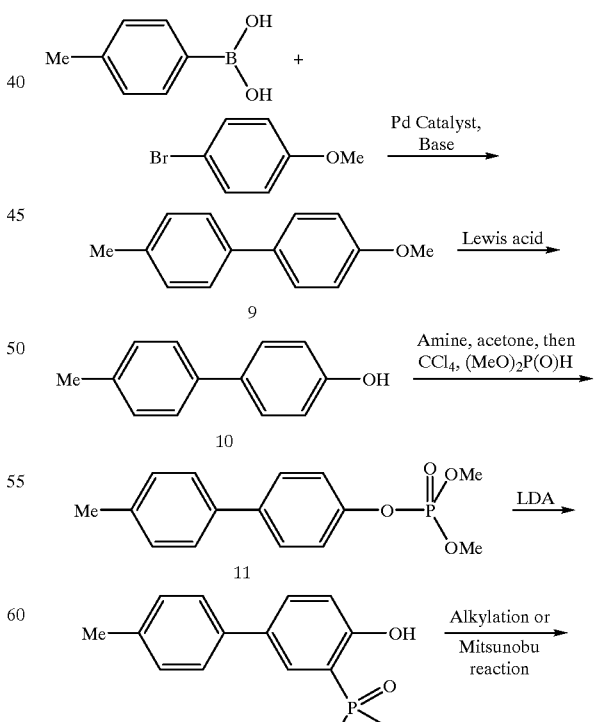

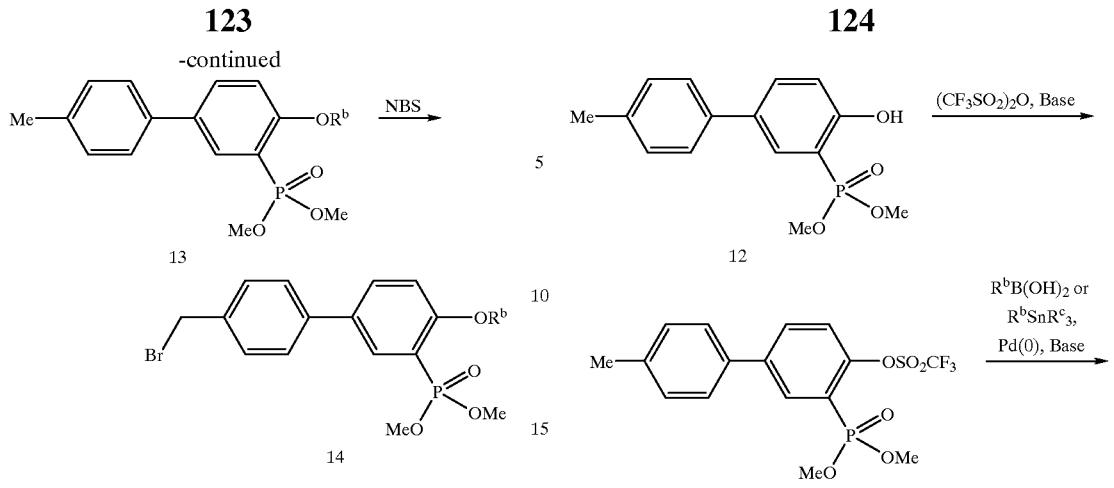

$R^b$ is a substituent, which is part of the coupling reagent, and can be selected independently.

Method D

An appropriately substituted iodo or bromo benzoate is coupled with a (hydroxymethyl)benzene boronic acid under Suzuki's condition to give an alcohol intermediate 15. Treatment of 15 with a brominating mixture such as NBS and Ph₃P gives bromide 16.

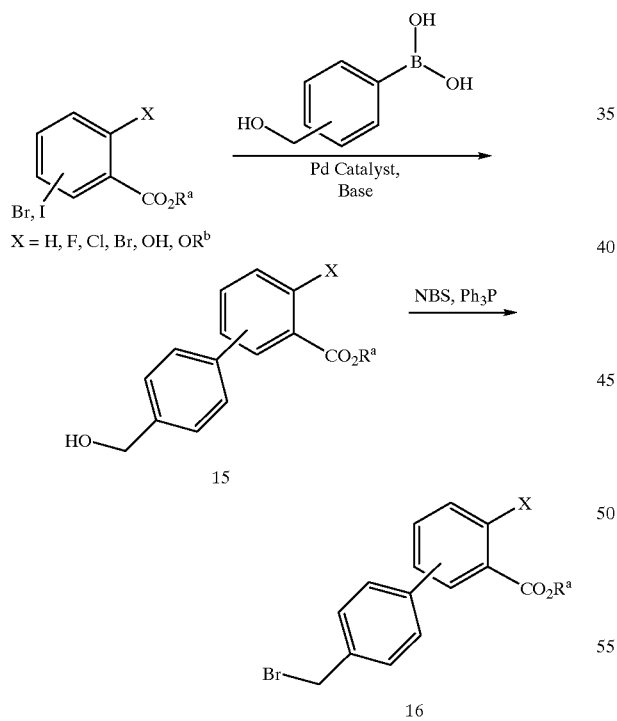

Method E

The phenol intermediate 12 from Method C is converted to the corresponding triflate 17, which is coupled with a boronic acid under Suzuki's conditions or a tin reagent under Still's conditions to provide 18. Bromination with NBS then gives bromide 19.

$R^c$ is a substituent which is part of the reagent.

Method F

2-Methyl-6,8-dibromo quinoline 20 is coupled with a boronic acid such as 4-(hydroxymethyl)benzene boronic acid under Suzuki's condition to give an alcohol intermediate. The hydroxyl group is protected as a silyl ether or a THP ether to provide 21. Monoalkylation gives 22. Repeating of the alkylation with a second electrophile yields 23. Treatment of 23 with a dialkyl phosphite in the presence of a Pd(O) catalyst affords 24. Deprotection of the hydroxyl protecting group gives 25, which is converted to the bromide 26 by POBr₃/DMF condition.

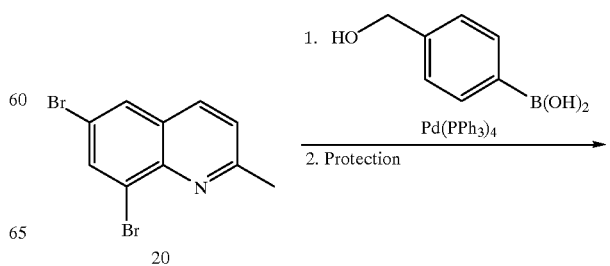

-continued

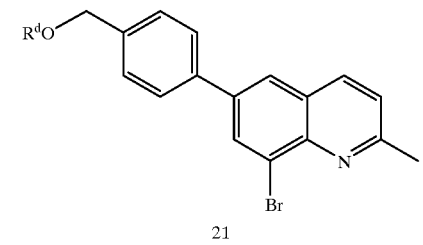
21

$R^d$ = OSiMe$_2$t-Bu, OTHP

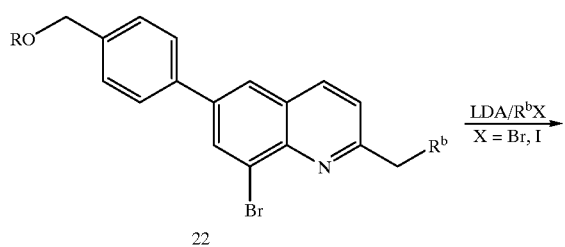
22

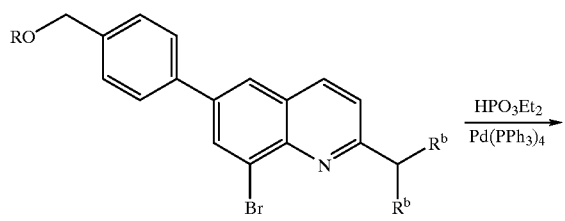
23

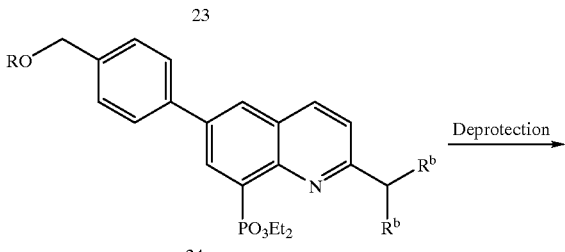
24

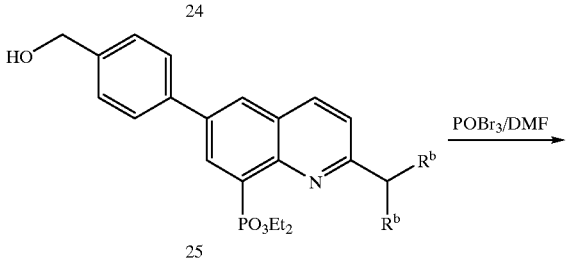
25

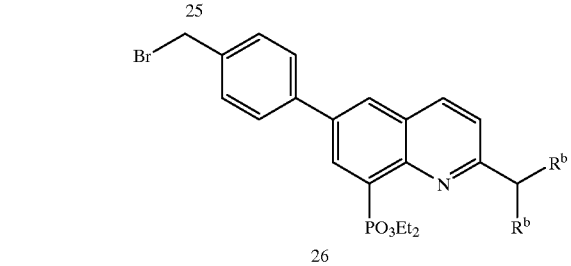
26

$R^b$ is a substituent, which is part of the reagent, and can be selected independently.

Method G

Bromoquinoline intermediate 23 from Method F is treated with n-BuLi, reacted with CO$_2$ and converted to the ester intermediate 27. Compound 27 is then transformed to the bromide 29 as described in Method F.

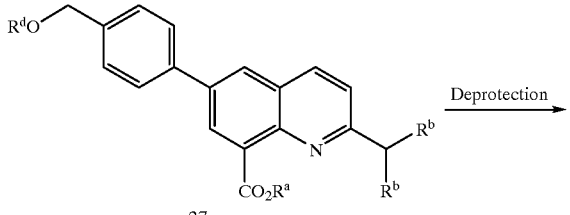
23

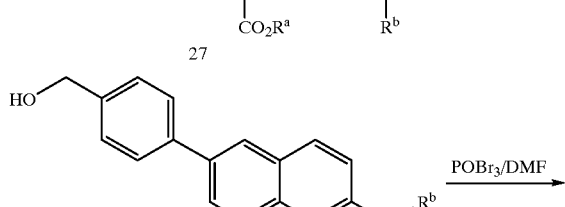
27

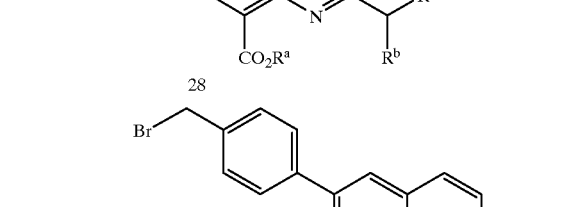
28

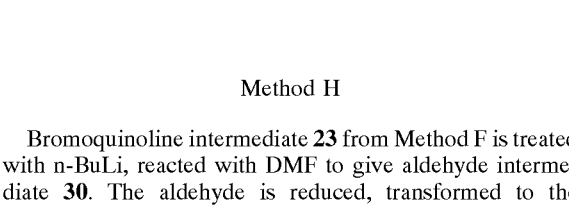
29

Method H

Bromoquinoline intermediate 23 from Method F is treated with n-BuLi, reacted with DMF to give aldehyde intermediate 30. The aldehyde is reduced, transformed to the bromide, reacted with NaCN and converted to the methyl ester 31. Compound 31 is then transformed to the bromide 33 as described in Method F.

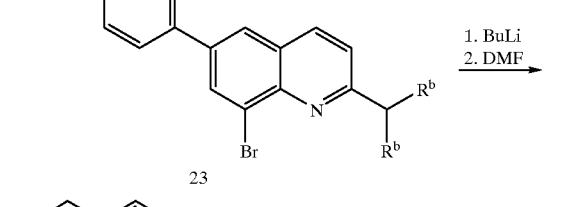
23

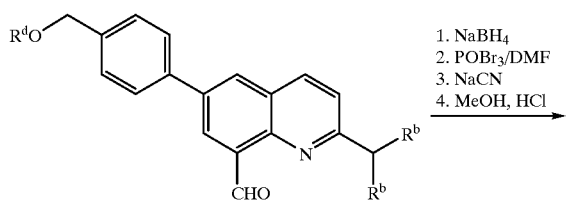
30

127
-continued

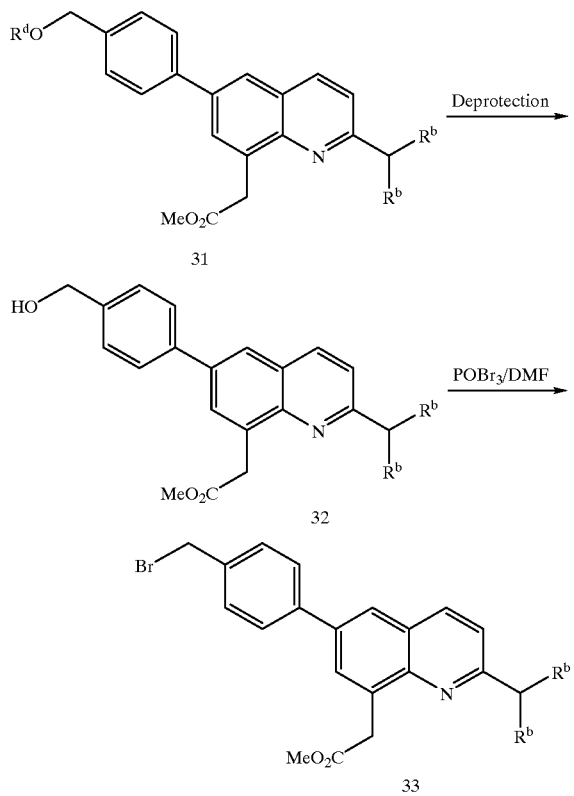

Method I

Bromoquinoline 21 from Method F is reacted with diethylphosphite in the presence of a Pd(O) catalyst to give 34. Reaction with SeO$_2$ provides aldehyde 35, which is reacted with a Grignard reagent to afford alcohol 36. Oxidation of 36 with MnO$_2$ yields ketone 37. The ketone intermediate is converted to the bromide 38 as described in Method F.

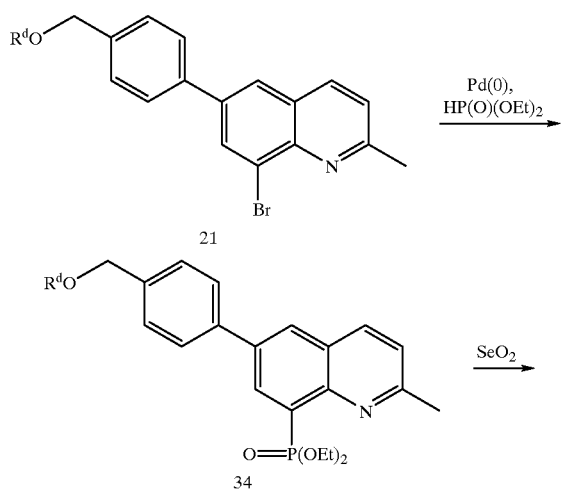

128
-continued

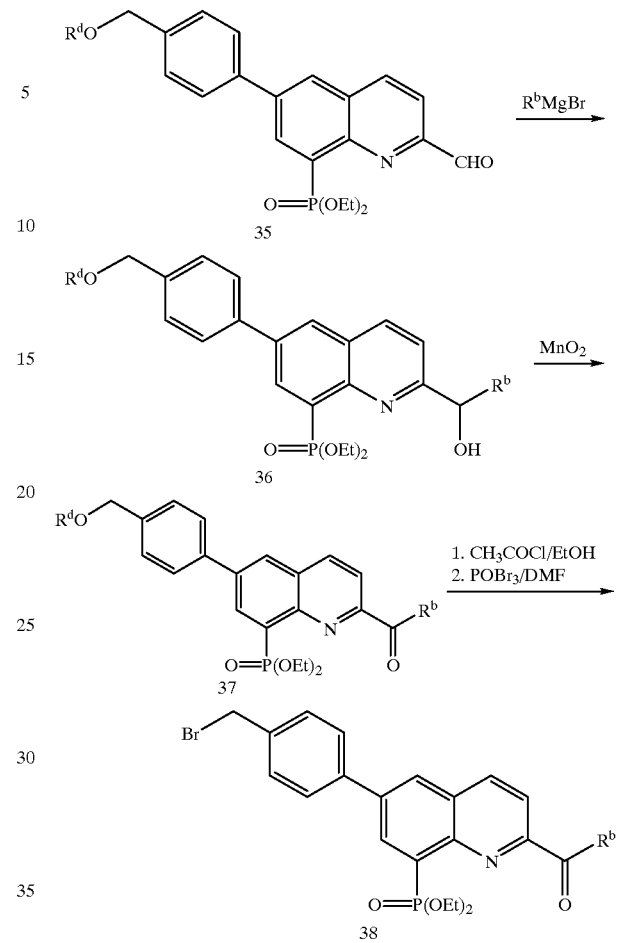

Method J

The ketone intermediate 37 from Method I is reacted with a Grignard reagent and converted to the methyl ether 39, which is transformed to the bromide 40 as described in Method F.

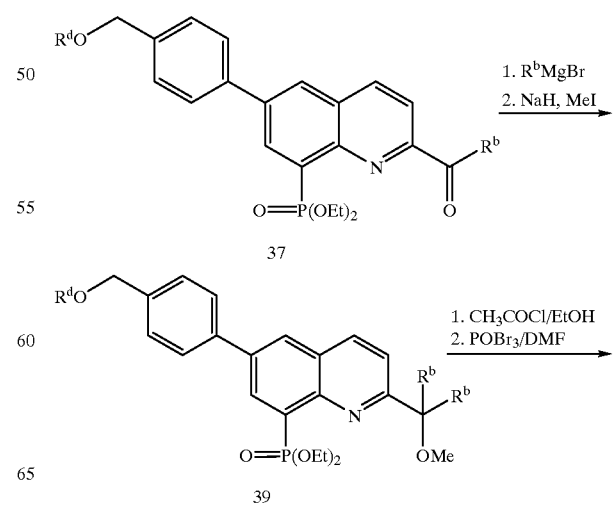

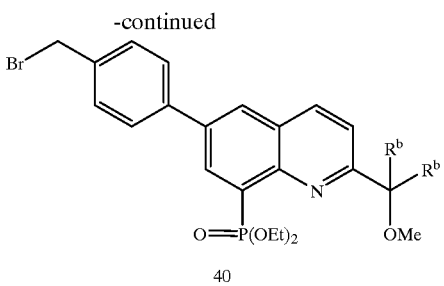

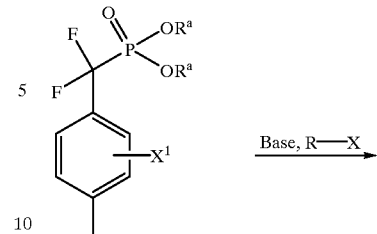

Method K

An appropriately substituted iodo-toluene 41 is brominated with NBS to give bromide 42, which is then coupled with a thiol or thioacetate to give sulfide 43. Sulfide 43 undergoes a copper halide-mediated cross coupling reaction with [(diethoxyphosphinyl)difluoromethyl]zinc bromide (Tetrahedron, 1997, 53, 815.) to give 44. Deprotection of 44 with TMS-Br or aqueous HOAc and may require additional deprotection reaction(s) for R to give 45.

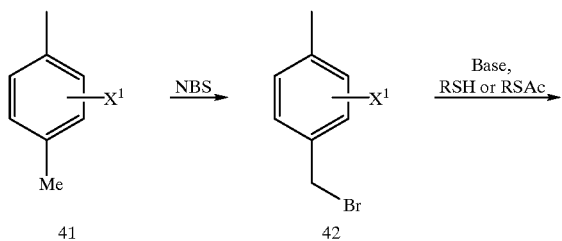

Method M

The sulfide intermediate 44 from Method L is oxidized to the sulfone 46, which is deprotected as described in Method L to give 47.

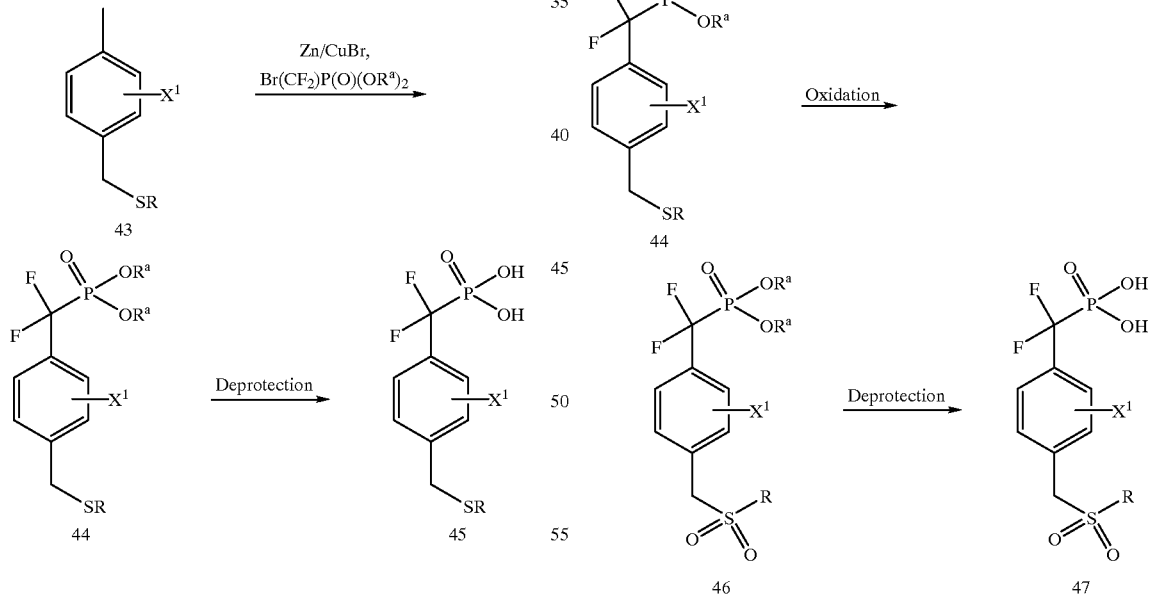

Method L

The thioacetate 8, prepared according to Method B, is reacted with an electrophile, either prepared from a suitable method as described for the present invention or from commercial sources, to give the sulfide intermediate 44. Deprotection of 44 with TMS-Br or aqueous HOAc and following by saponification for R containing an ester group to give 45.

Method N

Various substituted bromothioanisole 48 can be oxidized to the corresponding sulfone 49 by mCPBA. Palladium catalyzed coupling of the resulting bromosulfone with 4-hydroxymethylphenylboronic acid gives the corresponding biphenyl benzyl alcohol 50. Treatments of the alcohol 50 with POBr$_3$ gives the benzyl bromide 51.

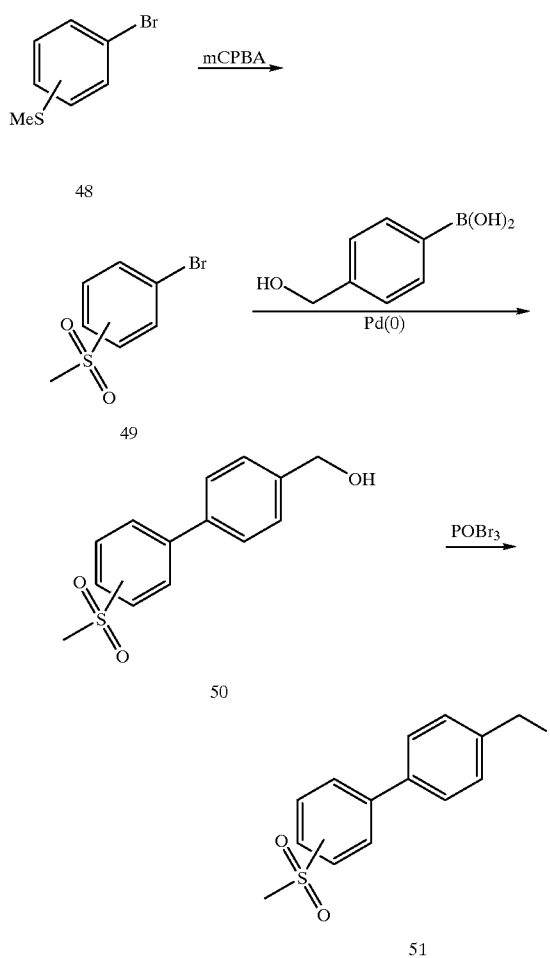

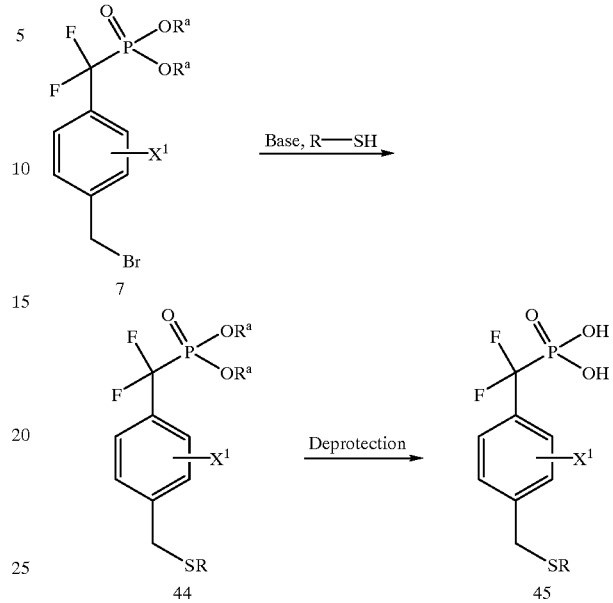

Method O

Compound 45 from Method L is treated with one equivalent or two equivalent of an oxidizing agent such as MMPP or mCPBA to give the corresponding sulfoxide 52 or sulfone 53 products.

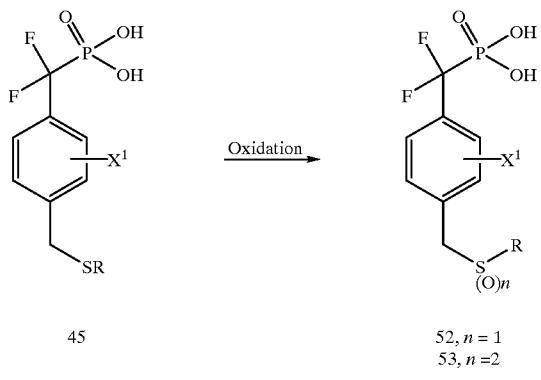

Method P

The bromide 7, prepared according to Method A, is reacted with an appropriate thiol to give the sulfide intermediate 44. Deprotection of 44 with TMS-Br or aqueous HOAc and following by soponification for R containing an ester group to give 45.

Method Q

Thioacetate 54 is reacted with bromide 7, prepared according to Method A, to give the sulfide intermediate 44. Deprotection of 44 with TMS-Br or aqueous HOAc and may require additional deprotection reaction(s) for R to give 45.

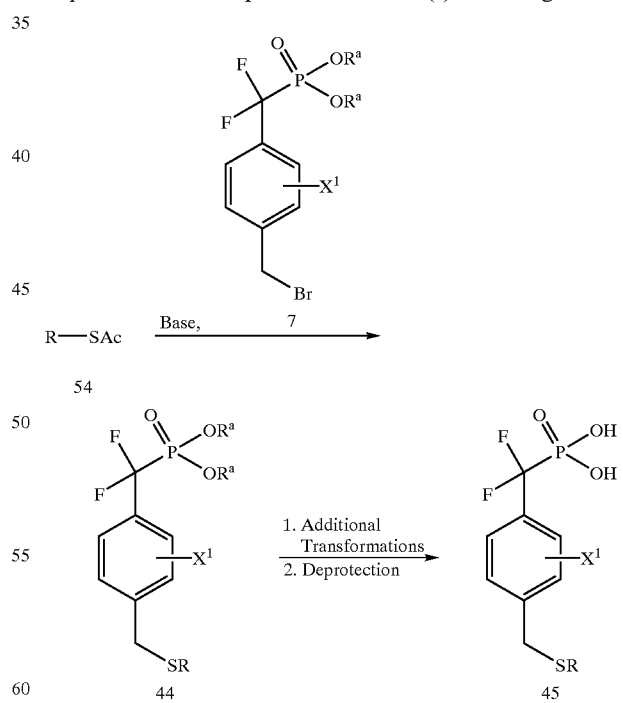

Method R

An appropriately substituted aniline 55 from commercial sources or prepared from readily available starting material, is diazotized and converted to the corresponding cyano intermediate 56 under Sandmyer's condition. Compound 56 is then reduced with DIBAL-H from −78° C. to room temperature to give the hydroxymethyl benzaldehyde 57. The hydroxyl group of 57 is converted to the bromo group by the treatment with a brominating mixture such as N-bromosuccinimde and triphenylphosphine to give bromide 58. The aldehyde of 58 is reacted with an anion derived from dialkyl phosphite and a base such as LiN(TMS)$_2$ to afford the hydroxy intermediate 59. Oxidation of 59 with MnO$_2$ or under Swem's condition provides the ketophosphonate 60. Treatment with DAST then gives bromide 61. Bromide 61 is then reacted with an appropriate thiol or thioacetate to give the sulfide intermediate 62. Deprotection of 62 with TMS-Br or aqueous HOAc and may require additional deprotection reaction(s) for R to give 63.

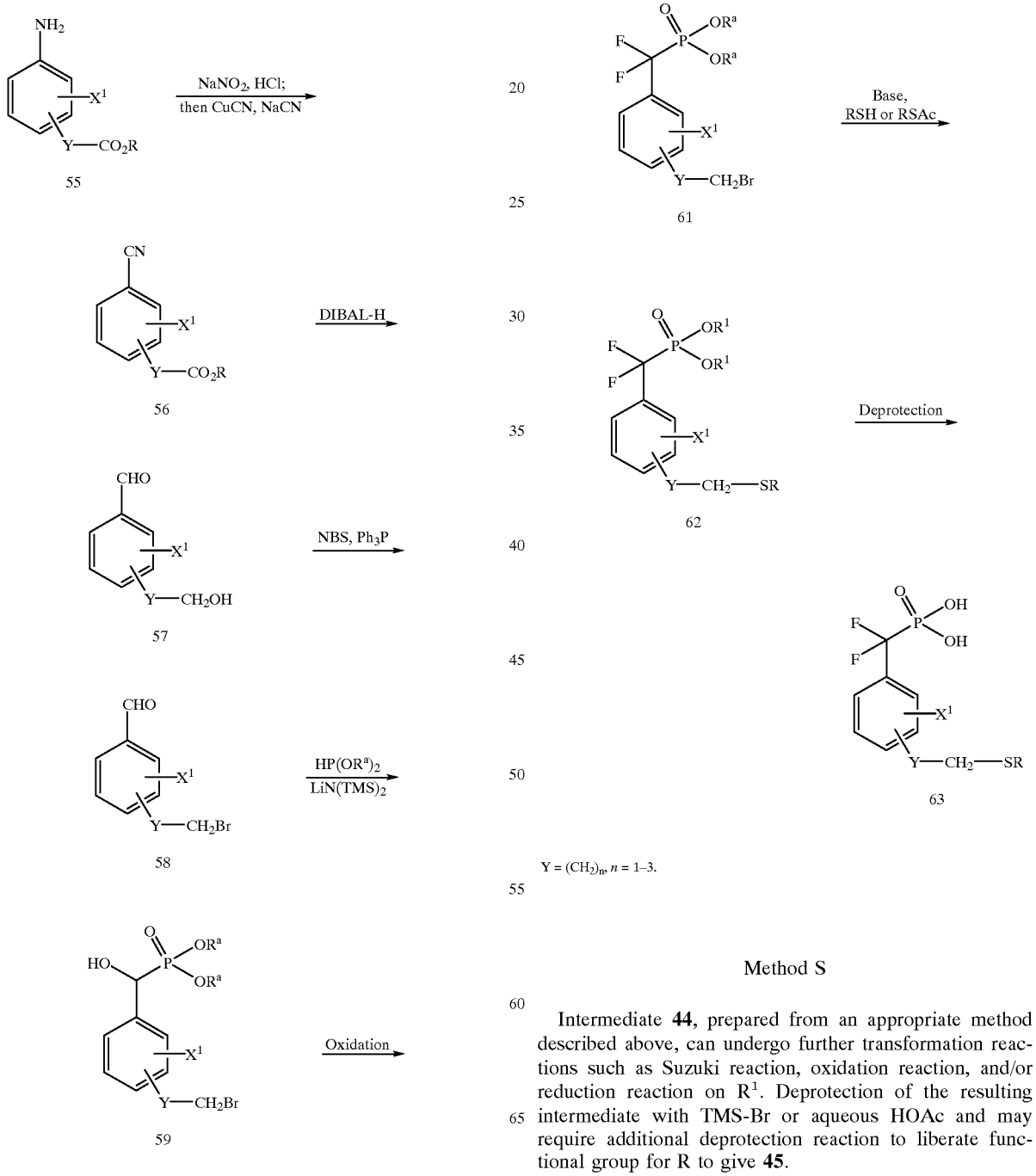

$Y = (CH_2)_n, n = 1–3.$

Method S

Intermediate 44, prepared from an appropriate method described above, can undergo further transformation reactions such as Suzuki reaction, oxidation reaction, and/or reduction reaction on $R^1$. Deprotection of the resulting intermediate with TMS-Br or aqueous HOAc and may require additional deprotection reaction to liberate functional group for R to give 45.

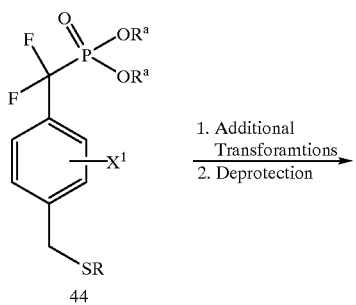

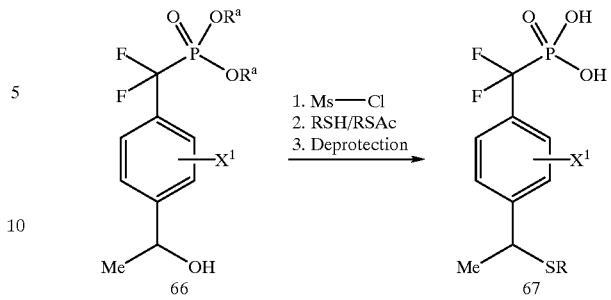

Method T

Bromide 7, prepared according to Method A is converted to aldehyde 64 using an amine-oxide such as N-methylmorpholine-N-oxide. Aldehyde 64 is then converted to olefin 65. Olefin 65 is further transform to alcohol intermediate 66 via an oxymercuration-demercuration squence. The hydroxy group of 66 is converted to a good leaving group such as mesylate, reacted with a thiol or thioacetate in the presence of a base and followed by deprotection reaction(s) to give 67.

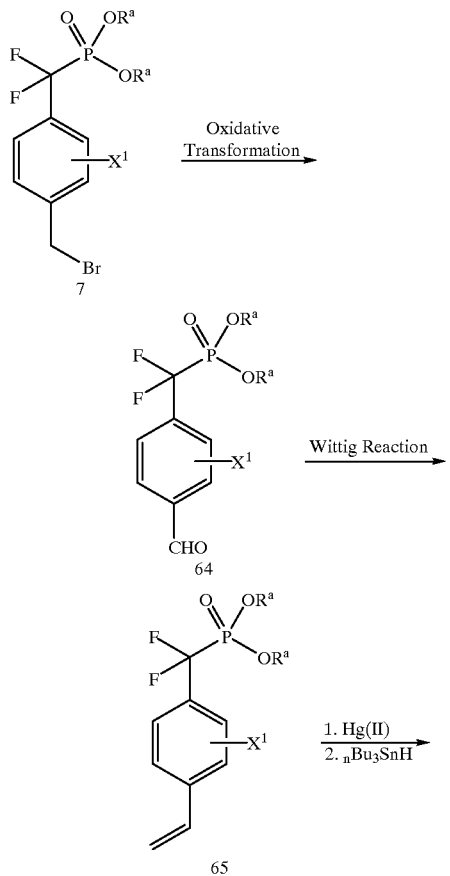

Method U

A heterocyclic(or aromatic) halide(or triflate) 68 is converted to a silyl sulfide intermediate 69 [Tetrahedron, 35, 3225–3226 (1994), Tetrahedron, 37, 4523-4524 (1996)]. Sulfide 69 is then reacted with bromide 7 in the presence of a fluoride ion to give the coupling product 44. Deprotection of 44 with TMS-Br or aqueous HOAc and may require additional deprotection reaction(s) for R to give 45.

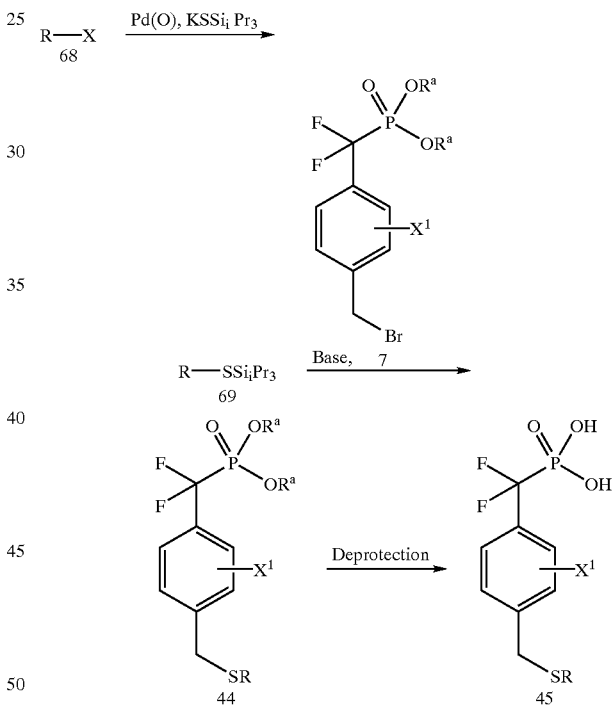

Synthesis of Intermediates for Use in Synthetic Examples

Thioacetic Acid S-{4-[(diethoxyphosphoryl) difluoromethyl]benzyl Ester

A solution of (4-bromomethylphenyl) difluoromethylphosphonic acid diethyl ester (4.0 g, 11.2 mmol) in DMF (30 mL) was purged with a stream of $N_2$ for 15 min, then cooled to 0° C. Powdered potassium thioacetate (1.5 g, 13.2 mmol) was added. The mixture was stirred at 0° C. for 1 h. After dilution with $H_2O$, the mixture was extracted with EtOAc. The EtOAc extract was washed with $H_2O$ (2×), dried ($MgSO_4$) and concentrated. Chromatography over silica gel and elution with hexanes:EtOAc (1.5:1) gave 3.5 g (89%) of the title compound as a light brown oil.

$^1H$ NMR (Acetone-$d_6$) δ 7.50 (m, 4H), 4.15 (m, 6H), 2.34 (s, 3H), 1.26 (t, 6H).

(2-Bromo-4-bromomethylphenyl)difluoromethylphosphonic Acid Diethyl Ester

Step 1: Ethyl 4-amino-3-bromobenzoate

To a mechanical stirred solution of ethyl 4-aminobenzoate (165 g, 1 mol) in THF (1.2 L) and pyridine (200 mL) at ~10° C. was added portionwise (~10–20 g each time) of pyridine hydrobromide perbromide (tech. 90%, 365 g, 1.02 mol) over a period of 1 h. Internal temperature was kept at 10–10° C. After completion of addition, the mixture was stirred for 30 min, then filtered through celite and the filter cake was washed with THF (1 L). The filtrate was diluted with $Et_2O$, washed with 0.5 M of aqueous $NaHSO_3$ (2×, 400 mL), brine, dried ($MgSO_4$) and concentrated. The residue contained too much $H_2O$ and therefore was dissolved in EtOAc (1L), washed with brine, dried ($MgSO_4$) and concentrated to give a semi-solid residue. The residue was swished with hexanes-$Et_2O$ (2:1) to yield 187 g (77%) of the title compound as a white powder. The mother liquor was evaporated and swished again to give 19 g (8%) of additional title compound as a light brown powder.

$^1$H NMR (Acetone-$d_6$) δ 8.00 (s, 1H), 7.72 (d, 1H), 6.88 (d, 1H), 5.68 (br s, 2H), 4.25 (q, 2H), 1.31 (t, 3H).

Step 2: Ethyl 3-bromo-4-cyanobenzoate

To a three necked 3L round bottomed flask with a mechanical stirrer was added 3M aqueous HCl (790 mL), followed by ethyl 4-amino-3-brombenzoate (195 g, 0.8 mol) and the mixture was stirred for 15 min. After cooling to 5° C., a solution of 4M aqueous $NaNO_2$ (240 mL, 0.96 mol) was added over a period of 30–45 min. The resulting mixture was further stirred for 30 min. and an almost homogenous solution was obtained. The mixture was filtered through glass wool to remove the insoluble residue. The solution was then added to a vigorously stirred solution of CuCN (111 g, 1.24 mol) and NaCN (162 g, 3.3 mol) in $H_2O$ (1 L) and EtOAc (500 mL) at room temperature in a 6L Erlenmeyer flask over ~45 min. The resulting mixture was further stirred at r.t. for 30 min., filtered through celite and extracted with EtOAc. The EtOAc extract was washed with brine, 0.5 M aqueous NaOH, dried ($MgSO_4$) and concentrated. Chromatography over silica gel and elution with hexanes:EtOAc (6:1), then (3:1), swished with hexanes and small amount of $Et_2O$ to give a light brown powder. The mother liquor was concentrated and swished again. Combined yield of the title compound was 119 g (58%).

$^1$H NMR (Acetone-$d_6$) δ 8.33 (s, 1H), 8.15 (d, 1H), 8.02 (d, 1H), 4.40 (q, 2H), 1.38 (t, 3H).

Step 3: 2-Bromo-4-hydroxymethyl-benzaldehyde

To a stirring cold (−78° C.) solution of ethyl 3-bromo-4-cyanobenzoate (0.41 mol, 104 g) in THF (2.3 L was added dropwise a solution of diisobutylaluminum hydride (2.0 mol, 1.36 L; 1.5 M in toluene) over a period of 1.5 h. After addition was completed, the mixture was warmed to rt over a period of 3 h. The mixture was then cooled to 0–5° C. and 40 ml of acetone was added slowly. The mixture was then transferred via a cannula to a cold (0° C.) stirring aqueous solution of HCl (2.2 L 3 N) over a period of 1.5 h, maintaining the temperature of the aqueous solution below 30° C. After the transfer was completed, the mixture was stirred for another 0.25 h. The organic solution was separated and the aqueous was extracted twice with EtOAc (3 L). The combined organic extracts were washed with brine, dried with $MgSO_4$ (anhyd.) and concentrated to give 74 g (83%) of the title compound as a light yellow solid.

$^1$H NMR (Acetone-$d_6$) δ 10.28 (s, 1H), 7.82 (d, 1H), 7.74 (s, 1H), 7.52 (d, 1H), 4.74 (d, 2H), 4.60 (t, 1H).

Step 4: 2-Bromo-4-bromomethyl-benzaldehyde

To a stirring cold (0° C.) solution of $POBr_3$ (0.6 mol, 171 g) in $CH_2Cl_2$ (1.6 L) was added dropwise DMF (0.75 L) over a period of 1 h. A solution of 2-bromo-4-hydroxymethyl-benzaldehyde (0.49 mol, 107 g) in $CH_2Cl_2$ (0.75 L) was then added dropwise over a period of 0.5 h. The resulting mixture was stirred at 0° C. for another 0.5 h and was then transferred via a cannula to a cold (0° C.) stirring aqueous solution of $NaHCO_3$ (3 L, 1M) while maintaining the temperature of the aqueous solution below 10° C. After the transfer was completed, the mixture was extracted with $CH_2Cl_2$ (2 L). The organic extract was separated and washed with $H_2O$ (3 L) and brine (3 L), dried with $MgSO_4$ (anhyd.) and concentrated to give an oil. The residue was extracted with 10% EtOAc/hexane (2 L). The organic extract was washed with $H_2O$ (2×1 L), dried with $MgSO_4$ (anhyd.) and concentrated to a solid which was swished with hexane to give 154 g (~100%) of the title compound as a beige solid.

$^1$H NMR (Acetone-$d_6$) δ 10.30 (s, 1H), 7.88 (s, 1H), 7.84 (d, 1H), 7.65 (d, 1H), 4.70 (s, 2H).

Step 5: (2-bromo-4-bromomethyl-phenyl)-hydroxy-methyl-phosphonic Acid Diethyl Ester To a −60–65° C. THF(200 mL) solution of diethyl phosphite (110 mmol., 15.2 g) was added 1.06 M (hexanes) LiHMDSi (110 mmol., 103 mL) dropwise (0.5 hour) and the mixture was stirred for 0.75 hour at −60–65° C. It was then transferred dropwise (1 hour) via a canula into a −60–65° C. THF (200 mL) solution of 2-bromo-4-bromomethyl-benzaldehyde (100 mmol., 27.8 g). The mixture was stirred for 1 hour at −60–65° C. The mixture was then transferred via a canula into a vigourously stirred mixture of ice, water (1.5 L), 1N HCl (300 mL), ether (500 mL) and ethyl acetate (100 mL). The organic layer was separated and the aqueous further extracted with 1:1 ether:ethyl acetate (200 mL). The combined organic layers were washed with water (IL), brine, dried with magnesium sulphate, filtered and the solvents were removed in vacuo. The residue was swished in ether at 0° C. to yield the title compound (38 g).

$^1$H NMR (Acetone-$d_6$) δ 7.8(1H, dd), 7.7(1H, s), 7.5(1H, d), 5.35-4.6(2H, m), 4.65(2H, s), 3.85-4.2(4H, m), 1.1-1.3 (6H, 2t).

Step 6: (2-bromo-4-bromomethyl-benzoyl)-phosphonic Acid Diethyl Ester

To −60–65° C. $CH_2Cl_2$ (100 mL) solution of oxalyl chloride (50 mmol., 6.35 g) was added dropwise a $CH_2Cl_2$ (40 mL) solution of DMSO (62 mmol., 4.8 g) over 0.2 hour and the mixture was stirred for 0.5 hour. A $CH_2Cl_2$ and DMSO solution (40 and 4 mL) of the hydroxy-phosphonate (40 mmol., 16.6 g) was then added via a canula over 0.2 hour and the mixture was stirred at −60–65° C. for 0.25 hour. Triethylamine (200 mmol., 20.2 g), as a $CH_2Cl_2$ (30 mL) solution was then added and the mixture was stirred at −60–65° C. for 0.25 hour. The dry ice bath was replaced by an ice bath and the mixture was allowed to warm up slowly. When the internal temperature of the mixture reached −5° C., 1N HCl (250 mL) was added and the mixture was stirred vigourously for 2 minutes. The dichloromethane layer was separated and the aqueous further extracted with dichloromethane (100 mL). The combined organic layers were washed with water, brine, dried with magnesium sulphate, filtered and the solvents were removed in vacuo. The residue (16 g) was used as such in the next step.

$^1$H NMR (Acetone-$d_6$) δ 8.15(1H, d), 7.9(1H, s), 7.65(1H, dd), 4.7(2H, s), 4.1-4.3(4H, q), 1.3(6H, t).

Step 7: (2-Bromo-4-bromomethylphenyl)difluoromethylphosphonic Acid Diethyl Ester DAST (145 mmol., 23 g) was added carefully (exotherm !) to −78° C. dichloromethane (15 mL) and immediately after, to prevent freezing, was added the benzoyl-phosphonate (29 mmol., 12.2 g) as a dichloromethane (15 mL) solution. The dry ice bath was replaced by an ice bath and the mixture was stirred for 16 hours while warming up slowly to room temperature. During that time, nitrogen was used to slowly blow away the dichloromethane from the reaction mixture. Dichloromethane (100 mL) was added to the mixture and it was transferred via a canula into a vigourously stirred mixture of ice, water and $NaHCO_3$. The organic layer was separated and the aqueous further extracted with dichloromethane. The combined organic layers were washed with brine, dried with magnesium sulphate, filtered and the solvent was removed in vacuo. The residue was purified by chromatography on a short pad of $SiO_2$ using ethyl acetate and hexanes (1:2) to yield the title compound (5.88 g).

$^1$H NMR (Acetone-$d_6$) δ 7.9(1H, s), 7.55-7.7(2H, m), 4.7(2H, s), 4.1-4.3(4H, m), 1.2-1.35(6H, t).

Thioacetic Acid S-{3-bromo-4-[(diethoxyphosphoryl)-difluoromethyl]benzyl Ester

To a solution of (2-bromo-4-bromomethylphenyl) difluoromethylphosphonic acid diethyl ester (1.0 g, 2.3 mmol) in DMF (6 mL) was passed $N_2$ for 15 min, then cooled to 0° C. Powdered potassium thioacetate (300 mg, 2.6 mmol) was added. The mixture was stirred at 0° C. for 1 h. After dilution with $H_2O$, the mixture was extracted with EtOAc. The EtOAc extract was washed with $H_2O$ (2×), dried ($MgSO_4$) and concentrated. Chromatography over silica gel and elution with hexanes:EtOAc (1.5:1) gave 850 mg (86%) of the title compound as a light brown oil.

$^1$H NMR (Acetone-$d_6$) δ 7.72 (s, 1H), 7.59 (d, 1H), 7.47 (d, 1H), 4.20 (m, 6H), 2.35 (s, 3H), 1.29 (t, 6H).

Example 1

4'-[4-(Difluorophosphonomethyl)benzylsulfanylmethyl]-4-hydroxy-biphenyl-3-yl-phosphonic Acid Tetrasodium Salt Step 1: 4'-Methoxy-4-methylbiphenyl A mixture of 4-methylbenzeneboronic acid (10 g, 73.5 mmol), 4-bromoanisole (25 g, 134 mmol) and 2M aqueous $Na_2CO_3$ (75 mL, 150 mmol) in DNW (350 mL) was passed $N_2$ for 15 min. [1,1'-Bis(diphenylphosphino)ferrocene] dichloropalladium (II), complex with dichloromethane (1:1) (200 mg, 0.24 mmol) was added and the mixture was heated at 85° C. for 4 h. After cooling to r.t., the mixture was diluted with $H_2O$ and extracted with EtOAc. The EtOAc extract was washed with brine (2×), dried (anhydrous $MgSO_4$) and concentrated. The residue was dissolved in small amount of $CH_2Cl_2$, filtered through a short pack (~2.5") of silica gel in a 600 mL sintered glass funnel and washed the silica with hexanes:EtOAc (4:1). The filtrate was evaporated. The residue was swished with hexanes to give a white flake. The mother liquor was concentrated and swished again with hexanes. After 4 cycles, the combined yield of title product was 10.5 g (72% based on the boronic acid used.).

$^1$H NMR (Acetone-$d_6$) δ 7.55 (d, 2H), 7.48 (d, 2H), 7.22 (d, 2H), 6.98 (d, 2H), 3.30 (s, 3H).

Step 2: 4'-Methy-4-hydroxybiphenyl

To a solution of 4'-methoxy-4-methylbiphenyl (10.5 g, 53 mmol) in $CH_2Cl_2$ (300 mL) at 0° C. was added a solution of 1M $BBr_3$ in $CH_2Cl_2$ (65 mL, 65 mmol). The mixture was slowly warmed to r.t. and stirred overnight. After cooling to 0° C. again, the mixture was quenched with $H_2O$. The $CH_2Cl_2$ layer was separated, washed with $H_2O$, dried ($MgSO_4$) and concentrated to give the title compound as a white solid (9.5 g, 97% yield).

$^1$H NMR (Acetone-$d_6$) δ 8.38 (br s, 1H), 7.45 (m, 4H), 7.20 (d, 2H), 6.88 (d, 2H), 2.32 (s, 3H).

Step 3: 4'-Methyl-biphenyl Dimethyl Phosphate

A mixture of 4'-methyl-4-hydroxybiphenyl (4.3 g, 23.4 mmol) and dicyclohexylamine (5.2 mL, 26.1 mmol) in acetone (30 mL) was refluxed for 1 h. Solvent was then evaporated in vacuo. The residue was dissolved in $CCl_4$ (120 mL) and mixed with dimethyl phosphite (2.4 mL, 26.2 mmol). The mixture was refluxed for 4 h., cooled to r.t. and filtered. The filtrate was concentrated and chromatographed over silica gel eluting with hexanes:EtOAc (2:3) to give 6.5 g (95%) of the title compound as a white solid.

$^1$H NMR (Acetone-$d_6$) δ 7.65 (d, 2H), 7.54 (d, 2H), 7.30 (d, 2H), 7.25 (d, 2H), 3.86 (s, 3H), 3.84 (s, 3l), 2.36 (s, 3H).

Step 4: 4-Hydroxy-4'-methylbiphenyl-3-yl-phosphonic Acid Dimethyl Ester

To a solution of LDA [prepared from diisopropylamine (3.5 mL, 24.5 mmol) and 2.2M n-butyllithium in hexanes (12 mL, 26.4 mmol)] in THF (120 mL) at −78° C. was added a solution of 4'-methyl-biphenyl dimethyl phosphate (6.1 g, 20.9 mmol) in THF (20 mL). The mixture was stirred at −78° C. for 1 h and then at r.t. for 1 h. After quenching with 2M aqueous HOAc (10 mL), solvent was removed in vacuo. The residue was diluted with $H_2O$ and extracted with EtOAc. The EtOAc extract was washed with $H_2O$ (2×), dried ($MgSO_4$) and concentrated. Chromatography over silica gel and elution with hexanes:EtOAc (3:2) provided 1.3 g of 4'-methyl-4-hydroxybiphenyl. Further elution gave 4.0 g (65.5%) of the title compound as a white solid.

$^1$H NMR (Acetone-$d_6$) δ 10.35 (br s, 1H), 7.80 (m, 1H), 7.60 (d, 1H), 7.48 (d, 2H), 7.25 (d, 2H), 7.02 (m, 1H), 3.80 (s, 3H), 3.77 (s, 3H), 2.34 (s, 3H).

Step 5: 4-Acetoxy-4'-methylbiphenyl-3-yl-phosphonic Acid Dimethyl Ester

A mixture of 4-hydroxy-4'-methylbiphenyl-3-yl-phosphonic acid dimethyl ester (1.6 g, 5.5 mmol), acetic anhydride (0.7 mL, 7.4 mmol), $Et_3N$ (1.5 mL, 10.8 mmol) and catalytic amount of DMAP in $CH_2Cl_2$ (50 mL) was stirred at r.t. for 1 h. After dilution with $H_2O$, the mixture was extracted with $CH_2Cl_2$. The $CH_2Cl_2$ layer was separated, washed with $H_2O$ and concentrated. Chromatography over silica gel and elution with hexanes:EtOAc (1:4) gave 1.8 g (98%) of the title compound as a colorless oil.

$^1$H NMR (Acetone-$d_6$) δ 8.02 (d, 1H), 7.90 (d, 1H), 7.55 (d, 2H), 7.30 (m, 3H), 3.74 (s, 3H), 3.70 (s, 3H), 2.36 (s, 3H), 2.28 (s, 3H).

Step 6: 4'-Bromomethyl-4-acetoxybiphenyl-3-yl-phosphonic Acid Dimethyl Ester

A mixture of 4-acetoxy-4'-methylbiphenyl-3-yl-phosphonic acid dimethyl ester (1.4 g, 4.2 mmol), N-bromosuccinimide (0.74 g, 4.4 mmol) and a few crystal of benzoyl peroxide in $CCl_4$ (30 mL) was refluxed and irradiated with a sun lamp for 1 h. Solvent was removed in vacuo. The residue was dissolved in $CH_2Cl_2$ and washed with $H_2O$ (3×), dried ($MgSO_4$) and concentrated. Chromatography over silica gel and elution with hexanes:EtOAc (1:3) afforded 1.8 g of title compound as a colorless oil.

$^1$H NMR (Acetone-$d_6$) δ 8.06 (d, 1H), 7.95 (m, 1H), 7.68 (d, 2H), 7.58 (d, 2H), 7.32 (m, 1H), 4.70 (s, 2H), 3.74 (s, 3H), 3.70 (s, 3H), 2.30 (s, 3H).

Step 7: 4'-[4-(Difluorophosphonomethyl)benzylsulfanylmethyl-4-hydroxy-biphenyl-3-yl-phosphonic Acid Tetrasodium Salt To a solution of thioacetic acid S-{4-[(diethoxyphosphoryl)-difluoromethyl]benzyl ester (450 mg, 1.3 mmol) in DMF (4 mL) and THF (2 mL) at 0° C. was added hydrazine hydrate (70 μL, 1.4 mmol), stirred for 15 min, then $Cs_2CO_3$ (450 mg, 1.4 mmol) was added and followed by a solution of 4'-bromomethyl-4-acetoxybiphenyl-3-yl-phosphonic acid dimethyl ester (560 mg, 1.4 mmol) in DMF (1 mL) and THF (0.5 mL). The mixture was stirred for 1 h, diluted with $H_2O$ and extracted with EtOAc. Chromatography over silica gel and elution with EtOAc, then EtOAc with 5% of MeOH gave 300 mg of coupling product as a brown oil.

A solution of above coupling product and bromotrimethylsilane (0.8 mL) in $CH_2Cl_2$ (4 mL) was stirred at r.t. overnight. Volatile materials were removed in vacuo. The residue was co-evaporated with ~90% aqueous EtOH (3×) to give the free acid as an oil. Tetrasodium salt was prepared by the additon of 4 equivalent of NaOH (1M aqueous solution) in a suspension of the free acid in $H_2O$ and freeze dried to give 270 mg of the title compound as a yellow foam.

$^1$H NMR (Methanol-$d_4$) δ 7.95 (d, 1H), 7.68 (d, 2H), 7.54 (d, 2H), 7.38 (m, 1H), 7.28 (m, 4H), 6.74 (m, 1H), 3.62 (s, 2H), 3.30 (s, 2H).

Example 2

{4-[4-(Difluorophosphonomethyl)benzylsulfanylmethyl] phenyl}difluoromethylphosphonic Acid Tetrasodium Salt Step 1: (4-{4-[(diethoxyphosphoryl)difluoromethyl] benzylsulfanylmethyl}-phenyl)difluoromethylphosphonic Acid Diethyl Ester To a solution of (4-bromomethylphenyl) difluoromethylphosphonic acid diethyl ester (357 mg, 1 mmol) and thioacetic acid S-{4-[(diethoxyphosphoryl) difluoromethyl]benzyl ester (352 mg, 1 mmol) in EtOH (10 mL) at 0° C. was passed $N_2$ for 15 min and 2M aqueous NaOH (1.1 mL, 2.2 mmol) was added. After stirring for 1 h at 0° C., the mixture was diluted with $H_2O$ and extracted with EtOAc. The EtOAc extract was washed with brine, dried ($MgSO_4$) and concentrated. Chromatography over silica gel and elution with hexanes:EtOAc (1:2) afforded 300 mg of title compound as a gum.

$^1$H NMR (Acetone-$d_6$) δ 7.58 (d, 4H), 7.46 (d, 4H), 4.15 (m, 8H), 3.74 (s, 4H), 1.26 (t, 12H).

Step 2: {4-[4-(Difluorophosphonomethyl) benzylsulfanylmethyl]-phenyl}difluoro-methylphosphonic Acid Tetrasodium Salt A solution of above coupling product (100 mg, 0.19 mmol) and bromotrimethylsilane (0.5 mL) in $CH_2Cl_2$ (3 mL) was stirred at r.t. overnight. Volatile materials were removed in vacuo. The residue was co-evaporated with ~90% aqueous EtOH (3×) to give the free acid as an oil.

$^1$H NMR (Methanol-$d_4$) δ 7.55 (d, 4H), 7.39 (d, 4H), 3.67 (s, 4H).

Tetrasodium salt was prepared by the additon of 4 equivalent of NaOH (1M aqueous solution) to a suspension of the free acid in $H_2O$ and freeze dried to give 110 mg of the title compound as a yellow foam.

$^1$H NMR (Methanol-$d_4$) δ 7.60 (d, 4H), 7.42 (d, 4H), 3.74 (s, 4H).

Example 3

{4-[4-(Difluorophosphonomethyl)benzylsulfonylmethyl] phenyl}difluoromethyl-phosphonic Acid Step 1: 4-{4-[(diethoxyphosphoryl)difluoromethyl] benzylsulfonylmethyl}-phenyl)difluoromethylphosphonic Acid Diethyl Ester To a solution of 4-{4-[(diethoxyphosphoryl) difluoromethyl]benzylsulfanylmethyl}-phenyl) difluoromethylphosphonic acid diethyl ester (200 mg, 0.34 mmol) in $CH_2Cl_2$ (5 mL) was added mCPBA (57–86%, 200 mg) at room temperature. After stirring for 30 min., the mixture was diluted with more $CH_2Cl_2$, washed successively with 0.5 M aqueous NaOH (2×), brine, dried ($MgSO_4$) and concentrated. Chromatography over silica gel and elution with EtOAc gave 170 mg of the title compound as colorless oil.

$^1$H NMR (Acetone-$d_6$) δ 7.62 (m, 8H), 4.53 Z(s, 4H), 4.15 (m, 8H), 1.26 (t, 12H).

Step 2: 14-[4-(Difluorophosphonomethyl) benzylsulfonylmethyl]-phenyl}difluoro-methylphosphonic Acid A solution of above coupling product (170 mg, 0.30 mmol) and bromotrimethylsilane (0.5 mL) in $CH_2Cl_2$ (3 mL) was stirred at r.t. overnight. Volatile materials were removed in vacuo. The residue was co-evaporated with ~90% aqueous EtOH (3×) to give the title compound as an oil.

$^1$H NMR (Methanol-$d_4$) δ 7.64 (d, 4H), 7.53 (d, 4H), 4.47 (s, 4H).

Example 4

{2-Bromo-4-[4-(difluorophosphonomethyl) benzylsulfanylmethyl]-phenyl}difluoromethylphosphonic Acid Tetrasodium Salt Step 1: (4-{3-Bromo-4-[(di-tert-butoxy-phosphoryl) difluoromethyl]-benzylsuflanylmethyl}phenyl) difluoromethylphosphonic Acid Diethyl Ester The title compound was prepared in a similar manner as described in step 1, Example 2, from thioacetic acid S-{4-[(diethoxyphosphoryl)-difluoromethyl]benzyl ester and (2-bromo-4-bromomethylphenyl)difluoromethylphosphonic di-tert-butyl ester.

$^1$H NMR (Acetone-$d_6$) δ 7.68 (s, 1H), 7.58 (m, 3H), 7.48 (m, 3H), 4.15 (m, 4H), 3.78 (s, 2H), 3.76 (s, 2H), 1.48 (s, 181H), 1.26 (t, 6H).

Step 2: {2-Bromo-4-[4-(difluorophosphonomethyl) benzylsulfanylmethyl]-phenyl}difluoromethylphosphonic Acid Tetrasodium Salt The title compound was prepared in a similar manner as described in step 2, Example 2 from (4-{3-bromo-4-[(di-tert-butoxy-phosphoryl)difluoromethyl] benzylsuflanylmethyl}phenyl)difluoromethylphosphonic acid diethyl ester.

$^1$H NMR ($D_2O$) δ 7.74 (d, 1H), 7.68 (s, 1H), 7.60 (d, 2H), 7.42 (m, 3H), 3.75 (s, 2H), 3.70 (s, 2H).

Example 5

(2-Bromo-4-{4-[(diethoxyphosphoryl)difluoromethyl] benzylsulfonyl-methyl}phenyldifluoromethylphosphonic Acid A solution of (4-{3-bromo-4-[(di-tert-butoxy-phosphoryl) difluoromethyl]benzylsuflanylmethyl}phenyl) difluoromethylphosphonic acid diethyl ester, from step 1, Example 4 (100 mg, 0.14 mmol) and 30% $H_2O_2$ in 80% aqueous HOAc (4 ml) was stirred at room temperature for 1 h. Volatile materials were removed in vacuo. The residue was co-evaporated with EtOH and small amount of $H_2O$ to give the title compound as a white foam.

$^1$H NMR (Acetone-$d_6$) δ 7.78 (s, 1H), 7.65 (m, 5H), 7.52 (d, 1H), 4.58 (s, 2H), 4.52 (s, 2H), 4.16 (m, 4H), 1.26 (t, 6H).

Example 6

{2-Bromo-4-[4-(difluorophosphonomethyl) benzylsulfonylmethyl]-phenyl}difluoromethylphosphonic Acid The title compound was prepared in a similar manner as described in step 2, Example 2, from (2-bromo-4-{4-[(diethoxyphosphoryl)difluoromethyl] benzylsulfonylmethyl}-phenyldifluoromethylphosphonic acid.

$^1$H NMR (Acetone-$d_6$) δ 7.82 (s, 1H), 7.64-7.45 (m, 6H), 4.60 (s, 2H), 4.56 (s, 2H).

Example 7
4'-[4-(Difluorophosphonomethyl)benzylsulfanylmethyl]-4-(3-methylbutoxy)biphenyl-3-yl-phosphonic Acid
Step 1: 4'-Methyl-4-(3-methyl-but-2-enyloxy)-biphenyl-3-yl-phosphonic Acid Dimethyl Ester A mixture of 4-hydroxy-4'-methylbiphenyl-3-yl-phosphonic acid dimethyl ester (1.3 g, 4.5 mmol) from step 4, Example 1,4-bromo-2-methyl-2-butene (650 μg, 5.6 mmol) and 10M aqueous NaOH (500 μL, 5.0 mmol) in DMF (15 mL) was stirred at r.t. for 1 h. After dilution with $H_2O$, the mixture was extracted with EtOAc. Chromatography over silica gel and elution with hexanes:EtOAc (1:1.5) gave 1.5 g (93%) of title compound as a white solid.

$^1$H NMR (Acetone-$d_6$) δ 8.00 (d, 1H), 7.79 (m, 1H), 7.49 (d, 2H), 7.25 (d, 2H), 7.20 (m, 1H), 5.52 (m, 1H), 4.70 (d, 2H), 3.74 (s, 3H), 3.72 (s, 3H), 2.35 (s, 3H), 1.78 (s, 6H).
Step 2: 4'-Methyl-4-(3-methyl-butoxy)-biphenyl-3-yl-phosphonic Acid Dimethyl Ester A mixture of 4'-methyl-4-(3-methyl-but-2-enyloxy)-biphenyl-3-yl-phosphonic acid dimethyl ester (750 mg, 2.1 mmol) and 10% palladium on carbon in EtOAc (20 mL) was hydrogenated under a hydrogen ballon at room temperature for 2 h. The catalyst was filtered off and the filtrate was concentrated. Chromatography over silica gel and elution with hexanes:EtOAc (1:1.5) afforded 650 mg (86%) of title compound as a colorless oil.

$^1$H NMR (Acetone-$d_6$) δ 8.00 (d, 1H), 7.80 m, 1H), 7.49 (d, 2H), 7.26 (d, 2H), 7.19 (m, 1H), 4.16 (t, 2H0, 3.74 (s, 3H), 3.72 (s, 3H), 2.35 (s, 3H), 1.98 (m, 1H0, 1.72 (m, 2H), 0.97 (d, 6H).
Step 3: 4'-Bromomethyl-4-(3-methylbutoxy)biphenyl-3-yl-phosphonic Acid Dimethyl Ester A mixture of 4'-methyl-4-(3-methyl-butoxy)-biphenyl-3-yl-phosphonic acid dimethyl ester (650 mg, 1.8 mmol), N-bromosuccinimide (380 mg, 2.1 mmol) and a few crystal of benzoyl peroxide in $CCl_4$ (20 mL) was refluxed and irradiated with a sun lamp for 1 h. After cooling to r.t., the mixture was diluted with $CH_2C_2$ and washed with $H_2O$ (3×), dried ($MgSO_4$) and concentrated. The solid residue was swished with $Et_2O$ to give 580 mg (73%) of the title compound as a white solid.

$^1$H NMR (Acetone-$d_6$) δ 8.03 (m, 1H), 7.85 (m, 1H), 7.62 (d, 2H), 7.54 (d, 2H), 7.23 (m, 1H), 4.70 (s, 2H), 4.19 (t, 2H), 3.75 (s, 3H), 3.72 (s, 3H), 1.98 (m, 1H), 1.73 (m, 2H), 0.98 (d, 6H).
Step 4: 4'-[4-(Difluorophosphonomethyl)benzylsulfanylmethyl]-4-(3-methylbutoxy)biphenyl-3-yl-phosphonic Acid The title compound was prepared in a similar manner as described for Example 2 from thioacetic acid S-{4-[(diethoxyphosphoryl)-difluoromethyl]benzyl ester and 4'-bromomethyl-4-(3-methylbutoxy)biphenyl-3-yl-phosphonic acid dimethyl ester.

$^1$H NMR (Acetone-$d_6$) δ 8.01 (d, 1H), 7.77 (m, 1H), 7.52 (m, 4H), 7.39 (d, 2H), 7.34 (d, 2H), 7.14 (m, 1H), 4.16 (t, 2H), 3.68 (s, 2H), 3.66 (s, 2H), 1.96 (m, 1H), 1.75 (m, 2H), 0.98 (d, 6H).

Example 8
4'-[3-Bromo-4-(difluorophosphonomethyl)benzylsulfanylmethyl]-4-(3-methylbutoxy)biphenyl-3-yl-phosphonic Acid The title compound was prepared in a similar manner as described for Example 2 from thioacetic acid S-{3-bromo-4-[(diethoxyphosphoryl)difluoromethyl]benzyl ester and 4'-bromomethyl-4-(3-methylbutoxy)biphenyl-3-yl-phosphonic acid dimethyl ester.

$^1$H NMR (Acetone-$d_6$) δ 8.01 (d, 1H), 7.76 (m, 1H), 7.57 (m, 2H), 7.52 (d, 2H), 7.32 (m, 3H), 7.13 (m, 1H), 4.15 (t, 2H), 3.66 (s, 2H), 3.63 (s, 2H), 1.95 (m, 1H), 1.75 (m, 2H), 0.98 (d, 6H).

Example 9
{2-Bromo-4-[3-bromo-4-(difluorophosphonomethyl)benzylsulfonylmethyl]-phenyl}difluoromethylphosphonic Acid The title compound was prepared in a similar manner as described for Example 2 from thioacetic acid S-{3-bromo-4-[(diethoxyphosphoryl)difluoromethyl]benzyl ester and (2-bromo-4-bromomethylphenyl)difluoromethylphosphonic acid diethyl ester.

$^1$H NMR (Acetone-$d_6$) δ 7.63 (s, 2H), 7.59 (d, 2H), 7.35 (d, 2H), 3.65 (s, 4H).

Example 10
[2-Bromo-4-(3-phenylallylsulfanylmethyl)phenyl]difluoromethylphosphonic Acid Disodium Salt
Step 1: 2-Bromo-4-(3-phenylallylsulfanylmethyl)phenylphosphonic Acid Diethyl Ester To a solution of thioacetic acid S-{3-bromo-4-[(diethoxyphosphoryl)difluoromethyl]benzyl ester (3.1 g, 7.2 mmol) and cinnamyl bromide (1.8 g, 9.1 mmol) in EtOH (60 mL) at 0° C. was passed $N_2$ for 15 min and 2M aqueous NaOH (7.6 mL, 15.2 mmol) was added. After stirring for 15 min at 0° C., the mixture was diluted with $H_2O$ and extracted with EtOAc. The EtOAc extract was washed with brine, dried ($MgSO_4$) and concentrated. Chromatography over silica gel and elution with hexanes:EtOAc (1.5:1) afforded 2.6 g (72%) of title compound as a pale yellow oil.

$^1$H NMR (Acetone-$d_6$) δ 7.74 (s, 1H), 7.61 (d, 1H), 7.52 (d, 1H), 7.45-7.20 (m, 5H), 6.49 (d, 1H), 6.22 (m, 1H), 4.20 (m, 4H), 3.81 (s, 2H), 3.27 (d, 2H), 1.30 (t, 6H).
Step 2: [2-Bromo-4-(3-phenylallylsulfanylmethyl)phenyl]difluoromethyl-phosphonic Acid Disodium Salt A solution of above coupling product (410 mg, 0.81 mmol) and bromotrimethylsilane (3.2 mL) in $CH_2Cl_2$ (16 mL) was stirred at r.t. overnight. Volatile mateials were removed in vacuo. The residue was co-evaporated with ~90% aqueous EtOH (3×) to give the acid as a gum.

$^1$H NMR (Acetone-$d_6$) δ 7.70 (s, 1H), 7.63 (d, 1H), 7.47 (d, 1H), 7.44-7.20 (m, 5H), 6.50 (d, 1H), 6.24 (m, 1H), 3.78 (s, 2H), 3.27 (d, 2H).

The above acid was treated with 2 equivalent of 1M aqueous NaOH in $H_2O$ and freeze-dried to give 420 mg of the title compound as white foam.

$^1$H NMR (Methanol-$d_4$) δ 8.04 (d, 1H), 7.56 (s, 1H), 7.45-7.15 (m, 6H), 6.42 (d, 1H), 6.18 (m, 1H), 3.66 (s, 2H).

Example 11
4'-[3-Bromo-4-(difluorophosphonomethyl)benzylsulfanylmethyl]-4-(3-methylbutoxy)biphenyl-3-yl-carboxylic Acid Trisodium Salt
Step 1: tert-Butyl 5-iodo-2-(3-methylbutoxy)benzoate To a suspension of 5-iodosalicylic acid (2.7 g, 10.2 mmol) in benzene (15 mL) at refluxing was added N,N-dimethylformamide di-tert-butyl acetal (10 mL, 41.4 mmoL) over a period of 30 min. After further refluxing for 30 min, the mixture was diluted with $H_2O$, extracted with EtOAc. The EtOAc extract was washed with $H_2O$ (2×), dried ($MgSO_4$) and concentrated to give 3.1 g of the tert-butyl ester intermediate.

A mixture of 1.4 g (4.4 mmol) of above crude tert-butyl ester intermediate, 1-bromo-3-methylbutane (0.7 mL, 5.8 mmol) and $Cs_2CO_3$ (1.5 g, 4.6 mmol) in DMF (20 mL) was heated at 75° C. for 30 min. After cooling to room temperature, the mixture was diluted with $H_2O$ and extracted with $Et_2O$. The $Et_2O$ extract was washed with $H_2O$ (2×), dried ($MgSO_4$) and concentrated to give the title compound as a colorless oil, which solidified upon cooling in a fridge.

¹H NMR (Acetone-d₆) δ 7.82 (s, 1H), 7.75 (d, 1H), 6.95 (d, 1H), 4.08 (t, 2H), 1.90 (m, 1H), 1.70 (m, 2H), 1.54 (s, 9H), 0.95 (d, 6H).

Step 2: tert-Butyl 4'-hydroxymethyl-4-(3-methylbutoxy) biphenyl-3-carboxylate

A mixture of tert-butyl 5-iodo-2-(3-methylbutoxy) benzoate (1.0 g, 2.6 mmol), 4-(hydroxymethyl)benzene boronic acid (450 mg, 3.0 mmol), 2M aqueous Na₂CO₃ (3.0 mL, 3.0 mmol) and [1,1'-bis(diphenylphosphino)ferrocene] dichloropalladium(II), complex with dichloromethane (1:1) (20 mg) was heated at 85° C. for 1 h. After cooling to room temperature, the mixture was diluted with H₂O, extracted with EtOAc. The EtOAc extract was washed H₂O (2×), dried (MgSO₄) and concentrated. Chromatography over silica gel and elution with hexanes:EtOAc (1.5:1) yielded 650 mg (68%) of the title compound as a light brown solid.

¹H NMR (Acetone-d₆) δ 7.83 (s, 1H), 7.71 (d, 1H), 7.57 b(d, 2H), 7.42 (d, 2H), 7.17 (d, 1H), 4.66 (d, 2H), 4.21 (t, 1H), 4.12 (t, 2H), 1.95 (m, 1H), 1.72 (m, 2H), 1.57 (s, 9H), 0.97 (d, 6H).

Step 3: tert-Butyl 4'-bromomethyl-4-(3-methylbutoxy) biphenyl-3-carboxylate

To a solution of tert-butyl 4'-hydroxymethyl-4-(3-methylbutoxy)biphenyl-3-carboxylate (370 mg, 1 mmol) and triphenylphosphine (315 mg, 1.2 mmol) in THF (10 mL) at 0° C. was added N-bromosuccinimide (215 mg, 1.2 mmol). After stirring for 30 min. TLC showed starting alcohol remained. More triphenylphosphine (160 mg, 0.61 mmol) and N-bromosuccinimde (110 mg, 0.61 mmol) were added. After further stirring at 0° C. for 30 min, almost no starting alcohol remained. Solvent was removed in vacuo. The residue was chromatographed over silica gel and eluted with hexanes:EtOAc (5:1) to afford 420 mg (97%) of the title compound as a colorless oil.

¹H NMR (Acetone-d₆) δ 7.85 (s, 1H), 7.74 (d, 1H), 7.62 (d, 2H), 7.53 (d, 2H), 7.18 (d, 1H), 4.70 (s, 2H), 4.13 (t, 2H), 1.95 (m, 1H), 1.73 (m, 2H), 1.57 (s, 9H), 0.97 (d, 6H).

Step 4: 4'-[3-Bromo-4-(difluorophosphonomethyl) benzylsulfanylmethyl]-4-(3-methylbutoxy)biphenyl-3-yl-carboxylic Acid Trisodium Salt The title compound was prepared in a similar manner as described for Example 2 from thioacetic acid S-{3-bromo-4-[(diethoxyphosphoryl)difluoromethyl]benzyl ester and tert-butyl 4'-bromomethyl-4-(3-methylbutoxy)biphenyl-3-carboxylate. The corresponding tetrasodium salt was prepared from the acid intermediate.

¹H NMR (Acetone-d₆) δ 8.10 (d, 1H), 7.63 (s, 1H), 7.54 (m, 4H), 7.32 (d, 2H), 7.25 (d, 1H), 7.01 (d, 1H), 4.08 (t, 2H), 3.62 (s, 2H), 3.59 (s, 2H), 1.90 (m, 1H), 1.70 (m, 2H), 0.96 (d, 6H).

Example 12

4"-[4-(Difluorophosphonomethyl)benzylsulfanylmethyl]-[1,1';4',1"]terphenyl-2'ylphosphonic Acid Step 1: Trifluoromethanesulfonic Acid 3-(dimethoxyphosphoryl)-4'-methylbiphenyl-4-yl Ester.

To a solution of 4-hydroxy-4'-methylbiphenyl-3-ylphosphonic acid dimethyl ester (500 mg) and triethylamine (0.31 mL) in methylene chloride (18 mL) at 0° C., was added trifluoromethanesulfonic anhydride (0.33 mL). The resulting mixture was stirred at room temperature for 15 min. Then, brine was added, the mixture was extracted with methylene chloride, washed with brine, dried (MgSO₄) and concentrated. The residue was purified by silica gel chromatography, using 40% ethyl acetate in hexane, to afford 685 mg of the title compound.

¹H NMR (Acetone-d₆) δ 8.18 (d, 1H), 8.08 (d, 1H), 7.63 (m, 3H), 7.35 (m, 2H), 3.34 (s, 3H), 3.31 (s, 3H), 2.39 (s, 3H).

Step 2: 4"-Methyl-[1,1';4'1"]terphenyl-2'ylphosphonic Acid Dimethyl Ester

A mixture of trifluoromethanesulfonic acid 3-(dimethoxyphosphoryl)-4'-methylbiphenyl-4-yl ester (340 mg) from the previous step, phenyl boronic acid (117 mg), potassium phosphate (255 mg) and tetrakis (triphenylphosphine)palladium (2 mg) in 1,4-dioxane where cooled to −78° C., pumped under high vacuum for 5 min. then left to warm to room temperature under nitrogen, this process was repeated one more time, then the mixture was heated at 80° C. over night. Excess boronic acid and catalyst were added and the mixture was heated another 4 hrs. After cooling to room temperature, ethyl acetate was added and the mixture was washed with brine (2×), dried (MgSO₄), filtered and concentrated. The residue was purified by silica gel chromatography, to afford the title compound.

¹H NMR (Acetone-d₆) δ 8.22 (d, 1H), 7.90 (d, 1H), 7.63(d, 2H), 7.50-7.31 (m, 8H), 3.50 (d, 6H), 2.39 (s, 3H).

Step 3: 4"-Bromomethyl-[1,1';4,1"]terphenyl-2'-ylphosphonic acid dimethyl ester

A mixture of 4" methyl-[1,1';4'1"]terphenyl-2'ylphosphonic acid dimethyl ester (209 mg), N-bromosuccinimide (116 mg) and benzoyl peroxide (10 mg) in carbon tetrachloride (10 mL) was heated in an oil bath at 80° C. while being illuminated with a 150 watt lamp, for 3 hrs. After cooling to room temperature, water was added and the mixture was extracted with methylene chloride, washed with brine, dried (MgSO₄), filtered and concentrated. The residue was triturated in diethyl ether to afford 90 mg of the title compound.

¹H NMR (Acetone-d₆) δ 8.25 (d, 1H), 7.96 (d, 1H), 7.83(s, 1H), 7.76 (d, 2H), 7.62 (d, 2H), 7.50-7.39 (m, 5H), 3.50 (d, 6H), 2.39 (s, 3H).

Step 4: 4"-{4-[(Diethoxyphosphoryl)-difluoromethyl] benzylsulfanylmethyl}-{1,1';4',1"]terphenyl-2'-ylphosphonic Acid Dimethyl Ester A mixture of thioacetic acid S-{4-[(diethoxyphosphoryl) difluoromethyl]benzyl}ester (74 mg) and 4"-bromomethyl-[1,1';4,1"]terphenyl-2'-ylphosphonic acid dimethyl ester (90 mg) in ethanol (2 mL) at 0° C. was bubbled with nitrogen for 10 minutes, then 2N NaOH (0.23 mL) was added and the mixture was stirred at 0° C. for 30 minutes. The mixture was diluted with water, extracted with ethyl acetate, washed with brine (2×), dried (MgSO₄), filtered and concentrated. The residue was purified by silica gel chromatography, using 65% ethyl acetate in hexane, to afford 65 mg of the title compound.

¹H NMR (Acetone-d₆) δ 8.25 (d, 1H), 7.94 (d, 1H), 7.72(d, 2H), 7.60 (d, 2H), 7.54-7.38 (m, 10H), 4.22-4.10 (m, 4H), 3.80 (s, 2H), 3.78 (s, 2H), 3.50(s, 3H), 3.48(s, 3H), 1.28(t, 6H).

Step 5: 4"-[4-(Difluorophosphonomethyl) benzylsulfanylmethyl]-[1,1';4',1"]terphenyl-2'ylphosphonic Acid To a solution of 4"-{4-[(diethoxyphosphoryl)-difluoromethyl]benzylsulfanylmethyl}-{1,1';4',1"] terphenyl-2'-ylphosphonic acid dimethyl ester in chloroform (2 mL) at 0° C. was added bromotrimethylsilane (0.26 mL) and the mixture was left to stir over night at room temperature. The solvent was evaporated under vacuum and the residue was coevaporated with chloroform (3×). The residue was dissolved in methylene chloride (1 mL) cooled to 0° C. and then ethanol (5 mL) was added and stirring continued at room temperature for 3 hrs. The solvent was evaporated under vacuum and the residue was coevaporated with ethanol (4×). The residue was triturated with diethyl ether to afford after filtration 50 mg of the title compound.

¹H NMR (Acetone-d₆) δ 8.33 (d, 1H), 7.83 (d, 1H), 7.68(d, 2H), 7.57 (d, 2H), 7.46-7.30 (m, 10H), 3.78 (s, 2H), 3.76 (s, 2H).

Example 13

4'-[3-Bromo-4-(difluorophosphonomethyl)-benzylsulfanylmethyl]-4-(1,3-dimethylbutoxy)-biphenyl-3-ylphosphonic Acid Tetrasodium Salt.

Step 1: 4-(1,3-Dimethylbutoxy)-4'-methylbiphenyl-3-ylphosphonic Acid Dimethyl Ester To a solution of 4-hydroxy-4'-methylbiphenyl-3-ylphosphonic acid dimethyl ester (200 mg), 4-methylpentan-2-ol (0.087 mL) and triphenylphosphine (178 mg) in THF (3 mL) at 0° C. was added diethyl azodicarboxylate (0.11 mL) and the mixture was stirred for 2 hrs at RT. then more 4-methylpentan-2-ol (0.044 mL), triphenylphosphine (89 mg) and diethyl azodicarboxylate (0.11 mL) were added. The mixture was stirred another hour. The solvent was evaporated and the residue was purified by silica gel chromatography, to afford 200 mg of the title compound.

¹H NMR (Acetone-d₆) δ 8.04 (dd, 1H), 7.80 (dd, 1H), 7.50(d, 2H), 7.28-7.20(m, 31), 4.74 (m, 1H), 3.77 (s, 3H), 3.72 (s, 3H), 2.35 (s, 3H), 1.95(m, 1H), 1.79(m, 1H), 1.48-0.92(m, 10H).

Step 2: 4'-Bromomethyl-4(1,3-dimethylbutoxy)-biphenyl-3-ylphosphonic Acid Dimethyl Ester A mixture of 4-(1,3-dimethylbutoxy)-4'-methylbiphenyl-3-ylphosphonic acid dimethyl ester (200 mg), N-bromosuccinimide (105 mg) and benzoyl peroxide (10 mg) in carbon tetrachloride (10 mL) was heated in an oil bath at 80° C. while being illuminated with a 150 watt lamp, for 3 hrs. After cooling to room temperature, water was added and the mixture was extracted with methylene chloride, washed with brine, dried (MgSO₄), filtered and concentrated. To afford the title compound.

¹H NMR (Acetone-d₆) δ 8.05 (d, 1H), 7.86 (d, 1H), 7.63 (d, 2H), 7.56 (d, 2H), 7.28(m, 1H), 4.78 (m, 1H), 4.72(s, 2H), 3.76 (s, 3H), 3.72 (s, 3H), 1.95 (m, 1H), 1.79 (m, 1H), 1.45 (m, 1H), 1.35 (d, 3H), 0.95 (dd, 6H).

Step 3: 4'-{3-Bromo-4-[(diethoxyphosphoryl)difluoromethylbenzylsulfanylmethy}-4-(1,3-dimethylbutoxy)biphenyl-3-ylphosphonic Acid Dimethyl Ester.

A mixture of thioacetic acid S-{4-[(diethoxyphosphoryl)difluoromethyl]benzyl}ester (100 mg) and 4'-bromomethyl-4(1,3-dimethylbutoxy)-biphenyl-3-ylphosphonic acid dimethyl ester (116 mg) in ethanol (2 mL) at 0° C. was bubbled with nitrogen for 5 minutes, then NaOMe (27 mg) was added and the mixture was stirred at 0° C. for 30 minutes. The mixture was diluted with water, extracted with ethyl acetate, washed with saturated ammonium chloride, brine, dried (MgSO₄), filtered and concentrated. The residue was purified by silica gel chromatography, to afford 97 mg of the title compound.

¹H NMR (Acetone-d₆) δ 8.05 (dd, 1H), 7.83 (dd, 1H), 7.69(s, 1H), 7.62 (d, 1H), 7.58 (d, 2H), 7.48 (d, 1H), 7.39(d, 2H), 7.25 (dd, 1H), 4.76 (m, 1H), 4.21 (m, 4H), 3.73 (m, 10H), 1.94(m, 1H), 1.78(m, 1H), 1.44(m, 1H), 1.31 (m, 9H), 0.95 (dd, 6H).

Step 4: 4'-[3-Bromo-4-(difluorophosphonomethyl)-benzylsulfanylmethyl]-4-(1,3-dimethylbutoxy)biphenyl-3-ylphosphonic Acid Tetrasodium Salt.

To a solution of 4'-{3-bromo-4-[(diethoxyphosphoryl)-difluoromethyl]benzylsulfanylmethyl}-4-(1,3-dimethylbutoxy)-biphenyl-3-ylphosphonic acid dimethyl ester (97 mg)in chloroform (2.5 mL) at 0° C. was added bromotrimethylsilane (0.34 mL) and the mixture was left to stir over night at room temperature. The solvent was evaporated under vacuum and the residue was coevaporated with chloroform (4×). The residue was dissolved in methylene chloride (1 mL) cooled to 0° C. and then ethanol (5 mL) was added and stirring continued at room temperature for 3 hrs. The solvent was evaporated under vacuum and the residue was coevaporated with ethanol (4×). The residue was purified by reverse phase chromatography, to afford 92 mg of compound which was mixed with water (5 mL) and 1N NaOH (0.54 mL) and lyophylised over night to afford the title compound.

¹H NMR (MeOH-d₄) δ 8.28 (dd, 1H), 8.11 (d, 1H), 7.60(d, 2H), 7.50(m, 2H), 7.29 (d, 2H), 7.25(d, 1H), 6.96 (dd, 1H), 4.62 (m, 1H), 3.62(s, 2H), 3.58(s, 2H), 1.89(m, 2H), 1.56(m, 1H), 1.41(d, 3H), 0.98(dd, 6H),.

Example 14

4'-[3-Bromo-4-(difluorophosphonomethyl)-benzylsulfanylmethyl]-4-butoxybiphenyl-3-ylphosphonic Acid Tetrasodium Salt.

Step 1: 4-Butoxy-4'-methylbiphenyl-3-ylphosphonic Acid Dimethyl Ester.

To a solution of 4-hydroxy-4'-methylbiphenyl-3-ylphosphonic acid dimethyl ester (200 mg), butan-1-ol (0.09 mL) and triphenylphosphine (267 mg) in THF (3 mL) at 0° C. was added diethyl azodicarboxylate (0.16 mL) and the mixture was stirred for 3 hrs at RT. The solvent was evaporated and the residue was purified by silica gel chromatography, using 50% ethyl acetate/hexane, to afford 223 mg of the title compound.

¹H NMR (Acetone-d₆) δ 8.04 (d, 1H), 7.78 (d, 1H), 7.50(d, 2H), 7.25(d, 2H), 7.15(t, 1H), 4.10 (t, 1H), 3.78 (s, 3H), 3.74 (s, 3H), 2.35 (s, 3H), 1.80(m, 2H), 1.57(m, 2H), 0.98 (t, 3H).

Step 2: 4'-Bromomethyl-4-butoxybiphenyl-3-ylphosphonic Acid Dimethyl Ester

A mixture of 4-butoxy-4'-methylbiphenyl-3-ylphosphonic acid dimethyl ester (223 mg), N-bromosuccinimide (125 mg) and benzoyl peroxide (10 mg) in carbon tetrachloride (10 mL) was heated in an oil bath at 80° C. while being illuminated with a 150 watt lamp, for 2 hrs. After cooling to room temperature, water was added and the mixture was extracted with methylene chloride, washed with brine, dried (MgSO₄), filtered and concentrated. Trituration in diethyl ether/hexane afforded 95 mg of the title compound.

¹H NMR (Acetone-d₆) δ 8.04 (dd, 1H), 7.87 (dd, 1H), 7.62 (d, 2H), 7.55 (d, 2H), 7.22(m, 1H), 4.71 (s, 1H), 4.16(t, 1H), 3.78 (s, 3H), 3.73 (s, 3H), 1.82 (m, 2H), 1.59 (m, 1H), 0.99 (t, 3H).

Step 3: 4'-{3-Bromo-4-[(diethoxyphosphoryl)-difluoromethyl]benzylsulfanylmethyl}-4-butoxybiphenyl-3-ylphosphonic Acid Dimethyl Ester.

A mixture of thioacetic acid S-{4-[(diethoxyphosphoryl)difluoromethyl]benzyl}ester (88 mg) and 4'-bromomethyl-4-butoxybiphenyl-3-ylphosphonic acid dimethyl ester (95 mg) in ethanol (2 mL) was bubbled with nitrogen for 10 minutes, then the solution was cooled to 0° C. , NaOMe (24 mg) was added and the mixture was stirred at 0° C. for 30 minutes. The mixture was diluted with water, extracted with ethyl acetate, washed with saturated ammonium chloride, brine, dried (MgSO₄), filtered and concentrated. The residue was purified by silica gel chromatography, using 85%ethyl acetate/hexane, to afford 122 mg of the title compound.

¹H NMR (Acetone-d₆) δ 8.12 (dd, 1H), 7.91(dd, 1H), 7.76(s, 1H), 7.70-7.65 (m, 3H), 7.56 (d, 1H), 7.46 (d, 2H), 7.28(t, 1H), 4.33-4.20 (m, 6H), 3.83-3.80(m, 10H), 1.89 (m, 2H), 1.67(m, 2H), 1.37(t, 6H), 1.05(t, 3H).

Step 4: 4'-[3-Bromo-4-(difluorophosphonomethyl)-benzylsulfanylmethyl]-4-butoxybiphenyl-3-ylphosphonic Acid Tetrasodium Salt.

To a solution of 4'-{3-bromo-4-[(diethoxyphosphoryl)-difluoromethyl]benzylsulfanylmethyl}-4-butoxybiphenyl-3-ylphosphonic acid dimethyl ester (122 mg) in chloroform (2.5 mL) at 0° C. was added bromotrimethylsilane (0.45 mL) and the mixture was left to stir over night at room temperature. The solvent was evaporated under vacuum and the residue was coevaporated with chloroform (4×). The residue was dissolved in methylene chloride (1 mL) cooled to 0° C. and then ethanol (5L) was added and stirring continued at room temperature for 2 hrs. The solvent was evaporated under vacuum and the residue was coevaporated with ethanol (4×). To the residue was added water (5 mL) and 1N NaOH (0.54 mL) and the solution was lyophylised over night to afford 103 mg of the title compound.

$^1$H NMR (MeOH-d$_4$) δ 8.23 (dd, 1H), 8.12 (d, 1H), 7.59(d, 2H), 7.55-7.52(m, 3H), 7.31(d, 2H), 7.26(d, 1H), 6.96 (dd, 1H), 4.11 (t, 2H), 3.62(s, 2H), 3.58(s, 2H), 1.92(m, 2H), 1.53(m, 2H), 1.01(t, 3H).

Example 15

4'-[3-Bromo-4-(difluorophosphonomethyl)-benzylsulfanylmethyl-4-(1-cyclopentylethoxy)-biphenyl-3-ylphosphonic Acid.

Step 1: 4-(1-Cyclopentylethoxy)-4'-methylbiphenyl-3-ylphosphonic Acid Dimethyl Ester.

To a solution of 4-hydroxy-4'-methylbiphenyl-3-ylphosphonic acid dimethyl ester (200 mg), 1-cyclopentylethanol (116 mg) and triphenylphosphine (267 mg) in THF (3 mL) at 0° C. was added diethyl azodicarboxylate (0.16 mL) and the mixture was stirred over night at RT. Another 30% of 1-cyclopentylethanol, triphenylphosphine and diethyl azodicarboxylate were added and the stirring continued for another hour. The solvent was evaporated and the residue was purified by silica gel chromatography, using 45% ethyl acetate/hexane, to afford 223 mg of the title compound.

$^1$H NMR (Acetone-d$_6$) δ 8.04 (d, 1H), 7.79 (d, 1H), 7.50(d, 2H), 7.27(d, 2H), 7.20(t, 1H), 4.54 (m, 1H), 3.74 (s, 3H), 3.71 (s, 3H), 2.19(m, 1H), 1.92-1.38(m, 8H), 1.30(d, 3H).

Step 2: 4'-Bromomethyl-4-(1-cyclopentylethoxy)-biphenyl-3-ylphosphonic Acid Dimethyl Ester.

A mixture of 4-(1-cyclopentylethoxy)-4'-methylbiphenyl-3-ylphosphonic acid dimethyl ester (239 mg), N-bromosuccinimide (121 mg) and benzoyl peroxide (10 mg) in carbon tetrachloride (10 mL) was heated in an oil bath at 80° C. while being illuminated with a 150 watt lamp, for 1 hr. After cooling to room temperature, water was added and the mixture was extracted with methylene chloride, washed with brine, dried (MgSO$_4$), filtered and concentrated affording 286 mg of the title compound.

Step 3: 4'-{3-Bromo-4-[(diethoxyphosphoryl)-difluoromethyl]benzylsulfanylmethyl}-4-(1-cyclopentylethoxy)-biphenyl-3-ylphosphonic Acid Dimethyl Ester.

A mixture of thioacetic acid S-{4-[(diethoxyphosphoryl)difluoromethyl]benzyl}ester (100 mg) and 4'-bromomethyl-4-(1-cyclopentylethoxy)-biphenyl-3-ylphosphonic acid dimethyl ester (118 mg) in ethanol (2.5 mL) was bubbled with nitrogen for 10 minutes, then the solution was cooled to 0° C. , NaOMe (27 mg) was added and the mixture was stirred at 0° C. for 30 minutes. The mixture was diluted with water, extracted with ethyl acetate, washed with saturated ammonium chloride, brine, dried (MgSO$_4$), filtered and concentrated. The residue was purified by silica gel chromatography, using 80%ethyl acetate/hexane, to afford 110 mg of the title compound.

$^1$H NMR (Acetone-d$_6$) δ 8.07 (dd, 1H), 7.83(dd, 1H), 7.69(s, 1H), 7.64-7.56 (m, 3H), 7.50 (d, 1H), 7.49 (d, 2H), 7.22(t, 1H), 4.57 (m, 1H), 4.22 (m, 4H), 3.75 (m, 10H), 2.20(m, 1H), 1.96-1.26(m, 17H).

Step 4: 4'-[3-Bromo-4-(difluorophosphonomethyl)-benzylsulfanylmethyl-4-(1-cyclopentylethoxy)-biphenyl-3-ylphosphonic Acid.

To a solution of 4'-{3-bromo-4-[(diethoxyphosphoryl)-difluoromethyl]benzylsulfanylmethyl}-4-(1-cyclopentylethoxy)-biphenyl-3-ylphosphonic acid dimethyl ester. (110 mg) in chloroform (3 mL) at 0° C. was added bromotrimethylsilane (0.38 mL) and the mixture was left to stir over night at room temperature. The solvent was evaporated under vacuum and the residue was coevaporated with chloroform (4×). The residue was dissolved in methylene chloride (1 mL) cooled to 0° C. and then ethanol (5 mL) was added and stirring continued at room temperature for 3 hrs. The solvent was evaporated under vacuum and the residue was coevaporated with ethanol (4×). To the residue was added water (5 mL) and 1N NaOH (0.56 mL) and the solution was lyophylised over night to afford the title compound.

$^1$H NMR (MeOH-d$_4$) δ 8.23 (d, 1H), 8.12 (d, 1H), 7.59(d, 2H), 7.55-7.52(m, 3H), 7.31(d, 2H), 7.26(d, 1H), 6.98 (dd, 1H), 4.36 (m, 1H), 3.62(s, 2H), 3.59(s, 2H), 2.33(m, 1H), 2.10(m, 1H), 1.80(m, 1H), 1.72-1.29(m, 9H).

Example 16

4'-[3-Bromo-4-(difluorophosphonomethyl)-benzylsulfanylmethyl]-4-styrylbiphenyl-3-ylphosphonic Acid Tetrasodium Salt.

Step 1: 4'-Methyl-4-styrylbiphenyl-3-ylphosphonic Acid Dimethyl Ester

A solution of trifluoromethanesulfonic acid 3-(dimethoxyphosphoryl)-4'-methylbiphenyl-4-yl ester (200 mg), 4,4,5,5-tetramethyl-2-styryl-[1,3,2]dioxaborolane (141 mg), Cl$_2$Pd(dppf)$_2$CH$_2$Cl$_2$ (12 mg) and 2M Na$_2$CO$_3$ (1.2 mL) in DMF (6 mL) was cooled to −78° C., pumped under high vacuum for 5 min. then left to warm to room temperature under nitrogen, this process was repeated one more time, then the mixture was heated at 80° C. for 5 hrs. After cooling to room temperature, ethyl acetate was added and the mixture was washed with saturated NH$_4$Cl, brine, dried (MgSO$_4$), filtered and concentrated. The residue was purified by silica gel chromatography, using 45% ethyl acetate/hexane to afford 148 mg of the title compound.

$^1$H NMR (Acetone-d$_6$) δ 8.18 (d, 1H), 8.05-7.98 (m, 2H), 7.88(d, 1H), 7.62-7.60 (m, 4H), 7.40 (t, 2H), 7.34-7.29 (m, 4H), 3.80(s, 3H), 3.77(s, 3H), 2.37(s, 3H).

Step 2: 4'-Bromomethyl-4-styrylbiphenyl-3-ylphosphonic Acid Dimethyl Ester.

A mixture of 4'-methyl-4-styrylbiphenyl-3-ylphosphonic acid dimethyl ester (192 mg), N-bromosuccinimide (91 mg) and benzoyl peroxide (5 mg) in carbon tetrachloride (10 mL) was heated in an oil bath at 80° C. while being illuminated with a 150 watt lamp, for 3 hrs. After cooling to room temperature, water was added and the mixture was extracted with methylene chloride, washed with brine, dried (MgSO$_4$), filtered and concentrated. The residue was purified by silica gel chromatography to afford the title compound.

$^1$H NMR (Acetone-d$_6$) δ 8.20 (d, 1H), 8.10-7.93 (m, 3H), 7.73(d, 2H), 7.61 (t, 4H), 7.44-7.30(m, 4H), 4.72 (d, 2H), 3.80 (s, 3H), 3.77 (s, 3H).

Step 3: 4'-{3-Bromo-4-F(diethoxyphosphoryl)-difluoromethyl]-benzylsulfanylmethyl}-4-styrylbiphenyl-3-ylphosphonic Acid Dimethyl Ester.

A mixture of thioacetic acid S-{4-[(diethoxyphosphoryl)difluoromethyl]benzyl}ester (62 mg) and 4'-bromomethyl-4-styrylbiphenyl-3-ylphosphonic acid dimethyl ester (66 mg) in ethanol (1.5 mL) at 0° C. was bubbled with nitrogen for 10 minutes, then NaOMe (17 mg) was added and the mixture was stirred at 0° C. for 30 minutes. The mixture was diluted with water, extracted with ethyl acetate, washed with saturated ammonium chloride, brine, dried (MgSO$_4$), filtered and concentrated. The residue was purified by silica gel chromatography, using 80% ethyl acetate in hexane, to afford 77 mg of the title compound.

$^1$H NMR (Acetone-d$_6$) δ 8.19 (d, 1H), 8.08-7.92 (m, 3H), 7.66(dd, 6H), 7.50-7.30 (m, 7H), 4.21 (m, 4H), 3.78 (m, 10H), 1.31 (t, 6H).

Step 4: 4'-[3-Bromo-4-(difluorophosphonomethyl)-benzylsulfanylmethyl]-4-styrylbiphenyl-3-ylphosphonic Acid Tetrasodium Salt.

To a solution of 4'-{3-bromo-4-[(diethoxyphosphoryl)-difluoromethyl]-benzylsulfanylmethyl}-4-styrylbiphenyl-3-ylphosphonic acid dimethyl ester (77 mg) in chloroform (2 mL) at 0° C. was added bromotrimethylsilane (0.27 mL) and the mixture was left to stir over night at room temperature. The solvent was evaporated under vacuum and the residue was coevaporated with chloroform (4×). The residue was dissolved in methylene chloride (1 mL) cooled to 0° C. and then ethanol (5 mL) was added and stirring continued at room temperature for 3 hrs. The solvent was evaporated under vacuum and the residue was coevaporated with ethanol (4×). To the residue was added water (5 mL) and 1N NaOH (0.4 mL) and the solution was lyophylised over night to afford 76 mg of the title compound.

$^1$H NMR (MeOH-d$_4$) δ 8.56 (d, 1H), 8.41(d, 1H), 8.12(d, 1H), 7.85 (m, 1H), 7.70-7.69(m, 4H), 7.56(d, 1H), 7.51 (s, 1H), 7.37-7.09 (m, 7H), 3.65(s, 2H), 3.59(s, 2H).

Example 17

6-{4-[3-bromo-4-difluoro-phosphono-methyl)-benzylsulfanyl-methyl]-phenyl}-2-(1,3-dimethyl-butyl)-quinolin-8-yl-phosphonic Acid Step 1: 8-Bromo-6-(4-hydroxymethyl-phenyl)-2-methyl-quinoline To a degassed solution of 6,8-dibromo-2-methylquinoline (20 mmol., 6.02 g) prepared according to Song et al. J. Heterocyclic Chem. 1993, 39, 17.), 4-hydroxymethylbenzeneboronic acid (30 mmol., 4.56 g) in benzene (200 mL), ethanol (40 mL) and 2M Na$_2$CO$_3$ (80 mL) was added Pd(PPh$_3$)$_4$ (1 mmol., 1.15 g)and the mixture was heated to reflux for 4 hours. It was then cooled and poured over ice, H$_2$O and ethyl acetate. The organic layer was separated and the aqueous further extracted with ethyl acetate. The combined organic layers were washed with brine, dried with magnesium sulphate, filtered and the solvent was removed in vacuo. The residue was purified by chromatography on SiO$_2$ using a gradient of ethyl acetate and hexanes (3:5 to 1:1) to yield the title compound (3.93 g) contaminated with a small amount of the regioisomer.

$^1$H NMR (CD$_3$COCD$_3$) δ 8.3-8.4(1H, d), 8.25-8.35(1H, d), 8.15-8.2(1H, d), 7.75-7.8(2H, d), 7.4-7.5(3H, m), 4.7(2H, d), 4.25-4.35(1H, t), 2.75(3H, s); resonnances for regioisomers omitted.

Step 2: 8-Bromo-6-(4-t-butyldimethylsilyloxymethyl-phenyl)-2-methylquinoline

To a −5° C. solution of the alcohol from step 1 (3 mmol., 0.984 g) in dichloromethane (15 mL) and triethylamine (4 mmol., 0.404 g) was added t-butyldimethylsilyl chloride (3.5 mmol., 0.525 g) as a dichloromethane solution (5 mL) and a catalytic amount of DMAP. The mixture was warmed to room temperature and stirred for 2 hours. An additionnal 100 mg of the silyl chloride was added and the mixture reacted for a further 48 hours. It was then poured over ice, dilute NH$_4$Cl and dichloromethane. The organic layer was separated and the aqueous further extracted with dichloromethane. The combined organic layers were washed with brine, dried with magnesium sulphate, filtered and the solvent was removed in vacuo. The residue was purified by chromatography on SiO$_2$ using ethyl acetate and hexanes (1:10) to yield the title compound (0.9 g).

$^1$H NMR (CD$_3$COCD$_3$) δ 8.35(1H, d), 8.30(1H, d), 8.15 (1H, d), 7.75-7.85(2H, d), 7.45-7.55(3H, m), 4.85(2H, s), 2.70(3H, s), 0.95(9H, s), 0.15(6H, s).

Step 3: 8-Bromo-6-(4-t-butyldimethylsilyloxymethyl-phenyl)-2-ethylquinoline

The quinaldine from step 2 (1.55 mmol., 0.687 g) in THF (3 mL) was added to freshly prepared LDA (from 1.8 mmol. of triethylamine and 1.7 mmol. of n-BuLi in 7 mL of THF) at −78° C. and the dark red mixture was reacted for 1.5 hour. Methyl iodide (3 mmol., 0.426 g) was added and the mixture was slowly warmed to 0° C. It was then poured over ice, dilute NH$_4$Cl and ethyl acetate. The organic layer was separated and the aqueous further extracted with ethyl acetate. The combined organic layers were washed with brine, dried with magnesium sulphate, filtered and the solvent was removed in vacuo. The residue was purified by chromatography on SiO$_2$ using ethyl acetate and hexanes (1:30) to yield the title compound (0.638 g).

$^1$H NMR (CD$_3$COCD$_3$) δ 8.35(1H, d), 8.30(1H, d), 8.2 (1H, d), 7.75-7.85(2H, d), 7.45-7.55(3H, m), 4.85(2H, s), 3.0-3.1(2H, q), 1.45(3H, t), 0.95(9H, s), 0.15(6H, s).

Step 4: 8-Bromo-6-(4-t-butyldimethylsilyloxymethyl-phenyl)-2-(4-methylpentyl)-quinoline The quinoline from step 3 (1.32 mmol., 0.676 g) in THF (2 mL) was added to freshly prepared LDA (from 2.0 mmol. of triethylamine and 1.7 mmol. of n-BuLi in 8 mL of THF) at −78° C. The dark red mixture was reacted for 0.75 hour and warmed at −45° C. for 0.75 hour. Isobutyl iodide (2.5 mmol., 0.46 g) was added and the mixture was slowly warmed to 0° C. and reacted 16 hours. It was then poured over ice, dilute NH$_4$Cl and ethyl acetate. The organic layer was separated and the aqueous further extracted with ethyl acetate. The combined organic layers were washed with brine, dried with magnesium sulphate, filtered and the solvent was removed in vacuo. The residue was purified by chromatography on SiO$_2$ using ethyl acetate and hexanes (1:30) to yield the title compound (0.389 g).

$^1$H NMR (CD$_3$COCD$_3$) δ 8.4(1H, d), 8.35(1H, d), 8.2(1H, d), 7.75-7.85(2H, d), 7.45-7.55(3H, m), 4.85(2H, s), 3.15-3.35(1H, m), 1.8-2.0(1H, m), 1.4-1.55(1H, m), 1.3-1.4(3H, d), 0.8-1.0(15, m), 0.15(6H, s).

Step 5: 8-Diethylphosphono-6-(4-bromo-methyl-phenyl)-2-(4-methyl-pentyl)quinoline To the quinoline from step 4 (0.87 mmol., 0.449 g) in THF (5 mL) at 0° C. was added 1M TBAF (0.95 mmol., 0.95 mL) and the mixture was reacted 1 hours. It was then poured over ice, dilute NH$_4$Cl and ethyl acetate. The organic layer was separated and the aqueous further extracted with ethyl acetate. The combined organic layers were washed with brine, dried with magnesium sulphate, filtered and the solvent was removed in vacuo. The residue was purified by chromatography on SiO$_2$ using ethyl acetate and hexanes (1:2) to yield the alcohol (0.318 g) which was reacted with DHP in the following manner.

To the cold (0° C.)solution of the alcohol (0.79 mmol., 0.318 g) in dichloromethane (5 mL) was added DHP (1.6 mmol., 0.134 g) and PPTS (0.038 g) and the mixture was warmed to room temperature and stirred for 16 hours. It was then poured over ice, dilute NaHCO$_3$ and dichloromethane. The organic layer was separated and the aqueous further extracted with dichloromethane. The combined organic layers were washed with brine, dried with magnesium sulphate, filtered and the solvent was removed in vacuo. The residue was purified by chromatography on SiO$_2$ using ethyl acetate and hexanes (1:10) to yield a THP derivative (0.39 g).

$^1$H NMR (CD$_3$COCD$_3$) δ 8.4(1H, d), 8.35(1H, d), 8.2(1H, d), 7.75-7.85(2H, d), 7.45-7.55(3H, m), 4.7-4.9(2H, m), 4.45-4.55(1H, d), 3.8-4.0(1H, m), 3.45-3.55(1H, m), 3.15-3.35(1H, m), 1.4-2.0(9H, m), 1.35(3H, d), 0.8-1.0(6H, dd).

To a degassed solution of the bromide from above (0.8 mmol., 0.39 g) in toluene (0.5 mL), triethylamine (2.4 mmol., 0.242 g) and diethylphosphite (2.4 mmol., 0.331 g) was added Pd(PPh$_3$)$_4$ (0.04 mmol., 0.046 g) and the mixture was heated to reflux for 4 hours. It was then cooled and poured over ice, H$_2$O and ethyl acetate. The organic layer was separated and the aqueous further extracted with ethyl acetate. The combined organic layers were washed with brine, dried with magnesium sulphate, filtered and the solvent was removed in vacuo. The residue was purified by chromatography on SiO$_2$ using ethyl acetate and hexanes (3:1) to yield a phosphonate intermediate (0.262 g) used as such in the next step.

The THP derivative from above (0.262 g) in ethanol (1 mL) was added to a 0° C. solution of ethanol (3 mL) containing AcCl (0.1 mL) and the mixture was reacted for 2 hours. It was then poured over ice, dilute NaHCO$_3$ and ethyl acetate. The organic layer was separated and the aqueous further extracted with ethyl acetate. The combined organic layers were washed with brine, dried with magnesium sulphate, filtered and the solvent was removed in vacuo. The residue was used as such in the next step.

A dichloromethane (1 mL) solution of the alcohol from above was added to a 0° C. suspension of POBr$_3$ (0.6 mmol., 0.172 g) in dichloromethane (1 mL) and DMF (1 mL) and the mixture was reacted 1 hour at room temperature. It was then poured over ice, dilute NaHCO$_3$ and ethyl acetate. The organic layer was separated and the aqueous further extracted with ethyl acetate. The combined organic layers were washed with brine, dried with magnesium sulphate, filtered and the solvent was removed in vacuo. The residue was purified on SiO$_2$ using ethylacetate and hexanes (3:1) to yield the title compound (0.213 g).

$^1$H NMR (CD$_3$COCD$_3$) δ 8.55-8.65(1H, dd), 8.3-8.4(2H, m), 7.8(2H, d), 7.6(2H, d), 7.55(1H, d), 4.7(2H, s), 4.15-4.4(4H, m), 3.15-3.35(1H, m), 1.85-1.95(1H, m), 1.4-1.55(2H, m), 1.45(3H, d), (1.3, 6H, t), 0.8-0.95(6H, dd).

Step 6: Diethyl 6-{4-[3-bromo-4-difluoro-phosphono-methyl)-benzylsulfanylmethyl]-phenyl}-2-(1,3-dimethyl-butyl)-quinolin-8-yl-phosphonate To a degassed −5° C. solution of the bromide (0.4 mmol., 0.21 g) form the previous step and diethyl (2-bromo-4-acetylthiomethyl-phenyl)-difluoro-methyl-phosphonic acid (0.4 mmol., 0.172 g) in ethanol (3 mL) was added 2M NaOH (0.8 mmol., 0.4 mL) and the mixture was reacted for 20 minutes. It was then poured over ice, dilute NH$_4$Cl and ethyl acetate. The organic layer was separated and the aqueous further extracted with ethyl acetate. The combined organic layers were washed with brine, dried with magnesium sulphate, filtered and the solvent was removed in vacuo. The residue was purified on SiO$_2$ using ethyl acetate, hexanes and dichloromethane (3:1:0.1) to yield the title compound (0.23 g).

$^1$H NMR (CD$_3$COCD$_3$) δ 8.6(1H, dd), 8.3-8.4(3H, m), 7.8(2H, d), 7.7(1H, bs), 7.45-7.65(5H, m), 4.1-4.4(8H, m), 3.8(4H, 2s), 3.15-3.35(1H, m), 1.85-1.95(1H, m), 1.4-1.55(2H, m), 1.25-1.4(15H, m), 0.8-0.95(6H, dd).

Step 7: 6-{4-[3-bromo-4-difluoro-phosphono-methyl)-benzylsulfanyl-methyl]-phenyl}-2-(1,3-dimethyl-butyl)-quinolin-8-yl-phosphonic Acid To a room temperature solution of the diester (0.27 mmol., 0.23 g) from step 7 in chloroform (2 mL) was added TMSiBr (2.7 mmol., 0.35 mL) and the mixture was gently heated to reflux for 3 hours. The volatils were removed in vacuo and the residue was dissolved in dichloromethane and cooled to 0° C. Ethanol (1 mL) was added and the mixture was stirred at room temperature for 1 hour. The mixture was evaporated to dryness and co-evaporated with toluene (3×) to yield the title compound containing traces of toluene.

$^1$H NMR (CD$_3$SOCD$_3$) δ 8.9(1H, dd), 8.65(1H, bs), 8.45-8.55(1H, dd), 8.0(1H, d), 7.35-7.6(5H, m), 3.8(4H, 2s), 3.25-3.45(1H, m), 1.3-1.96(6H, m), 0.75-0.95(6H, dd).

Example 18

6-{4-[bromo-4-(difluoro-phosphono-methyl)-benzylsulfanyl-methyl]-phenyl-2-(1-methyl-2-phenyl-ethyl)-quinolin-8-yl-phosphonic Acid Step 1: 8-Bromo-6-(4-(tetrahydropyranyloxy-methyl)-phenyl)-2-methylquinoline To a 0° C. solution of the 8-bromo-6-(4-hydroxymethyl-phenyl)-2-methyl-quinoline (19.2 mmol., 6.3 g) in dichloromethane (100 mL) and dihydropyran (40 mmol., 3.36 g) was added PPTS (1 g) and the mixture was stirred for 16 hours at room temperature. It was then poured over ice, dilute NaHCO$_3$ and dichloromethane. The organic layer was separated and the aqueous further extracted with dichloromethane. The combined organic layers were washed with brine, dried with magnesium sulphate, filtered and the solvent was removed in vacuo. The residue was purified by chromatography on SiO$_2$ using ethyl acetate and hexanes (1:4) to yield the title compound (6 g).

$^1$H NMR (CD$_3$COCD$_3$) δ 8.4(1H, d), 8.3(1H, d), 8.2(1H, d), 7.8(2H, d), 7.5(3H, m), 4.8(1H, d), 4.7(1H, m), 4.55(1H, d), 3.85-3.95(1H, m), 3.45-3.55(1H, m), 2.7(3H, s), 1.8-1.9(1H, M), 1.4-1.8(5 h, m).

Step 2: 8-Diethylphosphono-6-(4-(tetrahydropyranyloxy-methyl)-phenyl)-2-methyl-quinoline To a degassed solution of the THP-ether from step 1 (10.7 mmol., 4.4 g) in toluene (5 mL), triethylamine (30 mmol., 3.03 g) and diethylphosphite (30 mmol., 4.14 g) was added Pd(PPh$_3$)$_4$ (1.5 mmol., 1.7 g) and the mixture was heated to reflux for 4 hours. It was then cooled and poured over ice, H$_2$O and ethyl acetate. The organic layer was separated and the aqueous further extracted with ethyl acetate. The combined organic layers were washed with brine, dried with magnesium sulphate, filtered and the solvent was removed in vacuo. The residue was triturated in diethylether and hexanes to yield the title compound (3.6 g); the mother liquors were purified by chromatography on SiO$_2$ using acetone and toluene (1:3) and furnished more title compound (0.851 g).

$^1$H NMR (CD$_3$COCD$_3$) δ 8.5-8.6(1H, d), 8.3-8.4(3H, m) 7.8(2H, d), 7.45-7.55(3H, m), 4.8(1H, d), 4.7(1H, m), 4.55 (1H, d), 4.35-4.45(4H, m), 3.85-3.95(1H, m), 3.45-3.55(1H, m), 2.7(3H, s), 1.8-1.9(1H, M), 1.4-1.8(5 h, m), 1.3-1.4(3H, t).

Step 3: 8-Diethylphosphono-6-(4-(tetrahydropyranyloxy-methyl)-phenyl)-2-ethyl-quinoline The quinaldine derivative from the previous step was treated with freshly prepared LDA and the resulting species reacted with methyl iodide in a manner similar to the one described in Example 17, step 3 to yield the 2-ethyl-quinoline derivative.

$^1$H NMR (CD$_3$COCD$_3$) δ 8.6(1H, dd), 8.3-8.4(3H, m), 7.8(2H, d), 7.45-7.55(3H, m), 4.8(1H, d), 4.75(1H, m), 4.55(1H, d), 4.25-4.45(4H, m), 3.85-3.95(1H, m), 3.45-3.55 (1H, m), 2.95-3.1(2H, q), 1.8-1.9(1H, M), 1.4-1.8(5 h, m), 1.25-1.45(61, 2t).

Step 4: 8-Diethylphosphono-6-(4-(tetrahydropyranyloxy-methyl)-phenyl)-2-(1-methyl-2-phenyl-ethyl)-quinoline The quinoline from step 2 (0.72 mmol., 0.400 g) in THF (2 mL) was added to freshly prepared LDA (from 0.9 mmol. of triethylamine and 0.8 mmol. of n-BuLi in 3 mL of THF) at −78° C. The dark red mixture was reacted for 1 hour. Benzyl bromide (1.5 mmol., 0.256 g) was added and the mixture was slowly warmed to 0° C. and reacted 16 hours. It was then poured over ice, dilute $NH_4Cl$ and ethyl acetate. The organic layer was separated and the aqueous further extracted with ethyl acetate. The combined organic layers were washed with brine, dried with magnesium sulphate, filtered and the solvent was removed in vacuo. The residue was purified by chromatography on $SiO_2$ using ethyl acetate and hexanes (1:30) to yield the title compound (0.282 g).

$^1$H NMR ($CD_3COCD_3$) δ 8.6-8.7(1H, d), 8.35(1H, d), 8.3(1H, dd), 7.8(2H, d), 7.55(2H, d), 7.4(1H, d), 7.05-7.2 (5H, m), 4.8(1H, d), 4.75(1H, m), 4.55(1H, d), 4.15-4.4(4H, m), 3.85-3.95(1H, m), 3.45-3.55(3H, m), 3.0(1H, m), 1.45-1.9(6H, m), 1.4(3H, d), 1.35-1.45(6H, m).

Step 5: 8-Diethylphosphono-6-(4-(bromo-methyl)-phenyl)-2-(1-methyl-2-phenyl-ethyl)-quinoline The conversion of the THP-protected alcohol to the bromo-methyl derivative was carried in a similar manner to the one described in Step 5 of Example 17, using acid to deprotect and $POBr_3$ to produce the bromide.

$^1$H NMR ($CD_3COCD_3$) δ 8.6(1H, d), 8.4(1H, d), 8.3(1H, dd), 7.85(2H, d), 7.65(2H, d), 7.4(1H, d), 7.1-7.25(4H, m), 7.05-7.1(1H, m), 4.75(2H, s), 4.15-4.4(4H, m), 3.35-3.5(2H, m), 3.0(1H, m), 1.4(3H, d), 1.3-1.4(6H, m).

Step 6: Diethyl 6-{4-[3-bromo-4-(difluoro-phosphono-methyl)benzylsulfanyl-methyl]-phenyl}-2-(1-methyl-2-phenyl-ethyl)-quinolin-8-yl-phosphonate To a 0° C. degassed solution of the bromide (0.45 mmol., 0.248 g) and (2-bromo-4-acetylthiomethyl-phenyl)-difluoro-methyl-phosphonic acid (0.45 mmol., 0.194 g) in ethanol (4 mL) was added NaOMe (1 mmol., 0.054 g) and the mixture was reacted for 0.75 hour. It was then poured over ice, dilute $NH_4Cl$ and ethyl acetate. The organic layer was separated and the aqueous further extracted with ethyl acetate. The combined organic layers were washed with brine, dried with magnesium sulphate, filtered and the solvent was removed in vacuo. The residue was purified on $SiO_2$ using acetone and toluene(1:3) to yield the title compound (0.338 g).

$^1$H NMR ($CD_3COCD_3$) δ 8.6-8.7(1H, d), 8.4(1H, d), 8.3(1H, dd), 7.8(2H, d), 7.7(1H, s) 7.6(1H, d), 7.4-7.5(3H, m), 7.1-7.3(5H, m), 4.1-4.4(8H, m), 3.8(4H, 2s), 3.35-3.5 (2H, m), 3.0(1H, m), 1.4(3H, d), 1.25-1.35(6H, m).

Step 7: 6-{4-[3-bromo-4-(difluoro-phosphono-methyl)-benzylsulfanylmethyl]1-phenyl}-2-(1-methyl-2-phenyl-ethyl)-quinolin-8-yl-phosphonic Acid To a room temperature solution of the intermediate from Step 6 (0.39 mmol., 0.338 g) in chloroform (4 mL) was added TMSiBr (3.9 mmol., 0.596 mL) and the mixture was gently heated to reflux for 3 hours. The volatils were removed in vacuo and the residue was dissolved in dichloromethane and cooled to 0° C. Ethanol (1 mL) was added and the mixture was stirred at room temperature for 1 hour. The mixture was evaporated to dryness, co-evaporated with toluene (3×) and the residue was swished in ether to yield the title compound (0.224 g) containing traces of ether.

$^1$H NMR ($CD_3SOCD_3$) δ 8.7-8.8(1H, d), 8.6(1H, d), 8.5(1H, dd), 7.8(1H, d), 7.75(2H, d) 7.6(1H, s), 7.55(1H, d), 7.45(2H, d), 7.4(1H, d), 7.05-7.25(5H, m), 3.7-3.8(4H, 2s), 3.6(1H, m), 3.2(1H, m), 3.0(1H, m), 1.4(3H, d); traces of ether omitted.

Example 19

6-{4-[3-bromo-4-(difluoro-phosphono-methyl)-benzylsulfanyl-methyl]-phenyl}-2-(1,3-dimethyl-butyl)-quinoline-8-carboxylic Acid Step 1: 8-carboxy-6-((4-tetrahydropyranyloxy-methyl)-phenyl)-2-(1,3-dimethyl-butyl)-quinoline To a −78° C. THF (1.5 mL) solution of 8-bromo-6-(4-(tetrahydropyranyloxy-methyl)phenyl)-2-(1,3-dimethyl-butyl)-quinoline (0.195 mmol., 0.108 g), as prepared in Step 5 of Example 17, was added 2.38 M n-BuLi (hexanes; 0.21 mmol., 0.09 mL) and the mixture was reacted 3 minutes. Crushed dry ice was added and the mixture was allowed to slowly warm-up to room temperature. It was then poured over ice, dilute $NH_4Cl$ and ethyl acetate. The organic layer was separated and the aqueous further extracted with ethyl acetate. The combined organic layers were washed with brine, dried with magnesium sulphate, filtered and the solvent was removed in vacuo. The residue was purified on $SiO_2$ using of ethyl acetate and hexanes (1:2) followed by ethyl acetate, hexanes and acetic acid (1:2:0.01) to yield the title compound (0.077 g).

$^1$H NMR ($CD_3COCD_3$) δ 8.9(1H, d), 8.65(1H, d), 8.5(1H, d), 7.85(2H, d), 7.8(1H, d), 7.5(2H, d), 4.8(1H, d), 4.75(1H, m), 4.55(1H, d), 3.9(1H, m), 3.5(1H, m), 3.35(1H, m), 1.45-1.9(9H, m), 1.4(3H, d), 0.9(6H, dd).

Step 2: 8-methoxy-carbonyl-6-((4-tetrahydropyranyloxy-methyl)-phenyl)-2-(1,3-dimethyl-butyl)-quinoline To a 0° C. DMF (2 mL) solution of the carboxy derivative (0.49 mmol., 0.25 g) from the previous step was added iodomethane (0.8 mmol., 0.114 g) followed by cesium carbonate (0.6 mmol., 0.195 g) and the mixture was reacted at room temperature for 16 hours. It was then poured over ice, water and ethyl acetate. The organic layer was separated and the aqueous further extracted with ethyl acetate. The combined organic layers were washed with brine, dried with magnesium sulphate, filtered and the solvent was removed in vacuo. The residue was purified on $SiO_2$ using of ethyl acetate and toluene (1:20) to yield the title compound contaminated with a small amount of a long-wave positive impurity which could not be removed (0.194 g). The mixture was used as such in the next step.

$^1$H NMR ($CD_3COCD_3$) δ 8.35(1H, d), 8.3(1H, d), 8.15 (1H, d), 7.8 (2H, d), 7.5(3H, m), 4.8(1H, d), 4.75(1H, m), 4.55(1H, d), 4.0(3H, s), 3.85-3.95(1H, m), 3.5(1H, m), 3.2(1H, m), 1.45-1.9(9H, m), 1.4(3H, d), 0.9(6H, dd); resonances for the impurity omitted.

Step 3: 6-{4-[3-bromo-4-(difluoromethyl-diethoxy-phosphoryl)benzylsulfanyl-methyl]-phenyl}-2-(1,3-dimethyl-butyl)-quinolin-8-yl-carboxylic Acid The THP derivative from the previous step was converted to bromo-methyl intermediate using a procedure similar to the one described in the previous example and coupled to diethyl (2-bromo-4-acetylthiomethyl-phenyl)-difluoro-methyl-phosphonic acid as described earlier. It was dealkylated and hydrolysed as followed:

To a room temperature solution of the diethoxyphosphoryl/methoxycarbonyl intermediate (0.32 mmol., 0.242 g) in chloroform (3 mL) was added TMSiBr (3.2 mmol., 0.49 mL) and the mixture was gently heated to reflux for 3 hours. The volatils were removed in vacuo and the residue was dissolved in dichloromethane and cooled to 0° C. Ethanol (1 mL) was added and the mixture was stirred at room temperature for 1 hour. The mixture was evaporated to dryness, co-evaporated with toluene (3×) and the residue was suspended in ethanol (2 mL). Water (1.5 mL) and 1M NaOH (1.5 mL) were added. The mixture was warmed up to 40–50° C. for 25 minutes and then stirred at room temperature for 16 hours. Most of the ethanol/water mixture was removed in vacuo and the residue was diluted with water and acidify to pH of 2–3 with 1N HCl. The mixture was extracted with ethyl acetate (3×) and the combined organic layers were washed with brine, dried with magnesium sulphate, filtered and the solvent was removed in vacuo. The residue was swished in a mixture of ethyl acetate and ether to yield the title compound (0.056 g).

$^1$H NMR (CD$_3$SOCD$_3$) δ 8.8(1H, d), 8.6-8.7(2H, m), 7.8(2H, d), 7.3-7.65(6H, m), 3.65-3.85(4H, 2s), 3.2-3.4(1H, m), 1.65-1.85(1H, m), 1.3-1.6(5H, m), 0.75-0.95(6H, dd).

Example 20

3-(6-{4-[3-bromo-4-(difluoro-phosphono-methyl)-benzylsulfanyl-methyl]-phenyl}-8-phosphono-quinolin-2-yl)-butyric Acid The title compound was prepared from 8-Diethylphosphono-6-(4-(tetrahydropyranyl-oxy-methyl)-phenyl)-2-ethyl-quinoline in a manner similar to the one described in Example 18, step 4, but using ethyl iodoacetate as an electrophile. This derivative was then converted to the title compound in an analoguous manner to the one described for Example 18

$^1$H NMR (CD$_3$SOCD$_3$) δ 8.5-8.6(1H, d), 8.25-8.45(2H, m), 8.65-8.8(2H, m), 7.5(2H, d), 7.1-7.4(4H, m), 3.75-3.9 (4H, 2s), 3.55(1H, m), 2.9-3.0(1H, m), 2.6-2.7(1H, m), 1.3-1.4(3H, m); traces of ethanol present.

Example 21

6-{4-[3-bromo-4-(difluoro-phosphono-methyl)-benzylsulfanyl-methyl]-phenyl}-2-(cyclopentyl)-quinolin-8-yl-phosphonic Acid The title compound was prepared from 8-Diethylphosphono-6-(4-(tetrahydropyranyloxy-methyl)-phenyl)-2-methyl-quinoline in a similar manner the one described in Example 18, step 4, but using ethyl 1,4-diiodobutane as an electrophile. This derivative was then converted to the title compound in an analoguous manner to the one described for Example 18.

$^1$H NMR (CD$_3$SOCD$_3$) δ 8.9(1H, dd), 8.6(1H, d), 8.5(1H, dd), 7.95(1H, d), 7.75(2H, d), 7.5-7.6(2H, m), 7.45(2H, d), 7.4(1H, d), 3.75-3.85(4H, 2s), 3.5-3.6(1H, m), 2.15-2.3(2H, m), 1.65-1.95(6H, m).

Example 22

6-{4-[3-bromo-4-(difluoro-phosphono-methyl)-benzylsulfanyl-methyl]-phenyl}-2-(1,3-dimethyl-butyl)-quinolin-8-yl-acetic acid Step 1: 8-bromomethyl-6-(4-((tetrahydropyranyl-oxy)-methyl)-phenyl)-2-(1,3-dimethyl-butyl)-quinoline To a −78° C. THF (5 mL) solution of 8-bromo-6-(4-(tetrahydropyranyloxy-methyl)phenyl)-2-(1,3-dimethyl-butyl)-quinoline (1 mmol., 0.497 g), as prepared in Step 5 of Example 17, was added 2.38 M n-BuLi (hexanes; 1.1 mmol., 0.462 mL) and the mixture was reacted 5 minutes. Excess DMF was added and the mixture was allowed to slowly warm-up to room temperature. It was then poured over ice, dilute NH$_4$Cl and ethyl acetate. The organic layer was separated and the aqueous further extracted with ethyl acetate. The combined organic layers were washed with brine, dried with magnesium sulphate, filtered and the solvent was removed in vacuo. The residue (0.425 g) was dissolved in THF (1 mL) and methanol (3 mL), cooled to 0° C. and treated with NaBH$_4$ (0.05 g). After 1 hour, it was poured over ice, dilute NH$_4$Cl and ethyl acetate. The organic layer was separated and the aqueous further extracted with ethyl acetate. The combined organic layers were washed with brine, dried with magnesium sulphate, filtered and the solvent was removed in vacuo. The residue that consisted of the 8-(hydroxymethyl) derivative was converted to the bromomethyl derivative using POBr$_3$ as described before. The product was purified by chromatography on SiO$_2$ using ethyl acetate and hexanes (1:10) to yield the title compound (0.265 g).

$^1$H NMR (CD$_3$COCD$_3$) δ 8.3(1H, d), 8.25(1H, s), 8.2(1H, s), 7.8(2H, d), 7.5(3H, m), 5.3-5.4(2H, q), 4.8(1H, d), 4.75(1H, m), 4.5(1H, d), 3.8-3.9(1H, m), 3.5(1H, m), 3.2-3.3(1H, m), 1.4-2.0(9H, m), 1.45(3H, d), 0.8-1.0(6H, dd).

Step 2: 8-(methoxycarbonyl-)-6-((4-chloro-methyl)-phenyl)-2-(1,3-dimethylbutyl)-quinoline To 0° C. DMSO (3 mL) solution of the bromide (0.47 mmol., 0.236 g) from step 1 was added finely ground KCN (1.5 mmol., 0.098 g) and the mixture was stirred at room temperature for 3 hours. It was poured over ice, dilute NaHCO$_3$ and ether. The organic layer was separated and the aqueous further extracted with ether. The combined organic layers were washed with brine, dried with magnesium sulphate, filtered and the solvent was removed in vacuo. The product was purified by chromatography on SiO$_2$ using ethyl acetate and hexanes (1:5) to yield the title compound (0.187 g).

$^1$H NMR (CD$_3$COCD$_3$) δ 8.3-8.4(1H, d), 8.2 (2H, m), 7.8(2H, d), 7.5(3H, m), 4.8 (1H, d), 4.75(1H, m), 4.55(1H, d), 4.5(2H, s), 3.8-3.9(1H, m), 3.5(1H, m), 3.2-3.3(1H, m), 1.4-2.0(9H, m), 1.35(3H, d), 0.8-1.0(6H, dd).

The cyano derivative was dissolve in MeOH (4 mL) and the solution was saturated with dry HCl (g) at 0° C. The reaction vessel was sealed and warmed up to 60° C. for 3 hours then stirred at room temperature for 16 hours. It was then poured over ice, water and ethyl acetate. The organic layer was separated and the aqueous further extracted with ethyl acetate. The combined organic layers were washed with brine, dried with magnesium sulphate, filtered and the solvent was removed in vacuo. The product was purified by chromatography on SiO$_2$ using ethyl acetate and hexanes (1:10) to yield the title compound (0.115 g).

$^1$H NMR (CD$_3$COCD$_3$) δ 88.4(1H, d), 8.1 (1H, d), 8.0(1H, d), 7.8(2H, d), 7.6(2H, d), 7.45(1H, d), 4.8 (2H, s), 4.25(3H, s), 3.6(31H, s), 3.1-3.3(1H, m), 1.8-1.9(1H, m), 1.4-1.5(2H, m), 1.3(3H, d), 0.8-1.0(6H, dd).

Step 3: 6-{4-[3-bromo-4-(difluoro-phosphono-methyl)-benzylsulfanylmethyl]-phenyl}-2-(1,3-dimethyl-butyl)-quinolin-8-yl-acetic Acid The intermediate from the previous step was converted to the title compound using a procedure similar to as described for Example 19.

$^1$H NMR (CD$_3$OD) δ 8.25(1H, d), 8.05(1H, d), 7.05(1H, d), 7.65-7.75(3H, m), 7.55(1H, m), 7.4(3H, m), 7.3(1H, m), 3.6-3.7(4H, 2s), 3.15-3.25(1H, m), 1.8-1.9(1H, m), 1.4-1.55 (2H, m), 1.35(3H, d), 0.8-0.95(6H, dd); traces of acetic acid omitted.

Example 23

2-Benzoyl-6-{4-[3-Bromo-4-(difluoro-phosphono-methyl)-benzylsulfanyl-methyl]-phenyl}-quinolin-8-yl-phosphonic Acid Step 1: [4-(8-Bromo-2-methyl-quinolin-6-yl-phenyl]-methanol To a degassed solution of 6,8-dibromo-2-methylquinoline (6.7 g, 22.2 mmol, prepared according to Song et al. J. Heterocyclic Chem. 1993, 39, 17.), and 4-hydroxymethylphenylboronic acid (5.06 g, 33.3 mmol) in toluene (136 mL) was added Pd$_2$(dba)$_3$ (1.01 g, 1.11 mmol). The mixture was degassed and Ph$_3$P (2.3 g, 8.88 mmol), Et$_2$NH (2.43 g, 33.3 mmol), n-propanol (26 mL) and H$_2$O (26 mL) was added. The mixture was heated to reflux for 26 h. Aqueous NaHCO$_3$ was added and the resulting mixture was extracted with EtOAc. The combined organic extracts were washed with brine, dried (anhyd. MgSO$_4$) and concentrated in vacuo. The residue was purified by chromatography on silica gel to give 4.78 g (66%) of the title compound.

Step 2: 8-Bromo-2-methyl-6-[4-(tetrahydro-pyran-2-yloxymethyl)-phenyl]-quinoline To the product of step 1 (4.78 g, 14.5 mmol) in CH$_2$Cl$_2$ (65 mL) was added dihydropyran (2.44 g, 29 mmol) and Amberlyst 15 (600 mg). The mixture was heated to reflux for 8 h. The mixture was filtered and concentrated. The residue was purified by chromatography on silica gel to give 3.93 g (66%) of the title compound.

Step 3: 2-Methyl-6-[4-(tetrahydro-pyran-2-yloxymethyl)-phenyl]-quinolin-8-yl-phosphonic Acid Diethyl Ester To a solution of the product of step 2 (3.93 g, 9.54 mmol), diethylphosphite (3.95 g, 28.6 mmol) and Et$_3$N (2.89 g, 28.6 mmol) in toluene (4 mL) was added Pd(Ph$_3$P)$_4$ (551 mg, 0.477 mmol). The mixture was degassed and heated to 90° C. for 20 h, cooled, diluted with EtOAc (200 mL) and filtered through celite. The filtrate was concentrated in vacuo. The residue was purified by chromatography on silica gel to give 3.68 mg (83%) of the tiltle compound.

Step 4: 2-Formyl-6-[4-(tetrahydro-pyran-2-yloxymethyl)-phenyl]-quinolin-8-yl-phosphonic Acid Diethyl Ester To a solution of the product of step 3 (500 mg, 1.06 mmol) in dioxane (10 mL) was added Selenium dioxide (202 mg, 1.81 mmol). The mixture was stirred at 90° C. for 0.25 h. The mixture was diluted with EtOAc and filtered through a short column of silica gel. The filtrate was concentrated and the residue was purified by chromatography on silica gel to give 254 mg (50%) of the title compound.

Step 5: 2-(Hydroxy-phenyl-methyl)-6-[4-(tetrahydro-pyran-2-yloxymethyl)phenyl]-quinolin-8-yl-phosphonic Acid Diethyl Ester To a cold (0° C.) solution of the product of step 4 (1 g, 2.07 mmol) in THF (20 mL) was added PhMgCl (4.14 mmol, 1M in THF). The mixture was then stirred at rt for 1 h. Aqueous NH$_4$Cl was added, and the mixture was extracted with EtOAc. The combined organic extracts were washed with brine, dried (anhyd. MgSO$_4$) and concentrated in vacuo. The residue was purified by chromatography on silica gel to give 917 mg (79%) of the title compound.

Step 6: 2-Benzoyl-6-[4-(tetrahydro-pyran-2-yloxymethyl)-phenyl]-quinolin-8-yl-phosphonic Acid Diethyl Ester To a solution of the product of step 5 (559 mg, 0.99 mmol) in toluene (15 mL) at 90° C. was added portionwise MnO$_2$ (2.08 g, 24 mmol) over a period of 0.5 h. The mixture was then diluted with EtOAc and filtered through celite. The filtrate was concentrated and the residue was purified by chromatography on silica gel to give 270 mg (48%) of the tiltle compound.

Step 7: 2-Benzoyl-6-[4-(bromomethyl)-phenyl]-quinolin-8-yl-phosphonic Acid Diethyl Ester To a solution of the product of step 6 (270 mg, 0.48 mmol) in EtOH was added acetyl chloride (0.05 mL). The mixture was stirred at rt for 0.5 h. The mixture was then concentrated in vacuo and redissolved in CH$_2$Cl$_2$ (2 mL). The resulting solution was added to POBr$_3$ (165 mg, 0.58 mmol) in a mixture of DMF (2.6 mL) and CH$_2$Cl$_2$ (5.2 mL) and stirred at rt for 0.5 h. H$_2$O was added and the mixture was extracted with EtOAc. The combined organic extracts were washed with brine, dried (anhyd. MgSO$_4$) and concentrated in vacuo. The residue was purified by chromatography on silica gel to give 248 mg (96%) of the title compound.

Step 8: 2-Benzoyl-6-{4-[3-Bromo-4-(difluoro-phosphono-methyl)benzylsulfanyl-methyl]-phenyl}-quinolin-8-yl-phosphonic Acid Diethyl Ester To a cold (−5° C.) solution of the product of step 7 (75 mg, 0.14 mmol) and (4-acetylsulfanylmethyl-2-bromo-phenyl)-difluoro-methyl phosphonic acid diethyl ester (59.9 mg, 0.14 mmol) in EtOH (1.5 mL) and THF (0.5 mL) was added NaOH (0.28 mmol, 1N). The mixture was stirred at −5° C. for 0.5 h. Aqueous NH$_4$Cl was added, and the mixture was extracted with EtOAc. The combined organic extracts were washed with brine, dried (anhyd. MgSO$_4$) and concentrated in vacuo. The residue was purified by chromatography on silica gel to give 90 mg (82%) of the title compound.

Step 9: 2-Benzoyl-6-{4-[3-Bromo-4-(difluoro-phosphono-methyl)benzylsulfanyl-methyl]-phenyl}-quinolin-8-yl-phosphonic Acid To a solution of the product of step 8 (90 mg, 0.114 mmol) in CHCl$_3$ (1.5 mL) was added TMSBr (0.2 mL). The mixture was heated to 90° C. for 2 h. The solution was concentrated in vacuo. EtOH (2 mL) was added, and the mixture was stirred at rt for 0.5 h. Concentration of the EtOH solution in vacuo gave (80 mg, 96%) of the title compound.

$^1$H NMR (DMSO-d$_6$) δ 3.76 (s, 2H), 3.80 (s, 2H), 7.43 (d, 1H), 7.55 (m, 5H), 7.62 (s, 1H), 7.70 (t, 1H), 7.81 (d, 2H), 8.19 (d, 1H), 8.60 (m, 4H), 8.72 (d, 1H).

Example 24

6-{4-[3-Bromo-4-(difluoro-phosphono-methyl)-benzylsulfanyl-methyl]-phenyl}-2-(1-methoxy-3-methyl-1-phenyl-butyl)-quinolin-8-yl-phosphonic Acid Step 1: 2-(1-Hydroxy-3-methyl-1-phenyl-butyl)-6-[4-(tetrahydro-pyran-2-yloxymethyl)-phenyl]-quinolin-8-yl-phosphonic Acid Diethyl Ester To a cold (0° C.) solution of the product of step 6 of Example 1 (180 mg, 0.322 mmol) in toluene (6 mL) was added isobutylmagnesium bromide (1.28 mmol; 2 M in Et$_2$O). The mixture was warmed to rt over 2 h. Aqueous NH$_4$Cl was added, and the mixture was extracted with EtOAc. The combined organic extracts were washed with brine, dried (anhyd. MgSO$_4$) and concentrated in vacuo. The residue was purified by chromatography on silica gel to give 140 mg (70%) of the title compound.

Step 2: 2-(1-Methoxy-3-methyl-1-phenyl-butyl)-6-[4-(tetrahydro-pyran-2-yloxymethyl)-phenyl]-quinolin-8-yl-phosphonic Acid Diethyl Ester To a cold (0° C.) solution of the product of step 1 (215 mg, 0.35 mmol) in THF (3 mL) was added NaH (28 mg, 0.7 mmol) and MeI (197 mg, 1.4 mmol). The mixture was warmed to rt for 2 h. Aqueous NH$_4$Cl was added, and the mixture was extracted with EtOAc. The combined organic extracts were washed with brine, dried (anhyd. MgSO$_4$) and concentrated in vacuo. The residue was purified by chromatography on silica gel to give 180 mg (81%) of the title compound.

Step 3: 6-{4-[3-Bromo-4-(difluoro-phosphono-methyl)-benzylsulfanylmethyl]-phenyl}-2-(1-methoxy-3-methyl-1-phenyl-butyl)-quinolin-8-yl-phosphonic Acid Following the procedure described in step 7 to step 9 of Example 1, the product of step 2 was converted to the title compound.

$^1$H NMR (DMSO-d$_6$) δ 0.68 (d, 3H), 0.79 (d, 3H), 3.75 (s, 2H), 3.78 (s, 2H), 7.23 (t, 1H), 7.35 (t, 2H), 7.40 (d, 1H), 7.47 (d, 4H), 7.55 (d, 1H), 7.60 (s, 1H), 7.75 (m, 3H), 8.48 (m, 2H), 8.61 (d, 1H).

Example 25

6-{4-[3-Bromo-4-(difluoro-phosphono-methyl)-benzylsulfanyl-methyl]-phenyl}-2-(1-methoxy-3-methyl-1-phenyl-propyl)-quinolin-8-yl-phosphonic acid Step 1: 2-(1-Hydroxy-3-methyl-1-phenyl-propyl)-6-[4-(tetrahydro-pyran-2-yloxymethyl)-phenyl]-quinolin-8-yl-phosphonic Acid Diethyl Ester To a cold (0° C.) solution of the product of step 6 of Example 1 (189 mg, 0.338 mmol) in toluene (6 mL) was added ethylmagnesium bromide (0.7 mmol; 1 M in Et$_2$O). The mixture was stirred at 0° C. for 1 h. Aqueous NH$_4$Cl was added, and the mixture was extracted with EtOAc. The combined organic extracts were washed with brine, dried (anhyd. MgSO$_4$) and concentrated in vacuo. The residue was purified by chromatography on silica gel to give 150 mg (74%) of the title compound.

Step 2: 2-(1-Methoxy-3-methyl-1-phenyl-propyl)-6-[4-(tetrahydro-pyran-2-yloxymethyl)-phenyl]-quinolin-8-yl-phosphonic Acid Diethyl Ester To a cold (0° C.) solution of the product of step 1 (150 mg, 0.25 mmol) in THF (2 mL) was added NaH (20 mg, 0.5 mmol; 60% in oil) and MeI (282 mg, 2 mmol). The mixture was warmed to rt for 2 h. Aqueous NH$_4$Cl was added, and the mixture was extracted with EtOAc. The combined organic extracts were washed with brine, dried (anhyd. MgSO$_4$) and concentrated in vacuo. The residue was purified by chromatography on silica gel to give 100 mg (64%) of the title compound.

Step 3: 6-{4-[3-Bromo-4-(difluoro-phosphono-methyl)-benzylsulfanylmethyl]-phenyl}-2-(1-methoxy-3-methyl-1-phenyl-propyl)-quinolin-8-yl-phosphonic Acid Following the procedure described in step 7 to step 9 of Example 1, the product of step 2 was converted to the title compound.

$^1$H NMR (DMSO-d$_6$) δ 0.68 (t, 3H), 2.70 (q, 2H), 3.18 (s, 3H), 3.75 (s, 2H), 3.78 (s, 2H), 7.21 (t, 1H), 7.31 (t, 2H), 7.42 (d, 1H), 7.49 (t, 4H), 7.55 (d, 1H), 7.60 (s, 1H), 7.70 (s, 1H), 7.74 (d, 2H), 8.49 (m, 2H), 8.55 (d, 1H)

Example 26

[4-(Biphenyl-4-ylmethylsulfanyl-methyl)-2-bromo-phenyl]-difluoro-methylphosphonic Acid Step 1: [4-(Biphenyl-4-ylmethylsulfanyl-methyl)-2-bromo-phenyl]-difluoromethyl-phosphonic Acid Diethyl Ester To a cold (−5° C.) solution of 4-(bromomethyl)-biphenyl (123 mg, 0.5 mmol) and (4-acetylsulfanylmethyl-2-bromo-phenyl)-difluoro-methyl phosphonic acid (215 mg, 0.5 mmol) in EtOH (4.5 mL) and THF (1.5 mL) was added NaOMe (54 mg, 1 mmol). The mixture was stirred at −5° C. for 0.5 h. Aqueous NH$_4$Cl was added, and the mixture was extracted with EtOAc. The combined organic extracts were washed with brine, dried (anhyd. MgSO$_4$) and concentrated in vacuo. The residue was purified by chromatography on silica gel to give 208 mg (83%) of the title compound.

Step 2: [4-(Biphenyl-4-ylmethylsulfanyl-methyl)-2-bromo-phenyl]-difluoromethyl-phosphonic Acid To a solution of the product of step 1 (200 mg, 0.4 mmol) in CHCl$_3$ (8 mL) was added TMSBr (613 mg, 4.0 mmol). The mixture was stirred at rt for 20 h. The solution was concentrated in vacuo. EtOH (2 mL) was added, and the mixture was stirred at rt for 0.5 h. Concentration of the EtOH solution in vacuo gave (200 mg, 100%) of the title compound.

$^1$H NMR (DMSO-d$_6$) δ 3.66 (s, 2H), 3.68 (s, 2H), 7.30 (m, 4H), 7.40 (t, 2H), 7.52 (s, 1H), 7.60 (q, 4H), 7.70 (d, 1H).

Example 27

[2-Bromo-4-(3'-methylsulfonyl-biphenyl-4-ylmethylsulfanyl-methyl)-phenyl]-difluoro-methyl-phosphonic Acid Step 1: 1-Bromo-3-methanesulfonylbenzene To a cold (0° C.) solution of 3-bromo-thioanisole (5.0 g, 24.6 mmol) in CH$_2$Cl$_2$ (100 mL) was added mcpba (15 g, 50 mmol, 56% pure). The mixture was stirred at 0° C. for 2 h and warmed to rt for 4 h. CH$_2$Cl$_2$ (150 mL) was added, the combined organic extracts were washed with NaOH (0.2 N), then with brine, dried (anhyd. MgSO$_4$) and concentrated in vacuo to give 5.7 g (98%) of the title compound.

Step 2: (3'-Methylsulfonyl-biphenyl-4-yl)-methanol

To a degassed solution of the product of step 1 (5.7 g, 24.2 mmol, ), and 4-hydroxymethylphenylboronic acid (5.47 g, 36 mmol) in toluene (150 mL) was added Pd$_2$(dba)$_3$ (1.09 g, 1.2 mmol). The mixture was degassed and Ph$_3$P (2.5 g, 9.6 mmol), Et$_2$NH (2.63 g, 36 mmol), n-propanol (18 mL) and H$_2$O (18 mL) was added. The mixture was heated to reflux for 26 h. Aqueous NaHCO$_3$ was added and the resulting mixture was extracted with EtOAc. The combined organic extracts were washed with brine, dried (anhyd. MgSO$_4$) and concentrated in vacuo. The residue was purified by chromatography on silica gel to give 6.06 g (95%) of the title compound.

Step 3: 4'-Bromomethyl-3-methanesulfonyl-biphenyl

To a cold (0° C.) solution of POBr$_3$ (1.37 g, 4.8 mmol) in a mixture of DMF (15 mL) and CH$_2$Cl$_2$ (30 mL) was added the product of step 2 (1.04 g, 42 mmol, ). The mixture was stirred at 0° C. for 1 h. H$_2$O was added and the mixture was extracted with EtOAc. The combined organic extracts were washed with brine, dried (anhyd. MgSO$_4$) and concentrated in vacuo. The residue was purified by chromatography on silica gel to give 1.2 g (92%) of the title compound.

Step 4: [2-Bromo-4-(3'-methylsulfonyl-biphenyl-4-ylmethylsulfanyl-methyl)phenyl]-difluoro-methyl-phosphonic Acid Diethyl Ester To a cold (−5° C.) solution of the product of step 3 (163 mg, 0.5 mmol) and (4-acetylsulfanylmethyl-2-bromo-phenyl)-difluoro-methyl phosphonic acid dtethyl ester (215 mg, 0.5 mmol) in EtOH (4.5 mL) nd THF (1.5 mL) was added NaOMe (54 mg, 1 mmol). The mixture was stirred at −5° C. for 0.5 h. Aqueous NH$_4$Cl was added, and the mixture was extracted with EtOAc. The combined organic extracts were washed with brine, dried (anhyd. MgSO$_4$) and concentrated in vacuo. The residue was purified by chromatography on silica gel to give 236 mg (74.5%) of the title compound.

Step 5: [2-Bromo-4-(3'-methylsulfonyl-biphenyl-4-ylmethylsulfanyl-methyl)phenyl]-difluoro-methyl-phosphonic Acid To a solution of the product of step 4 (236 mg, 0.37 mmol) in CHCl$_3$ (8 mL) was added TMSBr (627 mg, 4.1 mmol). The mixture was stirred at rt for 20 h. The solution was concentrated in vacuo. EtOH (2 mL) was added, and the mixture was stirred at rt for 0.5 h. Concentration of the EtOH solution in vacuo gave (230 mg, 100%) of the title compound.

$^1$H NMR (DMSO-d$_6$) δ 3.17 (s, 3H), 3.60 (s, 2HO, 3.66 (s, 2 h), 7.25 (d, 1H), 7.42 (d, 2H), 7.50 (s, 1H), 7.65 (d, 2H), 7.70 (t, 1H), 7.92 (d, 1H), 7.99 (d, 1H), 8.10 (d, 1H), 8.18 (s, 1H).

Example 28

[4-(Biphenyl-4-ylsulfanylmethyl)-2-bromo-phenyl]-difluoromethylphosphonic Acid Disodium Salt Step 1: Biphenyl-4-thiol To a suspension of 4-amino-biphenyl (5.1 g, 30.2 mmol) in 6M aqueous HCl (12 mL) at 0° C. was added 3 mL of acetone, followed by dropwise addition of 4M aqueous NaNO$_2$ (8 mL, 32 mmol) over ~15 min. After stirring for ~30 min., the mixture was added to a solution of potassium ethyl xanthate (6 g, 37.5 mmol) in $H_2O$ at 45° C. The diazonium salt solution was decomposed vigorously at one point. The mixture was further stirred for 30 min., cooled to r.t., diluted with $H_2O$ and extracted with EtOAc. The EtOAc extract was washed with diluted aqueous HCl, brine, dried (anhydrous $MgSO_4$) and concentrated. The crude xanthate intermediate was refluxed with KOH (8M, 12 mL; 96 mmol) in aqueous EtOH (EtOH: 50 mL; $H_2O$: 36 mL) for 1 h. After cooling to r.t., the mixture was diluted with $H_2O$, washed with $Et_2O$ (2×), the aqueous was then acidified and extracted with $Et_2O$. The ethereal extract was washed with $H_2O$ (2×), dried (anhydrous $MgSO_4$) and concentrated to give 2.8 g of the title compound as a white powder.

$^1H$ NMR (Acetone-$d_6$) δ 7.68-7.30 (m, 9H), 4.40 (s, 1H).
Step 2: [4-(Biphenyl-4-ylsulfanylmethyl)-2-bromo-phenyl]-difluoromethylphosphonic Acid Diethyl Ester To a solution of (2-bromo-4-bromomethylphenyl) difluoromethylphosphonic acid diethyl ester (320 mg, 0.73 mmol) and biphenyl-4-thiol (186 mg, 1.0 mmol) in EtOH (10 mL) at 0° C. was passed $N_2$ for 15 min and 2.6M NaOEt in EtOH (600 μL, 1.6 mmol) was added. After stirring for 15 min at 0° C., the mixture was diluted with $H_2O$ and extracted with EtOAc. The EtOAc extract was washed with brine, dried ($MgSO_4$) and concentrated. Chromatography over silica gel and elution with hexanes:EtOAc (1.5:1) afforded 280 mg (71%) of title compound as a pale yellow gum.

$^1H$ NMR (Acetone-$d_6$) δ 7.73 (s, 1H), 7.68-7.30 (m, 1H), 4.31 (s, 2H), 4.18 (m, 4H), 1.26 (t, 6H).
Step 3: [4-(Biphenyl-4-ylsulfanylmethyl)-2-bromo-phenyl]-difluoromethylphosphonic Acid Disodium Salt A solution of above coupling product (280 mg, 0.35 mmol) and bromotrimethylsilane (1.0 mL) in $CH_2Cl_2$ (5 mL) was stirred at r.t. overnight. Volatile materials were removed in vacuo. The residue was co-evaporated with ~90% aqueous EtOH (3×) to give the acid. Treatment with 2 equivalent of 1M aqueous NaOH in $H_2O$ and freeze-dried to give 250 mg of the title compound.

$^1H$ NMR (Methanol-$d_4$) δ 8.01 (d, 1H), 7.60-7.20 (m, 1H), 4.14 (s, 2H).

Example 29

[2-Bromo-4-(3-phenylallylsulfonylmethyl)phenyl]difluoromethylphosphonic Acid

The title compound was prepared in a similar manner as described for Example 3 from 2-bromo-4-(3-phenylallylsulfanylmethyl)phenylphosphonic acid diethyl ester, which was obtained from Example 10, step 1.

$^1H$ NMR (Acetone-$d_6$) δ 7.81 (s, 1H), 7.66 (d, 1H), 7.52 (d, 1H), 7.44 (d, 2H), 7.40-7.24 (m, 3H), 6.76 (d, 1H), 6.25 (m, 1H), 4.47 (s, 2H), 4.00 (d, 2H).

Example 30

[2-Bromo-4-(3-phenylallylsulfinylmethyl)phenyl]difluoromethylphosphonic Acid

To a 0° C. methanol (1 mL) and dichloromethane (1 mL) solution of {2-bromo-4-[(3-phenylprop-2-enylthio)methyl]phenyl}difluoromethylphosphonic acid (0.2 mmol., 0.1 g) was added magnesium monoperoxyphthalic acid (MMPP) (0.1 mmol., 0.062 g. of 80% MMPP) and the mixture was allowed to stir 1 hour at 0° C. and then 1 hour at room temperature. Acetic acid (0.1 mL) was added and the mixture was absorbed on Bondapak® C-18 125 Å silica and applied to a short column of the same absorbant using ethanol and water (1:1) to elute the title compound (0.06 g.).

$^1H$ NMR ($CD_3SOCD_3$) δ 7.85-8.0(1H, bm), 7.6(1H, s), 7.4-7.5(2H, d), 7.15-7.35(4H, m), 6.6-6.75(1H, d), 6.25-6.45 (1H, m), 4.15-4.25(1H, d), 3.9-4.0(1H, d), 3.7-3.8(1H, m), 3.5-3.6 (1H, m).

Example 31

(2-Bromo-4-methylsulfanylmethylphenyl)-difluoromethylphosphonic Acid Disodium Salt The title compound was prepared in a similar manner as described for Example 2 from thioacetic acid S-{3-bromo-4-[(diethoxyphosphoryl)difluoromethyl]benzyl ester and iodomethane.

$^1H$ NMR (MeOH-$d_4$) δ 8.10 (d, 1H), 7.55 (s, 1H), 7.27 (d, 1H), 3.63 (s, 2H), 1.96 (s, 3H).

Example 32

[2-Bromo-4-(cyclopropylmethylsulfanylmethyl)-phenyl]-difluoromethylphosphonic Acid Disodium Salt The title compound was prepared from thioacetic acid S-{3-bromo-4-[(diethoxyphosphoryl)difluoromethyl]benzyl ester and bromomethylcyclopropane in a similar manner as described for Example 10.

$^1H$ NMR ($CD_3OD$) δ 8.09 (d, 1H), 7.56 (s, 1H), 7.27(s, 1H), 3.72 (s, 2H), 2.33 (d, 2H), 0.93 (m, 1H), 0.51 (m, 2H), 0.15 (m, 2H).
M.S. (APCI) m/z 387 (M−H)⁻.

Example 33

[2-Bromo-4-(5-chloropyridin-2-ylsulfanylmethyl)-phenyl]-difluoromethylphosphonic Acid Disodium Salt
Step 1: [2-Bromo-4-(5-chloropyridin-2-ylsulfanylmethyl) phenyl]difluoromethylphosphonic Acid Diethyl Ester To a solution of 2-mercapto-5-chloropyridine (65 mg) (Biorg. & Med. Chem. Let. 1999, 9, 151) and (2-bromo-4-bromomethylphenyl)-difluoromethylphosphonic acid diethyl ester (150 mg) in acetonitrile was added cesium carbonate, the mixture was then stirred a R.T. for 2 hrs. then heated at 60° C. for 2 hrs. After cooling to R.T. ethyl acetate was added and the solution was washed with brine (2×), dried over magnesium sulfate, filtered and the solvent evaporated under vacuum. Purification by silica gel chromatography using 35% ethyl acetate/hexane afforded 114 mg of the title compound.
Step 2: [2-Bromo-4-(5-chloropyridin-2-ylsulfanylmethyl)-phenyl]-difluoromethylphosphonic Acid Disodium Salt The intermediate from step 1 was treated with bromotrimethylsilane as described for Example 10, step 2.

$^1H$ NMR ($CD_3OD$) δ 8.40 (s, 1H), 7.83 (d, 1H), 7.65(s, 2H), 7.60 (d, 1H), 7.36 (d, 1H), 7.22 (d, 1H), 4.38 (s, 2H).

Example 34

Methyl 2-[({[4-(difluorophosphonomethyl)-3-bromophenyl]methylthio}methyl)cyclopropyl]acetate
Step 1: Methyl 2-{[({4-[(diethylphosphono)difluoromethyl]-3-bromophenyl}methylthio)methyl] cyclopropyl}acetate To a 0° C. DMF (4 mL) suspension of diethyl (2-bromo-4-bromomethyl-phenyl)difluoro-methyl-phosphonic acid (0.75 mmol., 0.301 g.) and cesium carbonate (0.8 mmol., 0.26 g.) was added methyl 2-[(sulfanylmethyl)cyclopropyl]acetate (0.75 mmol., 0.12 g.) and the mixture was reacted for 30 minutes. It was then warmed to room temperature and aged for 1 hour. It was then poured over ice, diluted $NH_4Cl$ and ethyl acetate. The organic layer was separated and the aqueous further extracted with ethyl acetate. The combined organic layers were washed with brine, dried with magnesium sulphate, filtered and the solvent was removed in vacuo. The residue was purified by chromatography on $SiO_2$ using ethyl acetate and hexanes (1:1.5) to yield the title compound (0.333 g), slightly contaminated with unreacted bromide.

$^1H$ NMR ($CD_3COCD_3$) δ 7.75(1H, s), 7.6(1H, d), 7.5(1H, d), 4.1-4.3(4H, m), 3.85(2H, s), 3.6(3H, s), 2.65(2H, s), 2.45(2H, s), 1.35-1.45(6H, m), 0.55-0.4(4H, m); minor impurity at δ 3.3(s).

Step 2: Methyl 2-[({[4-(difluorophosphonomethyl)-3-bromophenyl]methylthio}methyl)cyclopropyl]acetate To a room temperature solution of the diester (0.676 mmol, 0.333 g) from step 1 in chloroform (3 mL) was added TMSiBr (5 mmol., 0.66 mL) and the mixture was stirred at room temperature for 16 hours. The volatils were removed in vacuo and the residue was dissolved in dichloromethane and cooled to $_0$° C. Ethanol (1 mL) was added and the mixture was stirred at room temperature for 1 hour. The mixture was evaporated to dryness and co-evaporated with toluene (3×) to yield the title compound slightly contaminated with [2-bromo-4-(bromomethyl)phenyl]difluoromethylphosphonic acid.

$^1$H NMR (CD$_3$COCD$_3$) δ 7.7(1H, s), 7.6-7.65(1H, d), 7.45(1H, d), 3.8(2H, s), 3.6(3H, s), 2.65(2H, s), 2.45(2H, s), 0.55-0.45(4H, m); minor impurity at δ 3.3(s).

Example 35
{2-Bromo-4-[(pyridin-3-ylthio)methyl]phenyl}(difluoro)methylphosphonic Acid Disodium Salt Step 1: 3-{[Tri(tert-butyl)silyl]thio}pyridine To a degassed solution of 3-bromopyridine (379 mg, 2.4 mmol) in benzene (7 mL) was added (Ph$_3$P)$_4$Pd (55 mg, 0.048 mmol). The mixture was degassed and a suspension of potassium triisopropylsilanethiolate (534 mg, 2.33 mmol) in THF (3 mL) was added. The mixture was heated to reflux for 0.5 h., NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 137 mg (20%) of the title compound.

Step 2: Diethyl {2-Bromo-4-[(pyridin-3-ylthio)methyl]phenyl}(difluoro)methylphosphonate To a degassed solution of the product of step 1 (128 mg, 0.5 mmol) and diethyl [2-bromo-4-(bromomethyl)phenyl](difluoro)methylphosphonate (0.5 mmol, 215 mg) in THF (4 mL) at 0° C. was added a solution of tetra-n-butylammonium fluoride (0.6 mL, 1M in THF). The mixture was stirred at 0° C. for 1.5 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 147 mg (63%) of the title compound.

Step 3: {2-Bromo-4-[(pyridin-3-ylthio)methyl]phenyl}(difluoro)methylphosphonic Acid Disodium Salt To a solution of the product of step 2 (147 mg, 0.32 mmol) in CHCl$_3$ (6.0 mL) was added TMSiBr (3.2 mmol, 489 mg). The mixture was stirred at r.t. for 24 h. The solution was concentrated in vacuo. MeOH (5 mL) was added, and the mixture was stirred at rt for 0.5 h. Concentration of the MeOH solution in vacuo gave an oil. The oil was dissolved in H$_2$O and EtOH, aqueous NaOH (0.63 mmol, 1N) was added and the solution was evaporated to dryness. The residue was redissolved in H$_2$O and freeze dried to give the title compound.

$^1$H NMR (MeOH-d$_4$) δ 4.19 (s, 2H), 7.28 (d, 1H), 7.34 (m, 1H), 7.54 (s, 1H), 7.79 (dt, 1H), 8.01 (d, 1H), 8.37 (d, 1H), 8.47 (s, 1H).

Example 36
2-[({[4-(Difluorophosphonomethyl)-3-bromophenyl]methylthio}methyl)cyclopropyl]acetic Acid To an ethanol (2 mL) solution of methyl 2-[({[4-(difluorophosphonomethyl)-3-bromophenyl]methylthio}methyl)cyclopropyl]acetate (0.52 mmol., 0.239 g.) from Example 34 was added 1M NaOH (2.5 mmol., 2.5 mL) and the mixture was stirred overnight. Most of the ethanol was removed in vacuo and the resisue was made slightly acidic (pH<6) with 3M HCl. Most of the water was coevaporated with ethanol and the residue was applied to a short pad of Bondapak® C18 125 Å silica eluting with a gradient of water and ethanol (2:1 to 1:2). The fractions containing the product were evaporated to dryness to yield the pure title compound.

$^1$H NMR (CD$_3$COCD$_3$) δ 7.65(1H, s), 7.6(1H, d), 7.4(1H, d), 3.7(2H, s), 2.5(2H, s), 2.3(2H, s), 0.4(4H, m); residues of ethanol present.

Example 37
({2-[4-({[4-(Difluorophosphonomethyl)-3-bromophenyl]methylthio}methyl)phenyl]phenyl}sulfonyl)(tert-butyl)amine Step 1: {[4-({[4-(2-{[(tert-Butyl)amino]sulfonyl}phenyl)phenyl]methylthio}methyl)-2-bromophenyl]difluoromethyl}diethoxyphosphino-1-one To a −78° C. dichloromethane (4 mL) solution of (tert-butyl)({2-[4-(hydroxymethyl)phenyl]phenyl}sulfonyl)amine (1 mmol., 0.319 g.; Ruel, R. et. al., Bioorg. Med. Chem. Lett. 9(1999) 2699–2704) was added methanesulfonyl chloride (1.1 mmol., 0.126 g.) and the mixture was warmed to 0° C. It was diluted with dichloromethane and poured on ice and diluted NaHCO$_3$. The organic layer was separated and the mixture was extracted again with dichloromethane. The combined organic layers were washed with brine, dried with magnesium sulphate, filtered and the solvent was removed in vacuo. The residue was used as such in the coupling reaction with diethyl (2-bromo-4-acetylthiomethyl-phenyl)-difluoro-methylphosphonic acid following the usual manner to give the title compound (0.258 g.).

$^1$H NMR (CD$_3$COCD$_3$) δ 8.15(1H, d), 7.7(1H, bs), 7.55-7.35(9H, m), 4.65(1H, NH), 4.15-4.35(4H, m), 3.75(4H, bs), 1.25-1.35(6H, t), 1.0(9H, s).

Step 2: ({2-[4-({[4-(Difluorophosphonomethyl)-3-bromophenyl]methylthio}methyl)phenyl]phenyl}sulfonyl)(tert-butyl)amine To a room temperature solution of the diester (0.37 mmol., 0.258 g) from step 1 in chloroform (3 mL) was added TMSiBr (3.7 mmol., 0.488 mL) and the mixture was stirred at room temperature for 16 hours. The volatils were removed in vacuo and the residue was dissolved in dichloromethane and cooled to 0° C. Ethanol (1 mL) was added and the mixture was stirred at room temperature for 1 hour. The mixture was evaporated to dryness and co-evaporated with toluene (3×) to yield the title compound (0.22 g.).

$^1$H NMR (CD$_3$COCD$_3$) δ 8.1(1H, d), 7.7-7.3(10H, m), 4.8-5.0(1H, NH), 3.7-3.8(4H, 2s), 1.0(9H, s).

Example 38
2-[4-({[4-(Difluorophosphonomethyl)-3-bromophenyl]methylthio}methyl)phenyl]benzenesulfonamide.

To a 0° C. solution of intermediate (0.17 mmol., 0.110 g) from step 2 of Example 37 in dichloromethane (3 mL) was added TFA (2 mL) and the mixture was stirred at room temperature for 16 hours. The volatiles were removed in vacuo to yield the title compound.

$^1$H NMR (CD$_3$COCD$_3$) δ 8.1(1H, d), 7.75-7.6(3H, m), 7.6-7.5(1H, m), 7.3-7.4(6H, m), 4.9-5.3(broad, exchangeable), 3.7-3.8(4H, 2s).

Example 39
(2-Bromo-4-{[(2-naphthylmethyl)thio]methyl}phenyl)(difluoro)methylphosphonic Acid The title compound was prepared from thioacetic acid S-{3-bromo-4-[diethoxyphosphoryl)difluoromethyl]benzyl ester and 2-(bromomethy)naphthalene in a similar manner as described for Example 10.

$^1$H NMR (Acetone-d$_6$) δ 3.70 (s, 2H), 3.86 (s, 2H), 7.45 (m, 4H), 7.63 (m, 2H), 7.75 (s, 1H), 7.86 (m, 3H).

Example 40
(2-Bromo-4-{[(quinolin-2-ylmethyl)thio]methyl}phenyl)(difluoro)methylphosphonic Acid The title compound was prepared from thioacetic acid S-{3-bromo-4-[diethoxyphosphoryl)difluoromethyl]benzyl ester and α-chloroquinaldine in a similar manner as described for Example 10.

$^1$H NMR (MeOH-d$_4$) δ 3.66 (s, 2H), 3.92 (s, 2H), 7.26 (d, 1H), 7.54 (m, 3H), 7.74 (t, 1H), 7.89 (d, 1H) 7.94 (d, 1H), 8.05 (d, 1H), 8.26 (d, 1H).

Example 41
{2-Bromo-4-[4-(1-H-tetrazol-5-yl)benzylsulfanylmethyl]phenyl}difluoromethylphosphonic Acid Trisodium Salt Step 1: 4-(1H-Tetrazol-5-yl)benzoic Aicd Methyl Ester A mixture of methyl 4-cyanobenzoate (3.3 g, 20.5 mmol), sodium azide (4.0 g, 61.5 mmol) and pyridine hydrochloride (3.7 g, 32.0 mmol) in 1-methyl-2-pyrrolidine (100 mL) was heated at 100° C. overnight. After cooling, the mixture was diluted with H$_2$O, acidified with 6M aqueous HCl. The precipitate formed was collected, washed with H$_2$O and dried under vacuum to give 3.0 g (73%) of the title compound as a white powder.

$^1$H NMR (Acetone-d$_6$) δ 8.24 (m, 4H), 3.94 (s, 3H).

Step 2: 4-(1-Trityl-1H-tetrazol-5-yl)benzoic Aicd Methyl Ester

A mixture of 4-(1H-tetrazol-5-yl)benzoic aicd methyl ester (1.0 g, 5.0 mmol), triphenylmethyl chloride (1.6 g, 5.7 mmol) and triethylamine (1.5 mL, 10.8 mmol) in DMF (30 mL) was stirred at r. t. for 4 h. After diluting with H$_2$O, the precipitate formed was collected, washed with H$_2$O and dissolved in EtOAc. The EtOAc solution was washed with H$_2$O, dried (MgSO$_4$) and concentrated to give 2.5 g of the crude title compound as a white powder.

$^1$H NMR (Acetone-d$_6$) δ 8.20 (m, 4H), 7.45-7.15 (m, 15H), 3.90 (s, 3H).

Step 3: 4-(1-Trityl-1H-tetrazol-5-yl)methanol

To a solution of 4-(1-trityl-1H-tetrazol-5-yl)benzoic aicd methyl ester (1.4 g, 3.1 mmol) in THF (40 mL) at −78° C. was added DIBAL-H (1.5 mL, 8.4 mmol). The cooling bath was then removed and the mixture was slowly warmed to r. t. After cooling back to −78° C., the mixture was carefully quenched with H$_2$O, saturated aqueous NaHCO$_3$ and Et$_2$O were added. The mixture was stirred at r. t. for 30 min. and filtered through celite. The filter cake was washed with Et$_2$O. The combined filtrates were washed with H$_2$O, dried (MgSO$_4$) and concentrated. Chromatography over silica gel and elution with hexanes:EtOAc (1.5:1) gave 750 mg of the title compound.

$^1$H NMR (Acetone-d$_6$) δ 8.04 (d, 2H), 7.51 (d, 2H), 7.38 (m, 9H), 7.18 (m, 6H), 4.70 (m, 2H), 4.35 (t, 1H).

Step 4: 5-(4-Bromomethylphenyl)-1-trityl-1H-tetrazole

To a solution of 4-(1-trityl-1H-tetrazol-5-yl)methanol (720 mg, 1.7 mmol) and triphenylphosphine (590 mg, 2.3 mmol) in THF (15 mL) at 0° C. was added N-bromosuccinimde (400 mg, 2.3 mmol) and stirred for 15 min. The cooling bath was removed and the mixture was stirred for another 15 min. Sovent was then removed in vacuo. Chromatography over silica gel and elution with hexanes:EtOAc (5:1) yielded 700 mg of white powders, which was swished with Et$_2$O to give 480 mg (59%) of the title compound as a white powder.

$^1$NMR (Acetone-d$_6$) δ 8.07 (d, 2H), 7.62 (d, 2H), 7.40 (m, 9H), 7.18 (m, 6H), 4.71 (s, 2H).

Step 5: {2-Bromo-4-[4-(1-H-tetrazol-5-yl)benzylsulfanylmethyl]phenyl}-difluoromethylphosphonic Acid Trisodium Salt To a solution of thioacetic acid S-{3-bromo-4-[(diethoxyphosphoryl)difluoromethyl]benzyl ester (220 mg, 0.51 mmol) and -(4-bromomethylphenyl)-1-trityl-1H-tetrazole (270 mg, 0.56 mmol) in EtOH (6 mL) at 0° C. was passed N$_2$ for 15 min and 2M aqueous NaOH (520 μL, 1.04 mmol) was added. After stirring for 15 min at 0° C., the mixture was diluted with H$_2$O and extracted with EtOAc. The EtOAc extract was washed with brine, dried (MgSO$_4$) and concentrated. Chromatography over silica gel and elution with hexanes:EtOAc (1.5:1) afforded 170 mg of coupling intermediate. The trityl group was then removed with catalytic amount of p-TsOH (20 mg) in EtOH (5 mL) and acetone (2 mL) at r.t. for 2 h. Further deprotection with bromotrimethysilane gave the free acid and tri-sodium salt was prepared.

$^1$H NMR (Methanol-d$_4$) δ 8.04 (d, 1H), 7.98 (d, 2H), 7.54 (s, 1H), 7.38 (d, 2H), 7.27 (d, 1H), 3.65 (s, 2H), 3.60 (s, 2H).

Example 42
(2-Bromo-4-{[(4-pyridin-3-ylbenzyl)thio]methyl}phenyl)(difluoro)methylphosphonic Acid Disodium Salt Step 1: Diethyl (2-bromo-4-{[(4-pyridin-3-ylbenzyl)thio]methyl}phenyl)(difluoro)methylphosphonate To a degassed solution of diethyl (2-bromo-4-{[(4-bromobenzyl)thio]methyl}phenyl)(difluoro)methylphosphonate (172 mg, 0.31 mmol), 3-(1,3,2-dioxaborinan-2-yl)pyridine (75.5 mg, 0.46 mmol) and Pd(dba)$_3$ (14.1 mg, 0.05 mmol) in toluene (3 mL) was added Ph$_3$P (32.5 mg, 0.124 mmol). The mixture was degassed, Et$_2$NH (34 mg, 0.465 mmol) and n-PrOH (0.38 mL) was added. The mixture was heated to 90° C. for 20 h. The mixture was cooled, diluted with EtOAc, and washed with H$_2$O and brine, dried (anhyd. MgSO$_4$) and concentrated in vacuo.

The residue was purified by chromatography on silica gel to give 56 mg (32%) of the title compound.

Step 2: (2-Bromo-4-{[(4-pyridin-3-ylbenzyl)thio]methyl}phenyl)(difluoro)methylphosphonic Acid Disodium Salt To a solution of the product of step 1 (56 mg, 0.1 mmol) in CHCl$_3$ (2 mL) was added TMSBr (153 mg, 1.0 mmol). The mixture was stirred at rt for 20 h. The solution was concentrated in vacuo. EtOH (2 mL) was added, and the mixture was stirred at rt for 0.5 h. Concentration of the EtOH solution in vacuo gave 66 mg of an oil. The oil was dissolved in H$_2$O and EtOH, aqueous NaOH (0.2 mmol, 1N) was added and the solution was evaporated to dryness. The residue was redissolved in H$_2$O and freeze dried to give the title compound.

$^1$H NMR (MeOH-d$_4$) δ 3.61 (s, 2H), 3.67 (s, 2H), 7.41 (m, 3H), 7.50 (m, 2H), 7.62 (d, 2H), 7.95 (d, 1H), 8.10 (d, 1H), 8.49 (d, 1H), 8.80 (s, 1H).

Example 43
4'-[({3-Bromo-4-[difluoro(phosphono)methyl]benzyl}thio)methyl]-1,1'-biphenyl-3-ylphosphonic Acid Step 1: Diethyl 3-iodophenylphosphonate The title compound was prepared as described by T. Hirad et al in Synthesis 1981, p. 56 using 1,3-diodobenzene.

Step 2: Diethyl 4'-(hydroxymethyl)-1,1'-biphenyl-3-ylphosphonate

To the product of Step 1 (680 mg, 2 mmol) in toluene (10 mL)—H$_2$O (3 mL)—n Propanol (3 mL) were added 4-hydroxymethyl phenyl boronic acid (607 mg, 4 mmol), Pd(dba)$_3$ (92 mg, 0.1 mmol), triphenylphosphine (209 mg, 0.8 mmol) and EtNH (175 mg, 2.4 mmol). After a period of 18 h at 90° C., the reaction mixture was partionned between EtOAc and H$_2$O. The organic phase was separated, dried over NaSO$_4$, filtered and evaporated under reduced pressure. The title compound was obtained after flash chromatography (446 mg, 69%).

Step 3: Diethyl 4'-(bromomethyl)-1,1'-biphenyl-3-ylphosphonate

To a solution of POBr$_3$ (1.13 g, 3.97 mmol) in CH$_2$Cl$_2$ (30 mL) was added DMF (15 mL) at 0° C. The mixture was stirred at 0° C. for 0.5 h, then a solution of the product of step 2 (1.06 g, 3.3 mmol) was added. The mixture was stirred at 0° C. for 1 h. The reaction mixture was partitioned between EtOAc and aqueous NaHCO$_3$. The organic phase was separated, dried over Na$_2$SO$_4$, filtered and evaporated under reduced pressure. The title compound was obtained after flash chromatography (1.1 g, 87%).

Step 4: Diethyl {2-bromo-4-[({[3'-(diethoxyphosphoryl)-1,1'-biphenyl-4-yl]methyl}thio)methyl]phenyl}(difluoro) methylphosphonate To a cold (−5° C.) solution of the product of step 3 (192 mg, 0.5 mmol) and S-{3-bromo-4-[(diethoxyphosphoryl) (difluoro)methyl]benzyl}ethanethioate (215 mg, 0.5 mmol) in EtOH (4.5 mL) and THF (1.5 mL) was added NaOMe (1.0 mmol, 54 mg). The mixture was stirred at −5° C. for 1 h. Aqueous NH$_4$Cl was added, and the mixture was extracted with EtOAc. The combined organic extracts were washed with brine, dried (anhyd. MgSO$_4$) and concentrated in vacuo. The residue was purified by chromatography on silica gel to give 246 mg (71%) of the title compound.

Step 5: 4'-[({3-Bromo-4-[difluoro(phosphono)methyl] benzyl}thio)methyl]-1,1'-biphenyl-3-ylphosphonic Acid To a solution of the product of step 4 (90 mg, 0.114 mmol) in CHCl$_3$ (1.5 mL) was added TMSBr (0.2 mL). The mixture was heated to 70° C. for 2.5 h. The solution was concentrated in vacuo. EtOH (2 mL) was added, and the mixture was stirred at rt for 0.5 h. Concentration of the EtOH solution in vacuo gave the title compound.

$^1$H NMR (MeOH-d$_4$) δ 3.29 (s, 2H), 3.30 (s, 2H), 7.36 (m, 3H), 7.60 (m, 5H), 7.80 (m, 2H), 8.04 (d, 1H).

Example 44

(2-Bromo-4-{[(2-phenoxyethyl)thio]methyl}phenyl) (difluoro)methylphosphonic Acid Disodium Salt Step 1: Diethyl (2-bromo-4-{[(2-phenoxyethyl)thio] methyl}phenyl)(difluoro)methylphosphonate To a mixture of diethyl (2-bromo-4-{[(2-hydroxyethyl) thio]methyl}phenyl)(difluoro)methylphosphonate (0.113 mmol, 49 mg), phenol (0.23 mmol, 21.6 mg), triphenylphosphine (0.23 mmol, 60 mg) in THF (1.5 mL) was added a solution of diisopropylazodicarboxylate (0.23 mmol, 46.5 mg) in THF (0.2 mL) slowly. The mixture was stirred at r.t. for 20 h. Chromatography of the mixture gave 42 mg (72%) of the title compound Step 2: (2-Bromo-4-{[(2-phenoxyethyl)thio] methyl}phenyl)(difluoro)methylphosphonic Acid Disodium Salt To a solution of the product of step 1 (42 mg, 0.082 mmol) in CHCl$_3$ (1.0 mL) was added TMSBr (0.82 mmol, 126 mg). The mixture was stirred at r.t. for 24 h. The solution was concentrated in vacuo. EtOH (2 mL) was added, and the mixture was stirred at rt for 0.5 h. Concentration of the EtOH solution in vacuo gave an oil. The oil was dissolved in H$_2$O and EtOH, aqueous NaOH (0.164 mmol, 1N) was added and the solution was evaporated to dryness. The residue was redissolved in H$_2$O and freeze dried to give the title compound.

$^1$H NMR (MeOH-d$_4$) δ 2.75 (t, 2H), 3.79 (s, 2H), 4.11 (t, 2H), 6.89 (m, 3H), 7.27 (m, 3H), 7.58 (s, 1H), 8.11 (d, 1H).

Example 45

2-Bromo-4-[({(2E)-3-[3-(methylsulfonyl)phenyl]prop-2-enyl}thio)methyl]phenyl}(difluoro)methylphosphonic Acid Disodium Salt Step 1: tert-Butyl (2E)-3-[3-(methylsulfonyl)phenyl] acrylate To a degassed solution of 1-bromo-3-(methylsulfonyl) benzene (1.17 g, 5 mmol) in DMF (10 mL) was added tert-butyl acrylate (1.28 g, 10 mmol), Pd(OAc)$_2$ (56 mg, 0.25 mmol), triphenylphosphine (196 mg, 0.75 mmol) and triethylamine (1.01 g, 10 mmol). The mixture was degassed and heated to 80° C. for 20 h. H$_2$O was added and the resulting mixture was extracted with EtOAc. The combined organic extracts were washed with brine, dried (anhyd. MgSO$_4$) and concentrated in vacuo. The residue was purified by chromatography on silica gel to give 1.1 g (78%) of the title compound.

Step 2: (2E)-3-[3-(Methylsulfonyl)phenyl]prop-2-en-1-ol

To a solution of tert-butyl (2E)-3-[3-(methylsulfonyl) phenyl]acrylate (818 mg, 2.9 mmol) in THF (12 mL) at −78° C. was added diisobutylaluminum hydride (10.5 mmol, 1.5 M in toluene). The mixture was stirred at −78° C. for 4 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 260 mg (42%) of the title compound.

Step 3: 1-[(1E)-3-Bromoprop-1-enyl]-3-(methylsulfonyl) benzene

To a solution of POBr$_3$ (420 mg, 1.47 mmol) in CH$_2$Cl$_2$ (8 mL) was added DMF (3 mL) at 0° C. The mixture was stirred at 0° C. for 0.25 h, then a solution of the product of step 2 (260 mg, 1.22 mmol) was added. The mixture was stirred at 0° C. for 1 h. The reaction mixture was partitioned between EtOAc and aqueous NaHCO$_3$. The organic phase was separated, dried over Na$_2$SO$_4$, filtered and evaporated under reduced pressure. The title compound was obtained after flash chromatography (317 mg, 94%).

Step 4: S-{(2E)-3-[3-(methylsulfonyl)phenyl]prop-2-enyl}ethanethioate

To a solution of the product of step 3 (317 mg, 1.15 mmol) in DMF (5 mL) was added potassium thioacetate (153 mg, 1.34 mmol). The mixture was stirred at r.t. for 4 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 270 mg (86%) of the title compound.

Step 5: di(tert-Butyl) {2-bromo-4-[({(2E)-3-[3-(methylsulfonyl)phenyl]prop-2-enyl}thio)methyl]phenyl} (difluoro)methylphosphonate To a degassed solution of the product of step 4 (135 mg, 0.5 mmol) in EtOH (3 mL) and THF (0.5 mL) at 0° C. was added NaOMe (54 mg, 1 mmol) and di(tert-butyl) [2-bromo-4-(bromomethyl)phenyl](difluoro)methylphosphonate (246 mg, 0.5 mmol). The mixture was stirred at 0° C. for 1 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 230 mg (71%) of the title compound.

Step 6: {2-Bromo-4-[({(2E)-3-[3-(methylsulfonyl)phenyl] prop-2-enyl}thio)methyl]phenyl}(difluoro) methylphosphonic Acid Disodium Salt To a solution of the product of step 5 (230 mg, 0.36 mmol) in HOAc (5.0 mL) was added H$_2$O (0.75 mL). The mixture was stirred at r.t. for 24 h. The solution was concentrated in vacuo. The residual oil was dissolved in H$_2$O and EtOH, aqueous NaOH (0.72 mmol, 1N) was added and the solution was evaporated to dryness. The residue was redissolved in H$_2$O and freeze dried to give the title compound.

$^1$H NMR (MEOH-D$_4$) Δ 3.16 (S, 3H), 3.27 (D, 2H), 3.72 (S, 2H), 6.38 (M, 1H), 6.55 (D, 1H), 7.32 (D, 1H), 7.60 (M, 2H), 7.76 (D, 1H) 7.82 (D, 1H) 7.99 (M, 2H).

Example 46

{4-[(Benzylthio)methyl]-2-bromophenyl}(difluoro) methylphosphonic acid disodium salt Step 1: Diethyl {4-[(benzylthio)methyl]-2-bromophenyl} (difluoro)methylphosphonate.

To a degassed solution of phenylmethanethiol (0.5 mmol, 62.1 mg) in EtOH (5 mL) was added NaOMe (1 mmol, 54 mg). The mixture was stirred at r.t. for 0.25 h and then a solution of diethyl [2-bromo-4-(bromomethyl)phenyl] (difluoro)methylphosphonate (0.5 mmol, 215 mg) in THF (0.5 mL) was added. The mixture was stirred at r.t. for 2 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 174 mg (73%) of the title compound.

Step 2: 4-[(Benzylthio)methyl]-2-bromophenyl}(difluoro) methylphosphonic Acid Disodium Salt To a solution of the product of step 1 (170 mg, 0.355 mmol) in CHCl$_3$ (6.0 mL) was added TMSBr (3.55 mmol, 550 mg). The mixture was stirred at r.t. for 24 h. The solution was concentrated in vacuo. MeOH (5 mL) was added, and the mixture was stirred at rt for 0.5 h. Concentration of the MeOH solution in vacuo gave an oil. The oil was dissolved in H$_2$O and EtOH, aqueous NaOH (0.71 mmol, 1N) was added and the solution was evaporated to dryness. The residue was redissolved in H$_2$O and freeze dried to give the title compound.

$^1$H NMR (MeOH-d$_4$) δ 3.54 (s, 2H), 3.59 (s, 2H), 7.25 (m, 6H), 7.48 (s, 1H), 8.10 (d, 1H).

Example 47

(2-Bromo-4-[(4-chlorobenzyl)sulfanyl]methylphenyl) (difluoro)methylphosphonic Acid Disodium Salt Step 1: (2-Bromo-4-{[(4-chlorobenzyl)thio]methyl}phenyl) (difluoro)methylphosphonic Acid Disodium Salt To a degassed solution of (4-chlorophenyl)methanethiol (0.5 mmol, 79 mg) in EtOH (5 mL) was added NaOMe (1 mmol, 54 mg). The mixture was stirred at r.t. for 0.25 h and then a solution of [2-bromo-4-(bromomethyl)phenyl] (difluoro)methylphosphonic acid diethyl ester (0.5 mmol, 215 mg) in THF (0.5 mL) was added. The mixture was stirred at r.t. for 2 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 189 mg (73%) of the title compound.

Step 2: Diethyl (2-bromo-4-{[(4-chlorobenzyl)thio] methyl}phenyl)(difluoro)methylphosphonate To a solution of the product of step 1 (180 mg, 0.35 mmol) in CHCl$_3$ (6.0 mL) was added TMSBr (3.5 mmol, 543 mg). The mixture was stirred at r.t. for 24 h. The solution was concentrated in vacuo. MeOH (5 mL) was added, and the mixture was stirred at rt for 0.5 h. Concentration of the MeOH solution in vacuo gave an oil. The oil was dissolved in H$_2$O and EtOH, aqueous NaOH (0.71 mmol, 1N) was added and the solution was evaporated to dryness. The residue was redissolved in H$_2$O and freeze dried to give 174 mg of the title compound.

$^1$H NMR (MeOH-d$_4$) δ 3.56 (s, 2H), 3.58 (s, 2H), 7.21 (d, 1H), 7.28 (m, 4H), 7.48 (s, 1H), 8.10 (d, 1H).

Example 48

(2-Bromo-4-{[(4-tert-butylbenzyl)thio]methyl}phenyl) (difluoro)methylphosphonic Acid Disodium Salt Step 1 4-(tert-Butyl)benzyl ethanethioate To a solution of 1-(bromomethyl)-4-(tert-butyl)benzene (4 mmol, 908 mg) in DMF (15 mL) was added potassium thioacetate (4.4 mmol, 501 mg). The mixture was stirred at r.t. for 3 h. H$_2$O was added and the resulting mixture was extracted with EtOAc. The combined organic extracts were washed with brine, dried (anhyd. MgSO$_4$) and concentrated in vacuo. The residue was purified by chromatography on silica gel to give 800 mg (90%) of the title compound.

Step 2: Ethyl (2-bromo-4-{[(4-tert-butylbenzyl)thio] methyl}phenyl)(difluoro)methylphosphonate To a solution of the product of step 1 (0.5 mmol, 111 mg) in EtOH (5 mL) was added NaOMe (1 mmol, 54 mg). The mixture was stirred at r.t. for 0.25 h and then a solution of diethyl [2-bromo-4-(bromomethyl)phenyl](difluoro) methylphosphonate (0.5 mmol, 215 mg) in THF (0.3 mL) was added. The mixture was stirred at r.t. for 3 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 170 mg (63%) of the title compound.

Step 3: (2-Bromo-4-{[(4-tert-butylbenzyl)thio]methyl] phenyl)(difluoro)methylphosphonic Acid Disodium Salt To a solution of the product of step 2 (170 mg, 0.317 mmol) in CHCl$_3$ (6.0 mL) was added TMSBr (3.17 mmol, 486 mg). The mixture was stirred at r.t. for 24 h. The solution was concentrated in vacuo. MeOH (5 mL) was added, and the mixture was stirred at rt for 0.5 h. Concentration of the MeOH solution in vacuo gave an oil. The oil was dissolved in H$_2$O and EtOH, aqueous NaOH (0.71 mmol, 1N) was added and the solution was evaporated to dryness. The residue was redissolved in H$_2$O and freeze dried to give the title compound.

$^1$H NMR (MeOH-d$_4$) δ 1.30 (s, 9H), 3.55 (s, 2H), 3.56 (s, 2H), 7.20 (m, 3H), 7.32 (d, 2H), 7.49 (s, 1H), 8.06 (d, 1H).

Example 49

[2-Bromo-4-({[4-(3-methyl-1,2,4-oxadiazol-5-yl)benzyl] thio}methyl)phenyl](difluoro)methylphosphonic Acid Disodium Salt Step 1: Ethyl 4-(3-methyl-1,2,4-oxadiazol-5-yl)benzoate A degassed solution of Ethyl 4-iodobenzoate (2.76 g, 10 mmol) in toluene (45 mL) was added (1Z)-N'-hydroxyethanimidamide (2.22 g, 30 mmol), Pd(PPh$_3$)$_2$Cl$_2$ (350 mg, 0.5 mmol), and Et$_3$N (2.02 g, 20 mmol). The mixture was purged with CO and heated to reflux under 1 atm of CO for 20 h. H$_2$O was added and the resulting mixture was extracted with EtOAc. The combined organic extracts were washed with brine, dried (anhyd. MgSO$_4$) and concentrated in vacuo. The residue was purified by chromatography on silica gel to give 455 mg (20%) of the title compound.

Step 2: [4-(3-Methyl-1,2,4-oxadiazol-5-yl)phenyl]methanol

To a cold (0° C.) solution of the product of step 1 (455 mg, 1.96 mmol) in toluene (5 mL) was added a solution of diisobutylaluminum hydride (4 mL, 1.5M in toluene). The mixture was stirred at 0° C. for 2 h. Aqueous HCl (1N) was added. The mixture was stirred at r.t. for 0.25 h and then extracted with EtOAc. The combined organic extracts were washed with brine, dried (anhyd. MgSO$_4$) and concentrated in vacuo. The residue was purified by chromatography on silica gel to give 130 mg (35%) of the title compound.

Step 3: 4-(3-Methyl-1,2,4-oxadiazol-5-yl)benzyl bromide

To a solution of POBr$_3$ (234 mg, 0.82 mmol) in CH$_2$Cl$_2$ (5 mL) was added DMF (2.5 mL) at 0° C. The mixture was stirred at 0° C. for 0.25 h, then a solution of the product of step 2 (130 mg, 0.68 mmol) was added. The mixture was stirred at 0° C. for 1 h. The reaction mixture was partionned between EtOAc and aqueous NaHCO$_3$. The organic phase was separated, dried over Na$_2$SO$_4$, filtered and evaporated under reduced pressure. The title compound was obtained after flash chromatography (160 mg, 92%).

Step 4: 4-(3-Methyl-1,2,4-oxadiazol-5-yl)benzyl ethanethioate

To a solution of the product of step 3 (160 mg, 0.63 mmol) in DMF (2.5 mL) was added potassium thioacetate (80 mg, 0.695 mmol). The mixture was stirred at r.t. for 3 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 124 mg (80%) of the title compound.

Step 5: Diethyl [2-bromo-4-({[4-(3-methyl-1,2,4-oxadiazol-5-yl)benzyl]thio}methyl)phenyl](difluoro)methylphosphonate To a degassed solution of the product of step 4 (0.5 mmol, 124 mg) in EtOH (5 mL) was added NaOMe (1 mmol, 54 mg). The mixture was stirred at r.t. for 0.25 h and then a solution of diethyl [2-bromo-4-(bromomethyl)phenyl](difluoro)methylphosphonate (0.5 mmol, 215 mg) in THF (0.5 mL) was added. The mixture was stirred at r.t. for 2 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 200 mg (35%) of the title compound.

Step 6: [2-Bromo-4-({[4-(3-methyl-1,2,4-oxadiazol-5-yl)benzyl]thio}methyl)phenyl](difluoro)methylphosphonic Acid Disodium Salt To a solution of the product of step 5 (200 mg, 0.35 mmol) in CHCl$_3$ (6.0 mL) was added TMSBr (3.5 mmol, 543 mg). The mixture was stirred at r.t. for 24 h. The solution was concentrated in vacuo. MeOH (5 mL) was added, and the mixture was stirred at rt for 0.5 h. Concentration of the MeOH solution in vacuo gave an oil. The oil was dissolved in H$_2$O and EtOH, aqueous NaOH (0.71 mmol, 1N) was added and the solution was evaporated to dryness. The residue was redissolved in H$_2$O and freeze dried to give the title compound.

Example 50
{2-Bromo-4-[(quinolin-3-ylthio)methyl]phenyl}(difluoro)methylphosphonic Acid Disodium Salt Step 1: 3-[(Triisopropylsilyl)thio]quinoline To a degassed solution of 3-bromoquinoline (452 mg, 2.17 mmol) in benzene (7 mL) was added (Ph$_3$P)$_4$Pd (50 mg, 0.043 mmol). The mixture was degassed and a suspension of potassium triisopropylsilanethiolate (475 mg, 2.07 mmol) in THF (3 mL) was added. The mixture was heated to reflux for 3 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 341 mg (50%) of the title compound.

Step 2: Diethyl{2-bromo-4-[(quinolin-3-ylthio)methyl]phenyl}(difluoro)methylphosphonate To a degassed solution of the product of step 1 (158 mg, 0.5 mmol) and diethyl [2-bromo-4-(bromomethyl)phenyl](difluoro)methylphosphonate (0.5 mmol, 215 mg) in THF (4 mL) at 0° C. was added a solution of tetra-n-butylammonium fluoride (0.6 mL, 1M in THF). The mixture was stirred at 0° C. for 1.5 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 167 mg (64%) of the title compound.

Step 3: {2-Bromo-4-[(quinolin-3-ylthio)methyl]phenyl}(difluoro)methylphosphonic Acid Disodium Salt To a solution of the product of step 2 (167 mg, 0.32 mmol) in CHCl$_3$ (6.0 mL) was added TMSBr (3.2 mmol, 489 mg). The mixture was stirred at r.t. for 24 h. The solution was concentrated in vacuo. MeOH (5 mL) was added, and the mixture was stirred at rt for 0.5 h. Concentration of the MeOH solution in vacuo gave an oil. The oil was dissolved in H$_2$O and EtOH, aqueous NaOH (0.64 mmol, 1N) was added and the solution was evaporated to dryness. The residue was redissolved in H$_2$O and freeze dried to give the title compound.

$^1$H NMR (MeOH-d$_4$) δ 4.27 (s, 2H), 7.28 (d, 1H), 7.58 (m, 2H), 7.71 (t, 1H), 7.85 (d, 1H), 7.96 (m, 2H), 8.24 (s, 1H), 8.73 (s, 1H).

Example 51
[2-Bromo-4-(4-fluorophenylsulfanylmethyl)phenyl]difluoromethylphosphonic Acid Disodium Salt Step 1: 2-Bromo-4-(4-fluorophenylsulfanylmethyl)phenylphosphonic Acid Diethyl Ester To a solution of (2-bromo-4-bromomethylphenyl)difluoromethylphosphonic acid diethyl ester (150 mg, 0.34 mmol) and 4-fluorothiophenol (48 mg, 0.38 mmol) in EtOH (4 mL) at 0° C. was passed N$_2$ for 15 min and 2M aqueous NaOH (180 μL, 0.36 mmol) was added. After stirring for 15 min at 0° C., the mixture was diluted with H$_2$O and extracted with EtOAc. The EtOAc extract was washed with brine, dried (MgSO$_4$) and concentrated. Chromatography over silica gel and elution with hexanes:EtOAc (1.5:1) afforded 170 mg (quantitative yield) of title compound as an oil.

$^1$H NMR (Acetone-d$_6$) δ 7.64 (s, 1H), 7.55(d, 1H), 7.40 (m, 3H), 7.06 (m, 2H), 4.26-4.08 (m, 6H), 1.28 (t, 6H).

Step 2: [2-Bromo-4-(4-fluorophenylsulfanylmethyl)phenyl]difluoromethylphosphonic Acid Disodium Salt A solution of above coupling product (170 mg, 0.35 mmol) and bromotrimethylsilane (0.8 mL) in CH$_2$Cl$_2$ (4 mL) was stirred at r.t. overnight. Volatile materials were removed in vacuo. The residue was co-evaporated with ~90% aqueous EtOH (3×) to give the acid. Treatment with 2 equivalent of 1M aqueous NaOH in H$_2$O and freeze-dried to give 150 mg of the title compound.

$^1$H NMR (Methanol-d$_4$) δ 8.04 (d, 1H), 7.43 (s, 1H), 7.33 (m, 2H), 7.16 (d, 1H), 7.01 (m, 2H), 4.03 (s, 2H).

Example 52
{2-Bromo-4-[({4-[3-(methylsulfonyl)phenyl]but-3-ynyl}thio)methyl]phenyl}(difluoro)methylphosphonic Acid Disodium Salt Step 1: 1-Bromo-3-(methylsulfonyl)benzene To a solution of 3-bromothioanisole (8.4 g, 41 mmol) in CH$_2$Cl$_2$ (150 mL) was added mcpba (19 g, 66 mmol) at 0° C. The mixture was warmed to r.t. and was stirred for 3 h. The mixture was diluted with CH$_2$Cl$_2$ and washed twice with aqueous NaOH (1N) and brine. The combined organic extracts were dried (anhyd. MgSO$_4$) and concentrated in vacuo to give 9.1 g (94%) of the title compound.

Step 2: 4-[3-(Methylsulfonyl)phenyl]but-3-yn-1-ol

To a degassed solution of 1-bromo-3-(methylsulfonyl)benzene (1.17 g, 5 mmol) in CH$_3$CN (29 mL) was added (Ph$_3$P)$_4$Pd (58 mg, 0.05 mmol), CuI (29 mg, 0.152 mmol), and Et$_3$N (5.8 mL). The mixture was heated to 80° C. for 2 h. The residue was dissolved in EtOAc and filtered through a short pad of silica gel. Concentration of the filtrate gave an oil. The oil was purified by chromatography on silica gel to give 957 mg (85%) of the title compound.

Step 3: 1-(4-Bromobut-1-ynyl)-3-(methylsulfonyl)benzene

To a solution of the product of step 2 (224 mg, 1 mmol) and triphenylphosphine (288 mg, 1.1 mmol) in THF (5 mL) was added at 0° C. N-bromosuccinimide (265 mg, 1.5 mmol). The mixture was stirred at 0° C. for 1 h. The solvent was concentrated in vacuo. The residue was purified by chromatography on silica gel to give 193 mg (67%) of the title compound.

Step 4: S-{4-[3-(Methylsulfonyl)phenyl]but-3-ynyl}ethanethioate

To a solution of the product of step 3 (950 mg, 3.3 mmol) in DMF (25 mL) was added potassium thioacetate (415 mg, 3.64 mmol). The mixture was stirred at r.t. for 3 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 888 mg (95%) of the title compound.

Step 5: Di(tert-butyl) 12-bromo-4-[({4-[3-(methylsulfonyl)phenyl]but-3-ynyl}thio)methyl]phenyl}(difluoro)methylphosphonate To a degassed solution of the product of step 4 (141 mg, 0.5 mmol) in EtOH (3 mL) and THF (0.5 mL) at 0° C. was added NaOMe (54 mg, 1 mmol) and di(tert-butyl) [2-bromo-4-(bromomethyl)phenyl](difluoro)methylphosphonate (246 mg, 0.5 mmol). The mixture was stirred at 0° C. for 1 h. NH$_4$Cl was added and the resulting mixture was extracted with EtOAc. The combined organic extracts were washed with brine, dried (anhyd. MgSO$_4$) and concentrated in vacuo. The residue was purified by chromatography on silica gel to give 220 mg (67%) of the title compound.

Step 6: {2-Bromo-4-[({4-[3-(methylsulfonyl)phenyl]but-3-ynyl}thio)methyl]phenyl}(difluoro)methylphosphonic Acid Disodium Salt To a solution of the product of step 5 (220 mg, 0.34 mmol) in HOAc (5.0 mL) was added H$_2$O (0.75 mL). The mixture was stirred at r.t. for 24 h. The solution was concentrated in vacuo. The residual oil was dissolved in H$_2$O and EtOH, aqueous NaOH (0.68 mmol, 1N) was added and the solution was evaporated to dryness. The residue was redissolved in H$_2$O and freeze dried to give the title compound.

$^1$H NMR (MeOH-d$_4$) δ 2.74 (m, 4H), 3.14 (s, 3H), 3.87 (s, 2H), 7.46 (d, 1H), 7.62 (m, 2H), 7.72 (m, 2H), 7.89 (d, 1H), 7.95 (s, 1H).

Example 53

[2-Bromo-4-(4-cyanobenzylsulfanylmethyl)phenyl]difluoromethylphosphonic Acid Disodium Salt The title compound was prepared from thioacetic acid S-{3-bromo-4-[diethoxyphosphoryl)difluoromethyl]benzyl ester and 4-cyanobenzyl bromide in a similar manner as described for Example 10.

$^1$H NMR (Methanol-d$_4$) δ 8.08 (d, 1H), 7.66 (d, 2H), 7.45 (m, 3H), 7.20 (d, 1H), 3.67 (s, 2H), 3.59 (s, 2H).

Example 54

[2-Bromo-4-(3-phenylpropylsulfanylmethyl)phenyl]difluoromethylphosphonic acid disodium salt Step 1: Thioacetic acid S-(3-phenylpropyl)ester To a solution of 1-bromo-3-phenylpropane (6.0 g, 30.1 mmol) in DMF (100 mL) at r.t. was added potassium thioacetate (4.0 g, 35.1 mmol) and stirred for 1 h. After dilution with H$_2$O, the mixture was extracted with EtOAc. The residue was then passed through a short pad of silica in a sintered glass funnel, washed with hexanes:EtOAc (4:1) to give 6.0 g of the title compound as a light brown oil.

$^1$H NMR (Acetone-d$_6$) δ 7.35-7.10 (m, 5H), 2.86 (t, 2H), 2.68 (t, 2H), 2.30 (s, 3H), 1.86 (m, 2H).

Step 2: [2-Bromo-4-(3-phenylpropylsulfanylmethyl)phenyl]difluoromethylphosphonic Acid Diethyl Ester To a solution of (2-bromo-4-bromomethylphenyl)difluoromethylphosphonic acid diethyl ester (450 mg, 1.03 mmol) and thio acetic acid S-(3-phenylpropyl)ester (220 mg, 1.13 mmol) in EtOH (12 mL) at 0° C. was passed N$_2$ for 15 min and 2M aqueous NaOH (1.1 mL, 2.2 mmol) was added. After stirring for 15 min at 0° C., the mixture was diluted with H$_2$O and extracted with EtOAc. The EtOAc extract was washed with brine, dried (MgSO$_4$) and concentrated. Chromatography over silica gel and elution with hexanes:EtOAc (2:1) afforded 240 mg (45%) of title compound.

$^1$H NMR (Acetone-d$_6$) δ 7.74 (s, 1H), 7.58 (d, 1H), 7.45 (d, 2H), 7.30-7.10 (m, 5H), 4.30-4.10 (m, 4H), 3.80 (s, 2H), 2.66 (t, 2H), 2.45 (t, 2H), 1.35 (m, 2H), 1.30 (t, 6H).

Step 3: [2-Bromo-4-(3-phenylpropylsulfanylmethyl)phenyl]difluoromethylphosphonic Acid Disodium Salt A solution of above coupling product (240 mg, 0.46 mmol) and bromotrimethylsilane (1.0 mL) in CH$_2$Cl$_2$ (5 mL) was stirred at r.t. overnight. Volatile materials were removed in vacuo. The residue was co-evaporated with ~90% aqueous EtOH (3×) to give the acid. Treatment with 2 equivalent of 1M aqueous NaOH in H$_2$O and freeze-dried to give the title compound.

$^1$H NMR (Methanol-d$_4$) δ 8.06 (d, 1H), 7.53 (s, 1H), 7.26-7.10 (m, 6H), 3.65 (s, 2H), 2.66 (t, 2H), 2.38 (t, 2H), 1.85 (m, 2H).

Example 55

[2-Bromo-4-(1-methyl-3-phenylpropylsulfanylmethyl)phenyl]difluoromethylphosphonic Acid Disodium Salt Step 1: (3-Bromobutyl)benzene To a solution of 4-phenyl-2-butanol (1.5 g, 10 mmol) and triphenylphosphine (3.5 g, 13.3 mmol) in THF (50 mL) at r.t. was added N-bromosuccinimide (2.4 g, 13.5 mmol) and the mixture was stirred for 1 h. Some alcohol starting material remained, more triphenylphosphine (1.5 g, 5.7 mmol) and N-bromosuccinimde (1.0 g, 5.6 mmol) was added. After further stirring for 30 min., no starting material remained and solvent was removed in vacuo. The residue was filtered through silica in a sintered glass funnel, washed with hexanes:EtOAc (9:1) to afford 2.3 g of the title compound as a pale yellow oil.

$^1$H NMR (Acetone-d$_6$) δ 7.35 (m, 5H), 4.16 (m, 1H), 2.90-2.65 (m, 2H), 2.10 (m, 2H), 1.72 (d, 3H).

Step 2: Thioacetic acid S-(1-methyl-3-phenylpropyl)ester

A mixture of (3-bromobutyl)benzene (2.3 g, 10.8 mmol) and potassium thioacetate (1.4 g, 12.3 mmol) in DMF (30 mL) was stirred at r.t. for 1 h, diluted with H$_2$O and extracted with EtOAc. The EtOAc extract was washed with H$_2$O (2×), dried (MgSO$_4$) and concentrated. Chromatography over silica gel, elution with hexanes:EtOAc (9:1) and the late fractions were polled to give 950 mg of the title compound, which contaminated with small amount of (3-bromobutyl)benzene.

$^1$HNMR (Acetone-d$_6$) δ 7.30-7.10 (m, 5H), 3.52 (m, 1H), 2.68 (m, 2H), 2.29 (s, 3H), 1.86 (m, 2H), 1.31 (d, 3H).

Step 3: [2-Bromo-4-(1-methyl-3-phenylpropylsulfanylmethyl)phenyl]difluoromethylphosphonic Acid Diethyl Ester To a solution of (2-bromo-4-bromomethylphenyl)difluoromethylphosphonic acid diethyl ester (230 mg, 0.53 mmol) and thioacetic acid S-(1-methyl-3-phenylpropyl) ester (130 mg, 0.63 mmol) in EtOH (6 mL) at 0° C. was passed $N_2$ for 15 min and 2M aqueous NaOH (0.65 mL, 1.3 mmol) was added. After stirring for 15 min at 0° C., the mixture was diluted with $H_2O$ and extracted with EtOAc. The EtOAc extract was washed with brine, dried ($MgSO_4$) and concentrated. Chromatography over silica gel and elution with hexanes:EtOAc (2:1) afforded 160 mg (58%) of title compound.

$^1$H NMR (Acetone-$d_6$) δ 7.75 (s, 1H), 7.60 (d, 1H), 7.47 (d, 1H), 7.30-7.10 (m, 5H), 4.20 (m, 4H), 3.83 (s, 2H), 2.65 (m, 3H), 1.90-1.70 (m, 2H), 1.28 (m, 9H).

Step 4: [2-Bromo-4-(1-methyl-3-phenylpropylsulfanylmethyl)phenyl]difluoromethylphosphonic Acid Disodium Salt A solution of above coupling product (160 mg, 0.31 mmol) and bromotrimethylsilane (1.0 mL) in $CH_2Cl_2$ (5 mL) was stirred at r.t. overnight. Volatile materials were removed in vacuo. The residue was co-evaporated with ~90% aqueous EtOH (3×) to give the acid. Treatment with 2 equivalent of 1M aqueous NaOH in $H_2O$ and freeze-dried to give the title compound.

$^1$H NMR (Methanol-$d_4$) δ 8.03 (d, 1H), 7.55 (s, 1H), 7.26-7.10 (m, 6H), 3.68 (s, 2H), 2.75-2.55 (m, 3H), 1.85-1.70 (m, 2H), 1.26 (d, 3H).

Example 56

{2-Bromo-4-[3'-methanesulfonylamino-4'-(3-methylbutoxy)biphenyl-4-ylmethylsulfanylmethyl]phenyl}difluoromethylphosphonic Acid Trisodium Salt Step 1: Ethyl 5-iodo-2-(3-methylbutoxy)benzoate To a solution of 5-iodosalicylic acid (26.4 g, 0.1 mol) in EtOH (300 mL0 at 0° C. was added dropwise acetyl chloride (30 mL). The mixture was then refluxed for 2 days. Volatile materials were removed in vacuo. The residue was diluted with EtOAc, washed with $H_2O$ (3×), dried ($MgSO_4$) and concentrated to give 29 g of ethyl 5-iodosalicylate as a light brown solid.

A mixture of ethyl 5-iodosalicylate (12.0 g, 41 mmol), 1-bromo-3-methylbutane (7.0 mL, 58 mmol) and $Cs_2CO_3$ (13.6 g, 41.7 mmol) in DMF (150 mL) was heated at 60° C. for 2 h and then 80° C. for 1 h. After cooling to room temperature, the mixture was diluted with $H_2O$ and extracted with $Et_2O$. The $Et_2O$ extract was washed with $H_2O$ (2×), dried ($MgSO_4$) and concentrated. Chromatography over silica gel and elution with hexanes:EtOAc (9:1) afforded 11.6 g (78%) of the title compound as a colorless oil.

$^1$H NMR (Acetone-$d_6$) δ 7.94 (s, 1H), 7.75 (d, 1H), 6.98 (d, 1H), 4.28 (q, 2H), 4.08 (t, 2H), 1.90 (m, 2H), 1.32 (t, 3H), 0.95 (d, 6H).

Step 2: N-[5-Iodo-2-(3-methylbutoxy)phenyl][(4-methoxyphenyl)methoxy]formamide

A mixture of ethyl 5-iodo-2-(3-methylbutoxy)benzoate (5.8 g, 16 mmol) and 1 M aqueous NaOH (40 mL, 40 mmol) in EtOH: $H_2O$ (2:1, 120 mL) was heated at 80° C. for 2 h. Volatile materials were removed in vacuo. The residue was diluted with $H_2O$ (100 mL), acidified with 1 M aqueous HCl (~50 mL) and extracted with EtOAc. The EtOAc extract was washed with $H_2O$ (2×), dried ($MgSO_4$) and concentrated to give 4.8 g (90%) of 5-iodo-2-(3-methylbutoxy)benzoic acid as a white solid.

A mixture of 5-iodo-2-(3-methylbutoxy)benzoic acid (2.4 g, 7.2 mmol), diphenylphosphoryl azide (1.7 mL, 7.9 mmol), 4-methoxybenzyl alcohol (2.0 mL, 16 mmol) and $Et_3N$ (1.1 mL, 7.9 mmol) in toluene (20 mL) was refluxed for 2 h. The reaction was quite vigorous at the beginning. Volatile materials were then removed in vacuo. The residue was chromatographed over silica gel and eluted with hexanes:EtOAc (9:1) to afford 3.2 g (95%) of the title compound as a colorless oil.

$^1$H NMR (Acetone-$d_6$) δ 8.43 (s, 1H), 7.77 (s, 1H), 7.37 (d, 2H), 7.31 (d, 1H), 6.93 (d, 2H), 6.84 (d, 1H), 5.10 (s, 2H), 4.08 (t, 2H), 3.79 (s, 3H), 1.80 (m, 1H), 1.70 (m, 2H), 0.92 (d, 6H).

Step 3: N-{5-[4-(Hydroxymethyl)phenyl]-2-(3-methylbutoxy)phenyl}[(4-methoxyphenyl)methoxy]formamide A mixture of N-[5-iodo-2-(3-methylbutoxy)phenyl][(4-methoxyphenyl)methoxy]formamide (3.2 g, 6.8 mmol), 4-(hydroxymethyl)benzene boronic acid (1.2 g, 7.8 mmol), 2M aqueous $Na_2CO_3$ (8.0 mL, 16.0 mmol) and [1,1'-bis(diphenylphosphino)ferrocene]dichloropalladium(II), complex with dichloromethane (1:1) (50 mg) was heated at 85° C. for 2 h. After cooling to room temperature, the mixture was diluted with $H_2O$, extracted with EtOAc. The EtOAc extract was washed with $H_2O$ (2×), dried ($MgSO_4$) and concentrated. Chromatography over silica gel and elution with hexanes:EtOAc (1:1) yielded 2.1 g (68%) of the title compound as a light brown solid.

$^1$H NMR (Acetone-$d_6$) δ 8.40 (s, 1H), 7.72 (s, 1H), 7.55 (d, 2H), 7.40 (m, 4H), 7.28 (d, 1H), 7.08 (d, 1H), 6.94 (d, 2H), 5.13 (s, 2H), 4.66 (d, 2H), 4.20 (t, 1H), 4.14 (t, 2H), 3.80 (s, 3H), 1.84 (m, 1H), 1.73 (m, 2H), 0.95 (d, 6H).

Step 4: N-{5-[4-(Bromomethyl)phenyl]-2-(3-methylbutoxy)phenyl}[(4-methoxyphenyl)methoxy]formamide To a solution of N-{5-[4-(hydroxymethyl)phenyl]-2-(3-methylbutoxy)phenyl}[(4-methoxyphenyl)methoxy]formamide (1.0 g, 2.2 mmol) and triphenylphosphine (650 mg, 2.5 mmol) in THF (15 mL) at 0° C. was added N-bromosuccinimide (450 mg, 2.5 mmol). After stirring for 30 min. TLC showed starting alcohol remained. More triphenylphosphine (130 mg, 0.5 mmol) and N-bromosuccinimde (90 mg, 0.5 mmol) were added. After further stirring at 0° C. for 15 min, almost no starting alcohol remained. Solvent was removed in vacuuo. The residue was chromatographed over silica gel and eluted with hexanes:EtOAc (4:1) to afford 1.2 g of the title compound as a yellow oil.

$^1$H NMR (Acetone-$d_6$) δ 8.41 (s, 1H), 7.75 (s, 1H), 7.59 (d, 2H), 7.53 (d, 2H), 7.39 (d, 2H), 7.31 (d, 1H), 7.10 (d, 1H), 6.94 (d, 2H), 5.13 (s, 2H), 4.70 (s, 2H), 4.15 (t, 2H), 3.80 (s, 3H), 1.84 (m, 1H), 1.74 (m, 2H), 0.95 (d, 6H).

Step 5: {2-Bromo-4-[3'-methanesulfonylamino-4'-(3-methylbutoxy)biphenyl-4-ylmethylsulfanylmethyl]phenyl}difluoromethylphosphonic Acid Trisodium Salt N-{5-[4-(Bromomethyl)phenyl]-2-(3-methylbutoxy)phenyl}[(4-methoxyphenyl)methoxy]formamide was converted to N-{5-[4-(acetylthiomethyl)phenyl]-2-(3-methylbutoxy)phenyl}[(4-methoxyphenyl)methoxy]formamide in a similar manner as described in step 1, Example 54. The thioacetate intermediate was then coupled with (2-bromo-4-bromomethylphenyl)difluoromethylphosphonic diethyl ester in step 2, Example 54.

$^1$H NMR (Acetone-$d_6$) δ 8.40 (s, 1H), 7.74 (s, 1H), 7.70 (s, 1H), 7.62 (d, 1H), 7.54 (d, 2H), 7.50 (d, 1H), 7.38 (m, 4H), 7.28 (d, 1H), 7.10 (d, 1H), 6.94 (d, 2H), 5.14 (s, 2H), 4.20 (m, 4H), 4.15 (t, 2H), 3.80 (s, 3H), 3.76 (s, 2H), 3.74 (s, 2H), 1.85 (m, 1H), 1.72 (m, 2H), 1.30 (t, 6H), 0.95 (d, 6H).

To a solution of the above coupling product (550 mg, 0.67 mmol) in $CH_2Cl_2$ at 0° C. was added trifluoroacetic acid (1 mL). The cooling bath was removed and the mixture was stirred for 1 h. After quenching with saturated aqueous $NaHCO_3$, the mixture was extracted with $CH_2Cl_2$. Chromatography over silica gel and elution with hexanes:EtOAc (1.5:1) afforded 290 mg of an amino intermediate. To a solution of the amino intermediate (290 mg, 0.44 mmol) and pyridine (200 µL) in CH$_2$Cl$_2$ (5 mL) at 0° C. was added methanesulfonyl chloride (100 µL). The cooling bath was removed and the mixture was stirred for 3 h. After dilution with more CH$_2$Cl$_2$, the mixture was washed successively with diluted aqueous HCl, brine, dried (MgSO$_4$) and concentrated. Chromatography over silica gel and elution with hexanes:EtOAc (1.5:1, then 1:1) gave 240 mg of a methanesufonamide intermediate as a pale yellow gum.

$^1$H NMR (Acetone-d$_6$) δ 7.82 (s, 1H), 7.75 (s, 1H), 7.69 (s, 1H), 7.62 (d, 1H), 7.56 (d, 2H), 7.45 (m, 2H), 7.38 (d, 2H), 7.18 (d, 1H), 4.20 (m, 6H), 3.76 (s, 2H), 3.74 (s, 2H), 2.99 (s, 3H), 1.90 (m, 1H), 1.76 (m, 2H), 1.30 (t, 6H), 0.97 (d, 6H).

The diethyl phosphonate group in the above methanesulfonamide intermediate was deprotected with bromotrimethylsilane as described in step 3, Example 54. Treatment of the acid intermediate with 3 equivalent of 1M aqueous NaOH in H$_2$O and freeze-dried provided the title compound as a white foam.

$^1$H NMR (Methanol-d$_4$) δ 8.12 (d, 1H), 7.60 (s, 1H), 7.52 (m, 3H), 7.32 (m, 3H), 7.24 (d, 1H), 7.03 (d, 1H), 4.10 (t, 2H), 3.62 (s, 2H), 3.58 (s, 2H), 2.89 (s, 3H), 1.89 (m, 1H), 1.75 (m, 2H), 0.99 (d, 6H).

Example 57

[2-Bromo-4-(3-methanesulfonylaminobenzylsulfanylmethyl)phenyl] difluoromethylphosphonic Acid Trisodium Salt Step 1: N-(3-Chloromethylphenyl)methanesulfonamide To a solution of 3-aminobenzyl alcohol (2.5 g, 20.3 mmol) and pyridine (6.5 mL) in CH$_2$Cl$_2$ (100 mL) at 0° C. was added methanesulfonyl chloride (4.0 mL). The cooling bath was removed, the mixture was warmed to r.t. and stirred overnight (TLC showed 2 spots after 1 h, but 1 spot after overnight). After dilution with H$_2$O, the mixture was acidified with 6M aqueous HCl. The CH$_2$Cl$_2$ layer was separated, washed with H$_2$O (2x), dried (MgSO$_4$) and concentrated. Chromatography over silica gel and elution with hexanes:E-tOAc (1:1) gave 1.9 g (43%) the title compound as a colorless oil.

$^1$H NMR (Acetone-d$_6$) δ 8.66 (s, 1H), 7.42 (s, 1H), 7.40-7.20 (m, 3H), 4.70 (s, 2H), 3.00 (s, 3H).

MS (API 2000, -ESI) m/z 218, 220 (M$^-$-1).

Step 2: [2-Bromo-4-(3-methanesulfonylaminobenzylsulfanylmethyl)phenyl] difluoromethylphosphonic Acid Trisodium Salt The chloride from step 1 was converted to a thioacetate, then coupled with (2-bromo-4-bromomethylphenyl) difluoromethylphosphonic acid diethyl ester and followed by the deprotection reaction as described for Example 54 to give the title compound.

$^1$H NMR (Methanol-d$_4$) δ 8.06 (d, 1H), 7.51 (s, 1H), 7.24 (d, 1H), 7.08 (m, 2H), 6.98 (d, 1H), 6.70 (d, 1H), 3.57 (s, 2H), 3.52 (s, 2H), 2.82 (s, 3H).

Example 58

{2-Bromo-4-[2-(4-bromophenyl)ethylsulfanylmethyl] phenyl}difluoromethylphosphoinc Acid Disodium Salt Step 1: 1-Bromo-(2-bromoethyl)benzene To a solution of 4-bromophenethyl alcohol (5.0 g, 24.9 mmol) and triphenylphosphine (8.5 g, 32.4 mmol) in THF (100 mL) at 0° C. was added N-bromosuccinimde (5.8 g, 32.6 mmol). The cooling bath was then removed and the mixture was stirred at r.t. for 1 h. Some alcohol starting material remained, more triphenylphosphine (1.0 g, 3.8 mmol) and N-bromosuccinimde (0.68 g, 3.8 mmol) was added. After further stirring for 30 min., no starting material remained and solvent was removed in vacuo. The residue was chromatographed over silica gel and eluted with hexanes:EtOAc (4:1) afforded 5.5 g (84%) of the title compound as a colorless oil.

$^1$H NMR (Acetone-d$_6$) δ 7.50 (d, 2H), 7.25 (d, 2H), 3.68 (t, 2H), 3.15 (t, 2H).

Step 2: Thioacetic acid S-[2-(4-bromophenyl)ethyl]ester

To a solution of 1-bromo-(2-bromoethyl)benzene (1.0 g, 3.8 mmol) in DMF (15 mL) at r.t. was passed N$_2$ for 15 min, cooled to 0° C. and potassium thioacetate (0.5 g, 4.4 mmol) was added. The mixture was slowly warmed to r.t., and stirred for 1 h, diluted with H$_2$O and extracted with EtOAc. The EtOAc extract was washed with H$_2$O (2x), dried (MgSO$_4$) and concentrated. Chromatography over silica gel and elution with hexanes:EtOAc (5:1) yielded 695 mg (71%) of the title compound as a colorless oil.

$^1$H NMR (Acetone-d$_6$) δ 7.46 (d, 2H), 7.22 (d, 2H), 3.08 (t, 2H), 2.83 (t, 2H).

Step 3: {2-Bromo-4-[2-(4-bromophenyl) ethylsulfanylmethyl]phenyl}difluoromethylphosphoinc acid diethyl ester To a solution of (2-bromo-4-bromomethylphenyl) difluoromethylphosphonic acid diethyl ester (250 mg, 0.57 mmol) and thioacetic acid S-[2-(4-bromophenyl)ethyl]ester (170 mg, 0.66 mmol) in EtOH (10 mL) at 0° C. was passed N$_2$ for 15 min and 2.6M sodium ethoxide in EtOH (0.5 mL, 1.3 mmol) was added. After stirring for 30 min at 0° C., the mixture was diluted with H$_2$O and extracted with EtOAc. The EtOAc extract was washed with brine, dried (MgSO$_4$) and concentrated. Chromatography over silica gel and elution with hexanes:EtOAc (1.5:1) afforded 250 mg (77%) of title compound as a pale yellow oil.

$^1$H NMR (Acetone-d$_6$) δ 7.75 (s, 1H), 7.61 (d, 1H), 7.51 (d, 1H), 7.44 (d, 2H), 7.17 (d, 2H), 4.20 (m, 4H), 3.84 (s, 2H), 2.80 (m, 2H), 2.68 (m, 2H), 1.28 (t, 6H).

Step 4: {2-Bromo-4-[2-(4-bromophenyl) ethylsulfanylmethyl]phenyl}difluoromethylphosphoinc Acid Disodium Salt A solution of above coupling product from step 3 (250 mg, 0.44 mmol) and bromotrimethylsilane (0.8 mL) in CH$_2$Cl$_2$ (4 mL) was stirred at r.t. overnight. Volatile materials were removed in vacuo. The residue was co-evaporated with ~90% aqueous EtOH (3x) to give the acid. Treatment with 2 equivalent of 1M aqueous NaOH in H$_2$O and freeze-dried to give the title compound as a white powder.

$^1$H NMR (Methanol-d$_4$) δ 8.08 (d, 1H), 7.52 (s, 1H), 7.40 (d, 2H), 7.24 (d, 2H), 7.10 (d, 2H), 3.66 (s, 2H), 2.80 (t, 2H), 2.60 (t, 2H).

Example 59

[2-Bromo-4-(4-bromophenylsulfanylmethyl)phenyl] difluoromethylphosphonic Acid Disodium Salt The title compound was prepared in a similar manner as described for Example 51 from 4-bromothiophenol and (2-bromo-4-bromomethylphenyl)difluoromethylphosphonic acid diethyl ester.

$^1$H NMR (Methaol-d$_4$) δ 8.04 (d, 1H), 7.51 (s, 1H), 7.38 (d, 2H), 7.20 (m, 3H), 4.10 (s, 2H).

Example 60

{2-Bromo-4-[4-(4-bromophenylsulfanyl)butyl] phenyl}difluoromethylphosphonic Acid Disodium Salt Step 1: Ethyl 4-(4-aminophenyl)butyrate To a solution of 4-(4-nitrophenyl)butyric acid (10.0 g, 47.8 mmol) in EtOH (200 mL) at 0° C. was added acetyl chloride (15 mL). The mixture was then refluxed for 2 h.

Most of the ethanol was removed in vacuo. The residue was diluted with EtOAc and washed with H₂O, dried (MgSO₄) and concentrated to give 11.0 g (97%) of ethyl 4-(4-nitrophenyl)butyrate as a pale yellow oil. A solution of ethyl 4-(4-nitrophenyl)butyrate (11.0 g, 46.4 mmol) and 10% palladium on carbon (0.5 g) in EtOAc (150 mL) was hydrogenated under 50 psi for 2 h. After filtration, solvent was evaporated in vacuo to give 9.5 g (99%) of the title compound as a pale yellow oil.

¹H NMR (Acetone-d₆) δ 6.87 (d, 2H), 6.57 (d, 2H), 4.40 (br s, 2H), 4.04 (d, 2H), 2.45 (t, 2H), 2.24 (t, 2H), 1.80 (m, 2H), 1.19 (t, 3H).

Step 2: 2-Bromo-4-(4-hydroxybutyl)benzaldehyde

The ethyl 4-(4-aminophenyl)butyrate intermediate from step 1 was converted to the title compound in a similar manner as described for the preparation of 2-bromo-4-hydroxymethyl-benzaldehyde (step 1, 2 and 3 in the synthesis of (2-bromo-4-bromomethylphenyl)difluoromethylphosphonic acid diethyl ester).

¹H NMR (Acetone-d₆) δ 10.26 (s, 1H), 7.80 (d, 1H), 7.62 (s, 1H), 7.40 (d, 1H), 3.55 (m, 2H), 3.45 (t, 1H), 2.74 (t, 2H), 1.74 (m, 2H), 1.54 (m, 2H).

Step 3: 2-Bromo-4-(4-bromobutyl)benzaldehyde

To a solution of 2-bromo-4-(4-hydroxybutyl)benzaldehyde (9.0 g, 35 mmol) and triphenylphosphine (12 g, 46 mmol) in THF (150 mL) at 0° C. was added N-bromosuccinimide (8.0 g, 45 mmol). The cooling bath was removed and the mixture was stirred at r.t. for 30 min. The whole mixture was passed through a short pad of silica in a sintered glass funnel, washed with hexanes:EtOAc (5:1). The filtrate was evaporated in vacuo. Chromatography over silica gel and elution with hexanes:EtOAc (10:1) afforded 10.9 g of the title compound as a pale yellow oil.

¹H NMR (Acetone-d₆) δ 10.26 (s, 1H), 7.80 (d, 1H), 7.65 (s, 1H), 7.44 (d, 1H), 3.52 (t, 2H), 2.26 (t, 2H), 1.95-1.75 (m, 4H).

Step 4: [2-Bromo-4-(4-bromobutyl)phenyl]difluoromethylphosphonic Acid Diethyl Ester)

The 2-bromo-4-(4-bromobutyl)benzaldehyde intermediate from step 3 was converted to the title compound in a similar manner as described for the preparation of 2-bromo-4-hydroxymethyl-benzaldehyde (step 5, 6 and 7 in the synthesis of (2-bromo-4-bromomethylphenyl)difluoromethylphosphonic acid diethyl ester).

¹H NMR (Acetone-d₆) δ 7.64 (s, 1H), 7.58 (d, 1H), 7.38 (d, 1H), 4.20 (m, 4H), 3.52 (t, 2H), 2.72 (t, 2H), 1.95-1.75 (m, 4H), 1.30 (t, 6H).

Step 5: {2-Bromo-4-[4-(4-bromophenylsulfanyl)butyl]phenyl}difluoromethylphosphonic Acid Disodium Salt The title compound was prepared in a similar manner as described for Example 51 from 4-bromothiophenol and [2-bromo-4-(4-bromobutyl)phenyl]difluoromethylphosphonic acid diethyl ester).

¹H NMR (Methaol-d₄) δ 8.02 (d, 1H), 7.42 (m, 3H), 7.21 (d, 2H), 7.12 (d, 1H), 2.94 (t, 2H), 2.59 (t, 2H), 1.80-1.55 (m, 4H).

Example 61

{2-Bromo-4-[3-(1H-tetrazol-5-yl)propylsulfanylmethyl]phenyl}difluoromethylphosphonic Acid Trisodium Salt The title compound was prepared in a similar manner as described for Example 41. Therefore, 5-(3-bromopropyl)-1-trityl-1H-tetrazole was prepared from methyl 3-cyanopropionate, converted to a thioacetate intermediate, then coupled with (2-bromo-4-bromomethylphenyl)difluoromethylphosphonic acid diethyl ester and followed by the deprotection reactions. The product obtained was ~80% pure.

¹H NMR (Methanol-d₄) δ 769 (d, 1H), 7.60 (s, 1H), 7.29 (d, 1H), 3.70 (s, 2H), 2.90 (t, 2H), 2.48 (t, 2H), 1.95 (m, 2H).

Example 62

[2-Bromo-4-(3-methyl-butylsulfanylmethyl)phenyl]difluoromethylphosphonic Acid Disodium Salt The title compound was prepared in a similar manner as described for Example 51 from 3-methyl-butanethiol and [2-bromo-4-(4-bromobutyl)phenyl]difluoromethylphosphonic acid diethyl ester).

¹H NMR (Methaol-d₄) δ 8.08 (d, 1H), 7.54 (s, 1H), 7.24 (d, 1H), 3.65 (s, 2H), 2.40 (t, 2H), 1.64 (m, 1H), 1.42 (m, 2H), 0.87 (d, 6H).

Example 63

(2-Brom-4-cyclohexylsulfanylmethyl-phenyl)difluoromethylphosphonic Acid Disodium Salt The title compound was prepared in a similar manner as described for Example 51 from cyclohexyl mercaptan and [2-bromo-4-(4-bromobutyl)phenyl]difluoromethylphosphonic acid diethyl ester).

¹H NMR (Methaol-d₄) δ 8.06 (d, 1H), 7.55 (s, 1H), 7.25 (d, 1H), 3.69 (s, 2H), 2.50 (m, 1H), 1.94 (m, 2H), 1.74 (m, 2H), 1.58 (m, 1H), 1.28 (m, 5H).

Example 64

{2-Bromo-4-[3-(4-bromophenyl)propylsulfanylmethyl]phenyl}-difluoromethylphosphonic Acid Disodium Salt Step 1: 3-(4-Bromophenyl)propan-1-ol A mixture of ethyl trans-4-bromocinnamate (3.0 g, 11.8 mmol) and 10% palladium on carbon (0.2 g) in EtOAc (50 mL) was hydrogenated under 50 psi for 36 h. Catalyst was then filtered off and the filtrate was concentrated in vacuo. Chromatography over silica gel and elution with hexanes:EtOAc (9:1) afforded 2.7 g of ethyl 3-(4-bromophenyl)propionate. To a solution of ethyl 3-(4-bromophenyl)propionate (2.7 g, 10.5 mmol) in THF (100 mL) at −78° C. was added DIABL-H (5.0 mL, 28.1 mmol). The cooling bath was removed and the mixture was slowly warmed to r.t. After cooling back to 0° C., the mixture was quenched with MeOH, diluted with H₂O (50 mL) and acidified with 6M aqueous HCl (30 mL) and stirred for 15 min. The whole mixture was then extracted with EtOAc. The EtOAc extract was washed with H₂O (2x), dried (MgSO₄) and concentrated. Chromatography over silica gel and elution with hexanes:EtOAc (2:1) yielded 1.5 g of 3-(4-bromophenyl)propan-1-ol.

¹H NMR (Acetone-d₆) δ 7.46 (d, 2H), 7.20 (d, 2H), 3.55 (m, 3H), 2.68 (t, 2H), 1.80 (m, 2H).

Step 2: {2-Bromo-4-[3-(4-bromophenyl)propylsulfanylmethyl]phenyl}-difluoromethylphosphonic Acid Disodium Salt The title compound was prepared in a similar manner as described for Example 58. Therefore, thioacetic acid S-[3-(4-bromophenyl)propyl]ester was prepared from 3-(4-bromophenyl)propan-1-ol, then coupled with (2-bromo-4-bromomethylphenyl)difluoromethylphosphonic acid diethyl ester and followed by the deprotection reaction.

¹H NMR (Methanol-d₄) δ 8.00 (d, 1H), 7.55 (s, 1H), 7.38 (d, 2H), 7.25 (d, 1H), 7.07 (d, 2H), 3.66 (s, 2H), 2.63 (t, 2H), 2.41 (t, 2H), 1.80 (m, 2H).

Example 65

{2-Bromo-4-[3-(4-bromophenyl)allylsulfanylmethyl]phenyl}-difluoromethylphosphonic Acid Disodium Salt Step 1: 1-Bromo-4-(3-bromopropenyl)benzene To a solution of ethyl trans-4-bromocinnamate (3.5 g, 13.7 mmol) in THF (100 mL) at −78° C. was added DIBAL-H (6.0 mL, 33.7 mmol) and the mixture was slowly warmed to 0° C. After quenching with MeOH, the mixture was diluted with $H_2O$, acidified with 6M aqueous HCl and stirred for 15 min. The whole mixture was extracted with EtOAc. The EtOAc extract was washed with 1M aqueous HCl, $H_2O$ (2×), dried ($MgSO_4$) and concentrated. The residue was swished with hexanes containing small amount of $Et_2O$ to give 2.1 g of 3-(4-bromophenyl)pro-2-en-1-ol as a white solid.

To a solution of 3-(4-bromophenyl)pro-2-en-1-ol (1.0 g, 4.7 mmol) and triphenylphosphine (1.5 g, 5.7 mmol) in THF (30 mL) at 0° C. was added N-bromosuccinimde (1.1 g, 0.57 mmol) and the mixture was stirred for 30 min. Solvent was then removed in vacuo. The residue was chromatographed over silica gel and eluted with hexanes:EtOAc (6:1) to give 1.3 g of the title compound as a pale yellow solid.

$^1$H NMR (Acetone-$d_6$) δ 7.52 (d, 2H), 7.44 (d, 2H), 6.75 (d, 1H), 6.55 (m, 1H), 4.26 (d, 2H).

Step 2: {2-Bromo-4-[3-(4-bromophenyl) allylsulfanylmethyl]phenyl}-difluoromethylphosphonic Acid Disodium Salt The title compound was prepared from thioacetic acid S-{3-bromo-4-[diethoxyphosphoryl)difluoromethyl]benzyl ester and 1-bromo-4-(3-bromopropenyl)benzene in a similar manner as described for Example 10.

$^1$H NMR (Methanol-$d_4$) δ 8.07 (d, 1H), 7.55 (s, 1H), 7.44 (d, 2H), 7.31 (d, 2H), 7.26 (d, 1H), 6.38 (d, 1H), 6.22 (m, 1H), 3.65 (s, 2H), 3.17 (d, 2H).

Example 66
{2-Bromo-4-[3-(3-ethoxycarbonylphenyl)-prop-2-ynylsulfanylmethyl]-phenyl}difluoromethylphosphonic Acid Disodium Salt Step 1: 3-(3-Hydroxyprop-1-ynyl)benzoic Acid Ethyl Ester.

A mixture of 3-iodobenzoic acid ethyl ester (3 g), propargyl alcohol (0.63 mL), bis(triphenylphosphine)palladium chloride, copper iodide (10.5 mg) and triethyl amine (6 mL) in acetonitrile (20 mL) was stirred at R.T. for 30 min. A saturated solution of ammonium chloride was added to the mixture which was extracted with ethyl acetate, washed with brine and dried over magnesium sulfate. Filtration and evaporation of the solvent, followed by silica gel chromatography using 15% ethyl acetate/hexane afforded 2.06 g of 3-(3-hydroxyprop-1-ynyl)benzoic acid ethyl ester.

Step 2: 3-(3-Bromoprop-1-ynyl)benzoic acid ethyl ester.

To triphenylphosphine (3.7 g) in methylene chloride (106 mL) at 0° C. was slowly added bromine (0.67 mL), the mixture was stirred for 10 min. then, 3-(3-hydroxyprop-1-ynyl)benzoic acid ethyl ester (2 g) in methylene chloride (10 mL) was slowly added. Stirring was continued at 0° C. for 30 min. then a saturated solution of sodium bicarbonate was added, the mixture was extracted with methylene chloride, washed with brine and dried over magnesium sulfate. Filtration and evaporation of the solvent, followed by silica gel chromatography afforded the title compound.

Step 3: {2-Bromo-4-[3-(3-ethoxycarbonylphenyl)-prop-2-ynylsulfanylmethyl]-phenyl}difluoromethylphosphonic Acid Disodium Salt.

The title compound was prepared from thioacetic acid S-{3-bromo-4-[diethoxyphosphoryl)difluoromethyl]benzyl ester and 3-(3-bromoprop-1-ynyl)benzoic acid ethyl ester in a similar manner as described for Example 10.

$^1$H NMR (CD$_3$OD) δ 8.15 (d, 1H), 8.06 (s, 1H), 7.97(d, 1H), 7.67 (d, 1H), 7.62 (s, 1H), 7.48 (t, 1H), 7.32 (s, 1H), 4.38 (q, 2H), 3.89 (s, 2H), 3.38 (s, 2H), 1.39 (t, 3H).

M.S. (APCI) m/z 519 (M–H)$^-$

Example 67
3-{3-[3-Bromo-4-(difluorophosphonomethyl) benzylsulfanyl]prop-1-ynyl}benzoic Acid Trisodium Salt To a solution of {2-bromo-4-[3-(3-ethoxycarbonylphenyl)-prop-2-ynylsulfanylmethyl]-phenyl}difluoromethylphosphonic acid disodium salt (20 mg) from Example 66 in ethanol (1 mL) and water (1 mL) was added NaOH 1N (0.036 mL), and the mixture was stirred at R.T. for 18 hrs. The solvent was evaporated under reduced pressure, the residue was triturated in ethyl acetate and filtered, giving 11 mg of the title compound.

$^1$H NMR (CD$_3$OD) δ 8.09 (d, 1H), 8.03 (s, 1H), 7.90(d, 1H), 7.63 (s, 1H), 7.49 (d, 1H), 7.37-7.29 (m, 2H), 3.91 (s, 2H), 3.38 (s, 2H).

M.S. (APCI) m/z 491 (M–H)$^-$

Example 68
[2-Bromo-4-(pyridin-2-ylmethylsulfanylmethyl)-phenyl]-difluoromethylphosphonic Acid Disodium Salt.

The title compound was prepared from thioacetic acid S-{3-bromo-4-[diethoxyphosphoryl)difluoromethyl]benzyl ester and 2-(chloromethyl) pyridine in a similar manner as described for Example 10.

$^1$H NMR (CD$_3$OD) δ 8.45 (d, 1H), 7.97 (d, 1H), 7.76(t, 1H), 7.50 (s, 1H), 7.47 (d, 1H), 7.26 (m, 2H), 3.25 (s, 2H), 3.17 (s, 2H).

M.S. (APCI) m/z 424 (M–H)$^-$

Example 69
[2-Bromo-4-(4-bromobenzylsulfanylmethyl)-phenyl]-difluoromethylphosphonic Acid Disodium Salt.

Step 1: [2-Bromo-4-(4-bromobenzylsulfanylmethyl)phenyl] difluoromethylphosphonic Acid Diethyl Ester.

To a solution of thioacetic acid S{3-bromo-4-[(diethoxyphosphoryl)difluoromethylbenzyl ester (650 mg), 4-bromobenzyl bromide (487 mg) in ethanol (20 mL) at 0° C. was added sodium methoxide (178 mg), the mixture was stirred at 0° C. for 1 hr, then at R.T. for 30 min. A saturated solution of ammonium chloride was added to the mixture which was extracted with ethyl acetate, washed with brine and dried over magnesium sulfate. Filtration and evaporation of the solvent, followed by silica gel chromatography using 40% ethyl acetate/hexane afforded 840 mg of [2-bromo-4-(4-bromobenzylsulfanylmethyl)-phenyl]-difluoromethylphosphonic Acid Diethyl Ester.

Step 2: [2-Bromo-4-(4-bromobenzylsulfanylmethyl)phenyl] difluoromethylphosphonic Acid Disodium Salt.

To a solution of [2-bromo-4-(4-bromobenzylsulfanylmethyl)-phenyl]-difluoromethylphosphonic acid diethyl ester (1.16 g) in chloroform (60 mL) was added bromotrimethylsilane (4.1 mL) and the mixture was stirred at R.T. overnight. The solvent was evaporated under vacuum, and the residue was coevaporated with chloroform (3×), then dissolved in dichloromethane (5 mL) and ethanol (20 mL) and stirred at R.T. for 1 hr. The solvent was evaporated under vacuum and the residue was coevaporated with ethanol (2×), pumped dry to give 1.114 g of the phosphonic acid. To 600 mg of the phosphonic acid, water (20 ML) and sodium hydroxide 1N (2.38 mL) were added and the mixture was freeze dried over night to give 575 mg of [2-bromo-4-(4-bromobenzylsulfanylmethyl)-phenyl]-difuoromethylphosphonic acid disodium salt.

$^1$H NMR (CD$_3$OD) δ 8.11 (d, 1H), 7.49 (s, 1H), 7.45(d, 2H), 7.21 (d, 2H), 3.56 (s, 4H).

Alternative Synthesis of [2-Bromo-4-(4-bromobenzylsulfanylmethyl)-phenyl]-difluoromethylphosphonic Acid Diethyl Ester.

Step 1: Thioacetic acid S-(4-bromobenzyl)ester

To a solution of 4-bromobenzyl bromide (5 g) in dimethyl formamide (75 mL) was added potassium thioacetate (2.74 g) and the mixture was stirred over night. A saturated solution of ammonium chloride was added to the mixture which was extracted with ethyl acetate, washed with brine (3×) and dried over magnesium sulfate. Evaporation of the solvent under reduced pressure followed by filtration on silica gel with 20%ethyl acetate/hexane afforded, after evaporation of the solvent, 4.4 g of thioacetic acid S-(4-bromobenzyl)ester.

Step 2: [2-Bromo-4-(4-bromobenzylsulfanylmethyl)phenyl] difluoromethylphosphonic Acid Diethyl Ester To a solution of thioacetic acid S-(4-bromobenzyl)ester (135 mg) and (2-bromo-4-bromomethylphenyl)-difluoromethylphosphonic acid diethyl ester (200 mg) in ethanol (5 mL) was added sodium methoxide (60 mg) and the mixture was stirred over night. A saturated solution of ammonium chloride was added to the mixture which was extracted with ethyl acetate, washed with brine and dried over magnesium sulfate. Purification by silica gel chromatography using 30% ethyl acetate/hexane afforded 196 mg of [2-bromo-4-(4-bromobenzylsulfanylmethyl)-phenyl]-difluoromethylphosphonic acid diethyl ester.

Second Alternative Synthesis of [2-bromo-4-(4-bromobenzylsulfanylmethyl)phenyl] difluoromethylphosphonic Acid Diethyl Ester via a CuBr-mediated Cross Coupling Reaction of [(diethoxyphosphinyl)difluoromethyl]Zinc Bromide with an Iodide Intermediate.

Step 1: 2-Bromo-4-(bromomethyl)-1-iodobenzene

To 2-bromo-1-iodo-4-methylbenzene (10 g, 33.8 mmol) was added N-bromosuccinimide (6.6 g, 37.1 mmol) in $CCl_4$ (150 mL) with catalytic amount of benzoyl peroxide and the mixture was irradiated with a sunlamp under refluxing for 1 h. The mixture was then filtered on a pad of celite and evaporated to dryness. The residue was purified by silica gel chromatography to provide 9.0 g of the title compound.

Step 2: 2-Bromo-4-{[(4-bromobenzyl)sulfanyl]methyl}-1-iodobenzene

To 2-bromo-4-(bromomethyl)-1-iodobenzene (0.49 g, 1.28 mmol) and thioacetic acid S-(4-bromobenzyl)ester (0.31 g, 1.28 mmol) in EtOH (6.4 mL) was added a solution of 1M potassium tert-butoxide (1.4 mL, 1.4 mmol) in THF at −78° C. The temperature was then raised to room temperature. The reaction mixture was quenched with saturated $NH_4Cl$ and extracted with EtOAc. The extract was dried over anhydrous $Na_2SO_4$ and concentrated. The residue was purified on silica gel leading to the title compound.

Step 3: [2-Bromo-4-(4-bromobenzylsulfanylmethyl)phenyl] difluoromethylphosphonic Acid Diethyl Ester To a stirred suspension od Zn dust (66 mg, 1.0 mmol) in dry DMA (0.5 mL) was added slowly a solution of bromodifluoromethyl diethylphosphonate (270 mg, 1 mmol). During addition of half the amount of the phosphonate, an exothermic reaction occurred. The addition was controlled so that the internal temperature was maintained at 50° C. After the addition was completed, the solution was stirred at room temperature for 3 h. Then CuBr (145 mg, 1mmol) was added in one portion. The mixture was stirred at room temperature for 30 min to give the organocopper reagent in DMA. The aryl iodide intermediate (250 mg, 0.5 mmol) from step 2 in DMA (0.2 mL) was added at room temperature. The mixture was then sonicated overnight, quenched with saturated aqueous $NH_4Cl$ and extracted with EtOAc. The extract was dried over $Na_2SO_4$ and evaporated. The residue was purified on silica gel to give 145 mg of the title compound.

Example 70

(2-Bromo-4-{[(1-phenylethyl)sulfanyl]methyl}phenyl)(difluoro)methylphosphonic Acid Step 1 Diethyl (2-bromo-4-{[(1-phenylethyl)ethyl)sulfanyl]methyl}phenyl) (difluoro)methylphosphonate To a degassed solution of (1-bromoethyl)benzene (0.94 g, 0.51 mmol) and S-{3-bromo-4-[(diethoxyphosphoryl)(difluoro)methyl]benzyl}ethanethioate (0.20 g, 0.46 mmol) in EtOH (2.0 mL) at 0° C. was added a THF solution (1.0 M) of potassium tert-butoxide (0.46 mL, 0.46 mmol). After a period of 0.5 h at room temperature, the reaction mixture was quenched by the addition of saturated $NH_4Cl$. After extraction with EtOAc, dried over $Na_2SO_4$, filtered and evaporated, the title compound was purified by flash chromatography.

Step 2: (2-Bromo-4-{[(1-phenylethyl)sulfanyl]methyl}phenyl)(difluoro) methylphosphonic Acid To the compound of Step 1 in $CH_2Cl_2$ was added an excess of TMS-Br. After a period of 18 h, the solvents were evaporated and the resulting mixture was co-evaporated with EtOH followed by toluene.

$^1$H NMR (400 MHz, $CD_3COCD_3$) δ 1.40 (3H, d), 3.55 (2H, m), 3.90 (1H, q), 7.10-7.70 (8H, m).

Example 71

(2-Bromo-4-{[(2-bromo-5-fluorobenzyl)sulfanyl]methyl}phenyl)(difluoro) methylphosphonic Acid The title compound was prepared as described in Example 70 using 2-bromo-5-fluorobenzyl bromide.

$^1$H NMR (400 MHz, $CD_3COCD_3$) δ 3.90 (4H, s), 7.05-7.80 (6H, m).

Example 72

(2-Bromo-4-[(isopropylsulfanyl)methyl]phenyl}(difluoro)methylphosphonic Acid

The title compound was prepared as described in Example 70 using 2-iodopropane.

$^1$H NMR (400 MHZ, $CD_3COCD_3$) δ 1.20 (6H, d), 2.80 (1H, m), 3.75 (2H, s), 7.30 (1H, d), 7.60 (1H, s), 8.10 (1H, d) (sodium salt).

Example 73

(2-Bromo-4-{[(2-oxo-1,2-diphenylethyl)sulfanyl]methyl}phenyl)(difluoro) methylphosphonic Acid The title compound was prepared as described in Example 70, using desyl bromide.

m/z 526.

Example 74

(2-Bromo-4-{[(1,2-diphenylethyl)sulfanyl]methyl}phenyl)(difluoro)methylphosphonic Acid The ester intermediate of Example 73 in EtOH was treated with an excess of $NaBH_4$. The reaction was quenched with saturated $NH_4Cl$ and extracted with EtOAc. The organic phase was filtered through silica gel. The crude product in $CH_2Cl_2$ was treated with an excess of TFA/$ET_3SiH$. After a period of 18 h, the reaction mixture was evaporated and purified by flash chromatography to provide the title compound.

$^1$H NMR (400 MHz, $CD_3OD$) δ 3.10 (2H, m), 3.45 (2H, m), 3.85 (1H, t), 6.90-7.40 (12H, m), 8.10 (1H, d), (sodium salt).

Example 75

[2-Bromo-4-({[2-(4-bromophenyl)-1-methylethyl]sulfanyl}methyl)phenyl](difluoro)methylphosphonic Acid Step 1 1-Bromo-4-(1-bromoethyl)benzene To a solution of $POBr_3$ (1.2 eq.) in $CH_2Cl_2$ (0.2M) at 0° C. were added DMF (50%) and 4-bromo-α-methylbenzyl alcohol in CH$_2$Cl$_2$. The reaction mixture was then extracted with CH$_2$Cl$_2$/NaHCO$_3$. The organic phase was separated, dried over Na$_2$SO$_4$, filtered and evaporated. The title compound was then purified by flash chromatography.

Step 2 [2-Bromo-4-({[2-(4-bromophenyl)-1-methylethyl]sulfanyl}methyl)phenyl](difluoro) methylphosphonic Acid The title compound was prepared as described in Example 70 using intermediate from step 1.

$^1$H NMR (400 MHz, CD$_3$COCD$_3$) δ 1.50 (3H, d), 3.65 (2H, dd), 3.95 (1H, m), 7.30-7.70 (7H, m).

Example 76

[2-Bromo-4-(1-methyl-2-phenylethylsulfanylmethyl)phenyl]difluoromethylphosphonic Acid Step 1: Thioacetic acid S-(1-methyl-2-phenyl-ethyl)ester A mixture of 2-bromo-1-phenylpropane and potassium thioacetic acid (2.0 eq.) in DMF (0.5 M) was heated at 55° C. After a period of 18 h, the reaction mixture was poured over saturated NH$_4$Cl and EtOAc. The organic phase was separated, dried over Na$_2$SO$_4$, filtered and evaporated under reduced pressure. The title compound was purified by flash chromatography.

Step 2: [2-Bromo-4-(1-methyl-2-phenylethylsulfanylmethyl)phenyl]difluoromethylphosphonic Acid Diethyl Ester To a mixture of diethyl [2-bromo-4-(bromomethyl)phenyl]difluoromethylphosphonate and the compound of step 1 (1.5 eq.) in Degassed EtOH (0.2 M) was added EtONa (2.6 M) (1.2 eq.). After a period 0.5 h at room temperature, the reaction mixture was poured over saturated NH$_4$Cl and EtOAc. The organic phase was separated, dried over Na$_2$SO$_4$, filtered and evaporated.

Step 3 [2-Bromo-4-(1-methyl-2-phenylethylsulfanylmethyl)phenyl]difluoromethylphosphonic Acid The title compound was prepared as described in Example 70, step 2.

$^1$H NMR (400 MHz, CD$_3$COCD$_3$) δ 1.15 (3H, d), 2.75 (1H, m), 3.00 (2H, m), 3.90 (2H, m), 7.10-7.85 (8H, m).

Example 77

[4-({[1,2-Bis(4-fluorophenyl)ethyl]sulfanyl}methyl)-2-bromophenyl](difluoro) methylphosphonic Acid Step 1 1,2-Bis(4-fluorophenyl)-1-ethanone To the TMS cyanohydrin of 4-fluorobenzaldehyde in THF (0.4 M) at −78° C. was added a 1.06 M THF solution of LiHMDS (1.1 eq.). After a period of 15 min. at −78° C. 4-fluorobenzyl bromide (1.0 eq.) in THF was added and stirred for 1 h at room temperature. The reaction mixture was then poured over saturated NH$_4$OAc and EtOAc. The organic phase was separated, dried over Na$_2$SO$_4$, filtered and evaporated under reduced pressure. To the resulting oil was added hexane to provide a solid which was filtered and used as such for the next step.

Step 2: 2-Bromo-1,2-bis(4-fluorophenyl)-1-ethanone

To the compound of Step 1 in benzene (0.4 M) was added Br$_2$ (1.05 eq.). After the reaction was completed, the mixture was poured over sodium thiosulfate and EtOAc.

The organic phase was separated, dried over Na$_2$SO$_4$, filtered and evaporated and the product was used as such for next step.

Step 3: 1-[2-Bromo-2-(4-fluorophenyl)ethyl]-4-fluorobenzene

To the compound of Step 2 in EtOAc (0.4 M) at 0° C. was added an excess of NaBH$_4$. After a period of 1 h at 0° C., the reaction mixture was poured over saturated NH$_4$Cl and EtOAc. The organic phase was separated, dried over Na$_2$SO$_4$, filtered and evaporated under reduced pressure. The alcohol was purified by flash chromatography. To the alcohol in CH$_2$Cl$_2$ (0.4 M) was added an excess of TFA and Et$_3$SiH. A few drops of CF$_3$SO$_3$H was then added to the reaction mixture. After a period of 1 h, the reaction mixture was poured over saturated NaHCO$_3$ and EtOAc. The organic phase was then separated, dried over Na$_2$SO$_4$, filtered and evaporated under reduced pressure.

Step 4: [4-({[1,2-Bis(4-fluorophenyl)ethyl]sulfanyl}methyl)-2-bromophenyl](difluoro)methylphosphonic Acid The title compound was prepared as described in Example 70 using intermediate from step 3.

$^1$H NMR (400 MHz, CD$_3$COCD$_3$) δ 3.15 (2H, m), 3.60 (2H, m), 4.10 (1H, t), 6.95-7.65 (11H, m).

Example 78

(2-Bromo-4-{[(2-oxo-2-phenylethyl)sulfanyl]methyl}phenyl)(difluoro methylphosphonic Acid The title compound was prepared as described in Example 70 using 2-bromoacetophenone.

$^1$H NMR (Acetone d$_6$) δ 3.77-3.83 (4H, m), 7.45-7.55 (3H, m), 7.60-7.67 (2H, m), 7.22-7.76 (1H, m), 7.96-8.04 (2H, m).

Example 79

(2-Bromo-4-{[(2-bromobenzyl)sulfanyl]methyl}phenyl)(difluoro)methylphosphonic Acid The title compound was prepared as described in Example 70 using 2-bromobenzyl bromide.

$^1$H NMR (Acetone d$_6$) δ 3.78-3.87 (4H, m), 7.14-7.22 (1H, m), 7.28-7.35 (1H, m), 7.36-7.44 (1H, m), 7.44-7.50 (1H, m), 7.55-7.65 (2H, m), 7.68-7.82 (1H, m).

Example 80

(2-Bromo-4-{[(3-bromobenzyl)sulfanyl]methyl}phenyl)(difluoro)methylphosphonic Acid The title compound was prepared as described in Example 70 using 2-bromobenzyl bromide.

$^1$H NMR (Acetone d$_6$) δ 3.69-3.76 (4H, m), 7.22-7.33 (2H, m), 7.40-7.46 (2H, m), 7.50-7.54 (1H, m), 7.60-7.66 (2H, m).

Example 81

(2-Bromo-4-{[(4-iodobenzyl)sulfanyl]methyl}phenyl)(difluoro)methylphosphonic Acid The title compound was prepared as described in Example 70 using 4-iodobenzyl bromide.

$^1$H NMR (Acetone d$_6$) δ 3.68 (2H, s), 3.72 (2H, s), 7.11-7.17 (2H, m), 7.38-7.44 (1H, m), 7.59-7.65 (2H, m), 7.65-7.71 (2H, m).

Example 82

(2-Bromo-4-{F(4-bromo-2-fluorobenzyl)sulfanyl]methyl}phenyl)(difluoro)methylphosphonic Acid The title compound was prepared as described in Example 70 using 4-bromo-2-fluorobenzyl bromide.

$^1$H NMR (Acetone d$_6$) δ 3.73 (2H, s), 3.80 (2H, s), 7.31-7.39 (3H, m), 7.43-7.48 (1H, m), 7.60-7.65 (1H, m), 7.65-7.70 (1H, m).

Example 83

[2-Bromo-4-({[4-(trifluoromethoxy)benzyl]sulfanyl}methyl)phenyl](difluoro)methylphosphonic Acid The title compound was prepared as described in Example 70 using 4-(trifluoromethoxy)benzyl bromide.

$^1$H NMR (Acetone d$_{16}$) δ 3.70-3.78 (4H, m), 7.23-7.30 (2H, m), 7.40-7.48 (3H, m) 7.59-7.68 (2H, m).

Example 84

[2-Bromo-4-({[4-(ethoxycarbonyl)benzyl]sulfanyl}methyl)phenyl](difluoro)methylphosphonic Acid The title compound was prepared as described in Example 70 using ethyl 4-(bromomethyl)benzoate.

$^1$H NMR (Acetone d$_6$) δ 1.34-1.41 (3H, m), 3.74 (2H, s), 3.80 (2H, s), 4.32-4.39 (2H, m), 7.42-7.50 (3H, m), 7.62-7.68 (2H, m), 7.95-8.01 (2H, m).

Example 85

[4-({[Bis(4-bromophenyl)methyl]sulfanyl}methyl)-2-bromophenyl](difluoro)methylphosphonic Acid The title compound was prepared as described in Example 70 using bis(4-bromophenyl)bromomethane.

1H NMR (Methanol-d$_4$) δ 3.52 (2H, s), 4.95 (1H, s), 7.15 (1H, d), 7.30 (4H, d), 7.38 (1H, s), 7.50 (4H, d), 8.15 (1H, d).

Example 86

{4-[(Benzhydrylsulfanyl)methyl]-2-bromophenyl}(difluoro)methylphosphonic Acid

The title compound was prepared as described in Example 70 using bromodiphenylmethane.

1H NMR (Acetone-d$_6$) δ 3.62 (2H, s), 5.15 (1H, s), 7.25 (2H, m), 7.35 (5H, m), 7.44 (4H, m), 7.50 (1H, s), 7.60 (1H, d).

Example 87

2-[({[4-({[4-(Difluorophosphonomethyl)-3-bromophenyl]methylthio}methyl)phenyl]methylthio}methyl)cyclopropyl]acetic acid Step 1: Methyl 2-[({[4-(bromomethyl)phenyl]methylthio}methyl)cyclopropyl]acetate A suspension of 1,4-dibromoxylene (3 mmol., 0.792 g.), methyl 2-[(sulfanylmethyl)cyclopropyl]acetate (1.1 mmol., 0.176 g.) and cesium carbonate (1.1 mmol., 0.358 g.) in DMF (5 mL) was stirred for 2 hours. The mixture was diluted with diethylether and water was added. The organic layer was separated and the aqueous further extracted with diethylether. The combined organic layers were washed with brine, dried with magnesium sulfate and the solvent were removed in vacuo. The residue was passed on a short pad of silica gel eluting first with a mixture of dichloromethane and hexanes (1:4), and followed by a mixture of ethyl acetate and hexanes (1:10). The compound, which contained some impurities, was used as such in the next step.

Step 2: Methyl 2-[({[4-({[4-(diethoxydifluorophosphonomethyl)-3-bromophenyl]methylthio}methyl)phenyl]methylthio}methyl)cyclopropyl]acetate To a 0° C. mixture of diethyl (2-bromo-4-acetylthiomethyl-phenyl)-difluoro-methylphosphonic acid (0.6 mmol., 0.259 g.) and the bromide from the previous step (0.62 mmol., 0.214 g.) in ethanol (4 mL) was added NaOMe (1.2 mmol., 0.065 g.) and the mixture was reacted as described earlier to provide the title compound (0.15 g.).

$^1$H NMR (CD$_3$COCD$_3$) δ 7.55-7.7(2H, m), 7.4-7.5(1H, m), 7.2-7.35(4H, m), 4.15-4.3(4H, m), 3.65-3.8(6H, 3s), 3.6(3H, s), 2.6(2H, s), 2.4(2H, s), 1.25-1.35(6H, m), 0.4-0.55(4H, m).

Step 3: 2-[({[4-({[4-(Difluorophosphonomethyl)-3-bromophenyl]methylthio}methyl)phenyl]methylthio}methyl)cyclopropyl]acetic Acid Using bromotrimethylsilane in a procedure analogous to what was described earlier to obtain the title compound as the sodium salt.

$^1$H NMR (CD$_3$OD) δ 7.95-8.0(1H, m), 7.5(1H, bs), 7.15-7.35(5H, m), 3.75(2H, s), 3.5-3.6(4H, 2s), 2.65(2H, s), 2.35(2H, s), 0.5-0.55(2H, m), 0.35-0.4(2H, m).

Example 88

(2-Bromo-4-{13-(3-phosphonophenyl)propylthio]methyl}phenyl)difluoromethylphosphonic Acid Step 1: [3-(3-Bromopropyl)phenyl]diethoxyphosphino-1-one A THF (100 mL) solution of 3-bromobenzaldehyde (35 mmol., 6.5 g.) and carbethoxymethylenetriphenylphosphorane (40 mmol., 13.9 g.) was refluxed overnight. The mixture was evaporated to dryness and then diethylether was added. Most triphenylphosphine oxide was filtered off and the residue was purified by chromatography on silica using ethyl acetate and hexanes (1:10) to yield ethyl 3-(3-bromophenyl)prop-2-enoate (9 g.).

To a −78° C. solution of the ester (35 mmol., 9 g.) in THF (150 mL) was added DIBAL-H (100 mmol., 14.2 g.) as a THF (10 mL) solution. The mixture was slowly warmed to 0° C. and reacted for 1 hour. It was poured carefully over ice, diluted tartaric acid and ethyl acetate. The ethyl acetate layer was separated and the aqueous further extracted with ethyl acetate. The combined organic extracts were washed with diluted bicarbonate, brine and dried with magnesium sulfate. Removal of the solvent left a residue which was purified by chromatography on silica using ethyl acetate and hexanes (1:3) to give 3-(3-bromophenyl)prop-2-en-1-ol (7.8 g.).

To a −5° C. chloroform (100 mL) solution of the alcohol (36.6 mmol., 7.8 g.), dihydropyran (75 mmol., 6.3 g.) was added PPTS (1.25 g.) and the mixture was stirred at room temperature for 5 hours. It was washed with diluted bicarbonate, brine and dried with magnesium sulfate. Removal of the solvent left a residue which was put on high vacuum to yield 2-[3-(3-bromophenyl)prop-2-enyloxy]perhydro-2H-pyran (11 g.) used as such in the next step.

To a solution of 2-[3-(3-bromophenyl)prop-2-enyloxy]perhydro-2H-pyran (3 g.) in ethyl acetate (25 m L) was added 10% Palladium on charcoal (0.2 g.) and the mixture was stirred for 4 hours under a 1 atmosphere pressure of hydrogen. The mixture was diluted with ethyl acetate, filtered over celite, evaporated to dryness and passed on a short pad of silica using ethyl acetate and hexanes (1:20) to yield 2-[3-(3-bromophenyl)propoxy]perhydro-2H-pyran (2.1 g.).

To a degassed toluene (10 mL) solution of 2-[3-(3-bromophenyl)propoxy]perhydro-2H-pyran (7 mmol., 2.1 g.), triethylamine (15 mmol., 1.52 g.) and diethyl phosphite (15 mmol., 2 g.) was added Pd(Ph$_3$P)$_4$ (0.7 mmol., 0.808 g.) and the mixture was refluxed overnight. It was cooled, poured carefully over ice and diluted HCl and ethyl acetate. The ethyl acetate layer was separated and the aqueous further extracted with ethyl acetate. The combined organic extracts were washed with brine and dried with magnesium sulfate. Removal of the solvent left a residue which was purified by chromatography on silica using ethyl acetate to give diethoxy[3-(3-perhydro-2H-pyran-2-yloxypropyl)phenyl]phosphino-1-one (1.6 g.).

To a 0° ethanol (20 mL) solution of the above THP derivative (4.5 mmol., 1.6 g.) was added dry HCl (produced by adding 0.5 mL of acetyl chloride to −78° C. ethanol (2 mL) and warming to 0° C. prior to transfer) and the mixture was stirred at room temperature for 4 hours. The mixture was diluted with ethyl acetate, washed with diluted bicarbonate, brine and dried with magnesium sulfate. Removal of the solvent left a residue consisting of the crude diethoxy[3-(3-hydroxypropyl)phenyl]phosphino-1-one.

The above alcohol was treated with triphenylphosphine and bromine in the usual manner to yield [3-(3-bromopropyl)phenyl]diethoxyphosphino-1-one (0.43 g.) after purification by trituration and chromatography on silica using ethyl acetate and hexanes (3:1 to 100% ethyl acetate).

Step 2: [4-({3-[3-(Diethoxycarbonyl)phenyl]propylthio}methyl)-2-bromophenyl]diethoxyphosphino-1-one To a 0° C. mixture of diethyl (2-bromo-4-acetylthiomethyl-phenyl)-difluoro-methylphosphonic acid (0.5 mmol., 0.216 g.) and the bromide from the previous step (0.55 mmol., 0.15 g.) in ethanol (3 mL) was added NaOMe (1.2 mmol., 0.065 g.) and the mixture was reacted as described earlier to provide the title compound (0.197 g.) after purification by chromatography on silica using ethyl acetate.

$^1$H NMR (CD$_3$COCD$_3$) δ 7.5 (1H, bs), 7.4-7.65(6H, m), 4.1-4.25(4H, m), 3.95-4.1(4H, m), 3.5(2H, s), 2.7-2.8(2H, t), 2.4-2.5(2H, t), 1.85-1.95(2H, m), 1.2-1.35(12H, m).

Step 3: Sodium (2-bromo-4-{[3-(3-phosphonophenyl)propylthio]methyl}phenyl)difluoromethylphosphonic Acid Using bromotrimethylsilane in a procedure analogous to what was described earlier, the title compound was obtained as the sodium salt.

$^1$H NMR (CD$_3$OD) δ 8.05(1H, d), 7.6-7.7(2H, m), 7.55 (1H, bs), 7.05-7.25(3H, m), 3.65(2H, s), 2.65-2.75(2H, t), 2.35-2.45(2H, t), 1.8-1.95(2H, m).

Example 89
5-{[(3-Bromo-4-phosphonophenyl)methylthio]methyl}-2-chlorobenzenesulfonamide Step 1: 5-(Bromomethyl)-2-chlorobenzenesulfonamide To a DMF (50 mL) solution of 4-chloro-3-sulfamoylbenzoic acid (20.3 mmol., 4.8 g.) and iodomethane (22 mmol., 3.12 g.) was added potassium carbonate (22 mmol., 3 g.) and the mixture was stirred until the reaction was completed. It was diluted with ethyl acetate and washed with water, brine, dried with magnesium sulfate and the solvent were removed in vacuo. NMR showed some residual DMF. The residue was dissolved in diethyl ether, washed with water, brine, dried with magnesium sulfate and the ether was removed in vacuo to yield methyl 4-chloro-3-sulfamoylbenzoate (3 g.), used as such in the next step.

To a −78° C. THF (50 mL) solution of the ester from above was added DIBAL-H (50 mmol., 7.1 g.). The mixture was stirred at this temperature for 1 hour then warmed to 0° C. and stirred for 1 hour. The mixture was poured on ice, 2M H$_2$SO$_4$ and ethyl acetate and stirred for 0.5 hour. The ethyl acetate layer was separated and the aqueous further extracted with ethyl acetate. The combined organic extracts were washed with brine and dried with magnesium sulfate. Removal of the solvent left a residue which was triturated in ethyl acetate and ether to yield 2-chloro-5-(hydroxymethyl) benzenesulfonamide (1.2 g.), used as such in the next step.

The above alcohol was converted to the bromide using POBr$_3$ and DMF as described earlier to yield the title bromide after purification on silica gel using ethyl acetate and hexanes (1:2).

$^1$H NMR (CD$_3$COCD$_3$) δ 8.15(1H, m), 7.6-7.7(2H, m), 6.8-6.9(2H, NH$_2$), 4.75(2H, s).

Step 2: Sodium 5-{[(3-bromo-4-phosphonophenyl)methylthio]methyl}-2-chlorobenzenesulfonamide The above bromide was coupled with diethyl (2-bromo-4-acetylthiomethyl-phenyl)difluoro-methyl-phosphonic acid in the usual manner and the product converted to the sodium salt using a procedure similar to the one described earlier to yield the title compound.

$^1$H NMR (CD$_3$OD) δ 8.0-8.1(2H, m), 7.4-7.55(3H, m), 7.2(1H, m), 3.65(2H, s), 3.6(2H, s); NH$_2$ hydrogens not observed.

Example 90
3-[4-({[4-(Difluorophosphonomethyl)-3-bromophenyl]methylthio}methyl)phenyl]benzenesulfonamide Step 1: [4-(3-Bromophenyl)phenyl]methan-1-ol To a degassed suspension of 4-hydroxymethylbenzeneboronic acid (30 mmol, 4.56 g.), 3-iodo-bromobenzene (40 mmol., 11.3 g.), 2M sodium carbonate (30 mL) in DMF (150 mL) was added PdCl$_2$·dppf (0.15 g.) and the mixture was heated at 90° C. for 4 hours. It was cooled, poured carefully over ice, water and ethyl acetate. The ethyl acetate layer was separated and the aqueous was further extracted with ethyl acetate. The combined organic extracts were washed with brine and dried with magnesium sulfate. Removal of the solvent left a residue which was purified by chromatography on silica using ethyl acetate and hexanes (1:2) to give [4-(3-bromophenyl)phenyl]methan-1-ol (4 g.).

$^1$H NMR (CD$_3$COCD$_3$) δ 7.8(1H, m), 7.6-7.7(3H, m), 7.45-7.55(4H, m), 4.7(2H, d), 4.2-4.3(1H, t(OH)).

Step 2: 2-{[4-(3-Bromophenyl)phenyl]methoxy}perhydro-2H-pyran

A chloroform (50 mL) solution of the alcohol from the previous step (15.2 mmol., 4 g.), dihydropyran (30 mmol., 2.5 g.) and PPTS (2 mmol., 0.5 g.) was stirred at r.t. overnight. It was poured on diluted HCl and dichloromethane. The dichloromethane layer was separated and the aqueous further extracted with dichloromethane. The combined organic extracts were washed with brine and dried with magnesium sulfate. Removal of the solvent left a residue which was put on high vacuum for 12 hours and used as such in the next step.

$^1$H NMR (CD$_3$COCD$_3$) δ 7.8(1H, m), 7.6-7.7(3H, m), 7.45-7.55(4H, m), 4.7-4.85(2H, m), 4.5-4.55(1H, m), 3.7-3.85(1H, m), 3.45-3.55(1H, m), 1.45-2.0(6H, m).

Step 3: 3-[4-(Bromomethyl)phenyl]benzenesulfonamide

To a −78° C. THF (15 mL) solution of the THP derivative from step 2 (3 mmol., 1.04 g.) was added 2,38 M n-butyl lithium (3.3 mmol., 1.38 mL) and the mixture was reacted 10 minutes. SO$_2$ (5 mL) condensed in cold THF (10 mL) was then added and the mixture was reacted for 1 hour at −78° C. It was allowed to warm to room temperature and volatile materials were removed in vacuo. The resulting solid was triturated in hexanes and ether and dried.

The lithio specie from above was suspended in hexanes (15 mL) and cooled to 0° C. SO$_2$Cl$_2$ (3 mmol., 0.405 g.) was added dropwise and the mixture was reacted 30 minutes at 0° C. and 30 minutes at room temperature. Most of the solvents were removed in vacuo and THF (10 mL) was added. The mixture was then transferred into a 1:1 mixture of concentrated NH$_4$OH (5 mL) and water (5 mL) under vigourous stirring. It was cooled, poured over ice, water and ethyl acetate. The ethyl acetate layer was separated and the aqueous further extracted with ethyl acetate. The combined organic extracts were washed with brine and dried with magnesium sulfate. Removal of the solvent left a residue which was purified by chromatography on silica using ethyl acetate and hexanes (1:1) to give 3-[4-(perhydro-2H-pyran-2-yloxymethyl)phenyl]benzenesulfonamide (0.55 g.).

The THP derivative was added to a 0° C. solution of ethanolic HCl prepared from ethanol (10 mL) and acetyl chloride (0.3 mL) and stirred for 2 hours. It was poured over ice, water and ethyl acetate. The ethyl acetate layer was separated and the aqueous further extracted with ethyl acetate. The combined organic extracts were washed with diluted aqueous sodium bicarbonate, brine and dried with magnesium sulfate. Removal of the solvent left a residue which was purified by chromatography on silica using ethyl acetate and hexanes (2:1) to give 3-[4-(hydroxymethyl) phenyl]benzenesulfonamide (0.3 g.).

$^1$H NMR (CD$_3$COCD$_3$) δ 8.15(1H, m), 7.85-7.95(2H, m), 7.6-7.7(3H, m), 7.45-7.55(2H, m), 6.7-6.7(2H, bs(NH$_2$), 4.7(2H, d), 4.3(1H, t).

The hydroxy intermediate was then converted to the title compound using POBr$_3$/DMF as described before.

Step 4: Sodium 3-[4-({[4-(difluorophosphonomethyl)-3-bromophenyl]methylthio}methyl)phenyl]benzenesulfonamide The bromide from the previous step was reacted with diethyl (2-bromo-4-acetylthiomethyl-phenyl)-difluoromethyl-phosphonic acid in the usual manner and the product was converted to the sodium salt using a procedure similar to the one described earlier to yield the title compound.

$^1$H NMR (CD$_3$OD) δ 8.15(1H, s), 8.05(1H, d), 7.8-7.9 (2H, m), 7.55-7.65(3H, m), 7.5(1H, s), 7.4(2H, m), 7.25(1H, m); partial exchange for NH$_2$ hydrogens.

Example 91

[2-Bromo-4-(4'-bromobiphenyl-4-ylmethylsulfanylmethyl)phenyl]difluoromethylphosphonic Acid Disodium Salt (4'-Bromobiphenyl-4-yl)methanol was prepared from 1-bromo-4-iodobenzene and 4-(hydroxymethyl)benzene in the same manner as described in step 2 of Example 11. This hydroxyl intermediate was converted to thioacetic acid S-(4'-bromobiphenyl-4-ylmethyl) ester via the bromide. Subsequently, the thioacetate intermediate was coupled with (2-bromo-4-bromomethylphenyl)difluoromethylphosphonic acid diethyl ester and deprotection in the usual manner as described for Example 55 gave the title compound.

$^1$H NMR (Methanol-d$_4$) δ 8.08 (d, 1H), 7.60-7.45 (m, 7H), 7.36 (d, 2H), 7.23 (d, 1H), 3.64 (s, 2H), 3.59 (s, 2H).

Example 92

({[4-({[4-(Difluorophosphonomethyl)-3-bromophenyl]methylthio}methyl)phenyl]methyl}sulfonyl)benzene Step 1: Diethyl ({[4-({[4-(difluorophosphonomethyl)-3-bromophenyl]methylthio}methyl)phenyl]methyl}sulfonyl)benzene The title compound was prepared using 1-bromomethyl-2-[(phenylsulfonyl)methyl]benzene and diethyl (2-bromo-4-acetylthiomethyl-phenyl)difluoro-methyl-phosphonic acid following a procedure similar to the one described above.

$^1$H NMR (CD$_3$COCD$_3$) δ 7.55-7.8(7H, m), 7.45-7.5(1H, d), 7.1-7.45(4H, m), 4.65(2H, s), 4.15-4.35(4H, m), 3.8(2H, s), 3.7(2H, s), 1.3-1.4(6H, m).

Step 2: Sodium ({[4-({[4-(difluorophosphonomethyl)-3-bromophenyl]methylthio}methyl)phenyl]methyl}sulfonyl)benzene The ester from above was dealkylated with TMSiBr and the sodium salt was obtained following a procedure as described for previous analogs.

$^1$H NMR (CD$_3$OD) δ 8.1 (1H, d), 7.75-7.1(12H, m), 4.65(2H, s), 3.6(2H, s), 3.45(2H,

Example 93

4-({[4-({[4-(Difluorophosphonomethyl)-3-bromophenyl]methylthio}methyl)phenyl]methylthio {methyl)benzenesulfonamide Step 1: (tert-Butyl){[4-(chloromethyl)phenyl]sulfonyl}amine To a 0° C. dichloromethane (200 mL) and methanol (200 mL) solution of 4-chloromethyl-thioanisole (60 mmol., 10.3 g.) was added MMPP (29 mmol., 18 g.) and the mixture was reacted 2 hours. It was poured over ice, diluted aqueous bicarbonate and dichloromethane. The dichloromethane layer was separated and the aqueous further extracted with dichloromethane. The combined organic extracts were washed with diluted aqueous hydrochloric acid, brine and dried with magnesium sulfate. Removal of the solvent left a residue of the sulfoxide which was used as such in the next step (11.3 g.).

The sulfoxide (30 mmol., 5.64 g.) in dichloromethane (10 mL) was added to trifluoroacetic anhydride (25 mL) in dichloromethane (50 mL) and the mixture was gently heated for 1 hour. The volatils were removed in vacuo and the residue coevaporated with toluene (3×). The residue was dissolved in dichloromethane (50 mL) and water (10 mL) was added. Nitrogen was passed through the mixture which was vigourously stirred for 45 minutes. Acetic acid (10 mL) was added and chlorine was introduced at a rate of about 2 bubbles per second for 30–45 minutes. A vacuum adaptor was fitted to the reaction vessel and excess chlorine was removed under gentle vacuum. The mixture was diluted with water and dichloromethane was added. The dichloromethane layer was separated and the aqueous was further extracted with dichloromethane. The combined organic extracts were washed with diluted aqueous bicarbonate, brine and dried with magnesium sulfate. Removal of the solvent left a residue of the sulfonyl chloride which was used as such in the next step (3.28 g.).

The sulfonyl chloride (3.28 g.) was dissolved in dichloromethane (50 mL) and, at 0° C., t-butylamine (30 mmol., 2.2 g.) was added. The mixture was reacted for 2 hours while warming to room temperature. The mixture was diluted with water and dichloromethane was added. The dichloromethane layer was separated and the aqueous further extracted with dichloromethane. The combined organic extracts were washed with diluted aqueous hydrochloric acid, brine and dried with magnesium sulfate. Removal of the solvent left a residue which was triturated in ether and hexanes to yield (tert-butyl) {[4-(chloromethyl)phenyl]sulfonyl}amine (3.96 g.).

$^1$H NMR (CD$_3$COCD$_3$) δ 7.85-7.95(2H, d), 7.6-7.7(2H, d), 6.4(2H, bs(NH$_2$)), 4.8(2H, s), 1.2(9H, s).

Step 2: (tert-Butyl){[4-(acetylthio)phenyl]sulfonyl}amine

To a 0° C. DMF (50 mL) solution of the chloride (15 mmol., 3.96 g.) was added potassium thioacetate (18 mmol., 2 g.) and the mixture was reacted for 3 hours. It was poured over ice, water and ethyl acetate. The ethyl acetate layer was separated and the aqueous further extracted with ethyl acetate. The combined organic extracts were washed with diluted aqueous sodium bicarbonate, brine and dried with magnesium sulfate. Removal of the solvent left a residue which was purified by chromatography on silica using ethyl acetate and hexanes (1:5) to give (tert-butyl){[4-(acetylthio)phenyl]sulfonyl}amine (2.9 g.)

$^1$H NMR (CD$_3$COCD$_3$) δ 7.8-7.85(2H, d), 7.45-7.55(2H, d), 4.2(2H, s), 2.35(3H, s), 1.2(9H, s).

Step 3: (tert-Butyl){[4-({[3-(bromomethyl)phenyl]methylthio}methyl)phenyl]sulfonyl}amine To a 0° C. dioxane (I mL) and ethanol (4 mL) solution of the thioacetate (1 mmol., 0.301 g.) and 1,3-bis(bromomethyl)benzene (4 mmol., 1.05 g.) was added sodium methoxide (2 mmol., 0.108 g.). After 1 hour, it was poured on ice, diluted aqueous HCl and ethyl acetate. The ethyl acetate layer was separated and the aqueous further extracted with ethyl acetate. The combined organic extracts were washed with diluted aqueous sodium bicarbonate, brine and dried with magnesium sulfate. Removal of the solvent left a residue which was purified by chromatography on silica using ethyl acetate and hexanes (1:3 to 1:2) to give (tert-butyl){[4-({[3-(bromomethyl)phenyl]methylthio}methyl)-phenyl]sulfonyl}amine(0.16 g.).

$^1$H NMR (CD$_3$COCD$_3$) δ 7.7-7.75(2H, d), 7.45-7.5(2H, d), 7.2-7.4(4H, m), 6.35(1H, bs), 4.65(2H, s), 3.75(2H, s), 3.7(2H, s), 1.25(9H, s).

Step 4: Diethyl 4-{[4-({[4-(difluorophosphonomethyl)-3-bromophenyl]methylthio}methyl)phenyl]methylthio}benzene-t-butylsulfonamide The title compound was prepared using the bromide from step 3 and diethyl (2-bromo-4-acetylthiomethyl-phenyl)- difluoro-methyl-phosphonic acid following a procedure similar to the one described above.

$^1$H NMR (CD$_3$COCD$_3$) δ 7.8-7.85(2H, m), 7.7(1H, m), 7.6(1H, m), 7.45-7.55(3H, m), 7.15-7.35(4H, m), 6.45(1H, NH), 4.15-4.35(4H, m), 3.65-3.8(8H, 4s), 1.35-1.45(6H, t), 1.25(9H, s).

Step 5: Sodium 4-{[4-({[4-(difluorophosphonomethyl)-3-bromophenyl]methylthio}methyl)phenyl]methylthio}benzenesulfonamide The ester from above was dealkylated with TMSiBr and the t-butyl group cleaved following a procedure as described for a previous analogs. The sodium salt was obtained in the usual manner.

$^1$H NMR (CD$_3$COCD$_3$), for the free acid, δ 7.8-7.9(2H, d), 7.7-7.8(1H, m), 7.6(1H, s), 7.5(2H, d), 7.45(1H, d), 7.15-7.30(4H, m), 3.75(2H, s), 3.65-3.75(6H, 3s).

Example 94

(2-Bromo-4-{[(4-bromophenyl)methylthio]ethyl}phenyl)difluoromethylphosphonic Acid Step 1: 4-[(Diethoxyphosphonyl)difluoromethyl]-3-bromobenzaldehyde A dioxane (25 mL) solution of diethyl (2-bromo-4-bromomethyl-phenyl)-difluoromethyl-phosphonic acid (6.88 mmo, 1.3 g.) and N-methylmorpholine-N-oxide (20 mmol., 2.34 g.) was heated at 95° C. for 3 hours. It was cooled and poured over ice, diluted aqueous HCl and ethyl acetate. The ethyl acetate layer was separated and the aqueous further extracted with ethyl acetate. The combined organic extracts were washed with diluted aqueous sodium bicarbonate, brine and dried with magnesium sulfate. Removal of the solvent left a residue which was purified by chromatography on silica using ethyl acetate and hexanes (1:1) to give 4-[(diethoxyphosphonyl)difluoromethyl]-3-bromobenzaldehyde (0.97 g.).

$^1$H NMR (CD$_3$COCD$_3$) δ 10.1(1H, s), 8.25(1H, s), 8.0-8.1(1H, d), 7.85-7.9)1H, d), 4.15-4.35(4H, m), 1.25-1.35 (6H, m).

Step 2: [(2-Bromo-4-vinylphenyl)difluoromethyl]diethoxyphosphino-1-one

To a −78° C. suspension of methyltriphenylphosphonium bromide (5 mmol., 1.79 g.) in THF (20 mL) was added 2.38 M n-butyl lithium in hexanes (1.93 mL) and the mixture was allowed to warm to 0° C. The ylid was transferred into a THF (15 mL) solution of the aldehyde from step 1 (4.58 mmol., 1.6 g.). The mixture was warmed slowly to room temperature and stirred 2 hours. It was poured over ice, diluted aqueous HCl and ethyl acetate. The ethyl acetate layer was separated and the aqueous was further extracted with ethyl acetate. The combined organic extracts were washed with diluted aqueous sodium bicarbonate, brine and dried with magnesium sulfate. Removal of the solvent left a residue which was purified by chromatography on silica using ethyl acetate and hexanes (1:2) to give [(2-bromo-4-vinylphenyl)difluoromethyl]diethoxyphosphino-1-one (0.63 g.).

$^1$H NMR (CD$_3$COCD$_3$) δ 7.85(1H, s), 7.65(2H, s), 6.75-6.85(1H, m), 6.0(1H, d), 5.45(1H, d), 4.15-4.25(4H, m), 1.25-1.35(6H, m).

Step 3: {[2-Bromo-4-(α-hydroxyethyl)phenyl]difluoromethyl}diethoxyphosphino-1-one Mercuric acetate (1 mmol., 0.318 g.) was added to water (2 mL) and the mixture stirred vigourously for 10 minutes. The vinyl intermediate from step 2 (1 mmol., 0.347 g.) was added as a THF (2 mL) solution and the mixture was stirred at room temperature for 2 hours and then at 60° C. for 1 hour. The mixture was cooled and more mercuric acetate (0.32 g.) was added. The mixture was stirred at 60° C. for 2 hours. It was cooled and poured over water and ethyl acetate. The ethyl acetate layer was separated and the aqueous further extracted with ethyl acetate. The combined ethyl acetate layers were mixed and stirred for 5 minutes with brine. The organic layer was dried with magnesium sulfate and the solvent removed in vacuo. To the residue in toluene (3 mL) was added AIBN (0.025 g.) followed by n-Bu$_3$SnH (2.5 mmol., 0.728 g.) and the mixture was stirred for 1 hour. It was then poured over 5% KF (10 mL) and ethyl acetate and stirred 5 minutes. It was diluted with water and aqueous ammonium chloride. The ethyl acetate layer was separated and the aqueous was further extracted with ethyl acetate. The combined organic extracts were washed with diluted aqueous sodium bicarbonate, brine and dried with magnesium sulfate. Removal of the solvent left a residue which was purified by chromatography on silica using ethyl acetate and hexanes (1:1 to 2:1) to give {[2-bromo-4-(α-hydroxyethyl)phenyl]difluoromethyl}diethoxyphosphino-1-one) 0.18 g.).

$^1$H NMR (CD$_3$COCD$_3$) δ 7.75(1H, s), 7.6(1H, d), 7.5(1H, d), 4.9(1H, m), 4.5(1H, d), 4.15-4.25(4H, m), 1.4(3H, d), 1.35-1.45(6H, t).

Step 4: Diethyl (2-bromo-4-{[(4-bromophenyl)methylthio]ethyl}phenyl)difluoromethylphosphonic Acid To a −40° C. dichloromethane (3 mL) solution of the alcohol from above (0.493 mmol., 0.18 g.) was added triethylamine (0.75 mmol., 0.075 g.) followed by methanesulfonyl chloride (0.6 mmol., 0.068 g.). The mixture was kept at 40° C. for 0.5 hour and then warmed to 0° C. for 2 hours. Dichloromethane was added and the mixture was poured on diluted aqueous sodium bicarbonate. The organic layer was separated and the aqueous was further extracted with dichloromethane. The combined organic layers were washed with brine, dried with magnesium sulfate and the solvent was removed in vacuo. The residue was used as such in the next step.

To a 0° C. ethanol (4 mL) solution of 4-(acetylthiomethyl)-bromobenzene (1 mmol., 0.245 g.) was added NaOMe (1.2 mmol., 0.065 g.). The mixture was stirred for 0.5 hour and then poured on ice, diluted aqueous HCl and ethyl acetate. The organic layer was separated. The aqueous was further extracted with ethyl acetate. The combined organic extracts were washed with diluted aqueous sodium bicarbonate, brine and dried with magnesium sulfate. Removal of the solvent left a residue which was dissolved in acetonitrile (2 mL) and added to a 0° C. acetonitrile (2 mL) suspension of the mesylate from the previous step and cesium carbonate (1.05 mmol., 0.35 g.). It was reacted 10 minutes at this temperature and then warmed to room temperature and stirred 2 hours. It was poured over ice, diluted aqueous HCl and ethyl acetate. The ethyl acetate layer was separated and the aqueous was further extracted with ethyl acetate. The combined organic extracts were washed diluted aqueous sodium bicarbonate, brine and dried with magnesium sulfate. Removal of the solvent left a residue which was purified by chromatography on silica using ethyl acetate and hexanes (1:2) to give diethyl (2-bromo-4-{[(4-bromophenyl)methylthio]ethyl}phenyl)difluoromethylphosphonic acid (0.139 g.).

$^1$H NMR (CD$_3$COCD$_3$) δ 7.65(1H, s), 7.6(1H, m), 7.4-7.55(3H, m), 7.3(1H, m), 7.15(2H, m), 4.15-4.25(4H, m), 3.9-4.0(1H, m), 3.5-3.65(2H, m), 1.5(3H, d), 1.25-1.35(6H, m).

Step 5: Sodium (2-bromo-4-{[(4-bromophenyl)methylthio]ethyl}phenyl)difluoromethylphosphonic Acid The ester from above was dealkylated with TMSiBr and the sodium salt was obtained in the usual manner.

¹H NMR (CD₃OD) δ 8.15(1H, d), 7.55(1H, s), 7.45(2H, d), 7.25(1H, d), 7.15(2H, d), 3.75-3.85(1H, m), 3.4-3.6(2H, m), 1.5(3H, d).

Example 95

1-({[4-(Difluorophosphonomethyl)-3-bromophenyl]methylthio}methyl)-4-(methylsulfinyl)benzene This compound was prepared by the usual manner from 4-(bromomethyl)-1-(methylsulfinyl)benzene and di-t-butyl (2-bromo-4-acetylthiomethyl-phenyl)-difluoromethyl-phosphonic acid. It was subsequently dealkylated and the sodium salt was obtained in the usual manner.

¹H NMR (CD₃OD) δ 8.0(1H, d), 7.65(2H, d), 7.5(3H, m), 7.25(1H, d)3.7(2H, s), 3.65(2H, s), 2.85(3H, s).

Example 96

5-[(3-{14-(Difluorophosphonomethyl)-3-bromophenyl]methylthio}phenylthio)methyl]-2,4-dichlorobenzenesulfonamide Step 1: 5-(Bromomethyl)-2,4-dichlorobenzenesulfonamide The title compound was prepared from 2,4-dichloro-5-sulfamoylbenzoic acid in the same manner as for the intermediate of step 1 in EXAMPLE 89.

¹H NMR (CD₃COCD₃) δ 8.25(1H, s), 7.8(1H, s), 6.9-7.0 (2H, bs), 4.8(2H, s).

Step 2: Diethyl 5-[(3-{[4-(difluorophosphonomethyl)-3-bromophenyl]methylthio}phenylthio)methyl]-2,4-dichlorobenzenesulfonamide To a 0° C. DMF (10 mL) solution of the bromide from step 1 (2 mmol., 0.638 g.) and 1,3-benzenedithiol (6 mmol., 0.852 g.) was added potassium carbonate (2 mmol., 0.276 g.) and the mixture was stirred for 1 hour and warmed to room temperature. After 2 hours, it was poured over ice, diluted aqueous HCl, ether and ethyl acetate. The organic layer was separated and the aqueous further extracted with ethyl acetate. The combined organic extracts were washed with diluted aqueous sodium bicarbonate, brine and dried with magnesium sulfate. Removal of the solvent left a residue which was passed on a short pad of silica using ethyl acetate and hexanes (1:2) to give impure 2,4-dichloro-5-[(3-sulfanylphenylthio)methyl]benzenesulfonamide used as such (0.694 g.).

To a 0° C. DMF (10 mL) solution of the thiol from above and diethyl (2-bromo-4-bromomethyl-phenyl)-difluoromethyl-phosphonic acid (1.8 mmol., 0.784 g.) was added cesium carbonate (2 mmol., 0.65 g.) and the mixture was stirred at room temperature. After 2 hours, it was poured over ice, diluted aqueous HCl and ethyl acetate. The organic layer was separated and the aqueous further extracted with ethyl acetate. The combined organic extracts were washed with diluted aqueous sodium bicarbonate, brine and dried with magnesium sulfate. Removal of the solvent left a residue which was purified by chromatography on silica using ethyl acetate and hexanes (1:1.5 to 1:1) to give diethyl 5-[(3-{[4-(difluorophosphonomethyl)-3-bromophenyl]methylthio}phenylthio)methyl]-2,4-dichlorobenzenesulfonamide (0.639 g.).

¹H NMR (CD₃COCD₃) δ 8.15(1H, s), 7.75(1H, s), 7.7 (1H, s), 7.6(1H, s), 7.5(1H, s), 7.35(1H, s), 7.15-7.25(3H, m), 6.8-6.9(2H, NH₂), 4.35(2H, s), 4.3(2H, s), 4.1-4.25(4H, m), 1.2-1.3(6H, t).

Step 3: Sodium 5-[(3-{[4-(difluorophosphonomethyl)-3-bromophenyl]methylthio}phenylthio)methyl]-2,4-dichlorobenzenesulfonamide The ester from above was dealkylated with TMSiBr and the sodium salt was obtained in the usual manner.

¹H NMR (CD₃OD) δ 8.05(1H, d), 7.95(1H, s), 7.65(1H, s), 7.55(1H, s), 7.1-7.3(5H, m), 4.2(2H, s), 4.1(2H, s).

Example 97

3-[5-({[4-(Difluorophosphonomethyl)-3-bromophenyl]methylthio}methyl)-2-pyridyl]benzenesulfonamide Step 1: 3-[5-(Bromomethyl)-2-pyridyl]benzenesulfonamide This intermediate was prepared from methyl 6-chloronicotinate and 3-bromobenzeneboronic acid using a procedure similar to EXAMPLE 90.

¹H NMR (CD₃COCD₃) δ 8.8(1H, s), 8.7(1H, s), 8.35(1H, d), 8.05(2H, m), 7.95(1H, m), 7.65(1H, m), 6.7(2H, NH₂), 4.75(2H, s).

Step 2: Diethyl 3-[5-({[4-(difluorophosphonomethyl)-3-bromophenyl]methylthio}methyl)-2-pyridyl]benzenesulfonamide This intermediate was obtained from the bromide in step 1 and (2-bromo-4-acetylthiomethyl-phenyl)-difluoromethyl-phosphonic acid in the usual manner.

¹H NMR (CD₃COCD₃) δ 8.7(1H, s), 8.65(1H, m), 8.3 (1H, d), 7.95-8.0(2H, m), 7.85(1H, m), 7.1-7.25(3H, m), 7.5(1H, m), 6.65-6.7(2H, NH₂), 4.15-4.3(4H, m), 3.85(4H, m), 1.25-1.35(6H, m).

Step 3: Sodium 3-[5-({[4-(difluorophosphonomethyl)-3-bromophenyl]methylthio}methyl)-2-pyridyl]benzenesulfonamide The intermediate from step 2 was dealkylated and the sodium salt was obtained in the ususal manner.

¹H NMR (CD₃OD) δ 8.55(1H, 2H, s), 8.20(1H, m), 7.95(1H, m), 7.8-7.9(2H, m), 7.75(1H, m), 7.65-7.7(1H, m), 7.55(1H, s), 7.35(1H, m), 3.75(2H, s), 3.7(2H, s).

Example 98

(2-Bromo-4-[(6-chloro(3-pyridyl))methylthio]methyl}phenyl)difluoromethylphosphonic Acid Step 1: Diethyl (2-bromo-4-{[(6-chloro(3-pyridyl))methylthio]methyl}phenyl)difluoromethylphosphonic Acid This compound was prepared from 5-(bromomethyl)-2-chloropyridine and (2-bromo-4-acetylthiomethyl-phenyl)-difluoro-methyl-phosphonic acid in the usual manner.

¹H NMR (CD₃COCD₃) δ 8.3(1H, s), 7.75(1H, m), 7.7 (1H, s), 7.6(1H, s), 7.5(1H, m), 7.4(1H, m), 4.15-4.25(4H, m), 3.8(2H, s), 3.75(2H, s), 1.25-1.35(6H, m).

Step 2: Sodium (2-bromo-4-{[(6-chloro(3-pyridyl))methylthio]methyl}phenyl)difluoromethylphosphonic Acid The compound was obtained in the usual manner from the intermediate of step 1.

¹H NMR (CD₃OD) δ 8.25(1H, s), 7.9(1H, d), 7.75(1H, dd), 7.55(1H, s), 7.4(1H, d), 7.25(1H, d), 3.65(4H, m).

Example 99

2-{3-[4-({[4-(Difluorophosphonomethyl)-3-bromophenyl]methylthio}methyl)phenyl]phenyl}-4-methylpentanoic Acid Step 1: 2-(3-Bromophenyl)-4-methylpentanoic Acid Under nitrogen a 72L round bottom flask equipped with a mechanical stirrer, a nitrogen inlet, a thermocouple and addition funnel was charged with 3-bromophenylacetic acid (1.8 kg), THF (9L), and DMPU (1.8L). The mixture was cooled to −20° C. with a MeOH/dry ice bath. 1-Iodo-2-methylpropane (1.6 Kg) was added and the temperature re-adjusted to −20° C. LiHNDS (1M in THF) 17.6L was added via addition funnel over ~3 hours maintaining a temperature of −19° C. to −22° C.

The batch was aged for 4 hours at −18° C. to −20° C. The batch was allowed to warm to room temperature overnight. A sample assayed by HPLC indicated that all starting material was consumed. The batch was cooled to −5° C. and HCl (6N, 5.5L) added over 2 hours maintaining the temperature <20° C. The batch was transferred to a 100L cylindrical vessel and the lower aqueous layer separated.

The TBF layer was concentrated on the rotavap (<40° C.) to yield a viscous oil (3.1Kg). The oil was dissolved in a pre-mixed solution of methanol (7.2L) and water (2.1L) in a 50L round bottom flask. The temperature was adjusted to 20–22° C., and water (0.5L) added, followed by seed (10 g). The batch was aged for 1 hour during which crystallization occurred. Water (8.1L) was added over 3 hours and the batch aged overnight at room temperature. The batch was filtered and the cake washed with methanol/water (2/3 v/v 2×3L). The cake was dried under vacuum at 30° C. for 24 hours to yield 2090 g, (92 wt % by HPLC), 1886 assay g, 85% yield.

Step 2: Methyl 2-{3-[4-(bromomethyl)phenyl]phenyl}-4-methylpentanoate

The title compound was obtained from the bromide of step 1 and 4-hydroxymethylbenzeneboronic acid in a similar manner to step 2-3 of Example 27.

$^1$H NMR (CD$_3$COCD$_3$) δ 7.65(2H, m), 7.55(2H, m), 7.45(1H, m), 7.35(1H, m), 7.15-7.25(2H, m), 4.7(2H, s), 3.8(1H, m), 3.6(3H, s), 1.95-2.05(1H, m), 1.65-1.75(1H, m), ¼-1.5(1H, m), 0.9(6H, m).

Step 3: 2-{3-[4-({[4-(Diethoxyphosphorydifluoromethyl)-3-bromophenyl]methylthio}methyl)phenyl]phenyl}-4-methylpentanoic acid methyl ester This compound was obtained from the bromide in step 2 and (2-bromo-4-acetylthiomethyl-phenyl)-difluoro-methyl-phosphonic acid in the usual manner.

$^1$H NMR (CD$_3$COCD$_3$) δ 7.75(1H, s), 7.6-7.7(4H, m), 7.6(1H, m), 7.5(1H, m), 7.35-7.45(4H, m), 4.15-4.3(4H, m), 3.75-3.85(5H, m), 3.65(3H, s), 1.95-2.05(1H, m), 1.7-1.8 (1H, m), 1.45-1.55(1H, m), 1.3-1.4(6H, t), 0.95(6H, m).

Step 4: 2-{3-[4-({[4-(Difluorophosphonomethyl)-3-bromophenyl]methylthio}methyl)phenyl]phenyl}-4-methylpentanoic acid The intermediate from step 3 was dealkylated and the sodium salt was obtained in the usual manner.

$^1$H NMR (CD$_3$OD) δ 8.1 (1H, m), 7.65(1H, s), 7.6(2H, m), 7.55(1H, s), 7.4(1H, m), 7.25-7.35(5H, m), 3.55-3.65 (4H, m), 1.9-2.05(1H, m), 1.5-1.65(2H, m), 0.95(6H, m).

Example 100

[2-Bromo-4-(4-fluorobenzylsulfanylmethyl)-phenyl]-difluoromethylphosphonic Acid Disodium Salt.

Step 1: [2-Bromo-4-(4-fluorobenzylsulfanylmethyl)-phenyl]-difluoromethylphosphonic acid diethyl ester.

To a solution of 4-fluorobenzyl mercaptan (72 mg) and (2-bromo-4-bromomethylphenyl)-difluoromethylphosphonic acid diethyl ester (200 mg) in ethanol (5 mL) was added sodium methoxide (74 mg) and the mixture was stirred for 30 min. A saturated solution of ammonium chloride was added to the mixture, which was extracted with ethyl acetate, washed with brine and dried over magnesium sulfate. Purification by silica gel chromatography using 30% ethyl acetate/hexane afforded 193 mg of the title compound.

Step 2: [2-Bromo-4-(4-bromobenzylsulfanylmethyl)-phenyl]-difluoromethylphosphonic Acid Disodium Salt.

The intermediate from step 1 was treated with bromotrimethylsilane as described for Example 10, step 2.

$^1$H NMR (CD$_3$OD) δ 8.10 (d, 1H), 7.49 (s, 1H), 7.29 (m, 2H), 7.22 (d, 1H), 7.04 (t, 2H), 3.58 (s, 2H), 3.57 (d, 2H).

M.S. (APCI) m/z 441 (M–H)$^-$

Example 101

[2-Bromo-4-(5-phenyl-[1,3,4]oxadiazol-2-ylsulfanylmethyl)-phenyl]-difluoromethylphosphonic Acid Disodium Salt.

Step 1: [2-Bromo-4-(5-phenyl-[1,3,4]oxadiazol-2-ylsulfanylmethyl)phenyl]-difluoromethylphosphonic Acid Diethyl Ester.

To a solution of 5-phenyl-1,3,4-oxadiazole-2-thiol (123 mg) and (2-bromo-4-bromomethylphenyl)-difluoromethylphosphonic acid diethyl ester (200 mg) in ethanol (5 mL) was added sodium methoxide (50 mg) and the mixture was stirred for 2 hrs. A saturated solution of ammonium chloride was added to the mixture which was extracted with ethyl acetate, washed with brine (2×) and dried over magnesium sulfate. Purification by silica gel chromatography using 40% ethyl acetate/hexane afforded 193 mg of [2-bromo-4-(5-phenyl-[1,3,4]oxadiazol-2-ylsulfanylmethyl)-phenyl]-difluoromethylphosphonic acid diethyl ester.

Step 2: [2-Bromo-4-(5-phenyl-[1,3,4]oxadiazol-2-ylsulfanylmethyl)phenyl]-difluoromethylphosphonic Acid Disodium Salt.

The intermediate from step 1 was treated with bromotrimethylsilane as described for Example 10, step 2.

$^1$H NMR (CD$_3$OD) δ 8.00 (m, 3H), 7.79 (s, 1H), 7.59 (m, 3H), 7.49 (d, 1H), 4.55 (s, 2H).

M.S. (APCI) m/z 477 (M–H)$^-$.

Example 102

{2-Bromo-4-[3-(3-methylsulfonylphenyl)-prop-2-ynylsulfanylmethyl]-phenyl}-difluoromethylphosphonic Acid Disodium Salt The title compound was obtained in a similar manner as described for Example 52, step 5–6, from di-(tert-butyl)[2-bromo-4-(bromomethyl)phenyl(difluoro)methylphosphonate and thioacetic acid S-[3-(3-methylsulfonylphenyl)-prop-2-ynyl]ester, which was prepared from the coupling reaction of 1-bromo-3-(methylsulfonyl)benzene and propargyl alcohol and the alcohol intermediate was subsequently converted to the thioacetate in a similar manner as, Example 52, step 1–4.

$^1$H NMR (Methanol-d$_4$) δ 8.14 (d, 1H), 8.01 (s, 1H), 7.93 (d, 1H), 7.77 (d, 1H), 7.64 (m, 2H), 7.34 (d, 1H), 3.92 (s, 2H), 3.42 (s, 2H), 3.16 (s, 3H).

Example 103

{2-Bromo-4-[3-(4-bromophenyl)-prop-2-ynylsulfanylmethyl]-phenyl}-difluoromethylphosphonic Acid Disodium Salt The tiltle compound was obtained in a similar manner as described for Example 52, step 5–6, from di-(tert-butyl)[2-bromo-4-(bromomethyl)phenyl(difluoro)methylphosphonate and thioacetic acid S-[4-bromophenyl)-prop-2-ynyl]ester, which was prepared from the coupling reaction of 1,4-dibromobenzene and propargyl alcohol and the alcohol intermediate was subsequently converted to the thioacetate in a similar manner as, Example 52, step 2–4.

$^1$H NMR (Methanol-d$_4$) δ 8.13 (d, 1H), 7.63 (s, 1H), 7.52 (d, 2H), 7.36 (m, 3H), 3.89 (s, 2H), 3.36 (s, 2H).

The following procedure was the general condition for synthesis from thioacetic acid S-{3-bromo-4-[(diethoxyphosphoryl)-difluoromethylbenzyl ester with a halide.

A stock solution of thioacetic acid S-{3-bromo-4-[(diethoxyphosphoryl)-difluoromethylbenzyl ester (840 mg) in ethanol (8.4 mL) was prepared, 0.2 mL (0.046 mM) of this stock solution was mixed with a solution (0.2 mL, 0.064 mM)) of halide in ethanol (0.64 mM in 2 mL), then 1N sodium methoxide (0.2 mL) was added. The mixture was stirred over night. The solvent was evaporated under vacuum, using a centrifuge.

To the above coupling intermediate was added 1.5 mL of a stock solution, prepared from bromotrimethylsilane (7.2 mL) in chloroform (82.8 mL), and the resulting mixture was stirred overnight. The solvent was evaporated under vacuum, then 1 mL of chloroform was added and the solvent was again evaporated under vacuum. To the residue was added 0.25 mL of dichloromethane and 1 mL of ethanol and the mixture was stirred 2 hrs. The solvent was evaporated under vacuum and the residue was purified by LC/MS (using an X-Terra MS $C_{18}$ 5 μM 19×50 mm HPLC column, with a gradient from 90% water-5% $CH_3CN$-5% 60 mM $NH_4OAc$ to 20% water-75% $CH_3CN$-5% 60 mM $NH_4OAc$ over 10 minutes using a Micromass ZMD mass spectrum, negative ion electrospray for detection) to afford the title compound. Example 104–155 were prepared in this manner.

Example 104
[2-Bromo-4-(4-methylsulfonylbenzylsulfanylmethyl)-phenyl]-difluoromethylphosphonic Acid
The title compound was prepared from 4-methylsulfonylbenzyl chloride.
M.S. (APCI) m/z 501 (M–H)⁻.

Example 105
[4-(4-Benzyloxybenzylsulfanylmethyl)-2-bromophenyl] difluoromethylphosphonic Acid.
The title compound was prepared from 4-benzyloxybenzyl chloride.
M.S. (APCI) m/z 529 (M–H)⁻

Example 106
{2-Bromo-4-[2-(2-methoxyethoxy)ethylsulfanylmethyl] phenyl}difluoromethylphosphonic Acid.
The title compound was prepared from 1-bromo-2-(2-methoxyethoxy)ethane.
M.S. (APCI) m/z 435 (M–H)⁻

Example 107
[4-(4-Acetylaminobenzylsulfanylmethyl)-2-bromophenyl] difluoromethylphosphonic Acid.
The title compound was prepared from 4-acetamidobenzyl chloride.
M.S. (APCI) m/z 480 (M–H)⁻.

Example 108
[4-(2-Benzenesulfinylethylsulfanylmethyl)-2-bromophenyl] difluoromethylphosphonic Acid.
The title compound was prepared from 2-chloroethyl phenyl sulphoxide.
M.S. (APCI) m/z 485 (M–H)⁻

Example 109
[2-Bromo-4-(3,3-dimethyl-2-oxobutylsulfanylmethyl) phenyl]difluoromethylphosphonic Acid.
The title compound was prepared from 1-bromopinacolone.
M.S. (APCI) m/z 431 (M–H)⁻

Example 110
[2-Bromo-4-(2,4,6-trimethylbenzylsulfanylmethyl) phenyl] difluoromethylphosphonic Acid.
The title compound was prepared from 2,4,6-trimethylbenzyl chloride.
M.S. (APCI) m/z 465 (M–H)⁻

Example 111
2-Bromo-4-(3-nitrobenzylsulfanylmethyl) phenyl] difluoromethylphosphonic Acid.
The title compound was prepared from m-nitrobenzyl bromide.
M.S. (APCI) m/z 468 (M–H)⁻

Example 112
[2-Bromo-4-(3-phenoxypropylsulfanylmethyl) phenyl] difluoromethylphosphonic Acid.
The title compound was prepared from 3-bromopropyl phenyl ether.
M.S. (APCI) m/z 467 (M–H)⁻

Example 113
[2-Bromo-4-(3-methoxybenzylsulfanylmethyl) phenyl] difluoromethylphosphonic Acid.
The title compound was prepared from 3-methoxybenzyl chloride.
M.S. (APCI) m/z 453 (M–H)⁻

Example 114
2-Bromo-4-(tetrahydropyran-2-ylmethylsulfanylmethyl) phenyl]difluoromethylphosphonic Acid.
The title compound was prepared from 2-(bromomethyl) tetrahydro-2H-pyran.
M.S. (APCI) m/z 431 (M–H)⁻

Example 115
{2-Bromo-4-[4-(1,3-dioxo-1,3-dihydroisoindol-2-yl) butylsulfanylmethyl]phenyl}difluoromethylphosphonic Acid.
The title compound was prepared from N-(4-bromobutyl) phthalimide.
M.S. (APCI) m/z 534 (M–H)⁻

Example 116
[2-Bromo-4-(4-nitrobenzylsulfanylmethyl) phenyl] difluoromethylphosphonic Acid.
The title compound was prepared from p-nitrobenzyl chloride.
M.S. (APCI) m/z 468 (M–H)⁻

Example 117
[2-Bromo-4-(6-cyanohexylsulfanylmethyl) phenyl] difluoromethylphosphonic Acid.
The title compound was prepared from 7-bromoheptanenitrile.
M.S. (APCI) m/z 442 (M–H)⁻

Example 118
[2-Bromo-4-(4,4,4-trifluorobutylsulfanylmethyl) phenyl] difluoromethylphosphonic Acid.
The title compound was prepared from 4,4,4-trifluoro-1-bromobutane.
M.S. (APCI) m/z 443 (M–H)⁻

Example 119
[2-Bromo-4-(7-hydroxyheptylsulfanylmethyl) phenyl] difluoromethylphosphophonic Acid.
The title compound was prepared from 7-bromo-1-heptanol.
M.S. (APCI) m/z 447 (M–H)⁻.

Example 120
[2-Bromo-4-(7-methoxy-2-oxo-2H-chromen-4-ylmethylsulfanylmethyl) phenyl]difluoromethylphosphonic Acid.
The title compound was prepared from 4-(bromomethyl)-7-methoxycoumarin.
M.S. (APCI) m/z 521 (M–H)⁻.

Example 121
(2-Bromo-4-hexylsulfanylmethylphenyl) difluoromethylphosphonic Acid.
The title compound was prepared from bromohexane.
M.S. (APCI) m/z 417 (M–H)⁻.

Example 122
[2-Bromo-4-(carbamoylmethylsulfanylmethyl)phenyl]difluoromethylphosphonic Acid.

The title compound was prepared from 2-chloroacetamide.

M.S. (APCI) m/z 390 (M−H)⁻.

Example 123
[4-(2-Benzenesulfonylmethylbenzylsulfanylmethyl)-2-bromophenyl]difluoromethylphosphonic Acid.

The title compound was prepared from 1-(bromomethyl)-2-[(phenylsulfonyl)methyl]benzene.

M.S. (APCI) m/z 577 (M−H)⁻.

Example 124
[2-Bromo-4-(2-piperidin-1-ylethylsulfanylmethyl)phenyl]difluoromethylphosphonic Acid.

The title compound was prepared from 1-(2-chloroethyl)piperidine hydrochloride.

M.S. (APCI) m/z 444 (M−H)⁻.

Example 125
[2-Bromo-4-(pyridin-4-ylmethylsulfanylmethyl)phenyl]difluoromethylphosphonic Acid.

The title compound was prepared from 4-(chloromethyl)pyridine hydrochloride.

M.S. (APCI) m/z 424 (M−H)⁻.

Example 126
[2-Bromo-4-(2-methylthiazol-4-ylmethylsulfanylmethyl)phenyl]difluoromethylphosphonic Acid.

The title compound was prepared from 4-chloromethyl-2-methylthiazole hydrochloride.

M.S. (APCI) m/z 444 (M−H)⁻.

Example 127
{4-[3-(4-Acetyl-3-hydroxy-2-propylphenoxy)-propylsulfanylmethyl]-2-bromophenyl}difluoromethylphosphonic Acid.

The title compound was prepared from 1-[4-(3-bromopropoxy)-2-hydroxy-3-propylphenyl]ethanone.

M.S. (APCI) m/z 567 (M−H)⁻.

Example 128
[2-Bromo-4-(3,5-difluorobenzylsulfanylmethyl)phenyl]difluoromethylphosphonic Acid.

The title compound was prepared from 3,5-difluorobenzyl bromide.

M.S. (APCI) m/z 459(M−H)⁻.

Example 129
[2-Bromo-4-(4-methylbenzylsulfanylmethyl)-phenyl]-difluoromethylphosphonic Acid.

The title compound was prepared from 4-methylbenzyl bromide.

M.S. (APCI) m/z 437 (M−H)⁻.

Example 130
2-Bromo-4-(3-ethoxycarbonylphenylsulfanylmethyl)phenyl]difluoromethylphoshonic Acid.

The title compound was prepared from methyl 3-bromomethylbenzoate.

M.S. (APCI) m/z 495 (M−H)⁻

Example 131
[2-Bromo-4-(2,3-difluorobenzylsulfanylmethyl)phenyl]difluoromethylphosphonic Acid.

The title compound was prepared from 2,3-difluorobenzyl bromide.

M.S. (APCI) m/z 459 (M−H)⁻

Example 132
[2-Bromo-4-(3,4-dichlorobenzylsulfanylmethyl)phenyl]difluoromethylphosphonic Acid.

The title compound was prepared from 3,4-dichlorobenzyl bromide.

M.S. (APCI) m/z 491 (M−H)⁻

Example 133
[2-Bromo-4-(2-phenylbenzylsulfanylmethyl)phenyl]difluoromethylphosphonic Acid.

The title compound was prepared from 2-(bromomethyl)biphenyl.

M.S. (APCI) m/z 499 (M−H)⁻

Example 134
[2-Bromo-4-(2,6-dichlorobenzylsulfanylmethyl)phenyl]difluoromethylphosphonic Acid.

The title compound was prepared from 2,6-dichlorobenzyl chloride.

M.S. (APCI) m/z 491 (M−H)⁻

Example 135
[2-Bromo-4-(3-cyanobenzylsulfanylmethyl)phenyl]difluoromethylphosphonic Acid.

The title compound was prepared from alpha-bromo-m-tolunitrile.

M.S. (APCI) m/z 448 (M−H)⁻

Example 136
[2-Bromo-4-(2-trifluoromethylbenzylsulfanylmethyl)phenyl]difluoromethylphosphonic Acid.

The title compound was prepared from 2-trifluoromethylbenzylbromide.

M.S. (APCI) m/z 491 (M−H)⁻

Example 137
[2-Bromo-4-(2-nitrobenzylsulfanylmethyl)phenyl]difluoromethylphosphonic Acid.

The title compound was prepared from 2-nitrobenzyl bromide.

M.S. (APCI) m/z 468 (M−H)⁻

Example 138
[2-Bromo-4-(3-trifluoromethylbenzylsulfanylmethyl)phenyl]difluoromethylphosphonic Acid.

The title compound was prepared from 3-trifluoromethylbenzylbromide.

M.S. (APCI) m/z 491 (M−H)⁻

Example 139
[2-Bromo-4-(2-iodobenzylsulfanylmethyl)phenyl]difluoromethylphosphonic Acid.

The title compound was prepared from 2-iodobenzyl bromide.

M.S. (APCI) m/z 549 (M−H)⁻

Example 140
[2-Bromo-4-(2-fluorobenzylsulfanylmethyl)phenyl]difluoromethylphosphonic Acid.

The title compound was prepared from 2-fluorobenzyl bromide,

M.S. (APCI) m/z 441 (M−H)⁻

Example 141
[2-Bromo-4-(3-fluorobenzylsulfanylmethyl)phenyl]difluoromethylphosphonic Acid.

The title compound was prepared from 3-fluorobenzyl bromide.

M.S. (APCI) m/z 441 (M−H)⁻

Example 142
[2-Bromo-4-(2-chloro-4-fluorobenzylsulfanylmethyl)phenyl]difluoromethylphosphonic Acid.

The title compound was prepared from 2-chloro-4-fluorobenzyl bromide.

M.S. (APCI) m/z 475 (M–H)⁻

Example 143
[2-Bromo-4-(3-iodobenzylsulfanylmethyl)phenyl]difluoromethylphosphonic Acid.

The title compound was prepared from 3-iodobenzyl bromide.

M.S. (APCI) m/z 549 (M–H)⁻

Example 144
[2-Bromo-4-(4-methylnaphthalen-1-ylmethylsulfanylmethyl)phenyl]difluoromethylphosphonic Acid.

The title compound was prepared from 1-chloromethyl-4-methylnaphthalene.

M.S. (APCI) m/z 487 (M–H)⁻

Example 145
[2-Bromo-4-(2-chloro-6-fluorobenzylsulfanylmethyl)phenyl]difluoromethylphosphonic Acid.

The title compound was prepared from 2-chloro-6-fluorobenzyl chloride.

M.S. (APCI) m/z 475 (M–H)⁻

Example 146
[2-Bromo-4-(3,5-dibromobenzylsulfanylmethyl)phenyl]difluoromethylphosphonic Acid.

The title compound was prepared from 3,5-dibromobenzyl bromide.

M.S. (APCI) m/z 581 (M–H)⁻

Example 147
[2-Bromo-4-(2-chlorobenzylsulfanylmethyl)phenyl]difluoromethylphosphonic Acid.

The title compound was prepared from 2-chlorobenzyl bromide.

M.S. (AP CI) m/z 457 (M–H)⁻

Example 148
[2-Bromo-4-(3-methylbenzylsulfanylmethyl)phenyl]difluoromethylphosphonic Acid.

The title compound was prepared from alpha-chloro-m-xylene.

M.S. (APCI) m/z 437 (M–H)⁻

Example 149
[2-Bromo-4-(2,3,5,6-tetrafluoro-4-trifluoromethylbenzylsulfanylmethyl)phenyl]difluoromethylphosphonic Acid.

The title compound was prepared from 1-(bromomethyl)-2,3,5,6-tetrafluoro-4-trifluoromethylbenzene.

M.S. (APCI) m/z 563 (M–H)⁻

Example 150
[2-Bromo-4-(3-chlorobenzylsulfanylmethyl)phenyl]difluoromethylphosphonic Acid.

The title compound was prepared from 3-chlorobenzyl bromide.

M.S. (APCI) m/z 457 (M–H)⁻

Example 151
[2-Bromo-4-(2,5-difluorobenzylsulfanylmethyl)phenyl]difluoromethylphosphonic Acid.

The title compound was prepared from 2,5-difluorobenzyl bromide.

M.S. (APCI) m/z 459 (M–H)⁻

Example 152
[2-Bromo-4-(2,6-difluorobenzylsulfanylmethyl)phenyl]difluoromethylphosphonic Acid.

The title compound was prepared from 2,6-difluorobenzyl bromide.

M.S. (APCI) m/z 459 (M–H)⁻

Example 153
[2-Bromo-4-(2,5-dichlorobenzylsulfanylmethyl)phenyl]difluoromethylphosphonic Acid.

The title compound was prepared from 2,5-dichlorobenzyl bromide.

M.S. (APCI) m/z 491 (M–H)⁻

Example 154
[2-Bromo-4-(2-methylbenzylsulfanylmethyl)phenyl]difluoromethylphosphonic Acid.

The title compound was prepared from 2-methylbenzyl bromide.

M.S. (APCI) m/z 437 (M–H)⁻

Example 155
[2-Bromo-4-(2,4-dichlorobenzylsulfanylmethyl)phenyl]difluoromethylphosphonic Acid.

The title compound was prepared from 2,4-dichlorobenzyl chloride.

M.S. (APCI) m/z 491 (M–H)⁻

The following procedure was the general condition for synthesis from (2-bromo-4-bromomethylphenyl)-difluoromethylphosphonic acid diethyl ester with a thiol:

A stock solution of (2-bromo-4-bromomethylphenyl)difluoromethylphosphonic acid diethyl ester (410 mg) in THF (4.7 mL) was prepared, 0.2 mL of this stock solution was mixed with a stock solution (0.25 mL) of a thiol and KOtBu (0.26 mM of thiol in 1 mL of ethanol and 0.26 mL of KOtBu 1M in THF). The mixture was stirred over night. The solvent was evaporated under vacuum. Chloroform (1 mL) was added and the mixture evaporated again.

To the above coupling product was added 1.5 mL of a stock solution, prepared from bromotrimethylsilane (8.5 mL) in chloroform (112 ML), and the resulting mixture was stirred over night. The solvent was evaporated under vacuum, then 1 mL of chloroform was added and the solvent was again evaporated under vacuum. To the residue was added 0.25 mL of dichloromethane and 1 mL of ethanol and the mixture was stirred 2 hrs. The solvent was evaporated under vacuum and the residue was purified by LC/MS (using an X-Terra MS $C_{18}$ 5 μM 19×50 mm HPLC column, with a gradient from 90% water-5% $CH_3CN$-5% 60 mM $NH_4OAc$ to 20% water-75% $CH_3CN$-5% 60 mM $NH_4OAc$ over 10 minutes using a Micromass ZMD mass spectrum, negative ion electrospray for detection) to afford the title compound. Example 156–172 were prepared in this manner.

Example 156
[2-Bromo-4-(1-methyl-1H-tetrazol-5-ylsulfanylmethyl)-phenyl]-difluoromethylphosphonic Acid.

The title compound was prepared from 5-mercapto-1-methyltetrazole.

M.S. (APCI) m/z 415 (M–H)⁻

Example 157
[2-Bromo-4-(4-oxo-3,4-dihydroquinazolin-2-ylsulfanylmethyl)-phenyl]-difluoromethylphosphonic Acid.

The title compound was prepared from 2-mercapto-4(3H)-quinazolinone.

M.S. (APCI) m/z 477(M–H)⁻.

Example 158
[2-Bromo-4-(pyrimidin-2-ylsulfanylmethyl)-phenyl]-difluoromethylphosphonic acid.
5-mercapto-1-methyltetrazole 2-mercaptopyrimidine.
M.S. (APCI) m/z 411(M−H)⁻.

Example 159
[2-Bromo-4-(5-pyridin-4-yl-[1,3,4]oxadiazol-2-ylsulfanylmethyl)-phenyl]-difluoromethylphosphonic Acid.
The title compound was prepared from 5-(4-pyridyl)-1,3,4-oxadiazole-2-thiol.
M.S. (APCI) m/z 478(M−H)⁻.

Example 160
[2-Bromo-4-(4-phenylthiazol-2-ylsulfanylmethyl)-phenyl]-difluoromethylphosphonic Acid.
The title compound was prepared from 2-mercapto-4-phenylthiazole.
M.S. (APCI) m/z 492(M−H)⁻.

Example 161
{2-Bromo-4-[5-(4-chlorophenyl)-2H-[1,2,4]triazol-3-ylsulfanylmethyl]-phenyl}-difluoromethylphosphonic Acid.
The title compound was prepared from 3-(4-chlorophenyl)-1,2,4-triazole-5-thiol.
M.S. (APCI) m/z 511(M−H)⁻.

Example 162
[2-Bromo-4-(pyridin-2-ylsulfanylmethyl)-phenyl]-difluoromethylphosphonic Acid.
The title compound was prepared from 2-mercaptopyridine.
M.S. (APCI) m/z 410(M−H)⁻.

Example 163
[2-Bromo-4-(quinolin-2-ylsulfanylmethyl)-phenyl]-difluoromethylphosphonic Acid.
The title compound was prepared from 2-quinolinethiol.
M.S. (APCI) m/z 460(M−H)⁻.

Example 164
[2-Bromo-4-(5-methyl-[1,3,4]thiadiazol-2-ylsulfanylmethyl)-phenyl]-difluoromethylphosphonic Acid.
The title compound was prepared from 2-mercapto-5-methyl-1,3,4-thiadiazole.
M.S. (APCI) m/z 431(M−H)⁻.

Example 165
[2-Bromo-4-(5-phenyl-1H-[1,2,4]triazol-3-ylsulfanylmethyl)-phenyl]-difluoromethylphosphonic Acid.
The title compound was prepared from 3-phenyl-1,2,4-triazole-5-thiol.
M.S. (APCI) m/z 476(M−H)⁻.

Example 166
[2-Bromo-4-(1-methyl-1H-imidazol-2-ylsulfanylmethyl)-phenyl]-difluoromethylphosphonic Acid.
The title compound was prepared from 2-mercapto-1-methylimidazole.
M.S. (APCI) m/z 413(M−H)⁻.

Example 167
[4-(4-Acetylaminophenylsulfanylmethyl)-2-bromophenyl]-difluoromethylphosphonic Acid.
The title compound was prepared from 4-acetamidothiophenol.
M.S. (APCI) m/z 466(M−H)⁻.

Example 168
[2-Bromo-4-(3-chlorophenylsulfanylmethyl)-phenyl]-difluoromethylphosphonic Acid.
The title compound was prepared from 3-chlorothiophenol.
M.S. (APCI) m/z 443(M−H)⁻.

Example 169
3-[3-Bromo-4-(difluorophosphonomethyl)-benzylsulfanyl]benzoic Acid.
The title compound was prepared from 3-mercaptobenzoic Acid.
M.S. (APCI) m/z 453(M−H)⁻.

Example 170
[2-Bromo-4-(3-bromophenylsulfanylmethyl)-phenyl]-difluoromethylphosphonic Acid.
The title compound was prepared from 3-bromothiophenol.
M.S. (APCI) m/z 489(M−H)⁻

Example 171
[2-Bromo-4-(3,5-dichlorophenylsulfanylmethyl)-phenyl]-difluoromethylphosphonic Acid.
The title compound was prepared from 3,5-dichlorothiophenol.
M.S. (APCI) m/z 479(M−H)⁻

Example 172
[2-Bromo-4-(4-chlorophenylsulfanylmethyl)-phenyl]-difluoromethylphosphonic Acid.
The title compound was prepared from 4-chlorothiophenol.
M.S. (APCI) m/z 445(M−H)⁻

Examples 173–191 were prepared from [2-bromo-4-(3-bromopropyl)phenyl]difluoromethylphosphonic acid diethyl ester with a thiol in a manner similar to Examples 155–173.

[2-Bromo-4-(3-bromopropyl)phenyl]difluoromethylphosphonic acid diethyl ester was prepared in a manner similar to that described in Example 60, step 2–4, from ethyl 3-(4-aminophenyl)propionate which was obtained by the hydrogenation of ethyl nitrocinnamate.

$^1$H NMR (Acetone-d$_6$) δ 7.65 (1H, s), 7.6 (1H, d), 7.4 (1H, d), 4.15-4.25 (4H, m), 3.5 (2H, t), 2.35(2H, t), 2.15-2.25 (2H, m), 1.3 (6H, t).

Example 173
{2-Bromo-4-[3-(1-methyl-1H-tetrazol-5-ylsulfanyl)-propyl]phenyl}-difluoromethylphosphonic Acid.
The title compound was prepared from 5-mercapto-1-methyltetrazole.
M.S. (APCI) m/z 443 (M−H)⁻.

Example 174
{2-Bromo-4-[3-(4-oxo-3,4-dihydroquinazolin-2-ylsulfanyl)-propyl]phenyl}-difluoromethylphosphonic Acid.
The title compound was prepared from 2-mercapto-4(3H)-quinazolinone.
M.S. (APCI) m/z 505(M−H)⁻.

Example 175
{2-Bromo-4-[3-(pyrimidin-2-ylsulfanyl)-propyl]phenyl}-difluoromethylphosphonic Acid.

The title compound was prepared from 2-mercaptopyrimidine.

M.S. (APCI) m/z 439(M–H)⁻.

Example 176
{2-Bromo-4-[3-(5-pyridin-4-yl-[1,3,4]oxadiazol-2-ylsulfanyl)-propyl]phenyl}-difluoromethylphosphonic Acid.

The title compound was prepared from 5-(4-pyridyl)-1,3,4-oxadiazole-2-thiol.

M.S. (APCI) m/z 506(M–H)⁻.

Example 177
{2-Bromo-4-[3-(4-phenylthiazol-2-ylsulfanyl)-propyl]phenyl}-difluoromethylphosphonic Acid.

The title compound was prepared from 2-mercapto-4-phenylthiazole.

M.S. (APCI) m/z 520(M–H)⁻.

Example 178
(2-Bromo-4-{3-[5-(4-chlorophenyl)-2H-[1,2,4]triazol-3-ylsulfanyl]-propyl}phenyl)difluoromethylphosphonic Acid.

The title compound was prepared from 3-(4-chlorophenyl)-1,2,4-triazole-5-thiol.

M.S. (APCI) m/z 538(M–H)⁻.

Example 179
{2-Bromo-4-[3-(pyridin-2-ylsulfanyl)-propyl]phenyl}-difluoromethylphosphonic Acid.

The title compound was prepared from 2-mercaptopyridine.

M.S. (APCI) m/z 438(M–H)⁻.

Example 180
{2-Bromo-4-[3-(quinolin-2-ylsulfanyl)-propyl]phenyl}-difluoromethylphosphonic Acid.

The title compound was prepared from 2-quinolinethiol.

M.S. (APCI) m/z 488(M–H)⁻.

Example 181
{2-Bromo-4-[3-(5-methyl-1H-benzoimidazol-2-ylsulfanyl)-propyl]phenyl}-difluoromethylphosphonic Acid.

The title compound was prepared from 2-mercapto-5-methylbenzimidazole.

M.S. (APCI) m/z 491(M–H)⁻.

Example 182
{2-Bromo-4-[3-(5-methyl-[1,3,4]thiadiazol-2-ylsulfanyl)-propyl]phenyl}-difluoromethylphosphonic Acid.

The title compound was prepared from 2-mercapto-5-methyl-1,3,4-thiadiazole.

M.S. (APCI) m/z 459(M–H)⁻.

Example 183
{2-Bromo-4-[3-(5-phenyl-[1H-[1,2,4]triazol-2-ylsulfanyl)-propyl]phenyl}-difluoromethylphosphonic Acid.

The title compound was prepared from 3-phenyl-1,2,4-triazole-5-thiol.

M.S. (APCI) m/z 504(M–H)⁻.

Example 184
{2-Bromo-4-[3-(1-methyl-1H-imidazol-2-ylsulfanyl)-propyl]phenyl}-difluoromethylphosphonic Acid.

The title compound was prepared from 2-mercapto-1-methylimidazole.

M.S. (APCI) m/z 441(M–H)⁻.

Example 185
{4-[3-(4-Acetylaminophenylsulfanyl)-propyl]-2-bromophenyl}-difluoromethylphosphonic Acid.

The title compound was prepared from 4-acetamidothiophenol.

M.S. (APCI) m/z 494(M–H)⁻.

Example 186
{2-Bromo-4-[3-(3-chlorophenylsulfanyl)-propyl]phenyl}-difluoromethylphosphonic Acid.

The title compound was prepared from 3-chlorothiophenol.

M.S. (APCI) m/z 471(M–H)⁻.

Example 187
3-{3-[3-Bromo-4-(difluorophosphonomethyl)-phenyl]propylsulfanyl}benzoic Acid.

The title compound was prepared from 3-mercaptobenzoic Acid.

M.S. (APCI) m/z 481(M–H)⁻.

Example 188
{2-Bromo-4-[3-(3-bromophenylsulfanyl)-propyl]phenyl}-difluoromethylphosphonic Acid.

The title compound was prepared from 3-bromothiophenol

M.S. (APCI) m/z 515(M–H)⁻.

Example 189
{2-Bromo-4-[3-(3,5-dichlorophenylsulfanyl)-propyl]phenyl}-difluoromethylphosphonic Acid.

The title compound was prepared from 3,5-dichlorothiophenol.

M.S. (APCI) m/z 505(M–H)⁻.

Example 190
{2-Bromo-4-[3-(1H-imidazol-2-ylsulfanyl)-propyl]phenyl}-difluoromethylphosphonic Acid.

The title compound was prepared from 2-mercaptoimidazole.

M.S. (APCI) m/z 427(M–H)⁻

Example 191
{2-Bromo-4-[3-(4-chlorophenylsulfanyl)-propyl]phenyl}-difluoromethylphosphonic Acid.

The title compound was prepared from 4-chlorothiophenol.

M.S. (APCI) m/z 471(M–H)⁻

Example 192–209 were prepared from [2-bromo-4-(4-bromobutyl)phenyl]difluoromethylphosphonic acid diethyl ester, obtained from step 4 of Example 60, with a thiol in a similar manner as Example 155–172.

Example 192
{2-Bromo-4-[4-(1-methyl-1H-tetrazol-5-ylsulfanyl)-butyl]phenyl}-difluoromethylphosphonic Acid.

The title compound was prepared from 5-mercapto-1-methyltetrazole.

M.S. (APCI) m/z 457 (M–H)⁻.

Example 193
{2-Bromo-4-[4-(4-oxo-3,4-dihydroquinazolin-2-ylsulfanyl)-butyl]phenyl}-difluoromethylphosphonic Acid.

The title compound was prepared from 2-mercapto-4(3H)-quinazolinone.

M.S. (APCI) m/z 519(M–H)⁻.

Example 194

{2-Bromo-4-[4-(pyrimidin-2-ylsulfanyl)-butyl]phenyl}-difluoromethylphosphonic Acid.

The title compound was prepared from 2-mercaptopyrimidine.

M.S. (APCI) m/z 453(M–H)⁻.

Example 195

{2-Bromo-4-[4-(5-pyridin-4-yl-[1,3,4]oxadiazol-2-ylsulfanyl)-butyl]phenyl}-difluoromethylphosphonic Acid.

The title compound was prepared from 5-(4-pyridyl)-1,3,4-oxadiazole-2-thiol.

M.S. (APCI) m/z 520(M–H)⁻.

Example 196

{2-Bromo-4-[4-(4-phenylthiazol-2-ylsulfanyl)-butyl]phenyl}-difluoromethylphosphonic Acid.

The title compound was prepared from 2-mercapto-4-phenylthiazole.

M.S. (APCI) m/z 534(M–H)⁻.

Example 197

(2-Bromo-4-{4-[5-(4-chlorophenyl)-2H-[1,2,4]triazol-3-ylsulfanyl]-butyl}phenyl)difluoromethylphosphonic Acid.

The title compound was prepared from 3-(4-chlorophenyl)-1,2,4-triazole-5-thiol.

M.S. (APCI) m/z 552(M–H)⁻.

Example 198

{2-Bromo-4-[4-(pyridin-2-ylsulfanyl)-butyl]phenyl}-difluoromethylphosphonic Acid.

The title compound was prepared from 2-mercaptopyridine.

M.S. (APCI) m/z 452(M–H)⁻.

Example 199

{2-Bromo-4-[4-(quinolin-2-ylsulfanyl)-butyl]phenyl}-difluoromethylphosphonic Acid.

The title compound was prepared from 2-quinolinethiol

M.S. (APCI) m/z 502(M–H)⁻.

Example 200

{2-Bromo-4-[4-(5-methyl-[1,3,4]thiadiazol-2-ylsulfanyl)-butyl]phenyl}-difluoromethylphosphonic Acid.

The title compound was prepared from 2-mercapto-5-methyl-1,3,4-thiadiazole.

M.S. (APCI) m/z 473(M–H)⁻.

Example 201

{2-Bromo-4-[4-(5-phenyl-1H-[1,2,4]triazol-2-ylsulfanyl)-butyl]phenyl}-difluoromethylphosphonic Acid.

The title compound was prepared from 3-phenyl-1,2,4-triazole-5-thiol.

M.S. (APCI) m/z 518(M–H)⁻.

Example 202

{2-Bromo-4-[4-(1-methyl-1H-imidazol-2-ylsulfanyl)-butyl]phenyl}-difluoromethylphosphonic Acid.

The title compound was prepared from 2-mercapto-1-methylimidazole.

M.S. (APCI) m/z 455(M–H)⁻.

Example 203

{4-[4-(4-Acetylaminophenylsulfanyl)-butyl]-2-bromophenyl}-difluoromethylphosphonic Acid.

The title compound was prepared from 4-acetamidothiophenol

M.S. (APCI) m/z 508(M–H)⁻.

Example 204

{2-Bromo-4-[4-(3-chlorophenylsulfanyl)-butyl]phenyl}-difluoromethylphosphonic Acid.

The title compound was prepared from 3-chlorothiophenol.

M.S. (APCI) m/z 485(M–H)⁻.

Example 205

3-{4-[3-Bromo-4-(difluorophosphonomethyl)-phenyl]butylsulfanyl}benzoic Acid.

The title compound was prepared from 3-mercaptobenzoic acid.

M.S. (APCI) m/z 495(M–H)⁻.

Example 206

{2-Bromo-4-[4-(3-bromophenylsulfanyl)-butyl]phenyl}-difluoromethylphosphonic Acid.

The title compound was prepared from 3-bromothiophenol.

M.S. (APCI) m/z 529(M–H)⁻.

Example 207

{2-Bromo-4-[4-(3,5-dichlorophenylsulfanyl)-butyl]phenyl}-difluoromethylphosphonic Acid.

The title compound was prepared from 3,5-dichlorothiophenol.

M.S. (APCI) m/z 519(M–H)⁻.

Example 208

{2-Bromo-4-[4-(1H-imidazol-2-ylsulfanyl)-butyl]phenyl}-difluoromethylphosphonic Acid.

The title compound was prepared from 2-mercaptoimidazole.

M.S. (APCI) m/z 441(M–H)⁻.

Example 209

{2-Bromo-4-[4-(4-chlorophenylsulfanyl)-butyl]phenyl}-difluoromethylphosphonic Acid.

The title compound was prepared from 4-chlorothiophenol.

M.S. (APCI) m/z 485(M–H)⁻

What is claimed is:

1. A compound represented by formula I:

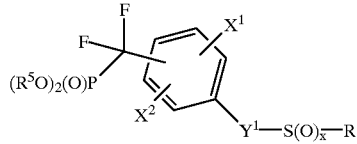

or a pharmaceutically acceptable salt or prodrug thereof, wherein:

$X^1$ and $X^2$ are each independently selected from the group consisting of: H, OH, halogen, CN, $CO_2H$, $CO_2C_{1-6}$alkyl, $CO_2C_{2-6}$alkenyl, $OC_{1-6}$alkyl, $OC_{2-6}$alkenyl, $C(O)C_{1-6}$alkyl, $C(O)C_{2-6}$alkenyl, $OC(O)C_{1-6}$alkyl, $OC(O)C_{2-6}$alkenyl, $S(O)_xC_{1-6}$alkyl, $S(O)_xC_{2-6}$alkenyl, $C_{1-6}$ alkyl, $C_{2-6}$alkenyl, $C_{2-6}$alkynyl, $S(O)_2NR^1R^2$, $C(O)NR^1R^2$, and $NR^1R^2$, wherein each alkyl group and each alkenyl group in each substituent is optionally substituted with one or more substituents independently selected from (a) 1–13 halogen atoms and (b) 1–2 substituents independently selected from $OC_{1-3}$ alkyl, C(O)C$_{1-3}$alkyl, OC(O)C$_{1-3}$alkyl, CO$_2$H, and CO$_2$C$_{1-3}$alkyl;

R$^5$ is H;

R$^1$ and R$^2$ are each independently selected from the group consisting of H and C$_{1-4}$alkyl, wherein said alkyl substituents are optionally substituted with 1–9 halogen atoms;

Each halogen is independently selected from I, Cl, Br and F;

Each x is independently 0, 1, or 2;

Y$^1$ is selected from the group consisting of a bond, a C$_{1-6}$ alkylene group, and a C$_{2-6}$ alkenylene group, wherein said alkylene group and said alkenylene group are optionally substituted with one or more substituents independently selected from (a) 1–12 halogen atoms and (b) 1–2 substituents independently selected from OH and OC$_{1-4}$ alkyl, said OC$_{1-4}$ alkyl being optionally substituted with 1–9 halogen atoms;

R is selected from the group consisting of C$_{1-10}$ alkyl, C$_{2-10}$alkenyl, C$_{2-10}$alkadienyl, C$_{2-10}$alkynyl, Ar$^1$, and Het$^1$, wherein said alkyl, alkenyl, alkadienyl, and alkynyl are optionally substituted with one or more substituents independently selected from (a) 1–21 halogen atoms, (b) one substituent selected from Ar$^1$ and Het$^1$, and (c) 1–2 substituents independently selected from OH, CN, CO$_2$H, CO$_2$C$_{1-6}$ alkyl, CO$_2$C$_{2-6}$ alkenyl, OC$_{1-3}$alkyleneOC$_{1-3}$alkyl, OC$_{1-6}$alkyl, OC$_{2-6}$ alkenyl, OC(O)C$_{1-6}$alkyl, OC(O)C$_{2-6}$alkenyl, C(O)C$_{1-6}$alkyl, C(O)C$_{2-6}$alkenyl, Aryl, C(O)Aryl, OC(O)Aryl, OAryl, CO$_2$Aryl, S(O)$_x$C$_{1-6}$alkyl, S(O) C$_{2-6}$alkenyl, S(O)$_x$ Aryl, S(O)$_2$NR$^1$R$^2$, C(O)NR$^1$R$^2$, NR$^1$R$^2$, and a 5–6-membered heterocycle having 1–2 heteroatoms selected from N, S and O in the ring, wherein said alkyl groups and said alkenyl groups of said substituents are optionally substituted with 1–13 halogen atoms;

Het$^1$ is a 5–10 membered aromatic ring system comprising 1 ring or 2 rings fused together and 1–4 heteroatoms selected from O, N, S(O)$_x$, and combinations thereof, and 0–2 carbonyl groups, wherein one of said fused rings is optionally a benzene ring, and said Het$^1$ is optionally substituted with one or more groups independently selected from (a) one group selected from CO$_2$H, CF$_2$CO$_2$H, P(O)(OR$^5$)$_2$, and SO$_2$R$^4$, and (b) 1–3 groups independently selected from R$^3$;

Ar$^1$ is phenyl or napthyl, wherein phenyl is optionally substituted with one or more groups independently selected from (a) one group selected from CF$_2$P(O)(OR$^5$)$_2$, CO$_2$H, CF$_2$CO$_2$H, P(O)(OR$^5$)$_2$, SO$_2$R$^4$, and Ar$^2$, and (b) 1–5 groups selected from R$^3$, and wherein naphthyl is optionally substituted with one or more groups independently selected from (a) one group selected from CO$_2$H, CF$_2$CO$_2$H, P(O)(OR$^5$)$_2$, SO$_2$R$^4$, and Ar$^2$, and (b) 1–5 groups selected from R$^3$;

Ar$^2$ is phenyl, naphthyl or a 5–10 membered aromatic ring system comprising 1 ring or 2 rings fused together and 1–4 heteroatoms independently selected from O, N, S(O)$_x$, and combinations thereof, and 0–2 carbonyl groups, wherein one of said fused rings is optionally a benzene ring, wherein Ar$^2$ is optionally substituted with one or more substituents independently selected from (a) one group selected from CF$_2$P(O)(OR$^5$)$_2$, CO$_2$H, CF$_2$CO$_2$H, P(O)(OR$^5$)$_2$, and SO$_2$R$^4$, and (b) 1–2 groups selected from R$^3$;

R$^3$ is selected from the group consisting of halogen, OH, CN, CO$_2$H, NO$_2$, CO$_2$C$_{1-10}$ alkyl, CO$_2$C$_{2-10}$ alkenyl, OC$_{1-10}$alkyl, OC$_{2-10}$ alkenyl, C$_{1-10}$ alkyl, C$_{2-10}$ alkenyl, OC(O)C$_{1-10}$alkyl, OC(O)C$_{2-10}$alkenyl, C(O)C$_{1-10}$alkyl, C(O)C$_{2-10}$alkenyl, C(O)Aryl, OC(O)Aryl, OAryl, CO$_2$Aryl, S(O)$_x$Cl$_{10}$alkyl, C$_{1-3}$alkyleneS(O)$_x$C$_{1-10}$ alkyl, S(O)$_x$C$_{2-10}$alkenyl, S(O)$_2$NR$^1$R$^2$, C(O)NR$^1$R$^2$, NR$^1$R$^2$, NR$^1$S(O)$_2$R$^2$ NR$^1$C(O)C$_{1-6}$alkyl, NR$^1$C(O)H, Aryl, and Het, wherein each alkyl group and each alkenyl group of each substituent is optionally substituted with one or more substituents independently selected from (a) 1–21 halogen atoms and (b) 1–2 substituents independently selected from OH, OC$_{1-3}$ alkyl, CO$_2$H, CO$_2$C$_{1-3}$alkyl, C(O)C$_{1-3}$alkyl, OC(O) C$_{1-3}$alkyl, S(O)$_x$Aryl, S(O)$_x$C$_{1-3}$alkyl and phenyl, wherein said phenyl is optionally substituted with 1–3 substituents independently selected from OCH$_3$, OCF$_3$, S(O)$_2$ NR$^1$R$^2$, Br, Cl, and F, wherein the C$_{1-3}$ alkyl groups of said substituents are optionally substituted with one or more substituents independently selected from (a) 1–7 halogen atoms and (b) 1–2 phenyls which are optionally substituted with 1–3 substituents independently selected from halogen and SO$_2$NR$^1$R$^2$;

Aryl is a 6–14 membered aromatic carbocyclic moiety comprising 1 ring or 2–3 fused rings, wherein said Aryl is optionally substituted with 1–3 substituents independently selected from C$_{1-3}$alkyl, halogen, OH, OC$_{1-3}$ alkyl, C(O)C$_{1-3}$alkyl, OC(O)C$_{1-3}$alkyl, CO$_2$H, CO$_2$ C$_{1-3}$alkyl, NR$^1$R$^2$, S(O)$_x$C$_{1-4}$alkyl and SO$_2$NR$^1$R$^2$, wherein said alkyl groups in said substituents are optionally substituted with 1–7 halogen atoms;

Het is a 5–10 membered aromatic ring system containing 1–4 heteroatoms selected from N, S(O)$_x$, O, and mixtures thereof, and 0–2 carbonyl groups, wherein said Het comprises 1 ring or 2 fused rings, one of which fused rings may be a benzene ring, and said Het is optionally substituted with 1–3 substituents independently selected from C$_{1-3}$alkyl, halogen, OC$_{1-3}$ alkyl, C(O)C$_{1-3}$alkyl, OC(O)C$_{1-3}$alkyl, CO$_2$H, CO$_2$C$_{1-3}$alkyl, NR$^1$R$^2$, S(O)$_x$C$_{1-4}$alkyl and SO$_2$NR$^1$R$^2$, wherein said alkyl groups are optionally substituted with 1–7 halogen atoms;

Alkyl, alkenyl, alkadienyl and alkynyl are linear, branched or cyclic hydrocarbon structures, or combinations thereof containing the indicated number of carbon atoms and substituted as indicated, wherein alkyl, alkenyl, alkadienyl and alkynyl are respectively saturated, contain one double bond, contain 2 double bonds, or contain one triple bond; and R$^4$ is phenyl or C$_{1-4}$ alkyl, wherein said phenyl is optionally substituted with one or more substituents independently selected from (a) 1–3 halogen atoms and (b) 1–2 C$_{1-3}$ alkyl or C$_{1-3}$alkoxy groups, which are optionally substituted with 1–7 halogen atoms, and said C$_{1-4}$ alkyl is optionally substituted with one or more substituents independently selected from (a) 1–9 halogen atoms and (b) 1–2 C$_{1-3}$ alkoxy groups, which are optionally substituted with 1–7 halogen atoms.

2. The compound having formula I as recited in claim 1, or a pharmaceutically acceptable salt or prodrug thereof, wherein:

X$^1$ and X$^2$ are each independently selected from the group consisting of: H, OH, halogen, CN, CO$_2$H, CO$_2$C$_{1-6}$ alkyl, CO$_2$C$_{2-6}$alkenyl, OC$_{1-6}$alkyl, OC$_{2-6}$alkenyl, C(O)C$_{1-6}$alkyl, C(O)C$_{2-6}$alkenyl, OC(O)C$_{1-6}$alkyl, OC(O)C$_{2-6}$alkenyl, S(O)$_x$C$_{1-6}$alkyl, S(O)$_x$C$_{2-6}$alkenyl, C$_{1-6}$ alkyl, C$_{2-6}$alkenyl, S(O)$_2$NR$^1$R$^2$, C(O)NR$^1$R$^2$, and NR$^1$R$^2$, wherein each alkyl group and each alkenyl group in each substituent is optionally substituted with one or more substituents independently selected from (a) 1–13 halogen atoms and (b) 1–2 substituents independently selected from $OC_{1-3}$ alkyl, $C(O)C_{1-3}$alkyl, $OC(O)C_{1-3}$alkyl, $CO_2H$, and $CO_2C_{1-3}$alkyl;

$R^5$ is H;

$R^1$ and $R^2$ are each independently selected from the group consisting of H and $C_{1-4}$alkyl, wherein said alkyl substituents are optionally substituted with 1–9 halogen atoms;

Each halogen is independently selected from I, Cl, Br and F;

Each x is independently 0, 1, or 2;

$Y^1$ is selected from the group consisting of a bond, a $C_{1-4}$ alkylene group, and a $C_{2-4}$ alkenylene group, wherein said alkylene group and said alkenylene group are optionally substituted with one or more substituents independently selected from (a) 1–8 halogen atoms and (b) 1–2 substituents independently selected from OH and $OC_{1-4}$ alkyl, said $OC_{1-4}$ alkyl being optionally substituted with 1–9 halogen atoms;

R is selected from the group consisting of $C_{1-10}$ alkyl, $C_{2-10}$alkenyl, $C_{2-10}$alkadienyl, $C_{2-10}$alkynyl, $Ar^1$, and $Het^1$, wherein said alkyl, alkenyl, alkadienyl, and alkynyl are optionally substituted with one or more substituents independently selected from (a) 1–21 halogen atoms, (b) one substituent selected from $Ar^1$ and $Het^1$, and (c) 1–2 substituents independently selected from OH, CN, $CO_2H$, $CO_2C_{1-6}$ alkyl, $CO_2C_{2-6}$ alkenyl, $OC_{1-6}$alkyl, $OC_{2-6}$ alkenyl, $OC(O)C_{1-6}$alkyl, $OC(O)C_{2-6}$alkenyl, $C(O)C_{1-6}$alkyl, $C(O)C_{2-6}$alkenyl, $C(O)$Aryl, $OC(O)$Aryl, OAryl, $CO_2$Aryl, $S(O)_xC_{1-6}$alkyl, $S(O)_xC_{2-6}$alkenyl, $S(O)_2NR^1R^2$, $C(O)NR^1R^2$, and $NR^1R^2$, wherein said alkyl groups and said alkenyl groups of said substituents are optionally substituted with 1–13 halogen atoms;

$Het^1$ is a 5–10 membered aromatic ring system comprising 1 ring or 2 rings fused together and 1–4 heteroatoms selected from O, N, $S(O)_x$, and combinations thereof, and 0–2 carbonyl groups, wherein one of said fused rings is optionally a benzene ring, and said $Het^1$ is optionally substituted with one or more substituents independently selected from (a) one group selected from $CO_2H$, $CF_2CO_2H$, $P(O)(OR^5)_2$, and $SO_2R^4$, and (b) 1–2 groups independently selected from $R^3$;

$Ar^1$ is phenyl or napthyl, wherein phenyl is optionally substituted with one or more groups independently selected from (a) one group selected from $CF_2P(O)(OR^5)_2$, $CO_2H$, $CF_2CO_2H$, $P(O)(OR^5)_2$, $SO_2R^4$, $Ar^2$, and (b) 1–2 groups selected from $R^3$, and wherein naphthyl is optionally substituted with one or more groups independently selected from (a) one group selected from $CO_2H$, $CF_2CO_2H$, $P(O)(OR^5)_2$, $SO_2R^4$, and $Ar^2$, and (b) 1–2 groups selected from $R^3$;

$Ar^2$ is phenyl, naphthyl or a 5–10 membered aromatic ring system comprising 1 ring or 2 rings fused together and 1–4 heteroatoms selected from O, N, $S(O)_x$, and combinations thereof, and 0–2 carbonyl groups, wherein one of said fused rings is optionally a benzene ring, wherein $Ar^2$ is optionally substituted with one or more substituents independently selected from (a) one group selected from $CF_2P(O)(OR^5)_2$, $CO_2H$, $CF_2CO_2H$, $P(O)(OR^5)_2$, and $SO_2R^4$, and (b) 1–2 groups selected from $R^3$;

$R^3$ is selected from the group consisting of halogen, OH, CN, $CO_2H$, $CO_2C_{1-10}$ alkyl, $CO_2C_{2-10}$ alkenyl, $OC_{1-10}$ alkyl, $OC_{2-10}$ alkenyl, $C_{1-10}$ alkyl, $C_{2-10}$ alkenyl, $OC(O)C_{1-10}$alkyl, $OC(O)C_{2-10}$alkenyl, $C(O)C_{1-10}$alkyl, $C(O)C_{2-10}$alkenyl, $C(O)$Aryl, $OC(O)$Aryl, OAryl, $CO_2$Aryl, $S(O)_xC_{1-10}$alkyl, $S(O)$ $C_{2-10}$alkenyl, $S(O)_2NR^1R^2$, $C(O)NR^1R^2$, $NR^1R^2$, Aryl, and Het, wherein each alkyl group and each alkenyl group of each substituent is optionally substituted with one or more substituents independently selected from (a) 1–21 halogen atoms and (b) 1–2 substituents independently selected from OH, $OC_{1-3}$ alkyl, $CO_2H$, $CO_2C_{1-3}$alkyl, $C(O)C_{1-3}$alkyl, $OC(O)C_{1-3}$alkyl, and phenyl, wherein said phenyl is optionally substituted with $OCH_3$, $OCF_3$, or 1–3 halogen atoms selected from Cl and F, and said $C_{1-3}$ alkyl groups of said substituents are optionally substituted with one or more substituents independently selected from (a) 1–7 halogen atoms and (b) 1–2 phenyls, wherein said phenyls are optionally substituted with 1–3 halogen atoms;

Aryl is a 6–14 membered aromatic carbocyclic moiety comprising 1 ring or 2–3 fused rings, wherein said Aryl is optionally substituted with 1–3 substituents independently selected from $C_{1-3}$alkyl, halogen, $OC_{1-3}$ alkyl, $C(O)C_{1-3}$alkyl, $OC(O)C_{1-3}$alkyl, $CO_2H$, and $CO_2C_{1-3}$ alkyl, wherein said alkyl groups in said substituents are optionally substituted with 1–7 halogen atoms;

Het is a 5–10 membered aromatic ring system containing 1–4 heteroatoms selected from N, $S(O)_x$, O, and mixtures thereof, and 0–2 carbonyl groups, wherein said Het comprises 1 ring or 2 fused rings, one of which fused rings may be a benzene ring, and said Het is optionally substituted with 1–3 substituents independently selected from $C_{1-3}$alkyl, halogen, $OC_{1-3}$alkyl, $C(O)C_{1-3}$alkyl, $OC(O)C_{1-3}$alkyl, $CO_2H$, and $CO_2C_{1-3}$ alkyl, wherein said alkyl groups are optionally substituted with 1–7 halogen atoms; and $R^4$ is phenyl or $C_{1-4}$ alkyl, wherein said phenyl is optionally substituted with one or more substituents independently selected from (a) 1–3 halogen atoms and (b) 1–2 $C_{1-3}$ alkyl or $C_{1-3}$alkoxy groups, which are optionally substituted with 1–7 halogen atoms, and said $C_{1-4}$ alkyl is optionally substituted with one or more substituents independently selected from (a) 1–9 halogen atoms and (b) 1–2 $C_{1-3}$ alkoxy groups, which are optionally substituted with 1–7 halogen atoms.

3. The compound as recited in claim 1, wherein said halogen atom substituents are independently selected from Cl, Br, and F.

4. The compound as recited in claim 1, wherein $X^1$ is H, and $X^2$ is selected from the group consisting of a halogen atom, $CH_3$, $OCH_3$, OH and $CO_2H$.

5. The compound as recited in claim 1, wherein $X^1$ is H, $X^2$ is selected from the group consisting of Cl, F, and Br, and the $Y^1$ substituent on the phenyl ring to which $Y^1$ is attached is in the position para to $CF_2 P(O)(OR^5)_2$.

6. The compound as recited in claim 5, wherein $X^2$ is Br and is ortho to $CF_2 P(O)(OR^5)_2$.

7. The compound as recited in claim 1, wherein $Y^1$ is a bond, $CH_2$, or a linear $C_{2-4}$alkylene.

8. The compound as recited in claim 1, wherein R is selected from the group consisting of $C_{1-4}$ alkyl, $C_{2-4}$ alkenyl and $C_{2-4}$alkynyl; wherein R is substituted with one $Ar^1$ and optionally substituted with 1–2 groups selected from Aryl and (C=O)Aryl; wherein $Ar^1$ is phenyl which is optionally substituted with one or more substituents independently selected from (a) one group $CF_2P(O)(OR^5)_2$ and (b) 1–2 groups $R^3$.

9. The compound as recited in claim 8, wherein R is selected from the group consisting of $C_{1-4}$ alkyl and $C_{2-4}$

217 alkenyl, wherein Ar¹ is phenyl which is optionally substituted with 1–2 groups R³, wherein R³ is selected from the group consisting of Br, Cl, F, OH, and $C_{1-3}$ alkyl.

10. The compound as recited in claim 9, wherein Y¹ is selected from the group consisting of a bond, $C_{1-4}$alkylene group, and $C_{1-4}$ alkenylene.

11. The compound as recited in claim 8, wherein R³ is Br.

12. The compound as recited in claim 1, wherein R is selected from the group consisting of $C_{1-4}$ alkyl, $C_{2-4}$ alkenyl, and $C_{2-4}$alkynyl, and R is substituted with one Ar¹;
Ar¹ is phenyl or naphthyl and is substituted with Ar²;
Ar² is a 5–10 membered aromatic ring system comprising 1 ring or 2 rings fused together and 1–4 heteroatoms selected from O, N, $S(O)_x$, and combinations thereof, and 0–2 carbonyl groups, wherein one of said fused rings is optionally a benzene ring, and Ar² is optionally substituted with one or more substituents independently selected from (a) one group selected from P(O)(OH)₂ and CO₂H and (b) 1–2 groups R³;
R³ is selected from halogen, $C_{1-10}$ alkyl, $OC_{1-10}$ alkyl, C(O)Aryl, and Aryl, where said $C_{1-10}$ alkyl and $OC_{1-10}$ alkyl are optionally substituted with 1–2 substituents independently selected from $OC_{1-3}$ alkyl, phenyl, and CO₂H; and
X¹, X², R¹, R², R⁴, R⁵, x, Y¹, Aryl, Het, and Het¹ are as defined in claim 1.

13. The compound as recited in claim 1, wherein R is selected from the group consisting of $C_{1-4}$ alkyl and $C_{2-4}$ alkenyl, and R is substituted with one Ar¹;
Ar¹ is phenyl or naphthyl and is substituted with Ar²;
Ar² is a 5–10 membered aromatic ring system comprising 1 ring or 2 rings fused together and 1–4 heteroatoms selected from O, N, $S(O)_x$, and combinations thereof, and 0–2 carbonyl groups, wherein one of said fused rings is optionally a benzene ring, and Ar² is optionally substituted with one or more substituents independently selected from (a) one group selected from P(O)(OH)₂ and CO₂H and (b) 1–2 groups R³;
R³ is selected from $C_{1-10}$ alkyl, $OC_{1-10}$ alkyl, C(O)Aryl, and Aryl, where said $C_{1-10}$ alkyl and $OC_{1-10}$ alkyl are optionally substituted with 1–2 substituents independently selected from $OC_{1-3}$ alkyl, phenyl, and CO₂H; and
X¹, X², R¹, R², R⁴, R⁵, x, Y¹, Aryl, Het, and Het¹ are as defined in claim 1.

14. The compound as recited in claim 12, wherein Ar² is quinoline.

15. The compound as recited in claim 1, wherein
R is selected from the group consisting of $C_{1-4}$ alkyl, $C_{2-4}$ alkenyl and $C_{2-4}$alkynyl and is substituted with one Ar¹;
Ar¹ is phenyl and is substituted with one Ar²;
Ar² is phenyl, and is optionally substituted with one or more substituents independently selected from (a) one substituent selected from P(O)(OR⁵)₂, CO₂H, and SO₂R⁴, and (b) 1–2 groups R³;
R⁴ is phenyl or $C_{1-4}$ alkyl;
R³ is selected from OH, Br, $OC_{1-10}$ alkyl, $C_{1-10}$ alkyl, Aryl, and $C_{2-10}$ alkenyl, where each alkyl group and each alkenyl group is optionally substituted with $OC_{1-3}$ alkyl or phenyl; and
X¹, X², R¹, R², R⁵, x, Y¹, Aryl, Het and Het¹ are as defined in claim 1.

16. The compound as recited in claim 1, wherein:
the first two carbons of Y¹ starting from S may be linear or monobranched, and

218 the first two carbons of R starting from S may be linear or monobranched.

17. A compound having the formula I as recited in claim 1, or a pharmaceutically acceptable salt thereof, wherein each group —OR⁵ is selected from —OH and a group that is converted to —OH under physiological conditions during or after administration to a mammalian patient, thereby yielding a phosphonic acid group, or a salt thereof, wherein at least one group —OR⁵ is not an —OH group, wherein all substituent groups other than R⁵ are as defined in claim 1.

18. A compound as recited in claim 17, wherein one group R⁵ is selected from $C_{1-6}$alkyl, phenyl, —CHR'phenyl and —CHR'OC(=O)R", and the remaining groups R⁵ are independently selected from H, $C_{1-6}$alkyl, phenyl, —CHR'phenyl and —CHR'OC(=O)R", wherein each R' is H or $C_{1-6}$alkyl, and each R" is —$C_{1-6}$alkyl or —$OC_{1-6}$alkyl, wherein $C_{1-6}$alkyl and —$OC_{1-6}$alkyl in each occurrence are optionally substituted with one or more substituents independently selected from 1–5 halogen atoms, a phenyl group, or a mixture of these, and each phenyl in each occurrence is optionally substituted with 1–3 substituents independently selected from halogen, —CH₃, —CF₃, —OCH₃ and —OCF₃.

19. A compound represented by formula I:

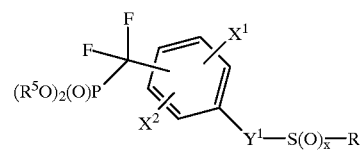

I or a pharmaceutically acceptable salt or prodrug thereof, wherein:

X¹ and X² are each independently selected from the group consisting of H, Cl, Br, F, $C_{1-3}$alkyl, $OC_{1-3}$alkyl, OH, CO₂H, and $CO_2C_{1-3}$alkyl;

R⁵ is H;

Y¹ is selected from the group consisting of a bond and a $C_{1-4}$ alkylene group;

R is selected from the group consisting of $C_{1-8}$ alkyl, $C_{2-8}$ alkenyl, $C_{2-8}$ alkynyl, Ar¹, and Het¹, wherein said $C_{1-8}$alkyl, $C_{2-8}$ alkenyl and $C_{2-8}$alkynyl are optionally substituted with one or more groups independently selected from (a) 1–5 halogen atoms selected from Cl, Br, and F, (b) one Ar¹ or Het¹, and (c) 1–2 substituents independently selected from OH, CN, CO₂H, $CO_2C_{1-6}$ alkyl, $CO_2C_{2-6}$ alkenyl, $OC_{1-6}$alkyl, $OC_{2-6}$ alkenyl, $OC(O)C_{1-6}$alkyl, $OC(O)C_{2-6}$ alkenyl, $C(O)C_{1-6}$alkyl, $C(O)C_{2-6}$alkenyl, Aryl, C(O)Aryl, OC(O)Aryl, OAryl, CO₂Aryl, $S(O)_xC_{1-6}$alkyl, $S(O)_xC_{2-6}$alkenyl, $S(O)_2NR^1R^2$, $C(O)NR^1R^2$, and $NR^1R^2$, wherein said alkyl groups and said alkenyl groups of said substituents are optionally substituted with 1–5 halogen atoms selected from Cl, Br, and F;

x is 0, 1, or 2;

R¹ and R² are each independently selected from the group consisting of H and $C_{1-4}$alkyl, wherein said alkyl substituents are optionally substituted with 1–5 halogen atoms selected from Cl, Br, and F;

Het¹ is a 5–10 membered aromatic ring system comprising 1 ring or 2 rings fused together and 1–4 heteroatoms selected from O, N, $S(O)_x$, and combinations thereof, and 0–2 carbonyl groups, wherein one of said fused rings is optionally a benzene ring, and said Het¹ is optionally substituted with (a) one group selected from $CO_2H$, $CF_2CO_2H$, $P(O)(OR^5)_2$, and $SO_2R^4$, and (b) 1–2 groups independently selected from $R^3$;

$Ar^1$ is phenyl, optionally substituted with (a) one group selected from $CF_2P(O)(OR^5)_2$, $CO_2H$, $CF_2CO_2H$, $P(O)(OR^5)_2$, $SO_2R^4$, and $Ar^2$, and (b) 1–2 groups selected from $R^3$;

$Ar^2$ is phenyl, naphthyl or a 5–10 membered aromatic ring system comprising 1 ring or 2 rings fused together and 1–4 heteroatoms selected from O, N, $S(O)_x$, and combinations thereof, and 0–2 carbonyl groups, wherein one of said fused rings is optionally a benzene ring, wherein $Ar^2$ is optionally substituted with (a) one group selected from $CF_2P(O)(OR^5)_2$, $CO_2H$, $CF_2CO_2H$, $P(O)(OR^5)_2$, and $SO_2R^4$, and (b) 1–2 groups selected from $R^3$;

$R^3$ is selected from the group consisting of Cl, Br, F, OH, CN, $CO_2H$, $CO_2C_{1-3}$ alkyl, $CO_2C_{2-3}$ alkenyl, $OC_{1-10}$alkyl, $OC_{2-10}$ alkenyl, $C_{1-10}$ alkyl, $C_{2-10}$ alkenyl, $OC(O)C_{1-3}$alkyl, $OC(O)C_{2-3}$alkenyl, $C(O)C_{1-3}$alkyl, $C(O)C_{2-3}$alkenyl, C(O)Aryl, OC(O)Aryl, OAryl, $CO_2$Aryl, $S(O)_xC_{1-6}$alkyl, $S(O)_xC_{2-6}$alkenyl, $S(O)_2NR^1R^2$, $C(O)NR^1R^2$, $NR^1R^2$, $NR^1S(O)_2R^2$, $NR^1C(O)C_{1-6}$alkyl, $NR^1C(O)H$, Aryl, and Het, wherein each alkyl group and each alkenyl group of each substituent is optionally substituted with one or more groups independently selected from (a) 1–3 halogen atoms selected from Cl, Br, and F, and (b) 1–2 substituents independently selected from OH, $OC_{1-3}$ alkyl, $CO_2H$, $CO_2C_{1-3}$alkyl, $C(O)C_{1-3}$alkyl, $OC(O)C_{1-3}$alkyl, and phenyl, wherein said phenyl is optionally substituted with 1–3 groups independently selected from $OCH_3$, $OCF_3$, Cl and F, and said $C_{1-3}$ alkyl groups of said substituents are optionally substituted with one or more substituents independently selected from (a) 1–3 halogen atoms independently selected from Cl, Br and F, and (b) 1–2 phenyl moieties;

Aryl is a phenyl or naphthyl moiety, wherein said Aryl is optionally substituted with 1–3 substituents independently selected from $C_{1-3}$alkyl, Cl, F, Br, $OC_{1-3}$ alkyl, $C(O)C_{1-3}$alkyl, $OC(O)C_{1-3}$alkyl, $CO_2H$, and $CO_2C_{1-3}$ alkyl, wherein said alkyl groups in said substituents are optionally substituted with 1–3 halogen atoms selected from Cl, Br, and F;

Het is a 5–10 membered aromatic ring system containing 1–4 heteroatoms selected from N, $S(O)_x$, O, and mixtures thereof, and 0–2 carbonyl groups, wherein x is 0, 1, or 2, wherein said Het comprises 1 ring or 2 fused rings, one of which fused rings may be a benzene ring, and said Het is optionally substituted with 1–3 substituents independently selected from $C_{1-3}$alkyl, Cl, Br, F, $OC_{1-3}$ alkyl, $C(O)C_{1-3}$alkyl, $OC(O)C_{1-3}$alkyl, $CO_2H$, and $CO_2C_{1-3}$alkyl, wherein said alkyl groups in said substituents are optionally substituted with 1–3 halogen atoms selected from Cl, Br, and F; and $R^4$ is phenyl or $C_{1-4}$ alkyl.

20. A compound having the formula I as recited in claim 19, or a pharmaceutically acceptable salt thereof, wherein $Y^1$ is selected from the group consisting of a bond and a $C_{1-3}$ alkylene group; and R is selected from the group consisting of $C_{1-8}$ alkyl, $C_{2-8}$ alkenyl, $Ar^1$, and $Het^1$, wherein said $C_{1-8}$alkyl and $C_{2-8}$ alkenyl are optionally substituted with one or more groups independently selected from (a) 1–5 halogen atoms selected from Cl, Br, and F, (b) one $Ar^1$ or $Het^1$, and (c) 1–2 substituents independently selected from OH, CN, $CO_2H$, $CO_2C_{1-6}$ alkyl, $CO_2C_{2-6}$ alkenyl, $OC_{1-6}$alkyl, $OC_{2-6}$ alkenyl, $OC(O)C_{1-6}$alkyl, $OC(O)C_{2-6}$ alkenyl, $C(O)C_{1-6}$alkyl, $C(O)C_{2-6}$alkenyl, C(O)Aryl, OC(O)Aryl, OAryl, $CO_2$Aryl, $S(O)_xC_{1-6}$alkyl, $S(O)_xC_{2-6}$alkenyl, $S(O)_2NR^1R^2$, $C(O)NR^1R^2$, and $NR^1R^2$, wherein said alkyl groups and said alkenyl groups of said substituents are optionally substituted with 1–5 halogen atoms selected from Cl, Br, and F.

21. A compound in accordance with claim 1 having the following structure:

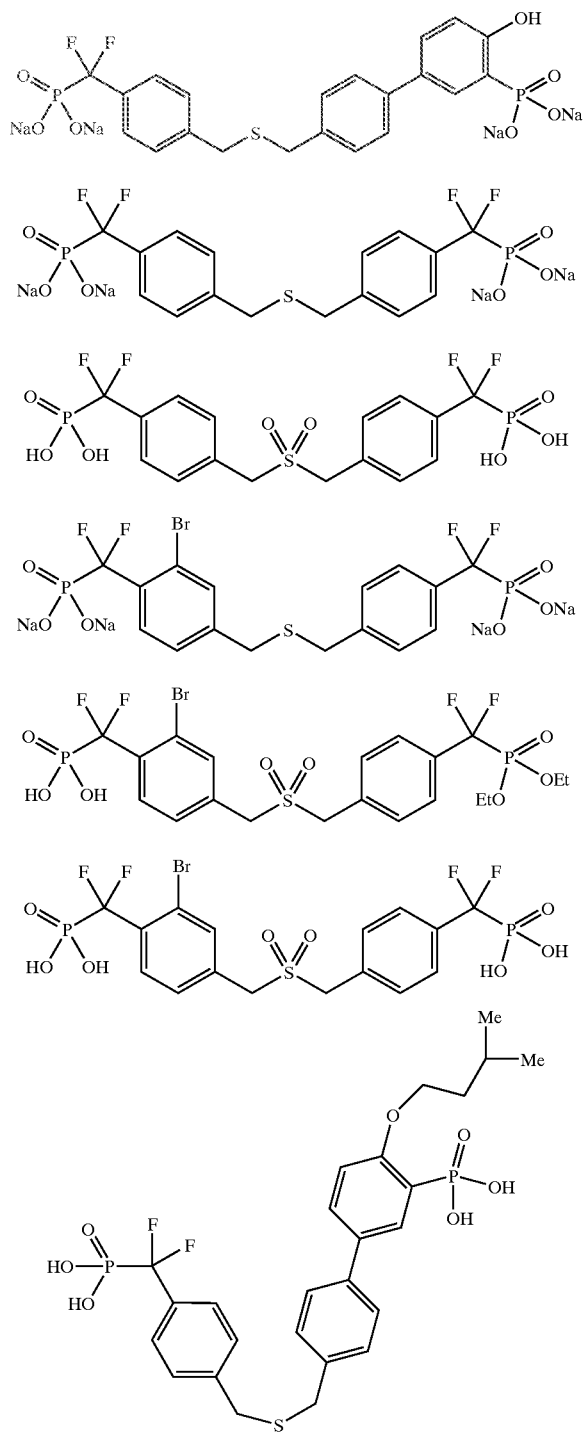

221
-continued
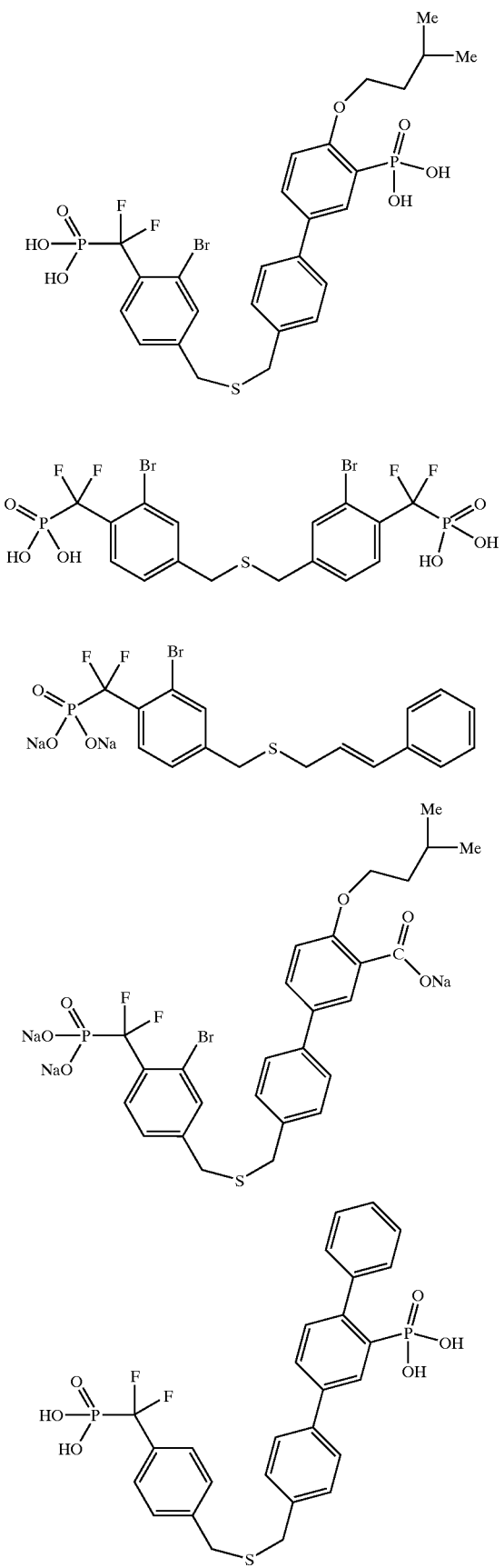
222
-continued
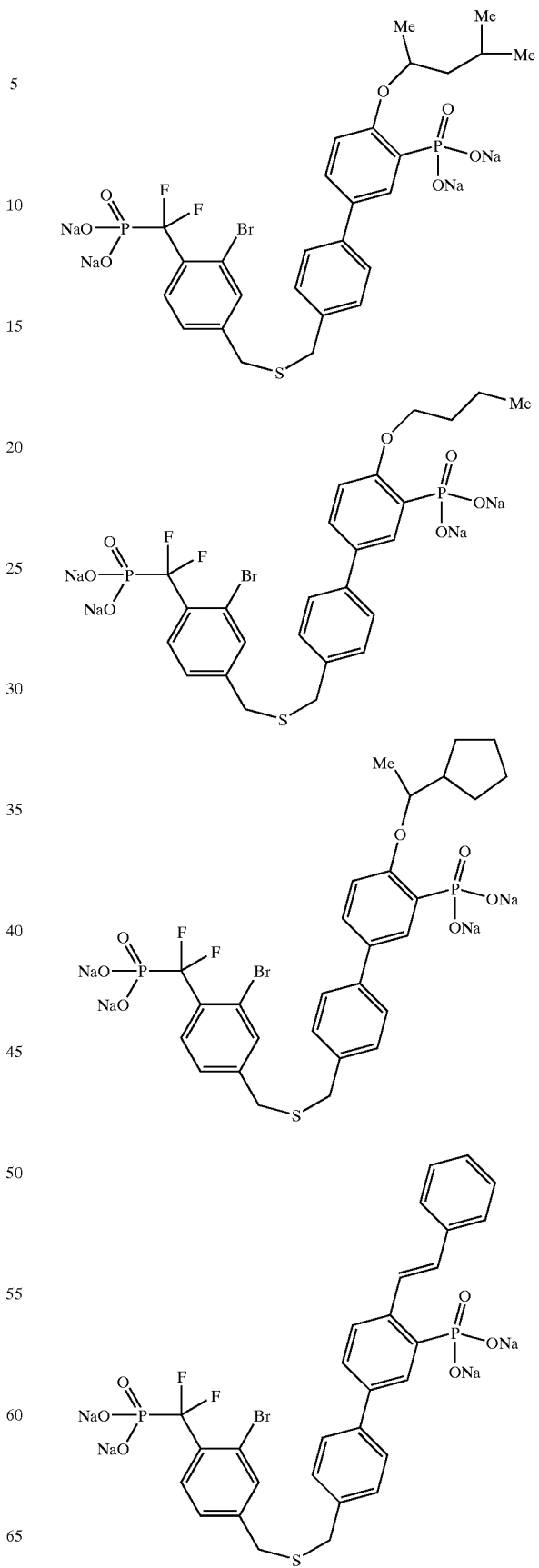

223
-continued
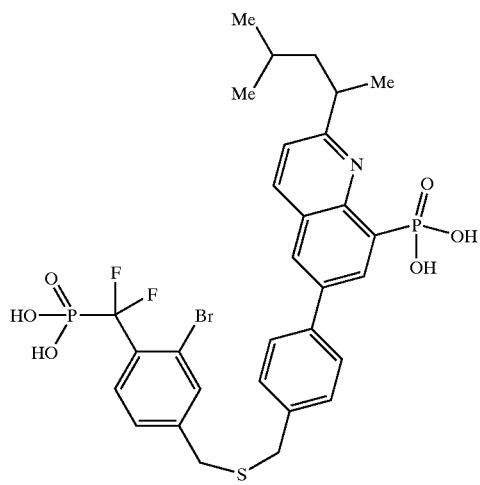
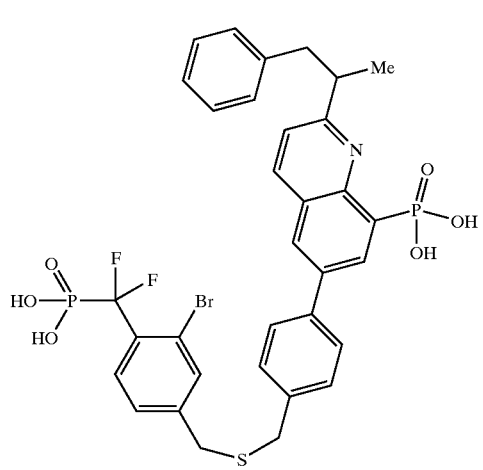
224
-continued
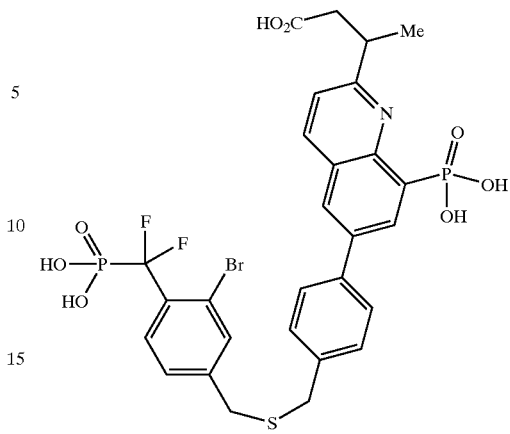
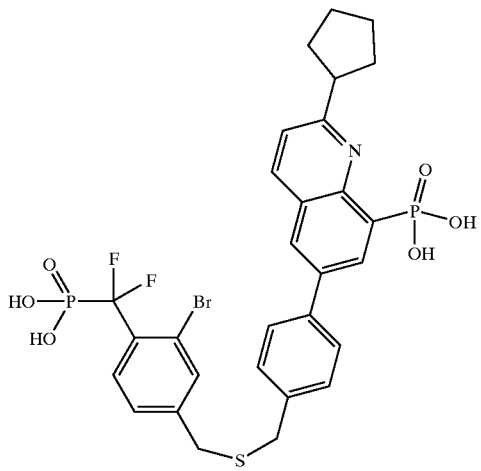
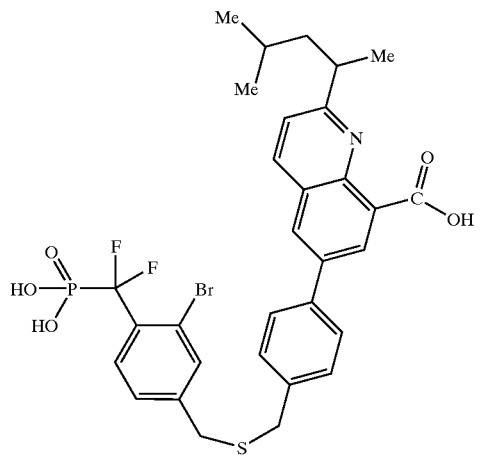
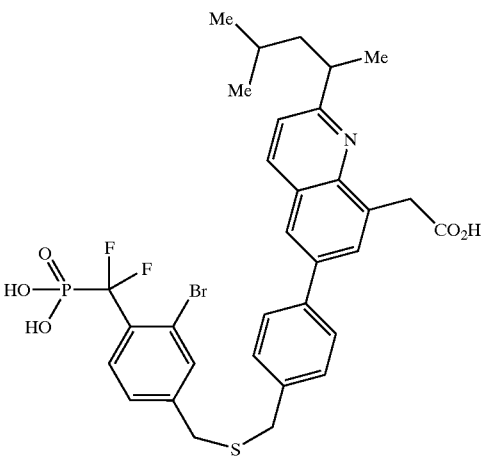

225
-continued
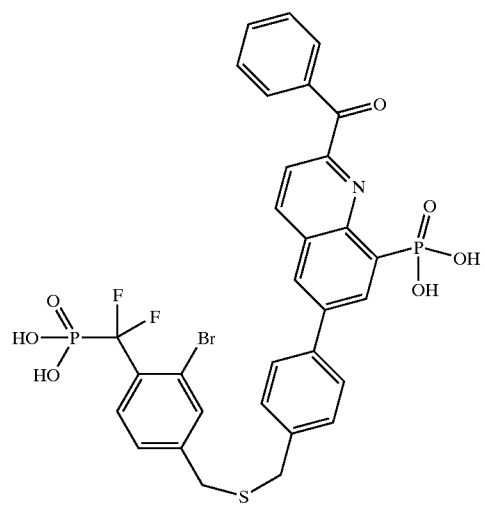
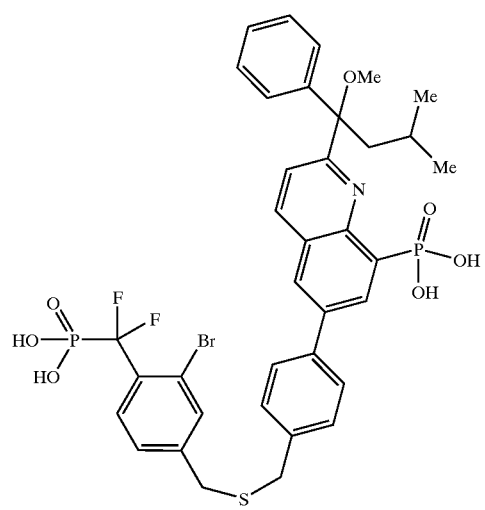
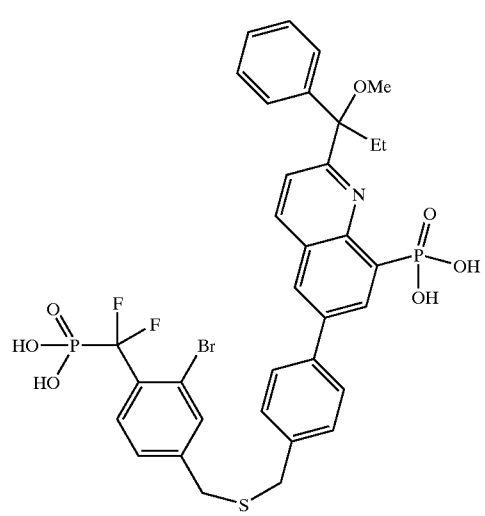
226
-continued
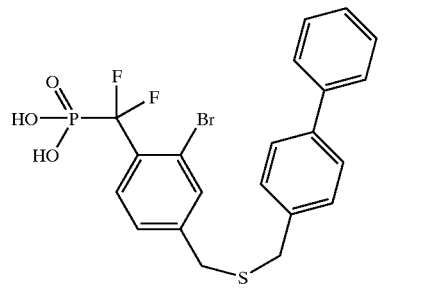
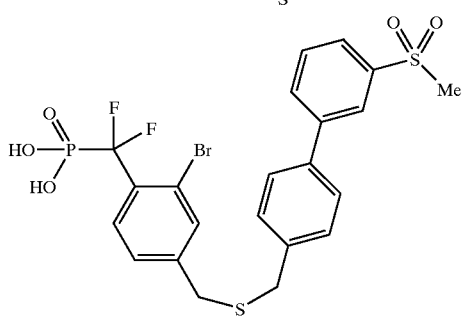
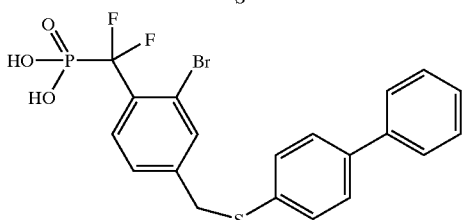
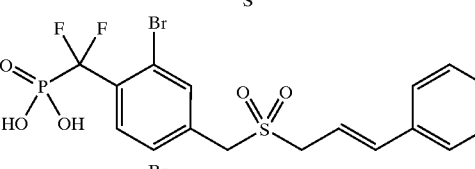
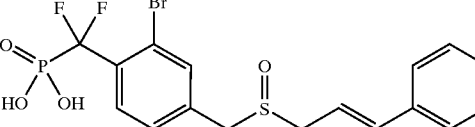
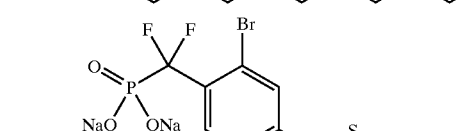
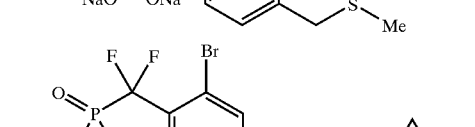
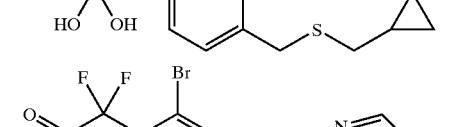
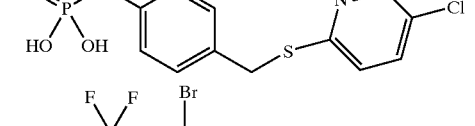
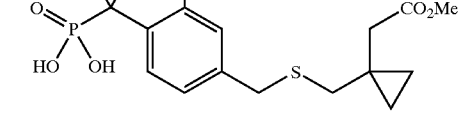

227
-continued
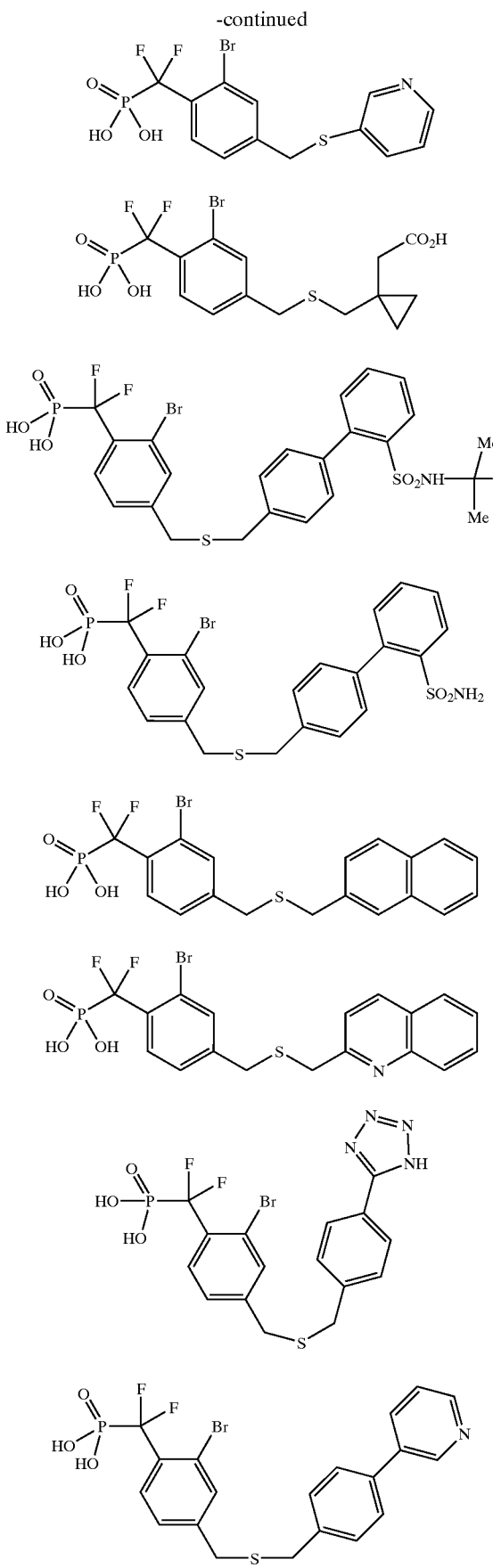
228
-continued
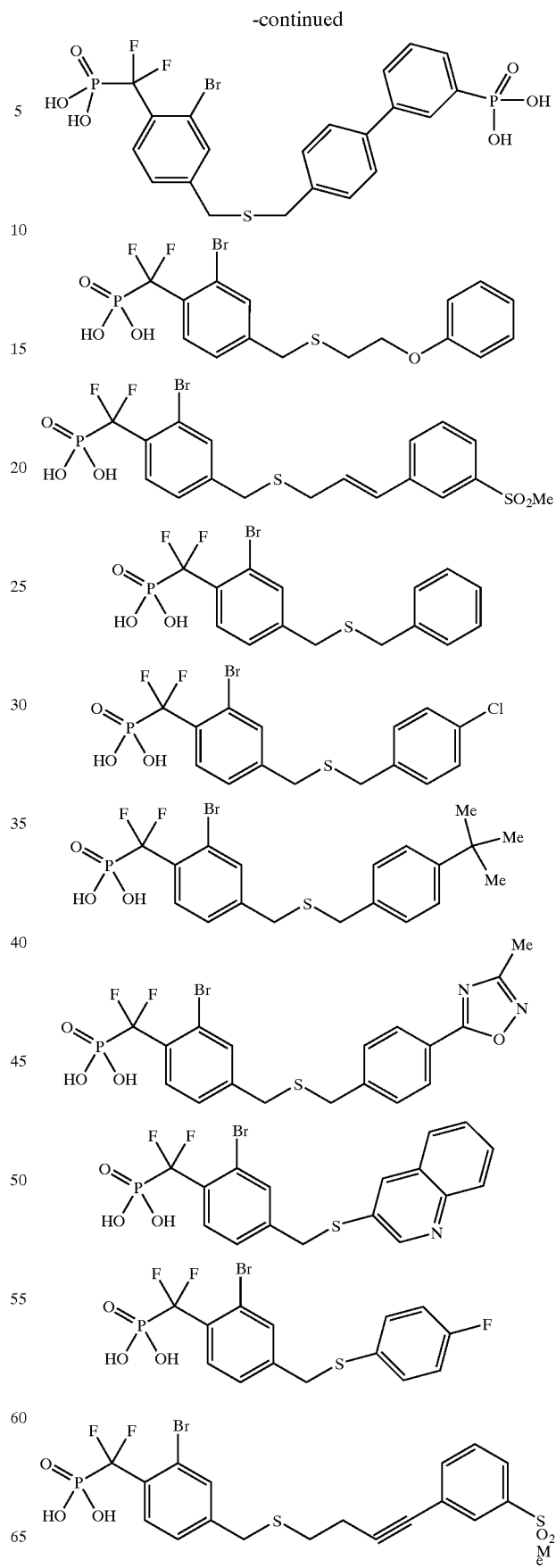

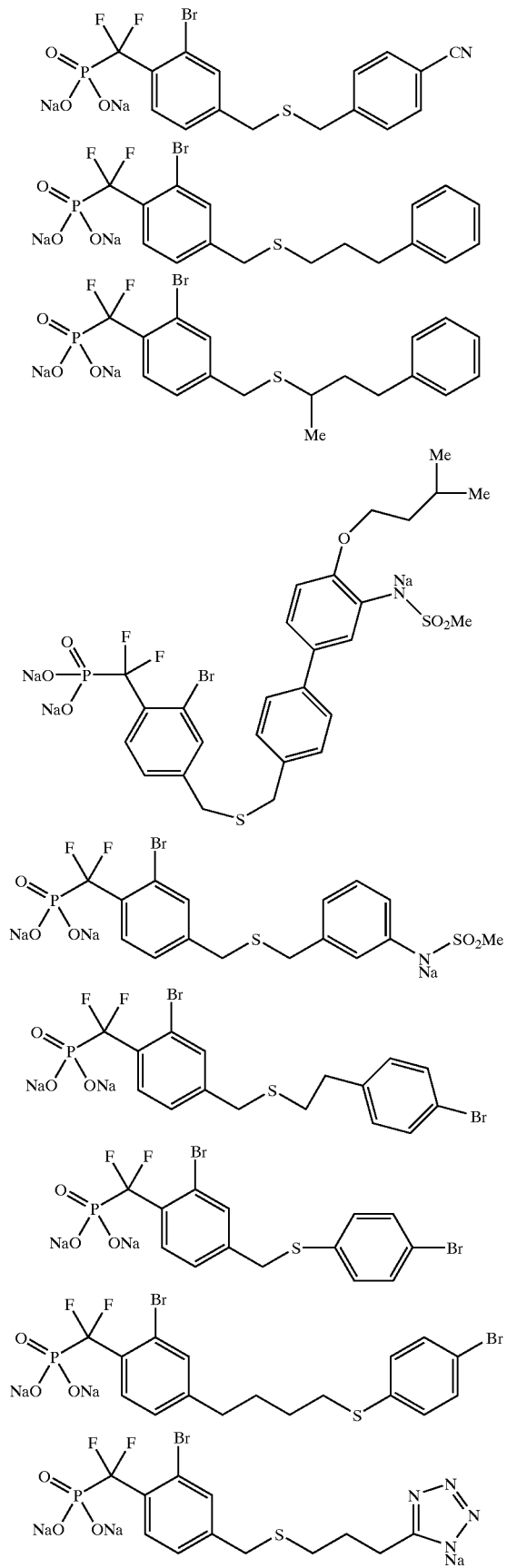
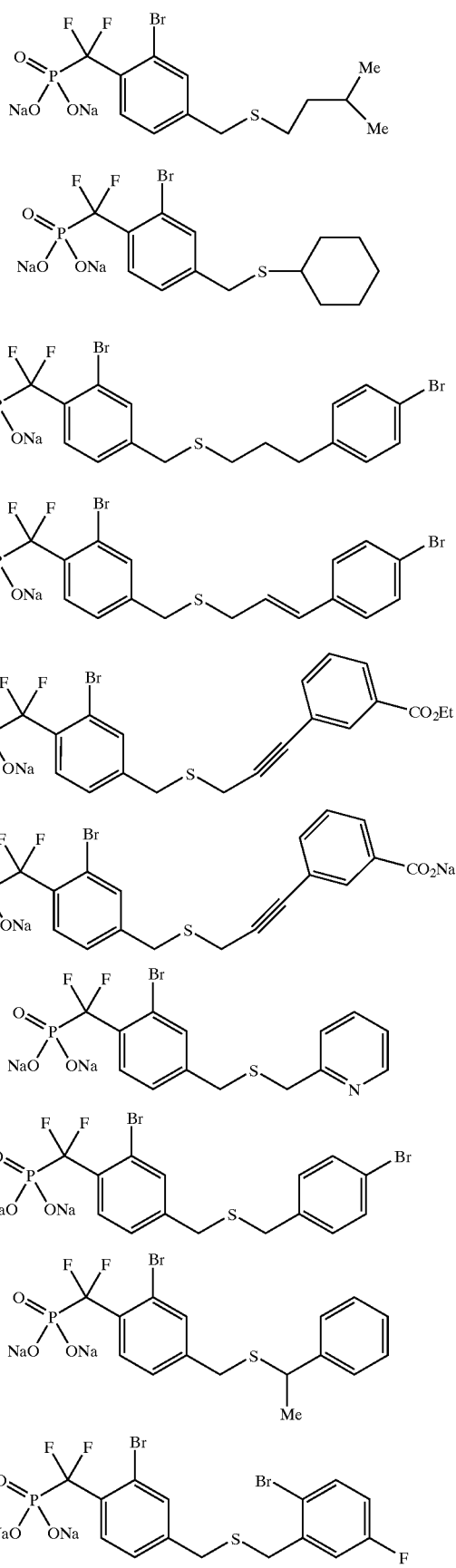

231
-continued
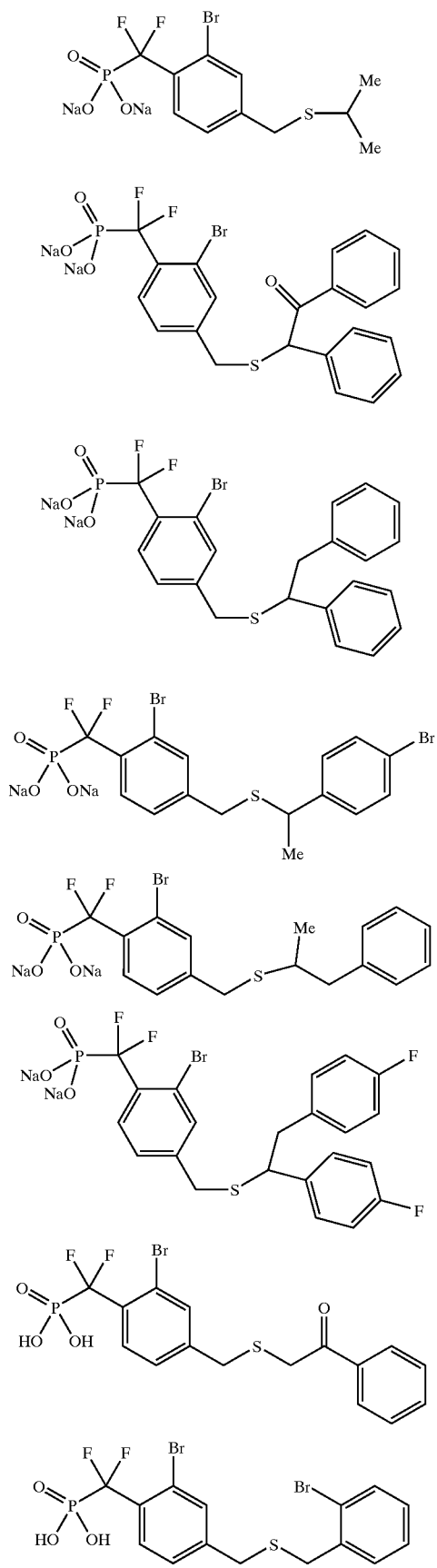
232
-continued
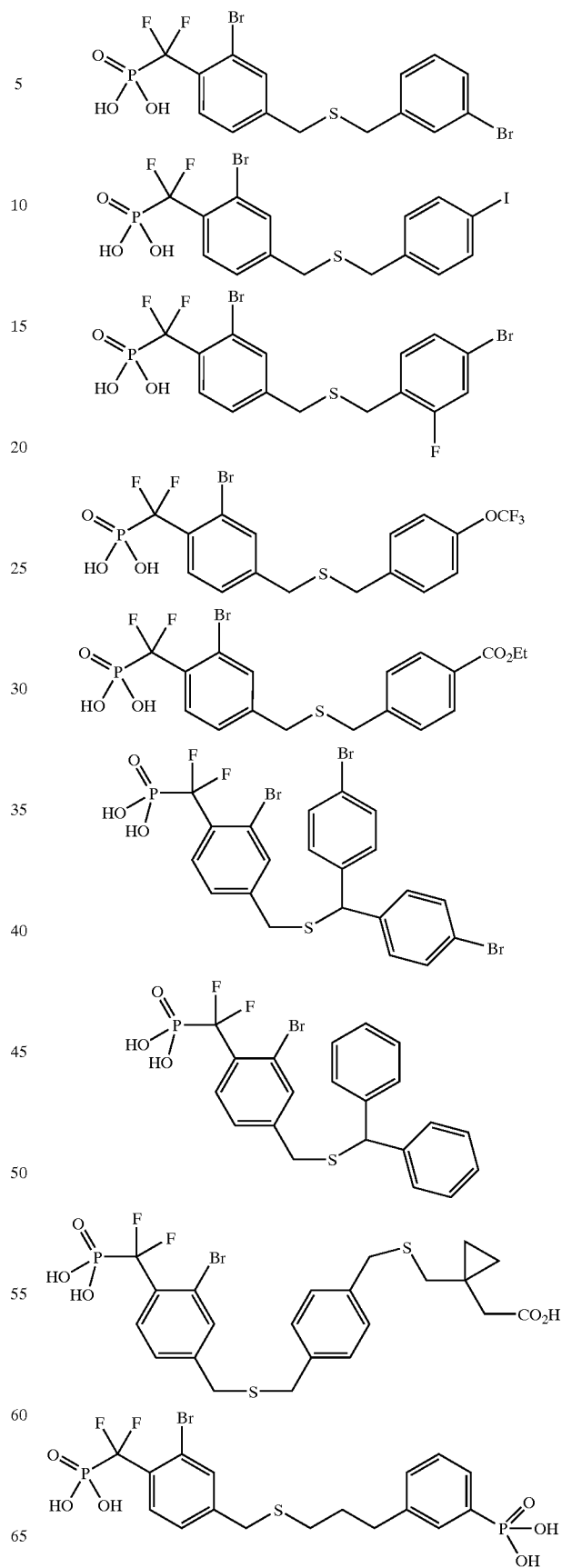

233
-continued
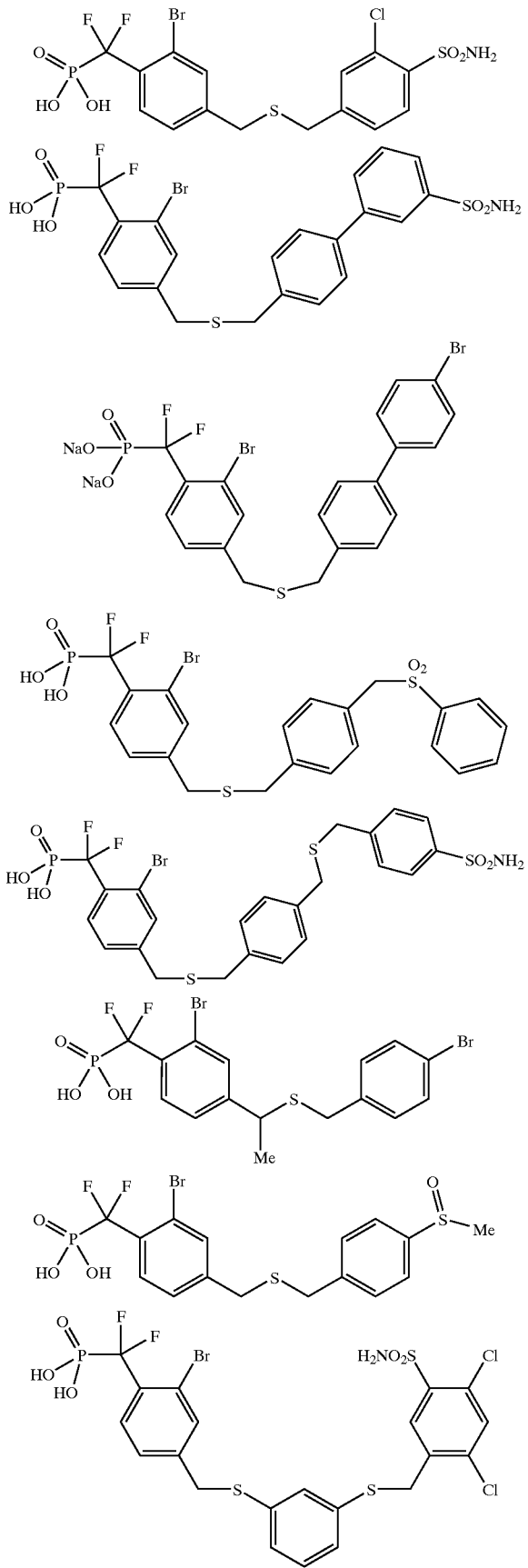
234
-continued
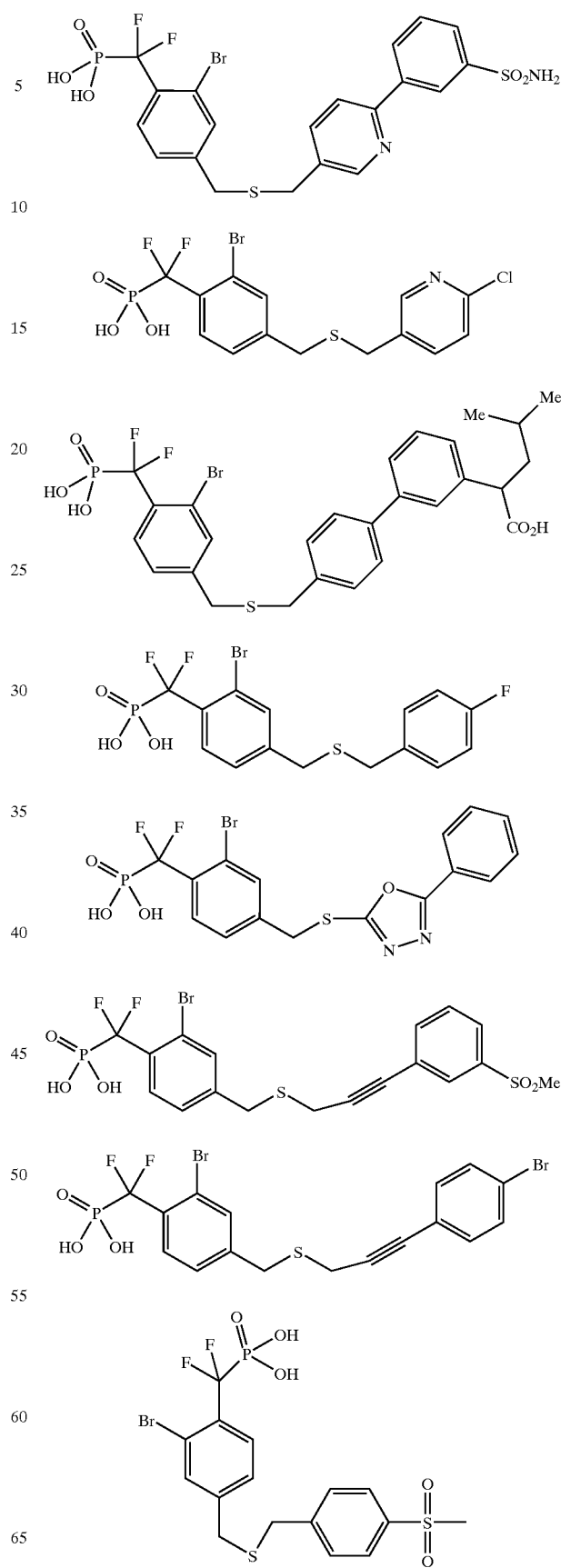

235
-continued
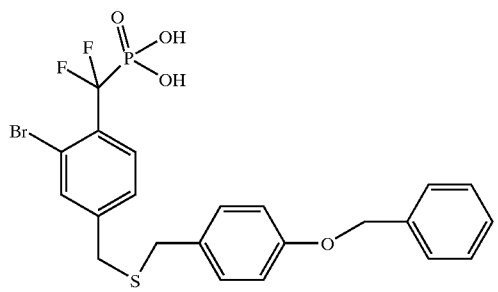
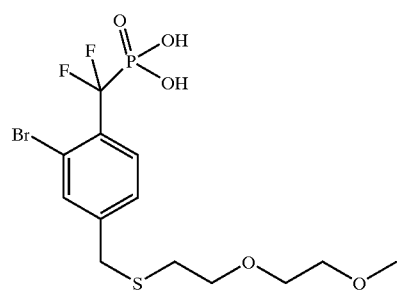
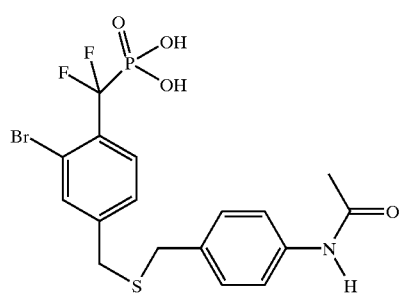
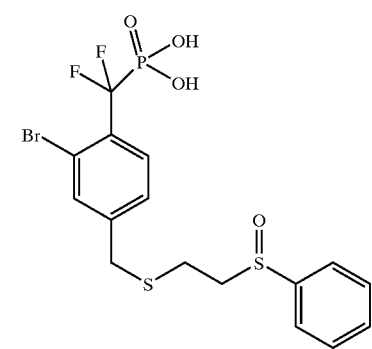
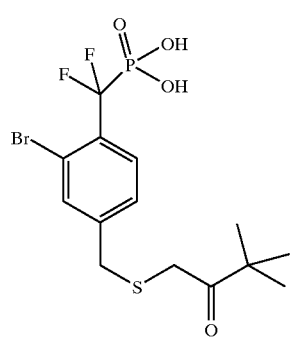
236
-continued
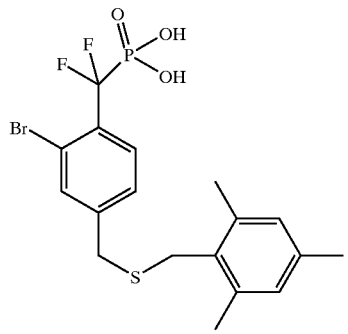
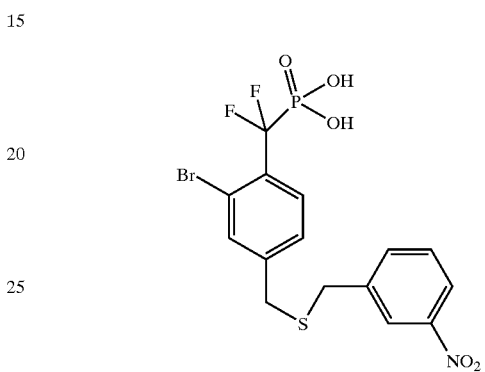
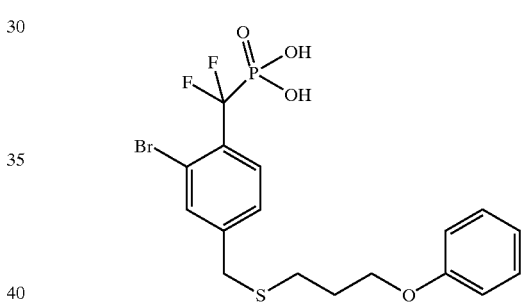
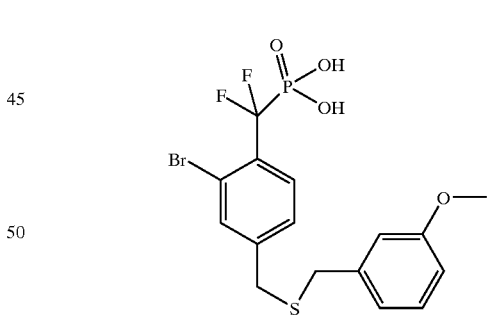
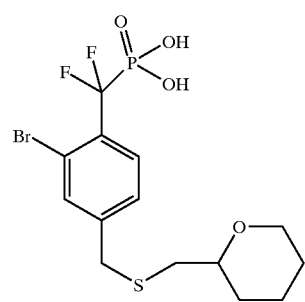

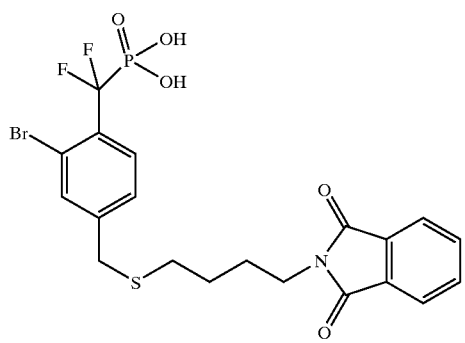
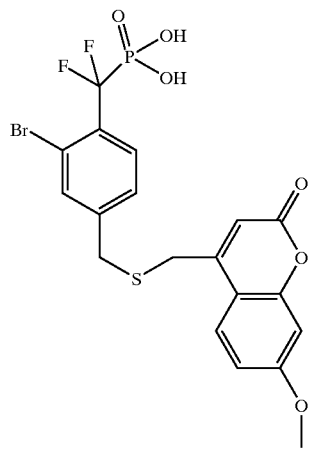
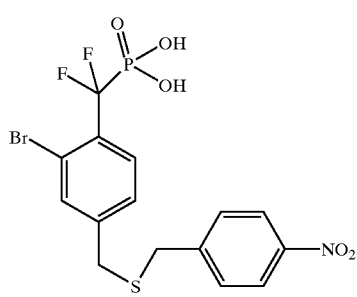
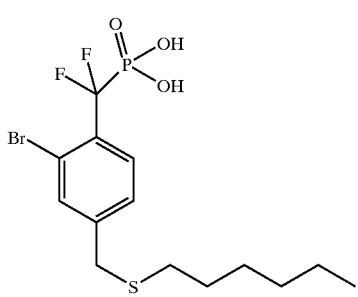
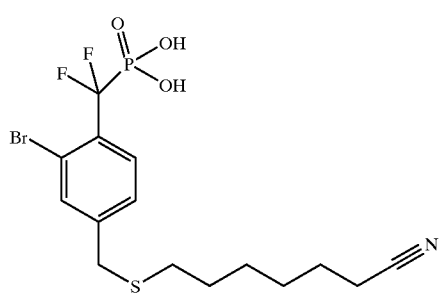
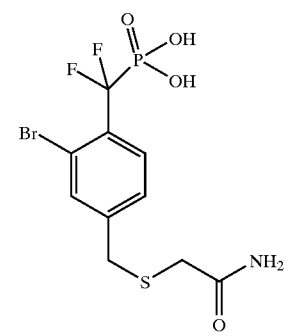
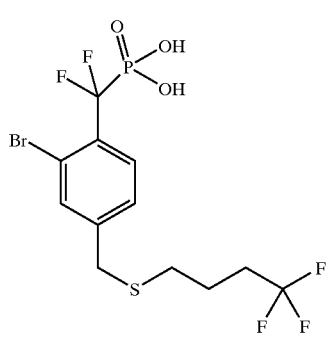
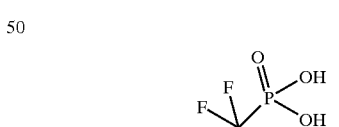
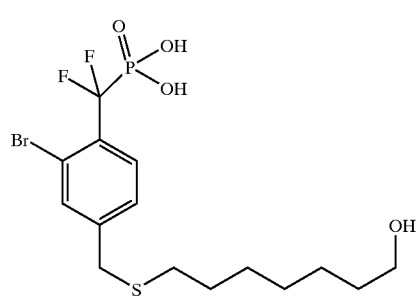
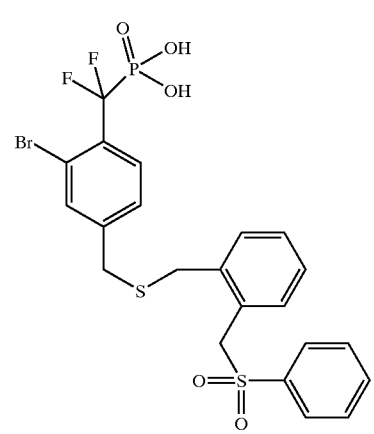

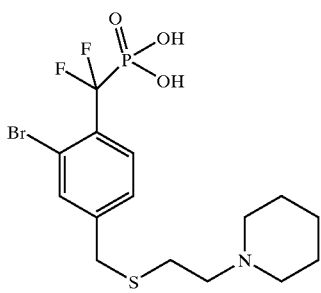
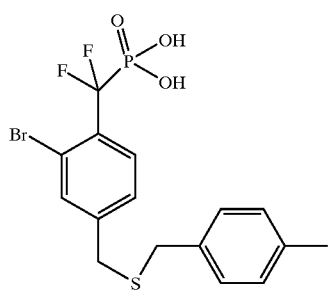

-continued
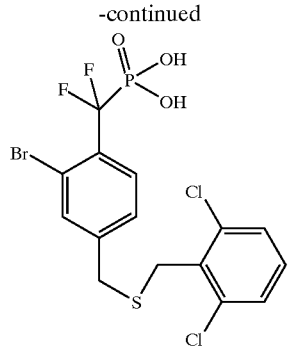
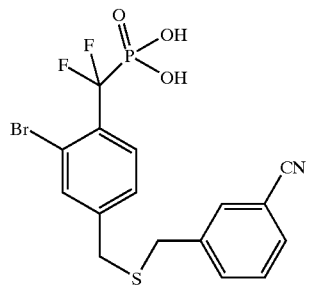
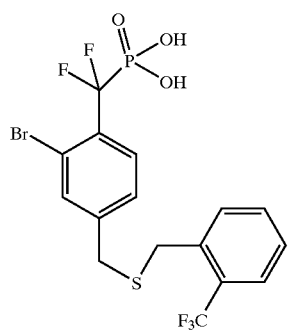
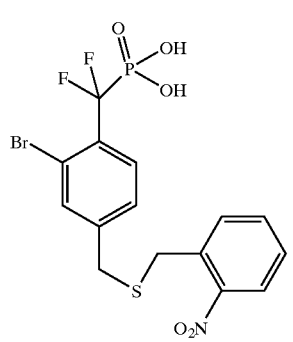
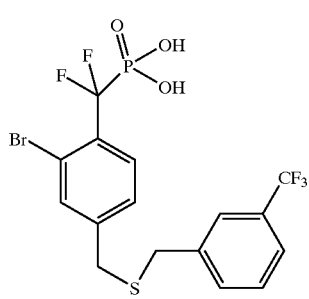
-continued
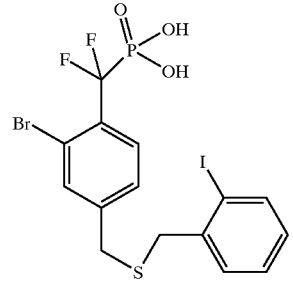
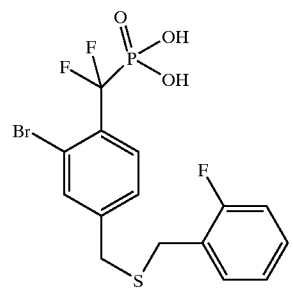
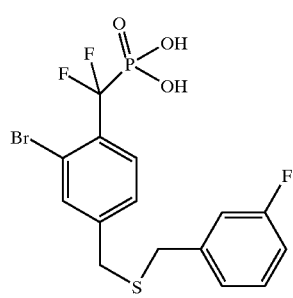
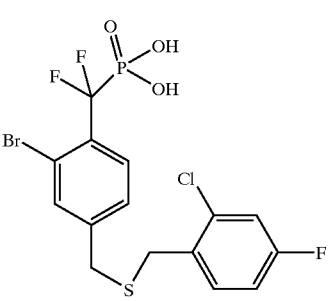
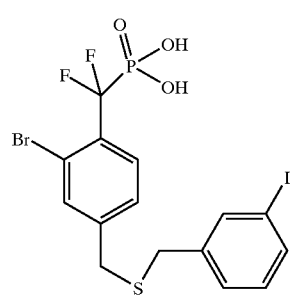

243
-continued
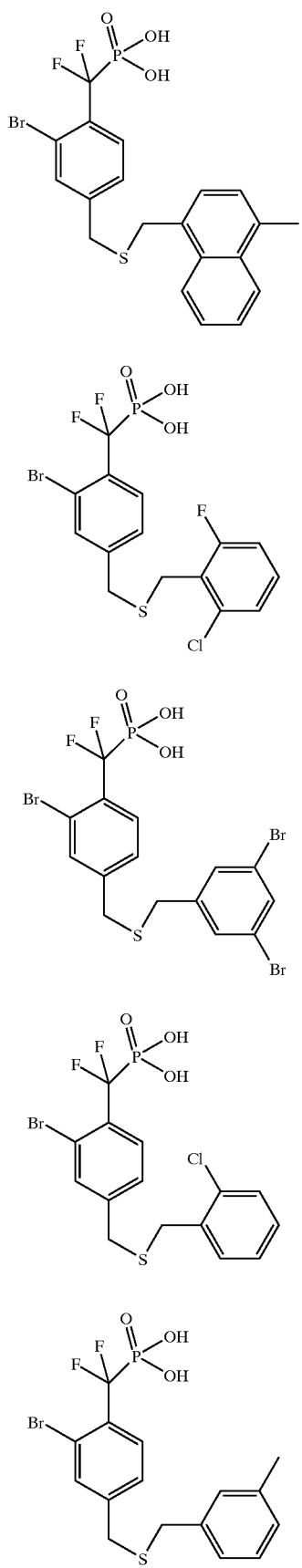
244
-continued
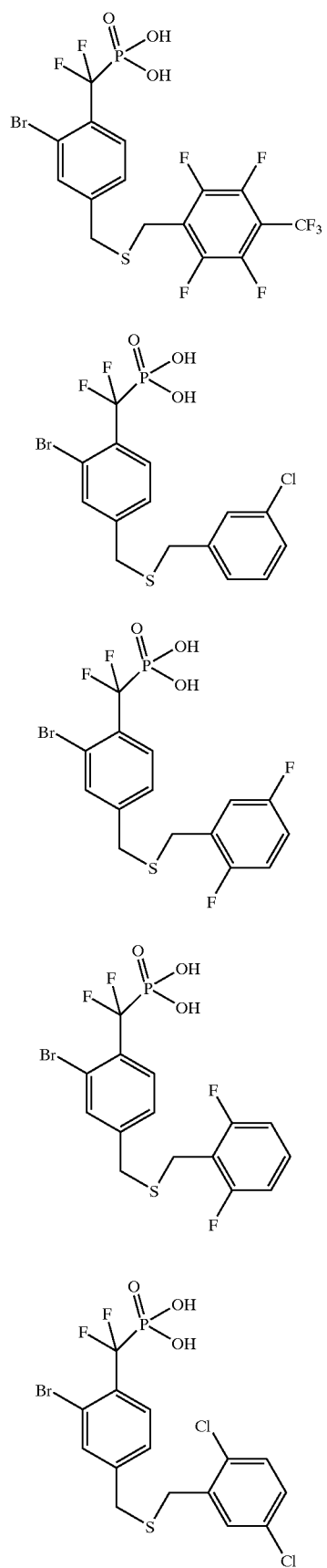

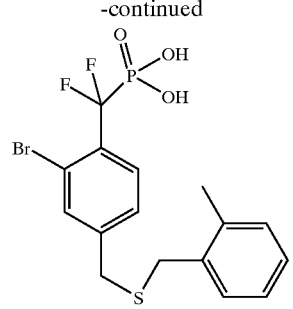
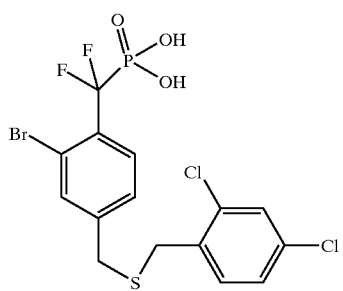
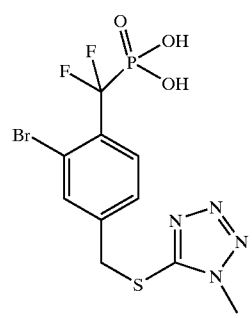
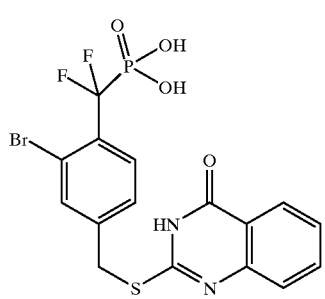
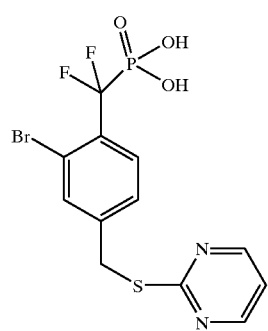
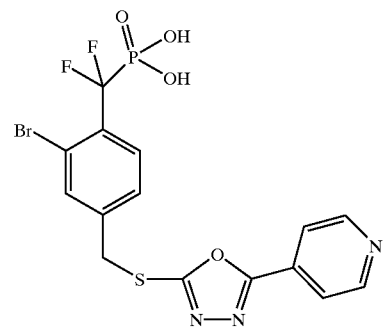
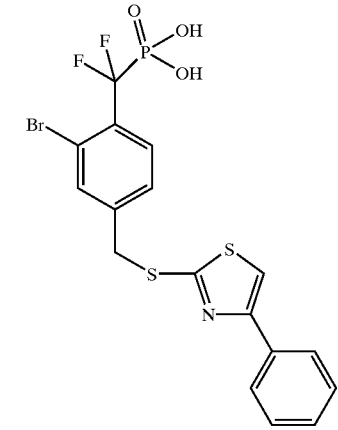
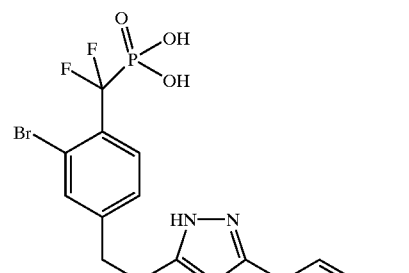
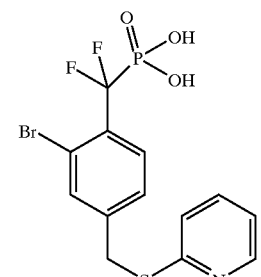
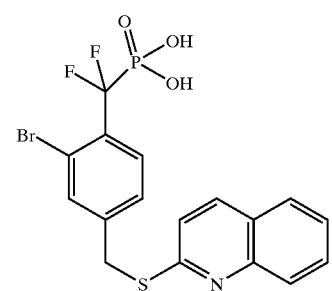

247 248

-continued
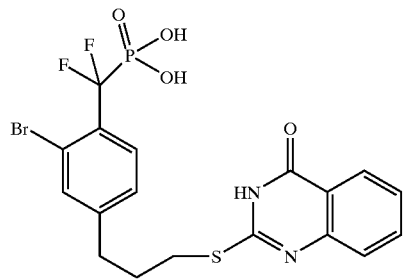
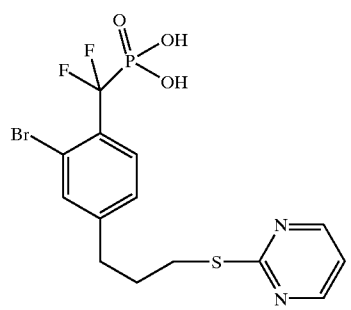
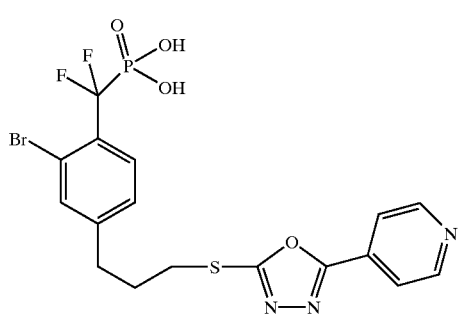
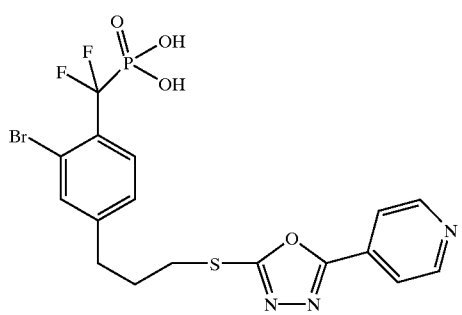
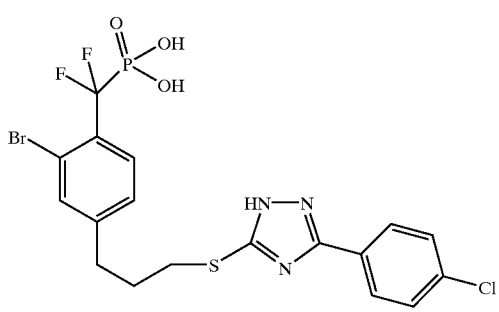
-continued
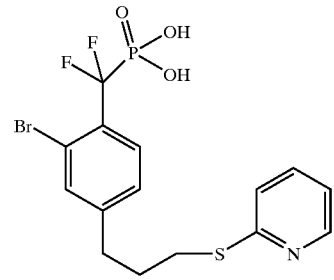
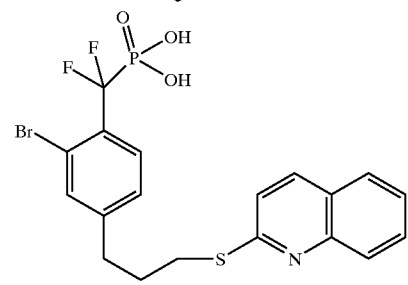
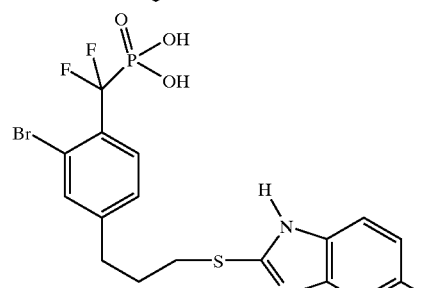
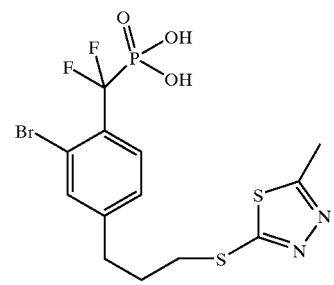
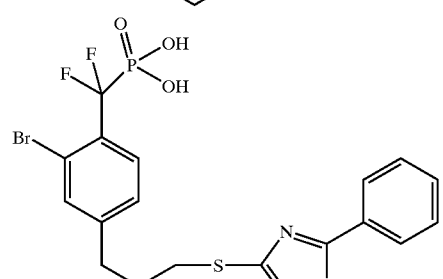
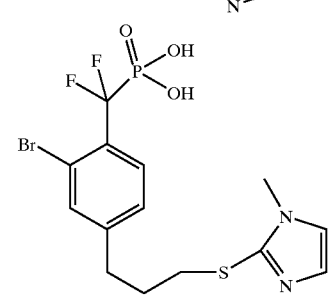

251
-continued

252
-continued

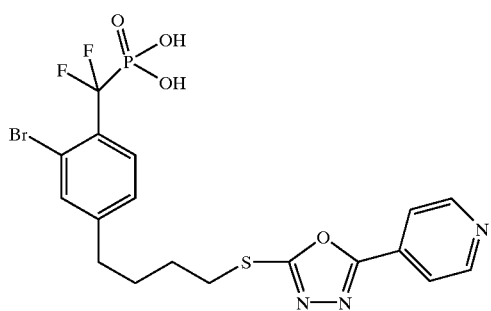
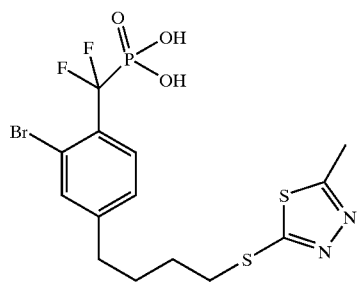
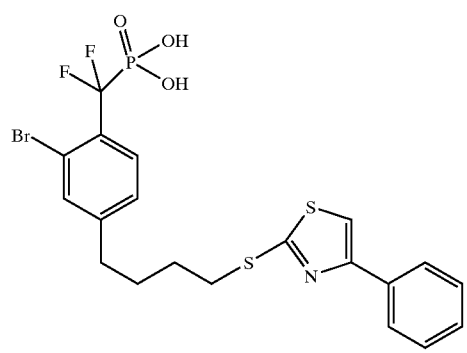
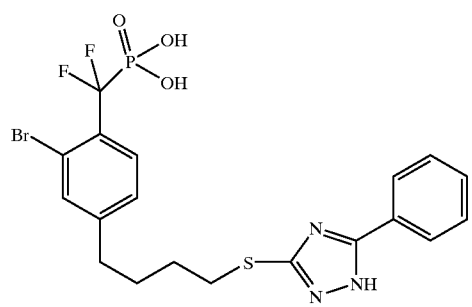
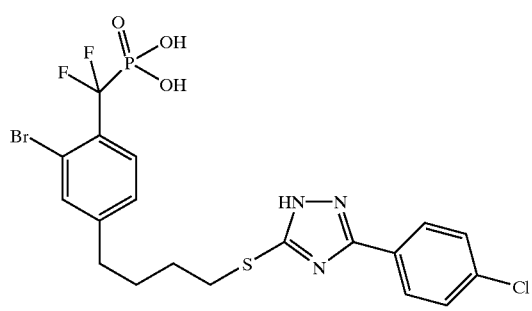
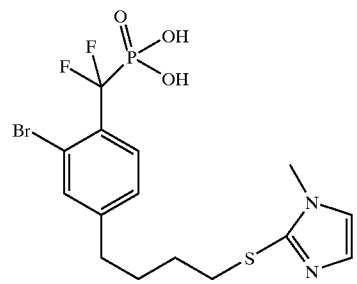
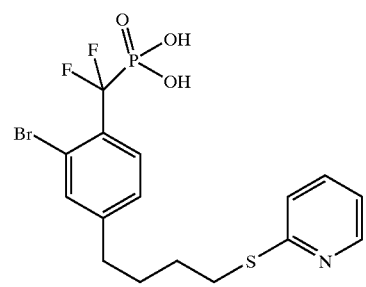
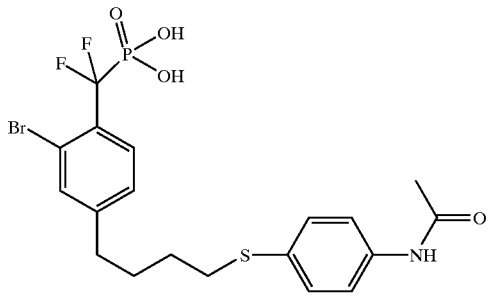
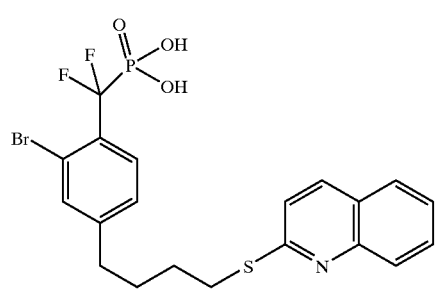
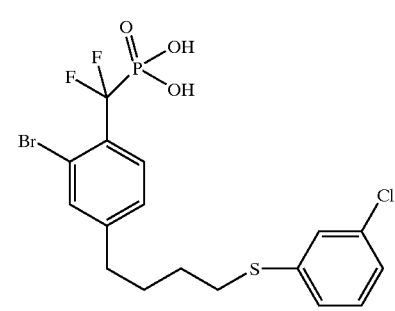

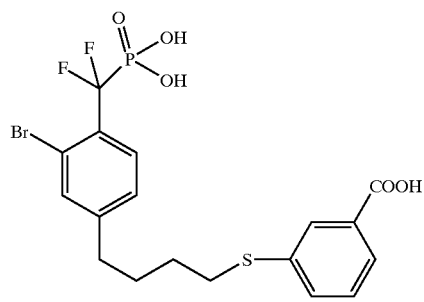
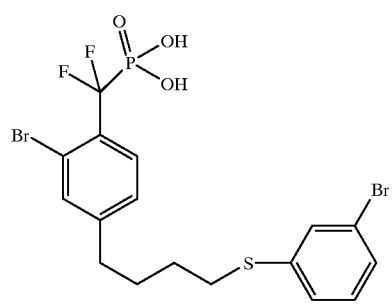
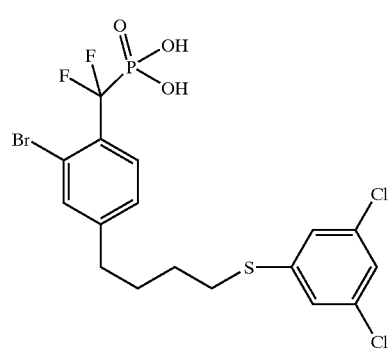
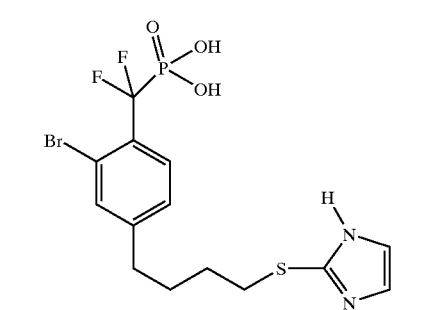
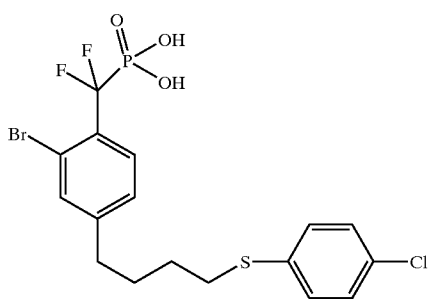
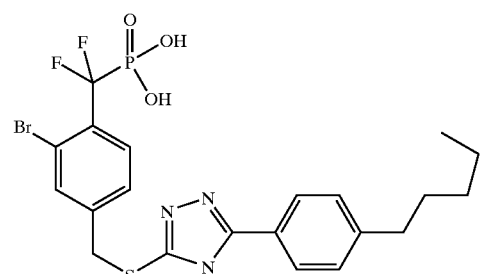
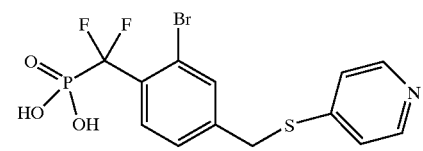
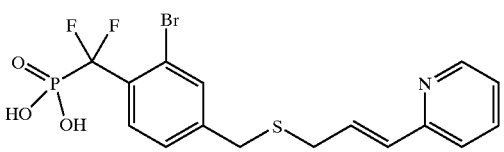
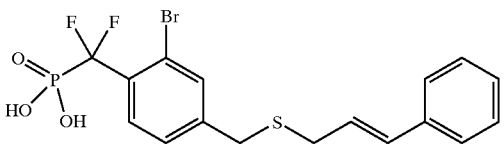
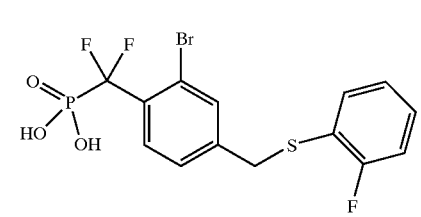
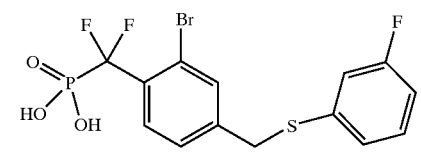
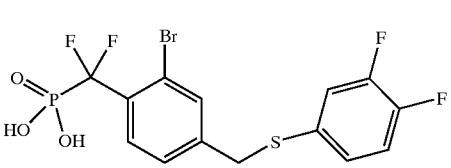
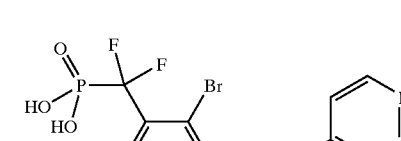
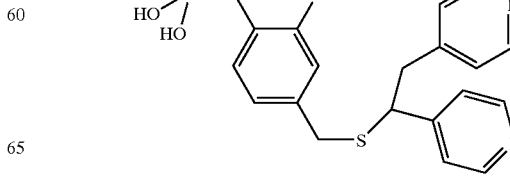

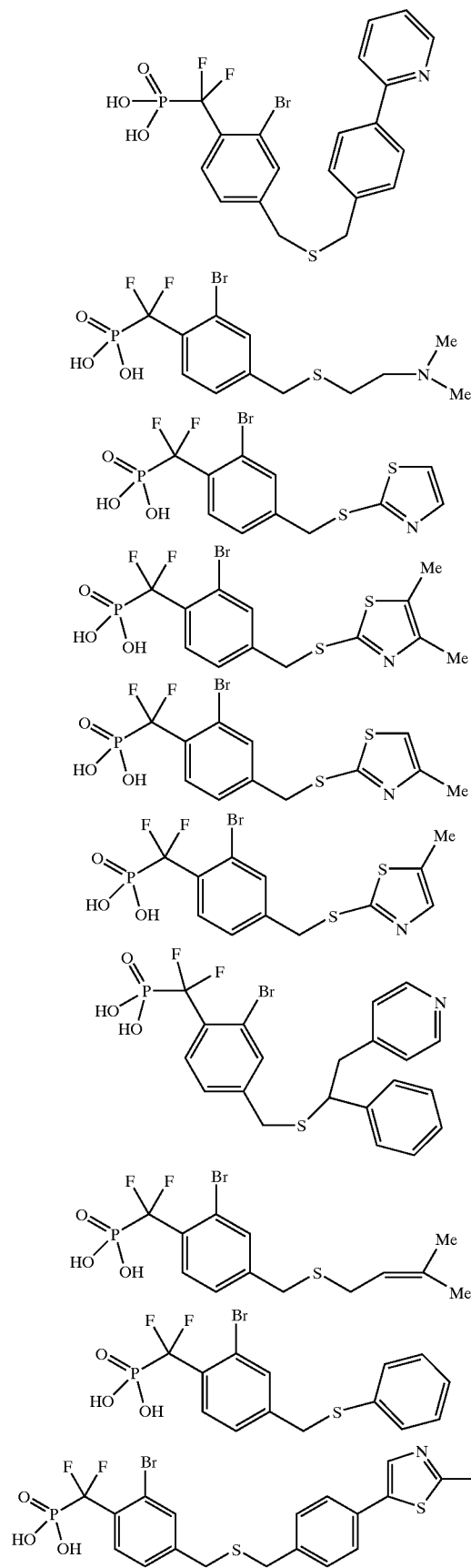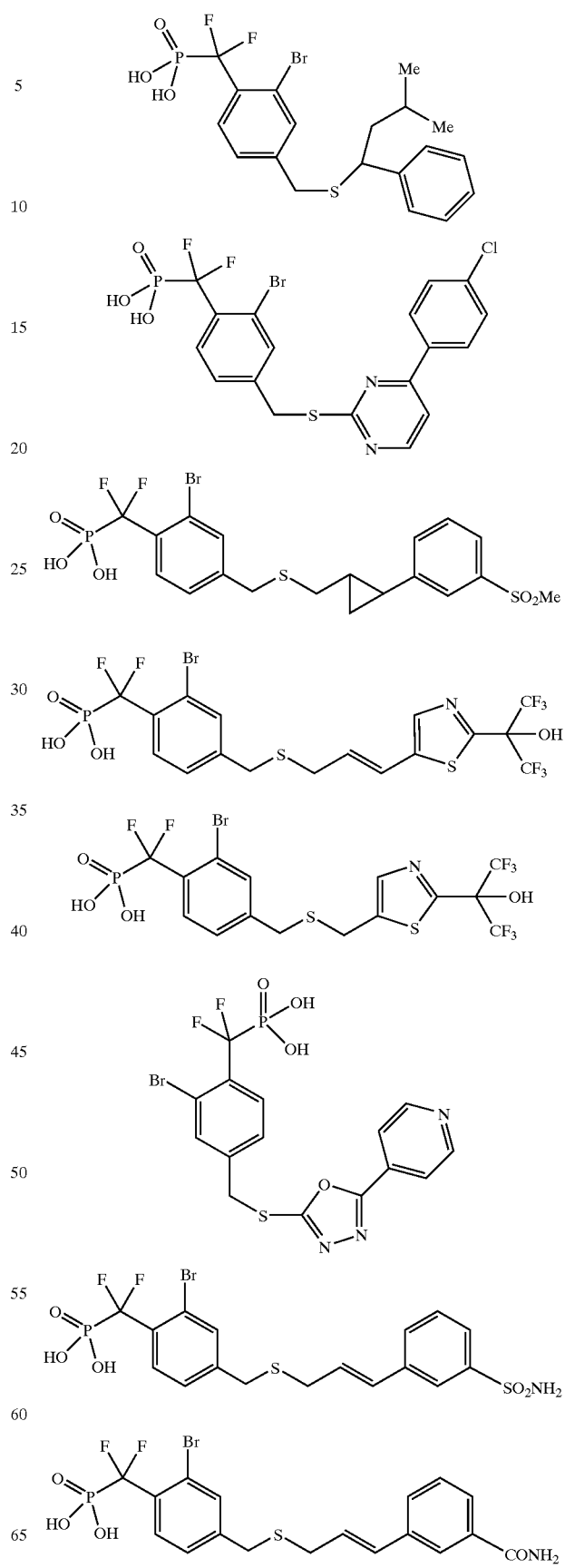

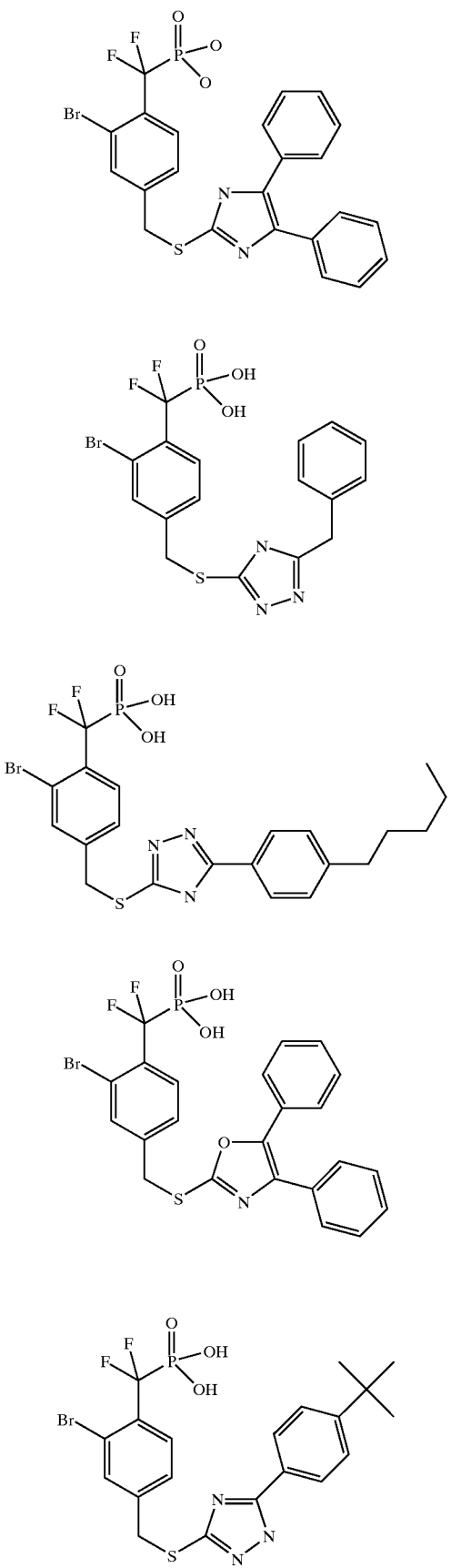
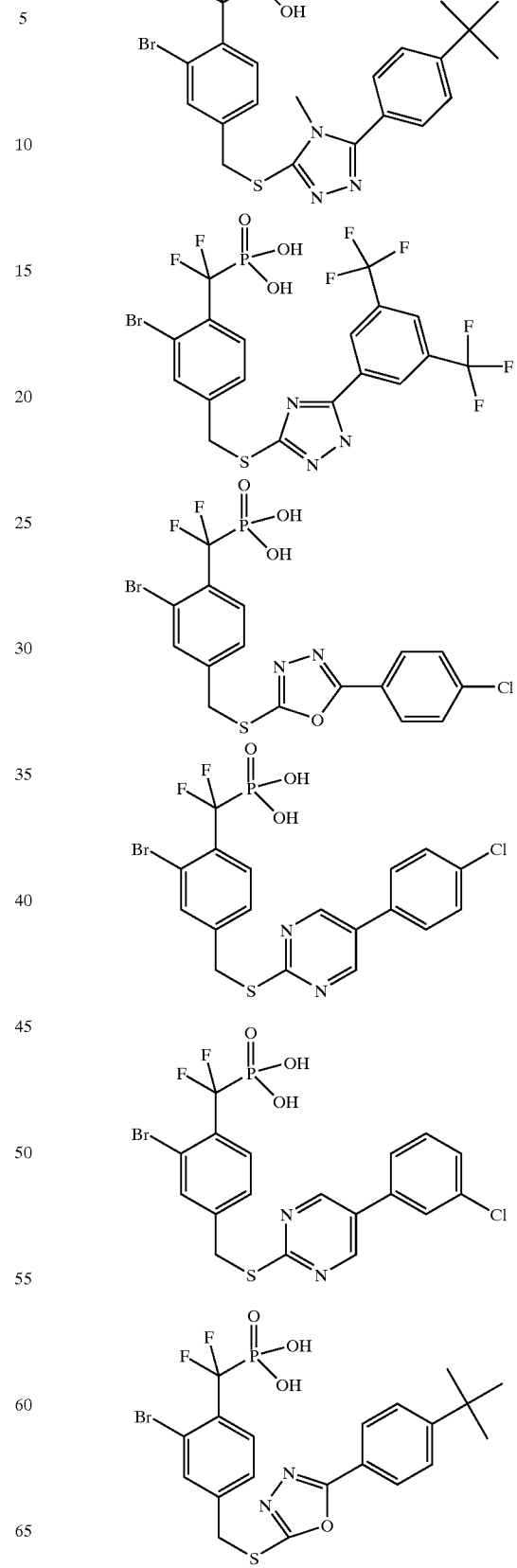

261
-continued
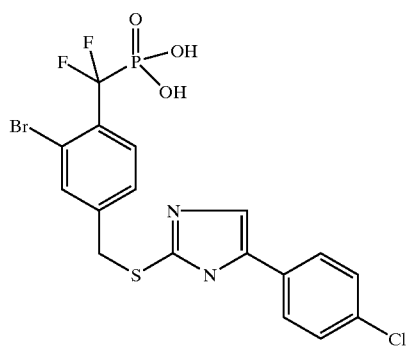
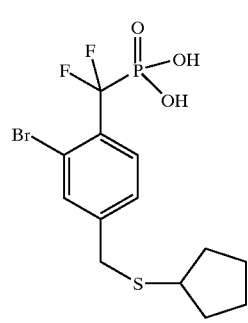
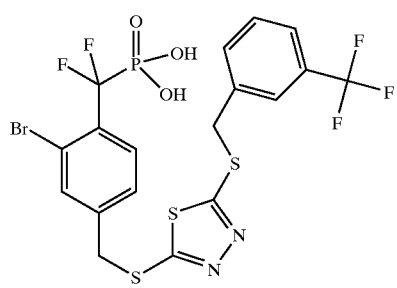
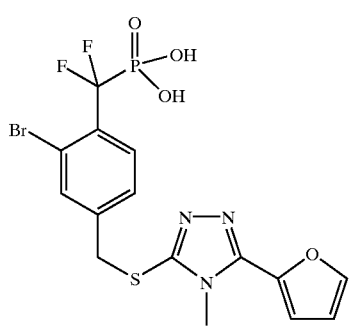
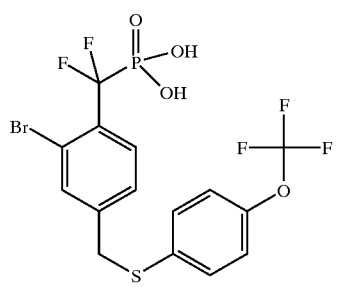
262
-continued
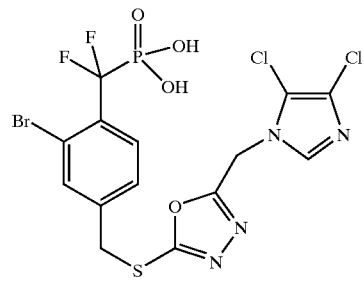
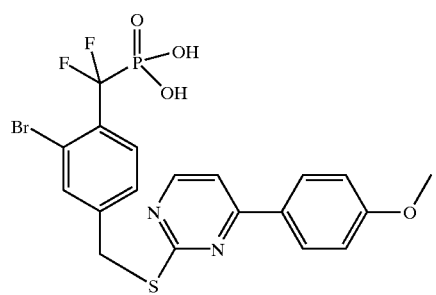
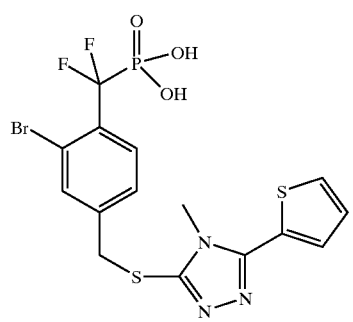
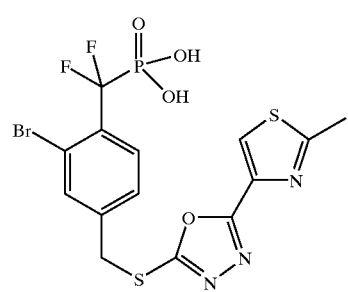
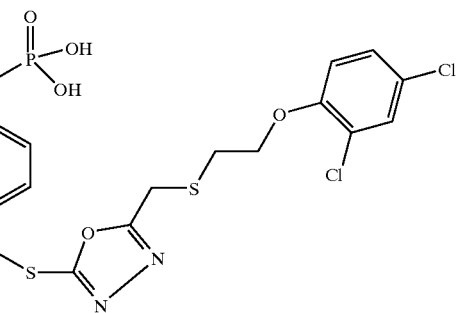

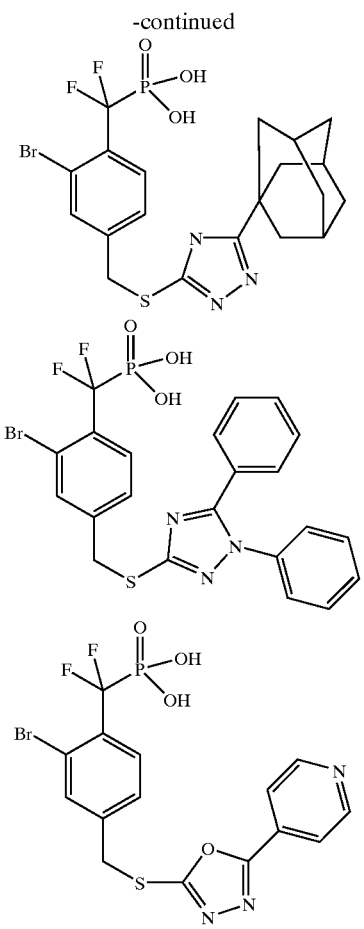

22. A compound in accordance with claim 1, as named below:

4'-[4-(Difluorophosphonomethyl)benzylsulfanylmethyl]-4-hydroxy-biphenyl-3-yl-phosphonic acid tetrasodium salt;
{4-[4-(Difluorophosphonomethyl)benzylsulfanylmethyl]phenyl}difluoromethyl-phosphonic acid tetrasodium salt;
{4-[4-(Difluorophosphonomethyl)benzylsulfanylmethyl]phenyl}difluoromethyl-phosphonic acid;
{2-Bromo-4-[4-(difluorophosphonomethyl)benzylsulfanylmethyl]-phenyl}difluoromethylphosphonic acid tetrasodium salt;
(2-Bromo-4-{4-[(diethoxyphosphoryl)difluoromethyl]benzylsulfonylmethyl}phenyldifluoromethylphosphonic acid;
}2-Bromo-4-[4-(difluorophosphonomethyl)benzylsulfonylmethyl]-phenyl}difluoromethylphosphonic acid;
4'-[4-(Difluorophosphonomethyl)benzylsulfanylmethyl]-4-(3-methylbutoxy)biphenyl-3-yl-phosphonic acid;
4'-[3-(Difluorophosphonomethyl)benzylsulfanylmethyl]-4-(3-methylbutoxy)biphenyl-3-yl-phosphonic acid;
4'-[3-Bromo-4-(difluorophosphonomethyl)benzylsulfanylmethyl]-4-(3-methylbutoxy)biphenyl-3-yl-phosphonic salt;
{2-Bromo-4-[3-bromo-4-(difluorophosphonomethyl)benzylsulfanylmethyl]-phenyl}difluoromethylphosphonic acid;
[2-Bromo-4-(3-phenylallylsulfanylmethyl)phenyl]difluoromethylphosphonic acid disodium salt;
4'-[3-Bromo-4-(difluorophosphonomethyl)benzylsulfanylmethyl]-4-(3-methylbutoxy)biphenyl-3-yl-carboxylic acid trisodium salt;
4''-[4-(Difluorophosphonomethyl)benzylsulfanylmethyl]-[1,1';4',1'']terphenyl-2'ylphosphonic acid;
4'-[3-Bromo-4-(difluorophosphonomethyl)-benzylsulfanylmethyl]-4-(1,3-dimethylbutoxy)-biphenyl-3-ylphosphonic salt tetrasodium salt;
4'-[3-Bromo-4-(difluorophosphonomethyl)-benzylsulfanylmethyl]-4-butoxybiphenyl-3-ylphosphonic acid tetrasodium salt;
4'-[3-Bromo-4-(difluorophosphonomethyl)-benzylsulfanylmethyl-4-(1-cyclopentylethoxy)-biphenyl-3-ylphosphonic salt;
4'-[3-Bromo-4-(difluorophosphonomethyl)-benzylsulfanylmethyl]-4-styrylbiphenyl-3-ylphosphonic acid tetrasodium salt;
6-{4-[3-Bromo-4-difluoro-phosphono-methyl)benzylsulfanyl-methyl]-phenyl}-2-(1,3-dimethyl-butyl)-quinolin-8-yl-phosphonic acid;
6-{4-[bromo-4-difluoro-phosphono-methyl)-benzylsulfanyl-methyl]-phenyl}-2-(1-methyl-2-phenyl-ethyl)-quinolin-8-yl-phosphonic acid;
6-{4-[3-bromo-4-difluoro-phosphono-methyl)-benzylsulfanyl-methyl]-phenyl}-2-(1,3-dimethyl-butyl)-quinoline-8-yl-carbonxylic acid;
3-(6-{4-[3-bromo-4-difluoro-phosphono-methyl)-benzylsulfanyl-methyl]-phenyl}-8-phosphono-quinolin-2-yl)-butyric acid;
6-{4-[3-bromo-4-difluoro-phosphono-methyl)-benzylsulfanyl-methyl]-phenyl}-2-(cyclopentyl)-quinolin-8-yl-phosphonic acid;
6-{4-[3-bromo-4-difluoro-phosphono-methyl)-benzylsulfanyl-methyl]-phenyl}-2-(1,3-dimethyl-butyl)-quinolin-8-yl-acetic acid;
2-Benzoyl-6-{4-[3-Bromo-4-difluoro-phosphono-methyl)-benzylsulfanyl-methyl]-phenyl}-quinolin-8-yl-phosphonic acid;
6-{4-[3-Bromo-4-difluoro-phosphono-methyl)-benzylsulfanyl-methyl]-phenyl}-2-(1-methoxy-3-methyl-1-phentl-butyl)-quinolin-8-yl-phosphonic acid;
6-{4-[3-Bromo-4-difluoro-phosphono-methyl)-benzylsulfanyl-methyl]-phenyl}-2-(1-methoxy-3-methyl-1-phenyl-propyl)-quinolin-8-yl-phosphonic acid;
[4-Biphenyl-4-ylmethylsulfanyl-methyl)-2-bromo-phenyl]-difluoro-methyl-phosphonic acid;
[2-Bromo-4-(3'-methylsulfonyl-biphenyl-4-ylmethylsulfanyl-methyl)-phenyl]-difluoro-methyl-phosphonic acid;
[4-Biphenyl-4-ylsulfanylmethyl)-2-bromo-phenyl]-difluoromethylphosphonic acid disodium salt;
[2-Bromo-4-(3-phenylallylsulfonylmethyl)phenyl] difluoromethylphosphonic acid;
[2-Bromo-4-(3-phenylallylsulfinylmethyl)phenyl] difluoromethylphosphonic acid;
(2-Bromo-4-methylsulfanylmethylphenyl)-difluoromethylphosphonic acid disodium salt;
[2-Bromo-4-(cyclopropylmethylsulfanylmethyl)-phenyl]-difluoromethylphosphonic acid disodium salt;
[2-Bromo-4-(5-chloropyridin-2-ylsulfanylmethyl)-phenyl]-difluoromethylphosphonic acid disodium salt;
Methyl 2-[({[4-(difluorophosphonomethyl)-3-bromophenyl]methylthio}methyl)cyclopropyl]acetate;
{2-Bromo-4-[(pyridin-3-ylthio)methyl]phenyl}(difluoro) methylphosphonic acid disodium salt;
2-[({[4-(Difluorophosphonomethyl)-3-bromophenyl]methylthio}methyl)cyclopropyl]acetic acid;
({2-[4-({[4-(Difluorophosphonomethyl)-3-bromophenyl]methylthio}methyl)phenyl]phenyl}sulfonyl(tert-butyl)amine;

2-[4-({[4-(Difluorophosphonomethyl)-3-bromophenyl]methylthio}methyl)phenyl]benzenesulfonamide;
(2-Bromo-4-{[(2-naphthylmethyl)thio]methyl}phenyl)(difluoro)methylphosphonic acid;
(2-Bromo-4-{[(quinolin-2-ylmethyl)thio]methyl}(difluoro)methylphosphonic acid;
{2-Bromo-4-[4-(1-H-tetrazol-5-yl)benzylsulfanylmethyl]phenyl}-difluoromethylphosphonic acid trisodium salt;
(2-Bromo-4-{[(4-pyridin-3-ylbenzyl)thio]methyl}phenyl)(difluoro)methylphosphonic acid disodium salt;
4'-[({3-Bromo-4-[difluoro(phosphono)methyl]benzyl}thio)methyl]-1,1'-biphenyl-3-ylphosphonic acid;
(2-Bromo-4-{[(2-phenoxyethyl)thio]methyl}phenyl)(difluoro)methylphosphonic acid disodium salt;
2-Bromo-4-[({(2E)-3-[3-(methylsulfonyl)phenyl]prop-2-enyl}thio)methyl]phenyl}(difluoro)methylphosphonic acid disodium salt;
{4-[(Benzylthio)methyl]-2-bromophenyl}(difluoro)methylphosphonic acid disodium salt;
(2-Bromo-4-[(4-chlorobenzyl)sulfanyl]methylphenyl)(difluoro)methylphosphonic acid disodium salt;
(2-Bromo-4-{[(4-tert-butylbenzyl)thio[methyl}phenyl)(difluoro)methylphosphonic acid disodium salt;
[2-Bromo-4-({[4-(3-methyl-1,2,4-oxadiazol-5-yl)benzyl]thio}methyl)phenyl](difluoro)methylphosphonic acid disodium salt;
{2-Bromo-4-[(quinolin-3-ylthio)methyl]phenyl}(difluoro)methylphosphonic acid disodium salt;
[2-Bromo-4-(4-fluorophenylsulfanylmethyl)phenyl]difluoromethylphosphonic acid disodium salt;
{2-Bromo-4-[({4-[3-methylsulfonyl)phenyl]but-3ynyl}thio)methyl]phenyl}(difluoro)methylphosphonic acid disodium salt;
[2-Bromo-4-(4-cyanobenzylsulfanylmethyl)phenyl]difluoromethylphosphonic acid disodium salt;
[2-Bromo-4-(3-phenylpropylsulfanylmethyl)phenyl]difluoromethylphosphonic acid disodium salt;
[2-Bromo-4-(1-methyl-3-phenylpropylsulfanylmethyl)phenyl]difluoromethylphosphonic acid disodium salt;
{2-Bromo-4-[3'-methanesulfonylamino-4'-(3-methylbutoxy)biphenyl-4-ylmethylsulfanylmethyl]phenyl}difluoromethylphosphonic acid trisodium salt;
[2-Bromo-4-(3-methanesulfonylamino-benzylsulfanylmethyl)phenyl]difluoromethylphosphonic acid trisodium salt;
{2-Bromo-4-[2-(4-bromophenyl)ethylsulfanylmethyl]phenyl}difluoromethylphosphoinc acid disodium salt;
[2-Bromo-4-(4-bromophenylsulfanylmethyl)phenyl]difluoromethylphosphonic acid disodium salt;
{2-Bromo-4-[4-(4-bromophenylsulfanyl)butyl]phenyl}difluoromethyphosphonic acid disodium salt;
{2-Bromo-4-[3-(1H-tetrazol-5-yl)propylsulfanylmethyl]phenyl}difluoromethylphosphonic acid trisodium salt;
[2-Bromo-4-(3-methyl-butylsulfanylmethyl)phenyl]difluoromethylphosphonic acid disodium salt;
(2-Bromo-4-cyclohexylsulfanylmethyl-phenyl)difluoromethylphosphonic acid disodium salt;
{2-Bromo-4-[3-(4-bromophenyl)propylsulfanylmethyl]phenyl}-difluoromethylphosphonic acid disodium salt;
{2-Bromo-4-[3-(4-bromophenyl)propylsulfanylmethyl]phenyl}-difluoromethylphosphonic acid disodium salt;
}2-Bromo-4-[3-(4-bromophenyl)allylsulfanylmethyl]phenyl}-difluoromethylphosphonic acid disodium salt;
{2-Bromo-4-[3-(3-ethyoxycarbonylphenyl)-prop-2-ynylsulfanylmethyl]phenyl}difluoromethylphosphonic acid disodium salt;
3-{3-[3-Bromo-4-(difluorophosphonomethyl)benzylsulfanyl]prop-1-ynyl}benzoic acid trisodium salt;
[2-Bromo-4-(pyridin-2-ylmethylsulfanylmethyl)-phenyl]-difluoromethylphosphonic acid disodium salt;
[2-Bromo-4-(4-bromobenzylsulfanylmethyl)-phenyl]-difluoromethylphosphonic acid disodium salt;
(2-Bromo-4-{[(1-phenylethyl)sulfanyl]methyl}phenyl)(difluoro)methylphosphonic acid;
(2-Bromo-4-{[(2-bromo-5-fluorobenzyl)sulfanyl]methyl}phenyl)(difluoro) methylphosphonic acid;
(2-Bromo-4-[(isopropylsulfanyl)methyl]phenyl}(difluoro)methylphosphonic acid;
(2-Bromo-4-{[(2-oxo-1,2-diphenylethyl)sulfanyl[methyl}phenyl)(difluoro) methylphosphonic acid;
(2-Bromo-4-{[(1,2-diphenylethyl)sulfanyl]methyl}phenyl)(difluoro)methylphosphonic acid;
[2-Bromo-4-({[2-(4-bromophenyl)-1-methylethyl]sulfanyl}methyl)phenyl](difluoro) methylphosphonic acid;
[2-Bromo-4-(1-methyl-2-phenyl-ethylsulfanylmethyl)phenyl]difluoromethylphosphonic acid;
[4-({[1,2-Bis(4-fluorophenyl)ethyl]sulfanyl}methyl)-2-bromophenyl](difluoro) methylphosphonic acid;
(2-Bromo-4-{[(2-oxo-2-phenylethyl)sulfanyl]methyl}phenyl)difluoro methylphosphonic acid;
(2-Bromo-4-{[(2-bromobenzyl)sulfanyl]methyl}phenyl)(difluoro)methylphosphonic acid;
(2-Bromo-4-{[(3-bromobenzyl)sulfanyl]methyl}phenyl)(difluoro)methylphosphonic acid;
(2-Bromo-4-{[(4-iodobenzyl)sulfanyl]methyl}phenyl)(difluoro)methylphosphonic acid;
(2-Bromo-4-{[(4-bromo-2-fluorobenzyl)sulfanyl]methyl}phenyl)(difluoro) methylphosphonic acid;
[2-Bromo-4-({[4-(trifluoromethoxy)benzyl]sulfanyl}methyl)phenyl](difluoro)methylphosphonic acid;
[2-Bromo-4-({[4-(ethoxycarbonyl)benzyl]sulfanyl}methyl)phenyl](difluoro)methylphosphonic acid;
[4-({[Bis(4-bromophenyl)methyl]sulfanyl}methyl)-2-bromophenyl](difluoro)methylphosphonic acid;
{4-[(Benzhydrylsulfanyl)methyl]-2-bromophenyl}(difluoro)methylphosphonic acid;
2-[({4-(Difluorophosphonomethyl)-3-bromophenyl]methylthio}methyl)phenyl]methylthio}methyl)cyclopropyl]acetic acid;
(2-Bromo-4-{[3-(3-phosphonophenyl)propylthio]methyl}phenyl)difluoromethylphosphonic acid;
5-{[(3-Bromo-4-phosphonophenyl)methylthio]methyl}-2-chlorobenzenesulfonamide;
3-[4-({[4-(Difluorophosphonomethyl)-3-bromophenyl]methylthio}methyl)phenyl]benzenesulfonamide;
[2-Bromo-4-(4'-bromobiphenyl-4-ylmethylsulfanylmethyl)phenyl]difluoromethylphosphonic acid disodium salt;
({[4-({[4-(Difluorophosphonomethyl)-3-bromophenyl]methylthio}methyl)phenyl]methyl}sulfonyl)benzene;
4-({[4-({[4-(Difluorophosphonomethyl)-3-bromophenyl]methylthio}methyl)phenyl]methylthio}methyl)benzenesulfonamide;
(2-Bromo-4-{[(4-bromophenyl)methylthio}phenyl)difluoromethylphosphonic acid;
1-({[4-(Difluorophosphonomethyl)-3-bromophenyl]methylthio}methyl)-4-(methylsulfinyl)benzene;
5-[(3-{[4-(Difluorophosphonomethyl)-3-bromophenyl]methylthio}phenylthio)methyl]2,4-dichlorobenzenesulfonamide;
3-[5-({[4-(Difluorophosphonomethyl)-3-bromophenyl]methylthio}methyl)-2-pyridyl]benzenesulfonamide;
(2-Bromo-4-{[(6-chloro(3-pyridyl))methylthio]methyl}phenyl)difluoromethylphosphonic acid;

2-{3-[4-({[4-(Difluorophosphonomethyl)-3-bromophenyl]methylthio}methyl)phenyl]phenyl}-4-methylpentanoic acid;
[2-Bromo-4-(4-fluorobenzylsulfanylmethyl)-phenyl]-difluoromethylphosphonic acid disodium salt;
[2-Bromo-4-(5-phenyl-[1,3,4]oxadiazol-2-ylsulfanymethyl)-pheyl]-difluoromethylphosphonic acid disodium salt;
{2-Bromo-4-[3-(3-methylsulfonylphenyl)-prop-2-ynylsulfanylmethyl]-phenyl}-difluoromethylphosphonic acid disodium salt;
{2-Bromo-4-[3-(4-bromophenyl)-prop-2-ynylsulfanylmethyl]-phenyl}-difluoromethylphosphonic acid disodium salt;
2-Bromo-4-(4-methylsulfonylbenzylsulfanylmethyl)-phenyl]-difluoromethylphosphonic acid;
[4-(4-Benzyloxybenzylsulfanylmethyl)-2-bromophenyl] difluoromethylphosphonic acid;
{2-Bromo-4-[2-(2-methoxyethoxy)ethylsulfanylmethyl] phenyl}difluoromethylphosphonic acid;
[4-(4-Acetylaminobenzylsulfanylmethyl)-2-bromophenyl] diflurormethylphosphonic acid;
[4-(2-Benzenesulfinylethylsulfanylmethyl)-2-bromophenyl] difluoromethylphosphonic acid;
[2-Bromo-4-(3,3-dimethyl-2-oxobutylsulfanylmethyl) phenyl]difluoromethylphosphonic acid;
[2-Bromo-4-(2,4,6-trimethylbenzylsulfanylmethyl) phenyl] difluoromethylphosphonic acid;
2-Bromo-4-(3-nitrobenzylsulfanylmethyl) phenyl] difluoromethylphosphonic acid;
[2-Bromo-4-(3-phenoxypropylsulfanylmethyl) phenyl] difluoromethylphosphonic acid;
[2-Bromo-4-(3-methoxybenzylsulfanylmethyl) phenyl] difluoromethylphosphonic acid;
[2-Bromo-4-(tetrahydropyran-2-ylmethylsulfanylmethyl) phenyl]difluoromethylphosphonic acid;
{2-Bromo-4-[4-(1,3-dioxo-1,3-dihydroisoindol-2-yl) butylsulfanylmethyl]phenyl}difluoromethylphosphonic acid;
[2-Bromo-4-(4-nitrobenzylsulfanylmethyl) phenyl] difluoromethylphosphonic acid;
2-Bromo-4-(6-cyanohexylsulfanylmethyl) phenyl] difluoromethylphosphonic acid;
[2-Bromo-4-(4,4,4-trifluorobutylsulfanylmethyl) phenyl] difluoromethylphosphonic acid;
[2-Bromo-4-(7-hydroxyheptylsulfanylmethyl) phenyl] difluoromethylphosphonic acid;
[2-Bromo-4-(7-methoxy-2-oxo-2H-chromen-4-ylmethylsulfanylmethyl) phenyl] difluoromethylphosphonic acid;
(2-Bromo-4-hexylsulfanylmethylphenyl) difluoromethylphosphonic acid
[2-Bromo-4-(carbamoylmethylsulfanylmethyl)phenyl] difluoromethylphosphonic acid;
[4-(2-Benzenesulfonylmethylbenzylsulfanylmethyl)-2-bromophenyl]difluoromethylphosphonic acid;
[2-Bromo-4-(2-piperidin-1-ylethylsulfanylmethyl)phenyl] difluoromethylphosphonic acid;
[2-Bromo-4-(pyridin-4-ylmethylsulfanylmethyl)phenyl] difluoromethylphosphonic acid;
[2-Bromo-4-(2-methylthiazol-4ylmethylsulfanylmethyl) phenyl]difluoromethylphosphonic acid;
{4-[3-(4-Acetyl-3-hydroxy-2-propylphenoxy)-propylsulfanylmethyl]-2-bromophenyl}difluoromethylphosphonic acid;
[2-Bromo-4-(3,5-difluorobenzylsulfanylmethyl)phenyl] difluoromethylphosphonic acid;
[2-Bromo-4-(4-methylbenzylsulfanylmethyl)-phenyl]-difluoromethylphosphonic acid;
[2-Bromo-4-(3-ethoxycarbonylphenylsulfanylmethyl) phenyl]difluoromethylphosphonic acid;
[2-Bromo-4-(2,3-difluorobenzylsulfanylmethyl)phenyl] difluoromethylphosphonic acid;
[2-Bromo-4-(3,4-dichlorobenzylsulfanylmethyl)phenyl] difluoromethylphosphonic acid;
[2-Bromo-4-(2-phenylbenzylsulfanylmethyl)phenyl] difluoromethylphosphonic acid;
[2-Bromo4-(2,6-dichlorobenzylsulfanylmethyl)phenyl] difluoromethylphosphonic acid;
[2-Bromo-4-(3-cyanobenzylsulfanylmethyl)phenyl] difluoromethylphosphonic acid;
[2-Bromo-4-(2-trifluoromethylbenzylsulfanylmethyl) phenyl]difluoromethylphosphonic acid;
[2-Bromo-4-(2-nitrobenzylsulfanylmethyl)phenyl] difluoromethylphosphonic acid;
[2-Bromo-4-(3-trifluoromethylbenzylsulfanylmethyl) phenyl]difluoromethylphosphonic acid;
[2-Bromo-4-(2-iodobenzylsulfanylmethyl)phenyl] difluoromethylphosphonic acid;
[2-Bromo-4-(2-fluorobenzylsulfanylmethyl)phenyl] difluoromethylphosphonic acid;
[2-Bromo-4-(3-fluorobenzylsulfanylmethyl)phenyl] difluoromethylphosphonic acid;
[2-Bromo-4-(2-chloro-4-fluorobenzylsulfanylmethyl) phenyl]difluoromethylphosphonic acid;
[2-Bromo-4-(3-iodobenzylsulfanylmethyl)phenyl] difluoromethylphosphonic acid;
[2-Bromo-4-(4-methylnaphthalen-1-ylmethylsulfanylmethyl)phenyl] difluoromethylphosphonic acid;
[2-Bromo-4-(2-chloro-6-fluorobenzylsulfanylmethyl) phenyl]difluoromethylphosphonic acid;
[2-Bromo-4-(3,5-dibromobenzylsulfanylmethyl)phenyl] difluoromethylphosphonic acid;
[2-Bromo-4-(2-chlorobenzylsulfanylmethyl)phenyl] difluoromethylphosphonic acid;
[2-Bromo-4-(3-methylbenzylsulfanylmethyl)phenyl] difluoromethylphosphonic acid;
[2-Bromo-4-(2,3,5,6-tetrafluoro-4-trifluorobenzylsulfanylmethyl)phenyl] difluoromethylphosphonic acid;
[2-Bromo-4-(3-chlorobenzylsulfanylmethyl)phenyl] difluoromethylphosphonic acid;
[2-Bromo-4-(2,5-difluorobenzylsulfanylmethyl)phenyl] difluoromethylphosphonic acid;
[2-Bromo-4-(2,6-difluorobenzylsulfanylmethyl)phenyl] difluoromethylphosphonic acid;
[2-Bromo-4-(2,5-dichlorobenzylsulfanylmethyl)phenyl] difluoromethylphosphonic acid;
[2-Bromo-4-(2-methylbenzylsulfanylmethyl)phenyl] difluoromethylphosphonic acid;
[2-Bromo-4-(2,4-dichlorobenzylsulfanylmethyl)phenyl] difluoromethylphosphonic acid;
[2-Bromo-4-(1-methyl-1H-tetrazol5-ylsulfanylmethyl)-phenyl]-difluoromethylphosphonic acid;
[2-Bromo-4-(4-oxo-3,4-dihydroquinazolin-2-ylsulfanylmethyl)-phenyl]-difluoromethylphosphonic acid;
[2-Bromo-4-(pyrimidin-2-ylsulfanylmethyl)phenyl]-difluoromethylphosphonic acid;
[2-Bromo-4-(5-pyridin-4-yl-[1,3,4]oxadiazol-2-ylsulfanylmethyl)-phenyl]-difluoromethylphosphonic acid;
[2-Bromo-4-(4-phenylthiazol-2-ylsulfanylmethyl)-phenyl]-difluoromethylphosphonic acid;

{2-Bromo-4-[5-(4-chlorophenyl)-2H-[1,2,4]triazol-3-ylsulfanylmethyl)-phenyl}-difluoromethylphosphonic acid;
[2-Bromo-4-(pyridin-2-ylsulfanylmethyl)-phenyl]-difluoromethylphosphonic acid;
[2-Bromo-4-(quinolin-2-ylsulfanylmethyl)-phenyl]-difluoromethylphosphonic acid;
[2-Bromo-4-(5-methyl-1,3,4]thiadiazol-2-ylsulfanylmethyl)-phenyl]-difluoromethylphosphonic acid;
[2-Bromo-4-(5-phenyl-1H-[1,2,4]triazol-3-ylsulfanylmethyl)-phenyl]-difluoromethylphosphonic acid;
[2-Bromo-4-(1-methyl-1H-imidazol-2-ylsulfanylmethyl)-phenyl]-difluoromethylphosphonic acid;
[4-(4-Acetylaminophenylsulfanylmethyl)-2-bromophenyl]-difluoromethylphosphonic acid;
[2-Bromo-4-(3-chlorophenylsulfanylmethyl)-phenyl]-difluoromethylphosphonic acid;
3-[3-Bromo-4-(difluorophosphonomethyl)-benzylsulfanyl]benzoic acid;
[2-Bromo-4-(3-bromophenylsulfanylmethyl)-phenyl]-difluoromethylphosphonic acid;
[2-Bromo-4-(3,5-dichlorophenylsulfanylmethyl)-phenyl]-difluoromethylphosphonic acid;
[2-Bromo-4-(4-chlorophenylsulfanylmethyl)-phenyl]-difluoromethylphosphonic acid;
{2-Bromo-4-[3-(1-methyl-1H-tetrazol-5-ylsulfanyl)-propyl]phenyl}-difluoromethylphosphonic acid;
{2-Bromo-4-[3-(4-oxo-3,4-dihydrouinazolin-2-ylsulfanyl)-propyl]phenyl}-difluoromethylphosphonic acid;
{2-Bromo-4-[3-(pyrimidin-2-ylsulfanyl)-propyl]phenyl}-difluoromethylphosphonic acid;
{2-Bromo-4-[3-(5-pyridin-4-yl-[1,3,4]oxadiazol-2-ylsulfanyl)-propyl]phenyl}-difluoromethylphosphonic acid;
{2-Bromo-4-[3-(4-phenylthiazol-2-ylsulfanyl)-propyl]phenyl}-difluoromethylphosphonic acid;
(2-Bromo-4-{3-[5-(4-chlorophenyl)-2H-[1,2,4]triazol-3-ylsulfanyl)-propyl}phenyl]-difluoromethylphosphonic acid;
{2-Bromo-4-[3-(pyridin-2-ylsulfanyl)-propyl]phenyl}-difluoromethylphosphonic acid;
{2-Bromo-4-[3-(quinolin-2-ylsulfanyl)-propyl]phenyl}-difluoromethylphosphonic acid;
{2-Bromo-4-[3-(5-methyl-1H-benzoimidazol-2-ylsulfanyl)-propyl]phenyl}-difluoromethylphosphonic acid;
{2-Bromo-4-[3-(5-methyl-[1,3,4]thiadiazol-2-ylsulfanyl)-propyl]phenyl}-difluoromethylphosphonic acid;
{2-Bromo-4-[3-(5-phenyl-1H-[1,2,4]triazol-2-ylsulfanyl)-propyl]phenyl}-difluoromethylphosphonic acid;
{2-Bromo-4-[3-(1-methyl-1H-imidazol-2-ylsulfanyl)-propyl]phenyl}-difluoromethylphosphonic acid;
{4-[3-(4-Acetylaminophenylsulfanyl)-propyl]-2-bromophenyl}-difluoromethylphosphonic acid;
{2-Bromo-4-[3-(3-chlorophenyslufanyl)-propyl]phenyl}-difluoromethylphosphonic acid;
3-{3-[3-Bromo-4-(difluorophosphonomethyl)-phenyl]-propylsulfanyl}benzoic acid;
{2-Bromo-4-[3-(3-bromophenylsulfanyl)-propyl]phenyl}-difluoromethylphosphonic acid;
{2-Bromo-4-[3-(3,5-dichlorophenylsulfanyl)-propyl]phenyl}-difluoromethylphosphonic acid;
{2-Bromo-4-[3-(1H-imidazol-2-ylsulfanyl)-propyl]phenyl}-difluoromethylphosphonic acid;
{2-Bromo-4-[3-(4-chlorophenylsulfanyl)-propyl]phenyl}-difluoromethylphosphonic acid;
{2-Bromo-4-[4-(1-methyl-1H-tetrazol-5-ylsulfanyl)-butyl]phenyl}-difluoromethylphosphonic acid;
{2-Bromo-4-[4-(4-oxo-3,4-dihydroquinazolin-2-ylsulfanyl)-butyl]phenyl}-difluoromethylphosphonic acid;
{2-Bromo-4-[4-(pyrimidin-2-ylsulfanyl)-butyl]phenyl}-difluoromethylphosphonic acid;
{2-Bromo-4-[4-(5-pyridin-4-yl-[1,3,4]oxadiazol-2-ylsulfanyl)-butyl]phenyl}-difluoromethylphosphonic acid;
{2-Bromo-4-[4-(4-phenylthiazol-2-ylsulfanyl)-butyl]phenyl}-difluoromethylphosphonic acid;
(2-Bromo-4-{4-5-(4-chlorophenyl)-2H-[1,2,4]triazol-3-ylsulfanyl]-butyl}phenyl) -difluoromethylphosphonic acid;
{2-Bromo-4-[4-(pyridin-2-ylsulfanyl)-butyl]phenyl}-difluoromethylphosphonic acid;
{2-Bromo-4-[4-(quinolin-2-ylsulfanyl)-butyl]phenyl}-difluoromethylphosphonic acid;
{2-Bromo-4-[4-(5-methyl-[1,3,4]thiadiazol-2-ylsulfanyl)-butyl]phenyl}-difluoromethylphosphonic acid;
{2-Bromo-4-[4-(5-phenyl-1H-[1,2,4]triazol-2-ylsulfanyl)-butyl]phenyl}-difluoromethylphosphonic acid;
{2-Bromo-4-[4-(1-methyl-1H-imidazol-2-ylsulfanyl)-butyl]phenyl}-difluoromethylphosphonic acid;
{4-[4-(4-Acetylaminophenylsulfanyl)-butyl]-2-bromophenyl}-difluoromethylphosphonic acid;
{2-Bromo-4-[4-(3-chlorophenylsulfanyl)-butyl]phenyl}-difluoromethylphosphonic acid;
3-{4-[3-Bromo-4-(difluorophosphonomethyl)-phenyl]butylsulfanyl}benzoic acid;
{2-Bromo-4-[4-(3-bromophenylsulfanyl)-butyl]phenyl}-difluoromethylphosphonic acid;
{2-Bromo-4-[4-(3,5-dichlorophenylsulfanyl)-butyl]phenyl}-difluoromethylphosphonic acid;
{2-Bromo-4-[4-(1H-imidazol-2-ylsulfanyl)-butyl]phenyl}-difluoromethylphosphonic acid; and
{2-Bromo- 4-[4-(4-chlorophenylsulfanyl)-butyl]phenyl}-difluoromethylphosphonic acid.

23. A pharmaceutical composition which is comprised of a compound in accordance with claim 1 in combination with a pharmaceutically acceptable carrier.

24. A method of treating or controlling diabetes and complications thereof in a mammalian patient in need of such treatment comprising administering to said patient an anti-diabetic effective amount of a compound in accordance with claim 1.

25. A method of treating, controlling or preventing obesity in a mammalian patient in need of such treatment comprising administering to said patient an anti-obesity effective amount of a compound in accordance with claim 1.

26. A method of treating or controlling one or more disease or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, and dyslipidemia, said method comprising the administration of an effective amount of the compound of claim 1.

* * * * *